(12) United States Patent
Connors et al.

(10) Patent No.: US 12,202,886 B2
(45) Date of Patent: *Jan. 21, 2025

(54) NEUTRALIZING ANTIBODIES TO GP120 AND THEIR USE

(71) Applicant: The United States of America, as represented by the Secretary, Department of Health and Human Services, Bethesda, MD (US)

(72) Inventors: Mark Connors, Bethesda, MD (US); Jinghe Huang, Derwood, MD (US); Byong Ha Kang, Rockville, MD (US); John Mascola, Rockville, MD (US); Elise Ishida, Chevy Chase, MD (US); Tongqing Zhou, Boyds, MD (US); Peter Kwong, Washington, DC (US); Anqi Zheng, Boyds, MD (US)

(73) Assignee: THE UNITED STATES OF AMERICA, as represented by the Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/855,553

(22) Filed: Jun. 30, 2022

(65) Prior Publication Data

US 2023/0060304 A1    Mar. 2, 2023

Related U.S. Application Data

(63) Continuation of application No. 17/358,522, filed on Jun. 25, 2021, now abandoned, which is a continuation of application No. 16/786,267, filed on Feb. 10, 2020, now abandoned, which is a continuation of application No. 15/559,791, filed as application No. PCT/US2016/023145 on Mar. 18, 2016, now Pat. No. 10,562,960.

(60) Provisional application No. 62/250,378, filed on Nov. 3, 2015, provisional application No. 62/136,228, filed on Mar. 20, 2015.

(51) Int. Cl.
| | |
|---|---|
| C07K 16/10 | (2006.01) |
| A61P 31/18 | (2006.01) |
| C07K 16/28 | (2006.01) |
| C07K 16/46 | (2006.01) |
| G01N 33/569 | (2006.01) |
| A61K 39/00 | (2006.01) |

(52) U.S. Cl.
CPC ......... *C07K 16/1063* (2013.01); *A61P 31/18* (2018.01); *C07K 16/2809* (2013.01); *C07K 16/468* (2013.01); *G01N 33/56988* (2013.01); *A61K 2039/505* (2013.01); *A61K 2039/545* (2013.01); *C07K 2317/21* (2013.01); *C07K 2317/31* (2013.01); *C07K 2317/52* (2013.01); *C07K 2317/76* (2013.01); *G01N 2333/162* (2013.01); *G01N 2800/26* (2013.01)

(58) Field of Classification Search
None
See application file for complete search history.

(56) References Cited

U.S. PATENT DOCUMENTS

| | | |
|---|---|---|
| 10,562,960 B2 | 2/2020 | Connors et al. |
| 2003/0118985 A1 | 6/2003 | Hunt et al. |
| 2012/0213783 A1 | 8/2012 | Rosenberg et al. |
| 2012/0288502 A1 | 11/2012 | Diskin et al. |
| 2013/0251726 A1 | 9/2013 | Mascola et al. |

FOREIGN PATENT DOCUMENTS

| | | |
|---|---|---|
| AU | 2013288641 A1 | 12/2014 |
| CN | 1227610 A | 9/1999 |
| WO | WO 1997/46697 | 12/1997 |
| WO | WO 2011/038290 | 3/2011 |
| WO | WO 2011/046623 | 4/2011 |
| WO | WO 2012/040562 | 3/2012 |
| WO | WO 2012/079000 | 6/2012 |
| WO | WO 2012/154312 | 11/2012 |
| WO | WO 2012/158948 | 11/2012 |
| WO | WO 2013/016468 | 1/2013 |
| WO | WO 2013/086533 | 6/2013 |
| WO | WO 2013/090644 | 6/2013 |
| WO | WO 2013/126726 | 8/2013 |
| WO | WO 2013/142324 | 9/2013 |
| WO | WO 2013/163427 | 10/2013 |
| WO | WO 2014/043386 | 3/2014 |
| WO | WO 2015/103549 | 7/2015 |

OTHER PUBLICATIONS

Barouch et al., "A Human T-Cell Leukemia Virus Type 1 Regulatory Element Enhances the Immunogenicity of Human Immunodeficiency Virus Type 1 DNA Vaccines in Mice and Nonhuman Primates," *J Virol.* 79.14: 8828-8834, Jul. 2005.

Brentjens et al., "Treatment of Chronic Lymphocytic Leukemia with Genetically Targeted Autologous T Cells: Case Report of an Unforeseen Adverse Event in a Phase I Clinical Trial." *Mol Ther.* 18.4: 666-668: Apr. 2010.

Brown et al., "Tolerance of Single, but not Multiple, Amino Acid Replacements in Antibody VH CDR 2: A Means of Minimizing B Cell Wastage from Somatic Hypermutation?" *J Immunol.* 156.9: 3285-3291, May 1996.

(Continued)

*Primary Examiner* — Nicole Kinsey White
(74) *Attorney, Agent, or Firm* — Klarquist Sparkman, LLP

(57) ABSTRACT

Antibodies and antigen binding fragments that specifically bind to gp120 and neutralize HIV-1 are disclosed. Nucleic acids encoding these antibodies, vectors and host cells are also provided. Methods for detecting HIV-1 using these antibodies are disclosed. In addition, the use of these antibodies, antigen binding fragment, nucleic acids and vectors to prevent and/or treat an HIV-1 infection is disclosed.

11 Claims, 37 Drawing Sheets

Specification includes a Sequence Listing.

(56) References Cited

OTHER PUBLICATIONS

Clark and Walsh, "Crystal Structure of a 3B3 Variant—A Broadly Neutralizing HIV-1 scFv Antibody," *Protein Sci. 18.12*: 2429-2441, Dec. 2009.
Craig et al., "Anti-HIV Double Variable Domain Immunoglobulins Binding Both gp41 and gp120 for Targeted Delivery of Immunoconjugates," *PLoS One 7.10*: e46778, Oct. 2012.
Diskin et al., "Increasing the Potency and Breadth of an HIV Antibody by Using Structure-Based Rational Design," *Science 334.6060*: 1289-1293, Dec. 2011.
Dondelinger et al., "Understanding the Significance and Implications of Antibody Numbering and Antigen-Binding Surface/Residue Definition," *Front Immunol. 9*: 2278, Oct. 2018 (15 pages).
Gardner et al., "AAV-Expressed eCD4-Ig Provides Durable Protection from Multiple SHIV Challenges," *Nature 519.7541*: 87-91, Feb. 2015.
GenBank Sequences AFQ31504 (heavy Chain) and AFQ3150 (light chain), Jun. 2012.
Georgiev et al., "Delineating Antibody Recognition in Polyclonal Sera from Patterns of HIV-1 Isolate Neutralization," *Science 340. 6133*: 751-756, May 2013.
Grupp et al., "Chimeric Antigen Receptor-Modified T Cells for Acute Lymphoid Leukemia," *N Engl J of Med. 368.16*: 1509-1518, Apr. 2013.
Han et al., "Chimeric Antigen Receptor-Engineered T Cells for Cancer Immunotherapy: Progress and Challenges," *Journal of Hematology & Oncology 6.1*: 47, Jul. 2013.
Haynes et al., "Cardiolipin Polyspecific Autoreactivity in Two Broadly Neutralizing HIV-1 Antibodies," *Science 308.5730*: 1906-1908, Jun. 2005.
Huang et al., "Identification of a CD4-Binding-Site Antibody to HIV that Evolved Near-Pan Neutralization Breadth," *Immunity 45.5*: 1108-1121, Nov. 2016.
Huang et al., "Isolation of Human Monoclonal Antibodies from Peripheral Blood B Cells," *Nature Protocols 8.10*: 1907-1915, Sep. 2013.
Jianhua et al., "Modification in Framework Region I Results in a Decreased Affinity of Chimeric Anti-TAG72 Antibody," *Mol Immunol. 28.1-2*: 141-148, Jan.-Feb. 1991.
Johnson et al., "Vector-Mediated Gene Transfer Engenders Long-Lived Neutralizing Activity and Protection Against SIV Infection in Monkeys," *Nat Med. 15.8*: 901-906, Aug. 2009.
Julg et al., "Virological Control by the CD4-Binding Site Antibody N6 in SHIV-Infected Rhesus Monkeys," *J Virol. 91.16*: e00498-17, Aug. 2017.
Klein et al., "Broad Neutralization by a Combination of Antibodies Recognizing the CD4 Binding Site and a New Conformational Epitope on the HIV-1 Envelope Protein," *J Exp Med. 209.8*: 1469-1479, Jul. 2012.
Kwong et al., "Human Antibodies that Neutralize HIV-1: Identification, Structures, and B Cell Ontogenies," *Immunity 37.3*:412-425, Sep. 2012.
Kwong et al., "Broadly Neutralizing Antibodies and the Search for an HIV-1 Vaccine: The End of the Beginning," *Nat Rev Immunol. 13.9*: 693-701, Sep. 2013.
Li et al., "Human Immunodeficiency Virus Type 1 env Clones from Acute and Early Subtype B Infections for Standardized Assessments of Vaccine-Elicited Neutralizing Antibodies," *J Virol. 79.16*: 10108-10125, Aug. 2005.
Li et al., "Mechanism of Neutralization by the Broadly Neutralizing HIV-1 Monoclonal Antibody VRC01," *J Virol. 85.17*: 8954-8967, Sep. 2011.
Lynch et al., "HIV-1 Fitness Cost Associated with Escape from the VRC01 Class of CD4 Binding Site Neutralizing Antibodies," *J Virol. 89.8*: 4201-4213, Apr. 2015.
Lynch et al., "The Development of CD4 Binding Site Antibodies During HIV-1 Infection," *J Virol. 86.14*: 7588-7595, Jul. 2012.
Matthews et al., "Prospects for Development of a Vaccine Against HTLV-III-Related Disorders," *AIDS Res Hum Retroviruses 3.Suppl 1*: 197-206, 1987.
Morgan et al., "Case Report of a Serious Adverse Event Following the Administration of T Cells Transduced with a Chimeric Antigen Receptor Recognizing ERBB2," *Mol Ther. 18.4*: 843-851, Apr. 2010.
Nakamura et al., "Coverage of Primary Mother-to-Child HIV Transmission Isolates by Second-Generation Broadly Neutralizing Antibodies," *AIDS (London, England) 27.3*: 337-346, Jan. 2013.
Neith, "Building Better HIV Antibodies," Caltech Media Relations, published Oct. 27, 2011, available at http://www.caltech.edu/article/13468 (last accessed May 28, 2013).
Park et al., "Treating Cancer with Genetically Engineered T Cells," *Trends in Biotechnology 29.11*: 550-557, Nov. 2011.
Rudicell et al., "Enhanced Potency of a Broadly Neutralizing HIV-1 Antibody In Vitro Improves Protection Against Lentiviral Infection In Vivo," *J Virol. 88.21*: 12669-12682, Nov. 2014.
Scheid et al., "Sequence and Structural Convergence of Broad and Potent HIV Antibodies that Mimic CD4 Binding," *Science 333. 6049*: 1633-1637, Sep. 2011.
Till et al., "Adoptive Immunotherapy for Indolent Non-Hodgkin Lymphoma and Mantle Cell Lymphoma Using Genetically Modified Autologous CD20-Specific T Cells," *Blood 112.6*: 2261-2271, Sep. 2008.
Tiller et al., "Efficient Generation of Monoclonal Antibodies from Single Human B Cells by Single Cell RT-PCR and Expression Vector Cloning," *J Immunol Methods 329.1*: 112-124: Jan. 2008.
Walker et al., "Mapping Broadly Neutralizing Antibody Specificities in Donor Sera," AIDS Vaccine 2010, Atlanta Georgia (2010), available at: http://www.vaccineenterprise.org/conference_archive/2010/pdf-presentations/Thursday/Symposium-06/WalkerL.pdf, last accessed Jun. 9, 2014.
West et al., "Structural Basis for Germ-Line Gene Usage of a Potent Class of Antibodies Targeting the CD4-Binding Site of HIV-1 gp120," *Proc Natl Acad Sci USA 109.30*: E2083-E2090, Jul. 2012.
Wu et al., "Focused Evolution of HIV-1 Neutralizing Antibodies Revealed by Structures and Deep Sequencing," *Science 333.6049*: 1593-1602, Sep. 2011.
Wu et al., "Rational Design of Envelope Identifies Broadly Neutralizing Human Monoclonal Antibodies to HIV-1," *Science, 329. 5993*: 856-861, Aug. 2010.
Wu et al., "Selection Pressure on HIV-1 Envelope by Broadly Neutralizing Antibodies to the Conserved CD4-Binding Site," *J Virol. 86.10*: 5844-5856, May 2012.
Zalevsky et al., "Enhanced Antibody Half-Life Improves In Vivo Activity," *Nat Biotechnol 28.2*: 157-159, Feb. 2010.
Zhao et al., "Study of HIV-1 gp120 monoclonal antibody blocking HIV infection of CD4 lymphocyte in vitro experiment," *Shaanxi Medical Journal* 39(7): 797-801 (Jul. 2010)(with English Translation).
Zhou et al., "Structural Basis for Broad and Potent Neutralization of HIV-1 by Antibody VRC01," *Science 329.5993*: 811-817, Aug. 2010.
Zhou et al., "Multidonor Analysis Reveals Structural Elements, Genetic Determinants, and Maturation Pathway for HIV-1 Neutralization by VRC01-Class Antibodies," *Immunity 39.2*: 245-258, Aug. 2013.
Zhu et al., "De Novo Identification of VRC01 Class HIV-1-Neutralizing Antibodies by Next-Generation Sequencing of B-Cell Transcripts," *Proc Natl Acad Sci USA* 110.43: E4088-E4097, Oct. 2013.

FIG. 1A

| SERUM | VRC01-like | b12-like | CD4-like | HJ16-like | 8ANC195-like | PG9-like | PGT128-like | 2G12-like | 2F5-like | 10E8-like | 35O22-like | Breadth (%) |
|---|---|---|---|---|---|---|---|---|---|---|---|---|
| 45 | 0.46 | | | | | | 0.25 | 0.25 | | 0.04 | | 81% |
| 127/C | 0.54 | 0.07 | | | | | | 0.12 | | 0.16 | 0.12 | 95% |
| Z258 | 0.4 | 0.08 | 0.12 | 0.18 | | 0.03 | | 0.2 | | | | 100% |
| N152 | | | | | | 0.08 | 0.29 | 0.05 | | 0.36 | 0.22 | 90% |

FIG. 1B

```
                     1         10         20         30             40           5052A      57
                     |          |          |          |              |           | ||        |
Heavy Chain           ____FR1_____    CDR1_   _____FR2____       _CDR2____
IGHV1-2*02   QVQLVQSGAEVKKPGASVKVSCKASGYTFT  GYYMH  WVRQAPGQGLEWMG   WINPNSGGT
        N6   RAHLVQSGTAMKKPGASVRVSCQTSGYTFT  AHILF  WFRQAPGRGLEWVG   WIKPQYGAV
       N17   RAHLVQSGTAVKRPGASVRVSCETSGYTFT  AHILY  WFRQAPGRGLEWVG   WIKPQYGAV
        F8   QVQLVQSGTAMKKPGASVRVSCQTSGYTFT  AHILF  WFRQAPGRGLEWVG   WIKPQYGAV
     VRC01   QVQLVQSGGQMKKPGESMRISCRASGYEFI  DCTLN  WIRLAPGKRPEWMG   WLKPRGGAV
     VRC27   Q-RLVQSGPQVRKPGSSVRISCETSGYTFN  AYILH  WFRQAPGRSFEWMG   WIKPKFGAV 60        70       8082ABC           90       100ABCDE102    110113
                     |          |        | ||||            |       |||||| |        | |
Heavy Chain          _CDR2____                  ___FR3_____   _CDR3_____   FR4(HJ5*01)
IGHV1-2*02   NYAQKFQG  RVTMTRDTSISTAYMELSRLRSDDTAVYYCAR  AYCGGDCYNWFDS   WGQGTLVTVSS
        N6   NFGGGFRD  RVTLTRDVYREIAYMDIRGLKPDDTAVYYCAR  DRSYGDSSWALDA   WGQGTTVVVSA
       N17   NFGGGFRG  RVTLTRDIYRDTAYMDISGLRFDDTAVYYCAR  DRSYDDSSWALDA   WGQGTTVVVSA
        F8   NFGGGFRD  RVTLTRDIYREIAYMDIRGLKLDDTAVYYCAR  DRSYGDSSWALDA   WGQGTTVVASA
     VRC01   NYARPLQG  RVTMTRDVYSDTAFLELRSLTVDDTAVYFCTR  GKNCDYN WDFEH  WGRGTPVIVSS
     VRC27   NYAHSFQG  RITLTRDIYRETAFLDLTGLRFDDTAVYYCAR  DRLYDGSSWRLDP   WGQGTRVVVSS 1         10         20         30             40           5052
                      |          |          |          |              |           | |
Kappa Chain            _____FR1_____    __CDR1___    ___FR2____   _CDR2___
IGKV1-33*01   DIQMTQSPSSLSASVGDRVTITC   QASQDISNYLN  WYQQKPGKAPKLLIY  DASNLET
         N6   YIHVTQSPSSLSVSIGDRVTINC   QTSQGVGSDLH  WYQHKPGRAPKLLIH  HTSSVED
        N17   YIHVTQSPSSLSVSAGDRVTINC   QTSQGVGRDLH  WYQHKPGRAPKLLIR  HASSVED
         F8   YIHVTQSPSSLSVSIGDRVTINC   QTSQGVGSDLH  WYQHKPGRAPKLLIH  HASSVED
      VRC01   EIVLTQSPGTLSLSPGETAIISC   RTSQYGSLA    WYQQRPGQAPRLVIY  SGSTRAA
      VRC27   FALMTQSPATLAVSVGDRVTITC   RASQGIGSDLH  WYQQKPGRPPKILIH  HASAREE 60         70        80          90         100       107
                       |          |         |           |          |         |
Kappa Chain           _____FR3_____  ____CDR3___   FR4(KJ5*01)
IGKV1-33*01   GVPSRFSGSGSGTDFTFTISSLQPEDIATYYC   QQYDNLPIT    FGQGTRLEIK
         N6   GVPSRFSGSGFHTSFNLTISDLQADDIATYYC   QVL-----QF   FGRGSRLHIK
        N17   GVPSRFSGTGFHTSFNLTINDLQSDDIATYYC   QVL-----ES   FGRGSRLDFK
         F8   GVPSRFSGSGFHTSFNLTINDLQADDIATYYC   QVL-----QF   FGRGSRLHIK
      VRC01   GIPDRFSGSRWGPDYNLTISNLESGDFGVYYC   QQY     EF   FGQGTKVQVDIKR
      VRC27   GVPSRFGGSGSHTSFIFTINDLQLDDVATYYC   QVL-----ES   FGQGTRLDIN
```

FIG. 1C

N6 Heavy Chain

| IGHV* | IGHD | IGHJ | CDR3 length (amino acid) | VH mutation frequency (nt) |
|---|---|---|---|---|
| 1-2*02 | 2-21*02 | 6*01 | 15 | 88/288 (31%) |

N6 Light Chain

| IGKV | IGKJ | CDR3 length (amino acid) | VK mutation frequency (nt) |
|---|---|---|---|
| 1-33*01 or 1D-33*01 | 5*01 | 5 | 69/279 (25%) |

FIG. 1D

| | N6 | VRC01 | 3BNC117 | VRC27 | PG9 | PGDM1400 | PGT121 | 10-1074 | 10E8 | 4E10 | 35O22 |
|---|---|---|---|---|---|---|---|---|---|---|---|
| No. of viruses | 181 | 177 | 180 | 175 | 177 | 171 | 177 | 178 | 180 | 180 | 181 |
| IC$_{50}$ <50 µg ml$^{-1}$ | 98% | 89% | 84% | 78% | 78% | 78% | 64% | 66% | 98% | 98% | 62% |
| IC$_{50}$ <1 µg ml$^{-1}$ | 96% | 75% | 77% | 56% | 65% | 70% | 51% | 46% | 72% | 37% | 49% |
| Geometric Mean IC$_{50}$* | 0.045 | 0.250 | 0.09 | 0.297 | 0.11 | 0.015 | 0.05 | 0.02 | 0.022 | 1.3 | 0.056 |
| Median IC$_{50}$ | 0.038 | 0.248 | 0.07 | 0.217 | 0.09 | 0.008 | 0.022 | 0.036 | 0.35 | 1.94 | 0.033 |
| Binding site | | CD4-binding site | | | V1V2 | | V3 | | gp41 MPER | | gp120-gp41 |

* Concentration is µg ml$^{-1}$

FIG. 1F

Neutralization of N6 and its variants against a 20-pseudovirus panel

IC50 (μg/ml)

| | Virus ID | Clade | N6 | F8 | N17 | N6 variant-1 N6H+F8K | N6 variant-2 N6H+N17K | N6 variant-3 N17H+F8K | N6 variant-4 N17H+N6K | N6 variant-5 F8H+N6K | N6 variant-6 F8H+N17K | VRC01 |
|---|---|---|---|---|---|---|---|---|---|---|---|---|
| 1 | 6540.v4.c1 | AC | 0.014 | 0.043 | 0.468 | 0.014 | 0.100 | 0.100 | 0.048 | 0.143 | 1.03 | >50 |
| 2 | 6545.V4.C1 | AC | 0.430 | >25 | >50 | 4.15 | 0.043 | >25 | >25 | >25 | 0.112 | >50 |
| 3 | 620345.c1 | AE | 0.398 | 0.045 | >50 | 1.09 | >50 | 0.662 | 1.28 | 1.69 | 6.17 | >50 |
| 4 | T278-50 | AG | >50 | >25 | >50 | >50 | >50 | >25 | >25 | >25 | >50 | >50 |
| 5 | 242-14 | AG | 0.256 | 1.50 | 1.16 | 0.269 | 1.57 | 0.255 | 0.307 | 3.78 | 1.03 | >50 |
| 6 | T250-4 | AG | 0.043 | 0.071 | 0.037 | 0.023 | 0.036 | 0.033 | 0.037 | 0.043 | 0.043 | >50 |
| 7 | 7165.18 | B | 0.708 | 1.38 | 19.2 | 0.764 | 2.13 | 4.61 | 7.20 | 2.90 | 2.02 | >50 |
| 8 | BL01.DG | B | >50 | >25 | >50 | >50 | >50 | >25 | >25 | >25 | >50 | >50 |
| 9 | HO86.8 | B | 0.045 | 0.043 | 0.387 | 0.043 | 0.043 | 0.118 | 0.153 | 0.148 | 0.237 | >50 |
| 10 | 6322.V4.C1 | C | 0.015 | 0.110 | 1.77 | 0.108 | 0.125 | 0.126 | 0.629 | 0.043 | 0.104 | >50 |
| 11 | DU422.01 | C | 0.043 | 0.228 | 0.278 | 0.106 | 1.04 | 0.255 | 0.123 | 0.258 | 1.94 | >50 |
| 12 | 8631.V3.C10 | C | 0.043 | 0.043 | 3.47 | 0.323 | 0.043 | 0.386 | 0.564 | 0.043 | 0.314 | >50 |
| 13 | TZA125.17 | C | 0.407 | 0.666 | >50 | 2.81 | >50 | >25 | >25 | 1.48 | 1.59 | >50 |
| 14 | CAP210.E8 | C | 0.043 | 0.043 | 0.043 | 0.043 | 0.748 | 0.042 | 0.028 | 0.043 | 0.043 | >50 |
| 15 | DU172.17 | C | 0.287 | 3.06 | 1.42 | 2.38 | 1.93 | 1.36 | 1.93 | 0.870 | 0.488 | >50 |
| 16 | 3817.v2.c59 | CD | 5.740 | 1.84 | 4.340 | 2.38 | 1.93 | 2.79 | 2.15 | 2.71 | 3.28 | >50 |
| 17 | 57128.vrc15 | D | 0.043 | 0.128 | 0.188 | 0.323 | 0.043 | 0.043 | 0.043 | 0.162 | 0.230 | >50 |
| 18 | X2088.c9 | G | 0.043 | >25 | >50 | >50 | >50 | >25 | >25 | >25 | >50 | >50 |
| 19 | 6471.V1.C16 | C | >50 | >25 | >50 | >50 | >50 | >25 | >25 | >25 | >50 | >50 |
| 20 | TV1.29 | C | >50 | >25 | >50 | >50 | >50 | >25 | >25 | >25 | >50 | >50 |

FIG. 2

| | Virus ID | Clade | IC50 (µg/ml) | | | |
|---|---|---|---|---|---|---|
| | | | N6 | VRC01 | VRC07-523-LS | 3BNC117 |
| 1 | 6540.v4.c1 | AC | 0.014 | >50 | >50 | >50 |
| 2 | 6545.V4.C1 | AC | 0.430 | >50 | >50 | >50 |
| 3 | 620345.c1 | AE | 0.338 | >50 | >50 | >50 |
| 4 | 242-14 | AG | 0.2559 | >50 | >50 | >50 |
| 5 | T250-4 | AG | 0.009 | >50 | >50 | >50 |
| 6 | 7165.18 | B | 0.709 | >50 | 1.430 | 6.540 |
| 7 | HO86.8 | B | 0.445 | >50 | >50 | >50 |
| 8 | 6322.V4.C1 | C | 0.027 | >50 | 0.023 | >50 |
| 9 | DU422.01 | C | 0.015 | >50 | 2.360 | >50 |
| 10 | 6631.V3.C10 | C | 0.065 | >50 | 0.148 | >50 |
| 11 | TZA125.17 | C | 0.407 | >50 | 1.410 | >50 |
| 12 | CAP210.E8 | C | 12.200 | >50 | >50 | 8.160 |
| 13 | DU172.17 | C | 0.016 | >50 | 0.065 | 0.289 |
| 14 | 3817.v2.c59 | CD | 0.2867 | >50 | 0.137 | >50 |
| 15 | 57128.vrc15 | D | 5.740 | >50 | 0.666 | 0.432 |
| 16 | X2088.c9 | G | 0.048 | >50 | >50 | >50 |
| 17 | T278-50 | AG | >50 | >50 | >50 | >50 |
| 18 | BL01.DG | B | >50 | >50 | >50 | >50 |
| 19 | 6471.V1.C16 | C | >50 | >50 | >50 | >50 |
| 20 | TV1.29 | C | >50 | >50 | 1.790 | >50 |

FIG. 3A
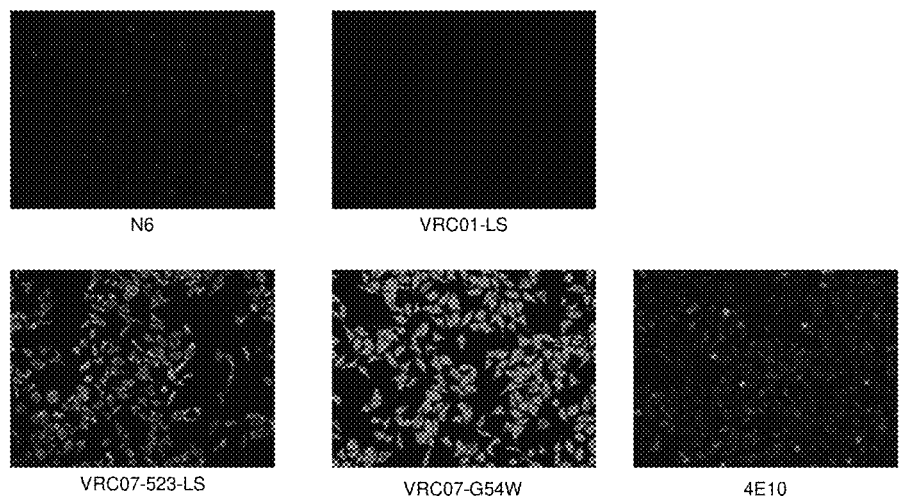
FIG. 3B
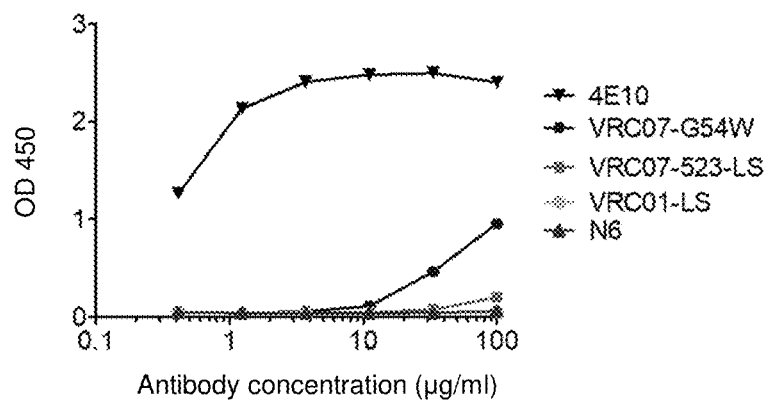
FIG. 3C
| Sample ID | SSA | SSB | Sm | RNP | Scl 70 | Jo 1 | dsDNA | Cent B | Histone |
|---|---|---|---|---|---|---|---|---|---|
| Neg Control | - | - | - | - | - | - | - | - | - |
| Pos Control 1 | | | | | | | | 319 | |
| Pos Control 2 | 496 | 878 | | | | 292 | 632 | | 423 |
| Pos Control 3 | | | 324 | 392 | 242 | | | | |
| synagis | 3.3 | 4.8 | 2.3 | 1.3 | 2 | 2.5 | 1.25 | 2 | 3 |
| 4E10 | 31 | 161 | 6.6 | 9 | 8 | 146 | 1 | 3 | 9 |
| N6 | 36.4 | 100.2 | 5.2 | 16.8 | 6 | 58.4 | 20.6 | 22 | 50.6 |

FIG. 4D

| gp120 domain | | Binding affinity relative to WT (%) | | | | | | | |
|---|---|---|---|---|---|---|---|---|---|
| | | N6 | VRC01 | 3BNC117 | VRC-PG04 | 12A21 | VRC27 | CD4-Ig | 2G12 |
| | WT | 100 | 100 | 100 | 100 | 100 | 100 | 100 | 100 |
| V2 | D167N | 83 | 77 | 95 | 42 | 108 | 37 | 58 | 100 |
| V1V2 stem | N197T | 80 | 72 | 101 | 39 | 131 | 28 | 25 | 100 |
| | N262A | 36 | 23 | 33 | 14 | 167 | 0 | 2 | 100 |
| | D279A | 15 | 0 | 0 | 247 | 188 | 7 | 49 | 100 |
| Loop D | N280A | 50 | 82 | 36 | 12 | 174 | 0 | 75 | 100 |
| | K282A | 28 | 33 | 3 | 12 | 29 | 57 | 53 | 100 |
| | T283A | 28 | 34 | 71 | 83 | 68 | 15 | 55 | 100 |
| V3 | N332A | 58 | 72 | 82 | 31 | 206 | 57 | 57 | 3 |
| | S365A | 28 | 63 | 90 | 34 | 454 | 107 | 34 | 100 |
| | G366A | 27 | 20 | 27 | 17 | 6 | 3 | 7 | 100 |
| | G367A | 19 | 18 | 25 | 19 | 2 | 0 | 3 | 100 |
| | D368A | 10 | 1 | 16 | 12 | 30 | 0 | 5 | 100 |
| CD4 binding loop | P369A | 57 | 50 | 75 | 44 | 122 | 38 | 54 | 100 |
| | E370A | 30 | 13 | 31 | 20 | 16 | 2 | 5 | 100 |
| | I371A | 31 | 16 | 40 | 21 | 17 | 0 | 12 | 100 |
| | V372A | 62 | 33 | 62 | 15 | 36 | 15 | 73 | 100 |
| | M373A | 67 | 56 | 133 | 44 | 63 | 23 | 91 | 100 |
| β23 | D457A | 13 | 22 | 84 | 0 | 23 | 19 | 3 | 100 |
| β24 | I467A | 77 | 42 | 87 | 40 | 49 | 27 | 115 | 100 |
| | R469A | 90 | 49 | 97 | 6 | 66 | 0 | 7 | 100 |
| | G471A | 113 | 108 | 164 | 64 | 162 | 131 | 141 | 100 |
| β24-α5 connection | G472A | 51 | 41 | 56 | 38 | 97 | 0 | 2 | 100 |
| | G473A | 103 | 48 | 40 | 34 | 53 | 6 | 0 | 100 |
| | D474A | 33 | 21 | 38 | 0 | 19 | 0 | 45 | 100 |
| | M475A | 82 | 75 | 169 | 90 | 76 | 35 | 117 | 100 |
| | R476A | 65 | 51 | 171 | 84 | 73 | 37 | 79 | 100 |

FIG. 4E

| gp120 domain | gp120 mutation | Neutralization fold change relative to WT | | | | | | | |
|---|---|---|---|---|---|---|---|---|---|
| | | N6 | VRC01 | 3BNC117 | VRC-PG04 | 12A21 | VRC27 | CD4-Ig | 2G12 |
| | WT | 1 | 1 | 1 | 1 | 1 | 1 | 1 | 1 |
| V2 | D167N | 1.6 | 1.4 | 1.1 | 1.1 | 1.9 | 2.7 | 0.4 | 2.9 |
| | N262A | 0.7 | 1.0 | 1.3 | 0.7 | 0.9 | 1.0 | 5.1 | 0.3 |
| | D279A | 0.7 | >312 | 2.0 | >269 | 34.1 | >1023 | 13.2 | 1.4 |
| Loop D | K282A | 0.8 | 0.8 | 12.4 | 25.0 | 62.1 | 1.6 | 6.9 | 1.1 |
| | T283A | 0.6 | 1.0 | 1.8 | 0.5 | 2.2 | 1.1 | 7.8 | 1.4 |
| V3 | N332A | 1.4 | 1.4 | 1.1 | 0.9 | 0.6 | 2.4 | 0.2 | >228 |
| | H363A | 0.8 | 0.8 | 1.5 | 0.7 | 1.1 | 1.1 | 2.4 | 1.7 |
| | S365A | 1.0 | 1.0 | 1.6 | 1.2 | 0.7 | 1.3 | 0.6 | 1.9 |
| CD4 binding loop | G366A | 1.0 | 0.6 | 0.4 | 0.3 | 3.1 | 2.3 | >17.6 | 2.0 |
| | P369A | 1.0 | 1.0 | 1.8 | 0.8 | 0.7 | 1.8 | 1.6 | 2.1 |
| | V372A | 0.6 | 0.9 | 1.9 | 1.0 | 3.3 | 3.0 | 4.4 | 2.0 |
| | M373A | 1.2 | 1.4 | 2.0 | 1.1 | 1.6 | 2.4 | 2.1 | 2.3 |
| β24-α5 connection | G471A | 0.7 | 0.6 | 1.8 | 0.7 | 0.6 | 1.3 | 1.7 | 2.0 |
| | D474A | 0.5 | 0.7 | 2.6 | 0.7 | 0.4 | 7.8 | 3.3 | 1.9 |
| | M475A | 0.7 | 0.4 | 1.7 | 0.7 | 1.1 | 0.6 | >17.6 | 0.6 |
| | R476A | 0.7 | 1.0 | 1.6 | 0.8 | 1.8 | 1.0 | >17.6 | 0.5 |

FIG. 5A

| Virus ID | | IC50 (μg/ml) | | Env sequence | | | |
|---|---|---|---|---|---|---|---|
| | | N6 | VRC01 | Loop D (276-283) | | CD4 BLP (362-374) | | β23-V5 (458-469) | |
| Reference viruses | HXB2 | | | NFTDNAKT | | KQSSGGDPEIVTH | | GGGNNNESE | TFR |
| | VRC57 | | 0.490 | (SEQ ID NO: 115) | | (SEQ ID NO: 117) | | (SEQ ID NO: 118) | |
| | 93TH057 | | 1.320 | NFTDNAKT | | TNSSGGNEFYWR | | GGNESSIE | IFR |
| | | | | (SEQ ID NO: 116) | | (SEQ ID NO: 119) | | (SEQ ID NO: 120) | |
| | | | | NLIRNAKT | | QFFSGGDLEITH | | GGSANTINE | TFR |
| | | | | (SEQ ID NO: 211) | | (SEQ ID NO: 122) | | (SEQ ID NO: 123) | |
| N6 sensitive viruses | 6540.v4.c1 | | >50 | NIGKSAMN | | RNSSGGDIETTR | | YGNRRSSNNE | TFR |
| | | | | (SEQ ID NO: 124) | | (SEQ ID NO: 125) | | (SEQ ID NO: 126) | |
| | 6545.v4.c1 | | >50 | NITRNAMN | | RNSSGGDIETTR | | YGNLSNNE | TFR |
| | | | | (SEQ ID NO: 127) | | (SEQ ID NO: 128) | | (SEQ ID NO: 129) | |
| | 620345.c1 | | >50 | DITTNAKT | | QFFSGGDIETTR | | GDGGFTADNE | TFR |
| | | | | (SEQ ID NO: 129) | | (SEQ ID NO: 130) | | (SEQ ID NO: 131) | |
| | 242-14 | | >50 | NISNRAKT | | TNRSGGDLEVTTR | | GPNSTYNE | TFR |
| | | | | (SEQ ID NO: 132) | | (SEQ ID NO: 133) | | (SEQ ID NO: 134) | |
| | T250-4 | | >50 | NFTDMAKT | | RKRSGGDLEVTTH | | GGGNKIDNGTE | IFR |
| | | | | (SEQ ID NO: 135) | | (SEQ ID NO: 136) | | (SEQ ID NO: 137) | |
| | 7165.18 | | >50 | NETDNVKT | | NQHSGGDFETTH | | GGGSRIGTE | IFR |
| | | | | (SEQ ID NO: 138) | | (SEQ ID NO: 139) | | (SEQ ID NO: 140) | |
| | H086.8 | | >50 | NFTDNBKT | | NQSTGGDFETAMP | | GGRSNSTE | VFR |
| | | | | (SEQ ID NO: 141) | | (SEQ ID NO: 142) | | (SEQ ID NO: 143) | |
| | 6322.V4.C3 | | >50 | NLTRNAXI | | QFHSGGDLEVTTR | | GGKGDNAMT | IFR |
| | | | | (SEQ ID NO: 144) | | (SEQ ID NO: 145) | | (SEQ ID NO: 146) | |
| | D0922-01 | | >50 | NLTRNAKT | | RFSSGGDLEVTTH | | GGSPSTNE | VFR |
| | | | | (SEQ ID NO: 147) | | (SEQ ID NO: 148) | | (SEQ ID NO: 149) | |
| | 6631.V3.C10 | | >50 | NLIRNAKT | | NSRSGGDLEITTR | | GGPPTSTE | IFR |
| | | | | (SEQ ID NO: 144) | | (SEQ ID NO: 150) | | (SEQ ID NO: 151) | |
| | TRA3.17 | | >50 | NLIRNAKT | | KFAVVGGDLEITTR | | GGRPFYNTE | IFR |
| | | | | (SEQ ID NO: 221) | | (SEQ ID NO: 152) | | (SEQ ID NO: 153) | |
| | DU172.17 | | >50 | NLIRNAKI | | APSSGGDLEITTR | | GGRKRSSYE | IFR |
| | | | | (SEQ ID NO: 144) | | (SEQ ID NO: 154) | | (SEQ ID NO: 155) | |
| | 3817.V2.c59 | | >50 | NVTDNAKT | | SFSSGGDFETTR | | GGLNSSONE | IFR |
| | | | | (SEQ ID NO: 156) | | (SEQ ID NO: 157) | | (SEQ ID NO: 158) | |
| | X2088.c9 | | >50 | NLTDNAKV | | NSFAKGDLEITTR | | GVNFTHNKENE | TFR |
| | | | | (SEQ ID NO: 159) | | (SEQ ID NO: 160) | | (SEQ ID NO: 161) | |
| | 57128.vrc15 | | >50 | NLIRNAKT | | NASSGGDFEITTR | | GGGADNRQNE | TFR |
| | | | | (SEQ ID NO: 144) | | (SEQ ID NO: 162) | | (SEQ ID NO: 163) | |
| | CAP210.E8 | | >50 | NISNRVKT | | APFVGGDLEITTR | | GGGNKTTNDTEIR | IFR |
| | | | | (SEQ ID NO: 164) | | (SEQ ID NO: 165) | | (SEQ ID NO: 166) | |

FIG. 5B

| | Virus ID | IC50 (μg/ml) | | Env sequence | | |

FIG. 5C

| Virus | Env sequence | | |
|---|---|---|---|
| | Loop D (276-283) | CD4 BLP (362-374) | β23-V5 (458-469) |
| HXBC2 | NFTDNAKT (SEQ ID NO: 116) | KQSSGGDPEIVTH (SEQ ID NO: 117) | GGNSNNESE IFR (SEQ ID NO: 118) |
| JRCSF | NFTDNAKT (SEQ ID NO: 116) | THSSGGDPEIVMH (SEQ ID NO: 119) | GGKNESEIE IFR (SEQ ID NO: 120) |
| 93TH057 | NLTDNAKT (SEQ ID NO: 121) | QPPSGGDLEITMH (SEQ ID NO: 122) | GGANNTSNE TFR (SEQ ID NO: 123) |
| T278-50 | NISANAKT (SEQ ID NO: 167) | TKPSGGDLEITTH (SEQ ID NO: 168) | GEGDEKANE TFR (SEQ ID NO: 169) |
| T278-50.V5 Swap | NISANAKT (SEQ ID NO: 167) | TKPSGGDLEITTH (SEQ ID NO: 168) | GGNSNNESE TFR (SEQ ID NO: 118) |
| T278-50.Loop D mut (A279D) | NIS<u>D</u>NAKT (SEQ ID NO: 187) | TKPSGGDLEITTH (SEQ ID NO: 168) | GEGDEKANE TFR (SEQ ID NO: 169) |
| T278-50.Loop D mut/V5 Swap | NISDNAKT (SEQ ID NO: 187) | TKPSGGDLEITTH (SEQ ID NO: 168) | GGNSNNESE TFR (SEQ ID NO: 118) |
| TV1.29 | NLTENTKT (SEQ ID NO: 173) | KPHAGGDIEITMH (SEQ ID NO: 174) | GGFNTTNNTE TFR (SEQ ID NO: 175) |
| TV1.29.V5 Swap | NLTENTKT (SEQ ID NO: 173) | KPHAGGDIEITMH (SEQ ID NO: 174) | GGKNESEIE TFR (SEQ ID NO: 188) |
| TV1.29.Loop D mut (E279D T281K) | NLTDNAKT (SEQ ID NO: 189) | KPHAGGDIEITMH (SEQ ID NO: 174) | GGFNTTNNTE TFR (SEQ ID NO: 175) |
| TV1.29.Loop D mut/V5 Swap | NLTDNAKT (SEQ ID NO: 189) | KPHAGGDIEITMH (SEQ ID NO: 174) | GGKNESEIE TFR (SEQ ID NO: 188) |
| TV1.29.Loop D/CD4 BLP mut/V5 Swap | NLTDNAKT (SEQ ID NO: 189) | KQSSGGDIEITMH (SEQ ID NO: 192) | GGKNESEIE TFR (SEQ ID NO: 188) |
| BL01 | NFTQNAKT (SEQ ID NO: 170) | NFPIRGGDPEIVMH (SEQ ID NO: 171) | GGKNGTEGTE IFR (SEQ ID NO: 172) |
| BL01.V5 Swap | NFTQNAKT (SEQ ID NO: 170) | NFPIRGGDPEIVMH (SEQ ID NO: 171) | GGKNESEIE IFR (SEQ ID NO: 120) |
| BL01.Loop D mut (Q279D E282K) | NFTDNAKT (SEQ ID NO: 116) | NFPIRGGDPEIVMH (SEQ ID NO: 171) | GGKNGTEGTE IFR (SEQ ID NO: 172) |
| BL01.Loop D mut/V5 Swap | NFTDNAKT (SEQ ID NO: 116) | NFPIRGGDPEIVMH (SEQ ID NO: 171) | GGKNESEIE IFR (SEQ ID NO: 120) |
| BL01.Loop D/CD4 BLP mut/V5 Swap | NFTDNAKT (SEQ ID NO: 116) | KQSSGGDPEIVMH (SEQ ID NO: 195) | GGKNESEIE IFR (SEQ ID NO: 120) |
| Z258.2012.SGA5 | NFSRNTKN (SEQ ID NO: 179) | QPHSGGDPEVVRH (SEQ ID NO: 180) | GGNNFEGKNNTEIFR (SEQ ID NO: 181) |
| Z258.2012.SGA5 V5 swap | NFSRNTKN (SEQ ID NO: 179) | QPHSGGDPEVVRH (SEQ ID NO: 180) | GGKNESEIE IFR (SEQ ID NO: 120) |
| Z258.2012.SGA5 CD4 BLP swap | NFSRNTKN (SEQ ID NO: 179) | THSSGGDPEIVMH (SEQ ID NO: 119) | GGNNFEGKNNTEIFR (SEQ ID NO: 181) |
| Z258.2012.SGA5 Loop D mut (R279D T281A N283T) | NFSDNAKT (SEQ ID NO: 196) | QPHSGGDPEVVRH (SEQ ID NO: 180) | GGNNFEGKNNTEIFR (SEQ ID NO: 181) |
| Z258.2012.SGA5 Loop D mut V5 swap | NFSDNAKT (SEQ ID NO: 196) | QPHSGGDPEVVRH (SEQ ID NO: 180) | GGKNESEIE IFR (SEQ ID NO: 120) |
| Z258.2012.SGA5 Loop D/CD4 BLP mut/V5 swap | NFSDNAKT (SEQ ID NO: 196) | THSSGGDPEIVMH (SEQ ID NO: 119) | GGKNESEIE IFR (SEQ ID NO: 120) |

FIG. 5D

| Virus | N6 | VRC01 | 3BNC117 | VRC-PG04 | 12A21 | VRC27 | CD4-Ig | 2G12 |
|---|---|---|---|---|---|---|---|---|
| | | | | IC50 (µg/ml) | | | | |
| HXBC2 | 0.005 | 0.048 | 0.017 | 0.034 | 23.600 | 0.310 | 0.030 | 1.01 |
| JRCSF | 0.056 | 0.160 | 0.041 | 0.186 | 0.230 | 0.186 | 2.84 | 0.220 |
| 93TH057 | 0.016 | 1.32 | 0.517 | 0.600 | 0.367 | 0.262 | 10.5 | >50 |
| T278-50 | >50 | >50 | >50 | >50 | >50 | >50 | 2.30 | >50 |
| T278-50.V5 Swap | 17.5 | >50 | >50 | >50 | 1.87 | >50 | 1.64 | >50 |
| T278-50.Loop D mut (A279D) | 0.271 | >50 | >50 | >50 | >50 | >50 | 0.635 | >50 |
| T278-50.Loop D mut/V5 Swap | 0.345 | 3.33 | 0.761 | 3.78 | 5.03 | 2.05 | 0.163 | >50 |
| TV1.29 | >50 | >50 | >50 | >50 | >50 | >50 | 1.56 | 3.33 |
| TV1.29 V5 Swap | 1.84 | >50 | >50 | >50 | >50 | >50 | 2.09 | 15.9 |
| TV1.29.Loop D mut (E279D T281K) | 0.320 | 2.39 | 4.20 | 2.68 | >50 | >50 | 3.39 | >50 |
| TV1.29.Loop D mut/V5 Swap | 0.159 | 9.63 | 0.656 | 4.01 | >50 | >50 | 16.3 | 3.29 |
| TV1.29.Loop D/CD4 BLP mut/V5 Swap | 0.095 | 2.40 | 0.339 | 0.291 | >50 | >50 | 7.41 | 2.34 |
| BL01 | >50 | >50 | >50 | >50 | >50 | >50 | 1.06 | 16.7 |
| BL01 V5 Swap | 0.659 | 5.52 | 2.7 | >50 | >50 | >50 | 0.676 | 2.17 |
| BL01.Loop D mut (Q279D E282K) | >50 | 27.9 | 20.0 | >50 | >50 | >50 | 0.243 | 0.423 |
| BL01.Loop D mut/V5 Swap | 1.47 | >50 | 2.9 | 9.68 | >50 | >50 | 0.340 | 29.5 |
| BL01.Loop D/CD4 BLP mut/V5 Swap | 0.263 | 0.711 | 0.326 | 20.0 | >50 | >50 | 0.211 | 15.5 |
| Z258.2012.SGA5 | >50 | >50 | >50 | >50 | >50 | >50 | 0.179 | >50 |
| Z258.2012.SGA5 V5 swap | >50 | >50 | >50 | >50 | >50 | >50 | 1.24 | >50 |
| Z258.2012.SGA5 CD4 BLP swap | 0.446 | 20.2 | 2.9 | 9.68 | >50 | >50 | 0.538 | >50 |
| Z258.2012.SGA5 Loop D mut (R279D T281A N283T) | 0.466 | 2.1 | 5.69 | 9.1 | >50 | >50 | 3.24 | >50 |
| Z258.2012.SGA5 Loop D mut V5 swap | 0.355 | 8.55 | 3.52 | 9.17 | >50 | >50 | 6.62 | >50 |
| Z258.2012.SGA5 Loop D/CD4 BLP mut/V5 swap | | | | | | | 30.0 | >50 |

FIG. 5E

| Virus | Env sequence | | |
|---|---|---|---|
| | Loop D (276-283) | CD4 BLP (362-374) | β23-V5 (458-469) |
| T278-50 | NISANAKT (SEQ ID NO: 167) | TKPSGGDLEITTH (SEQ ID NO: 168) | GEGDEKANE TFR (SEQ ID NO: 169) |
| T278-50 A279D | NISDNAKT (SEQ ID NO: 187) | TKPSGGDLEITTH (SEQ ID NO: 168) | GEGDEKANE TFR (SEQ ID NO: 169) |
| TV1.29 | NLTENTKT (SEQ ID NO: 173) | KPHAGGDIEITMH (SEQ ID NO: 174) | GGFNTTNNTE TFR (SEQ ID NO: 175) |
| TV1.29 E279D | NLTDNTKT (SEQ ID NO: 190) | KPHAGGDIEITMH (SEQ ID NO: 174) | GGFNTTNNTE TFR (SEQ ID NO: 175) |
| TV1.29 T281K | NLTENKKT (SEQ ID NO: 191) | KPHAGGDIEITMH (SEQ ID NO: 174) | GGFNTTNNTE TFR (SEQ ID NO: 175) |
| BL01 | NFTQNAET (SEQ ID NO: 170) | NFPIRGGDPEIVMH (SEQ ID NO: 171) | GGKNGTEGTE IFR (SEQ ID NO: 172) |
| BL01 Q279D | NFTDNAET (SEQ ID NO: 193) | NFPIRGGDPEIVMH (SEQ ID NO: 171) | GGKNGTEGTE IFR (SEQ ID NO: 172) |
| BL01 E282K | NFTQNAKT (SEQ ID NO: 194) | NFPIRGGDPEIVMH (SEQ ID NO: 171) | GGKNGTEGTE IFR (SEQ ID NO: 172) |
| Z258.2012.SGA5 | NFSRNTKN (SEQ ID NO: 179) | QPHSGGDPEVVRH (SEQ ID NO: 180) | GGNNPEGKNNTEIFR (SEQ ID NO: 181) |
| Z258.2012.SGA5 R279D | NFSDNTKN (SEQ ID NO: 197) | QPHSGGDPEVVRH (SEQ ID NO: 180) | GGNNPEGKNNTEIFR (SEQ ID NO: 181) |
| Z258.2012.SGA5 T281A | NFSRNAKN (SEQ ID NO: 198) | QPHSGGDPEVVRH (SEQ ID NO: 180) | GGNNPEGKNNTEIFR (SEQ ID NO: 181) |
| Z258.2012.SGA5 N283T | NFSRNTKT (SEQ ID NO: 199) | QPHSGGDPEVVRH (SEQ ID NO: 180) | GGNNPEGKNNTEIFR (SEQ ID NO: 181) |

FIG. 5F

| Virus | IC50 (µg/ml) | | | | | | | |
|---|---|---|---|---|---|---|---|---|
| | N6 | VRC01 | 3BNC117 | VRC-PG04 | 12A21 | VRC27 | CD4-Ig | 2G12 |
| T278-50 | >50 | >50 | >50 | >50 | >50 | >50 | 2.30 | >50 |
| T278-50 A279D | 0.271 | >50 | >50 | >50 | >50 | >50 | 0.635 | >50 |
| TV1.29 | >50 | >50 | >50 | >50 | >50 | >50 | 1.56 | 33.0 |
| TV1.29 E279D | 0.320 | >50 | 1.35 | 4.72 | >50 | >50 | >50 | 1.34 |
| TV1.29 T281K | 14.1 | >50 | 12.1 | >50 | >50 | >50 | >50 | 0.928 |
| BL01 | >50 | >50 | >50 | >50 | >50 | >50 | 1.06 | 19.3 |
| BL01 Q279D | 39.5 | 7.46 | 2.51 | >50 | >50 | >50 | >50 | 3.67 |
| BL01 E282K | 46.6 | >50 | 0.962 | >50 | >50 | >50 | >50 | 2.65 |
| Z258.2012.SGA5 | >50 | >50 | >50 | >50 | >50 | 0.179 | >50 | >50 |
| Z258.2012.SGA5 R279D | 0.758 | >50 | 3.65 | >50 | >50 | >50 | 1.75 | >50 |
| Z258.2012.SGA5 T281A | >50 | >50 | >50 | >50 | >50 | >50 | 3.38 | >50 |
| Z258.2012.SGA5 N283T | >50 | >50 | >50 | >50 | >50 | 1.38 | >50 | >50 |

FIG. 6A

| N6 Region | N6 Variant ID | Neutralization $IC_{50}$ 0439.v5.c1 Clade A | 93TH057 Clade AE | BG1168.01 Clade B | JRCSF.JB Clade B | 0013095-2.11 Clade C | 16936-2.21 Clade C | Median $IC_{50}$ (μg/ml)[a] | Fold Change[b] |
|---|---|---|---|---|---|---|---|---|---|
| | WT | 0.144 | 0.249 | 0.469 | 0.145 | 0.066 | 0.059 | 0.145 | |
| FRH1 | T28A | 0.117 | 0.229 | 0.183 | 0.068 | 0.053 | 0.063 | 0.093 | 1 |
| | T30A | 0.110 | 0.239 | 0.160 | 0.080 | 0.039 | 0.043 | 0.095 | 1 |
| CDRH1 | I33A | 0.151 | 0.172 | 0.278 | 0.147 | 0.068 | 0.069 | 0.149 | 1 |
| FRH2 | F35A | 0.147 | 0.279 | 0.326 | 0.189 | 0.069 | 0.084 | 0.168 | 1 |
| CDRH2 | W47A | 0.286 | 0.220 | 0.662 | 0.260 | 0.238 | 0.166 | 0.249 | 2 |
| | W50A | 0.102 | 0.089 | 0.236 | 0.089 | 0.048 | 0.034 | 0.089 | 1 |
| | K52A | 0.132 | 0.118 | 0.239 | 0.173 | 0.124 | 0.079 | 0.128 | 1 |
| | Q53A | 0.110 | 0.175 | 0.340 | 0.163 | 0.062 | 0.061 | 0.137 | 1 |
| | Y54A | 0.201 | 0.224 | 0.356 | 0.235 | 0.110 | 0.082 | 0.213 | 1 |
| | G55A | 0.105 | 0.153 | 0.338 | 0.103 | 0.082 | 0.028 | 0.104 | 1 |
| | V57A | 0.114 | 0.127 | 0.285 | 0.127 | 0.052 | 0.042 | 0.121 | 1 |
| | N58A | 0.071 | 0.090 | 0.268 | 0.122 | 0.040 | 0.058 | 0.081 | 1 |
| | F59A | 0.162 | 0.121 | 0.229 | 0.131 | 0.072 | 0.085 | 0.126 | 1 |
| | G60A | 0.104 | 0.149 | 0.178 | 0.084 | 0.050 | 0.038 | 0.094 | 1 |
| | G61A | 0.104 | 0.151 | 0.207 | 0.094 | 0.054 | 0.062 | 0.099 | 1 |
| | G62A | 0.140 | 0.187 | 0.304 | 0.118 | 0.082 | 0.076 | 0.129 | 1 |
| | R64A | 0.137 | 0.082 | 0.293 | 0.108 | 0.122 | 0.103 | 0.115 | 1 |
| | D65A | 0.082 | 0.123 | 0.145 | 0.074 | 0.037 | 0.012 | 0.078 | 1 |
| FRH3 | R71A | 0.359 | 0.447 | 0.860 | 0.449 | 0.417 | 0.231 | 0.432 | 3 |
| | V73A | 0.063 | 0.112 | 0.185 | 0.092 | 0.040 | 0.037 | 0.078 | 1 |
| | Y74A | 0.148 | 0.239 | 0.255 | 0.236 | 0.073 | 0.073 | 0.192 | 1 |
| CDRH3 | G99A | 0.074 | 0.131 | 0.151 | 0.058 | 0.038 | 0.022 | 0.066 | 0 |
| | D100A | 0.104 | 0.137 | 0.198 | 0.091 | 0.053 | 0.027 | 0.098 | 1 |
| | S100AA | 0.086 | 0.176 | 0.269 | 0.123 | 0.045 | 0.037 | 0.105 | 1 |
| | W100CA | 0.283 | 0.163 | 0.585 | 0.344 | 0.072 | 0.126 | 0.223 | 2 |
| FRL1 | Y1A | 0.106 | 0.141 | 0.130 | 0.092 | 0.033 | 0.037 | 0.099 | 1 |
| | I2A | 0.109 | 0.134 | 0.243 | 0.167 | 0.041 | 0.048 | 0.122 | 1 |
| CDRL1 | Q27A | 0.068 | 0.146 | 0.214 | 0.109 | 0.031 | 0.037 | 0.089 | 1 |
| | G28A | 0.067 | 0.074 | 0.096 | 0.111 | 0.050 | 0.034 | 0.081 | 1 |
| | V29A | 0.093 | 0.100 | 0.146 | 0.077 | 0.049 | 0.031 | 0.085 | 1 |
| | G30A | 0.079 | 0.117 | 0.286 | 0.116 | 0.061 | 0.046 | 0.098 | 1 |
| | D32A | 0.080 | 0.118 | 0.245 | 0.117 | 0.053 | 0.064 | 0.099 | 1 |
| CDRL3 | V90A | 0.115 | 0.121 | 0.212 | 0.083 | 0.053 | 0.032 | 0.099 | 1 |
| | L91A | 0.076 | 0.063 | 0.304 | 0.055 | 0.037 | 0.018 | 0.059 | 0 |
| | F96A | 0.106 | 0.194 | 0.396 | 0.147 | 0.059 | 0.036 | 0.127 | 1 |

FIG. 6B

| N6 Region | N6 Variant ID | Neutralization $IC_{80}$ 0439.v5.c1 Clade A | 93TH057 Clade AE | BG1168.01 Clade B | JRCSF.JB Clade B | 0013095-2.11 Clade C | 16936-2.21 Clade C | Median $IC_{80}$ (μg/ml)[a] | Fold Change[b] |
|---|---|---|---|---|---|---|---|---|---|
| | WT | 0.476 | 0.498 | 1.14 | 0.498 | 0.234 | 0.282 | 0.487 | |
| FRH1 | T28A | 0.467 | 0.483 | 0.605 | 0.378 | 0.212 | 0.316 | 0.423 | 1 |
| | T30A | 0.469 | 0.>509 | 0.542 | 0.403 | 0.171 | 0.215 | 0.436 | 1 |
| CDRH1 | I33A | 0.529 | 0.499 | 0.717 | 0.619 | 0.252 | 0.317 | 0.514 | 1 |
| FRH2 | F35A | 0.>501 | 0.638 | 0.788 | 0.756 | 0.225 | 0.289 | 0.570 | 1 |
| CDRH2 | W47A | 1.61 | 0.972 | 2.41 | 1.63 | 0.792 | 1.00 | 1.305 | 3 |
| | W50A | 0.524 | 0.335 | 0.742 | 0.411 | 0.217 | 0.230 | 0.373 | 1 |
| | K52A | 0.579 | 0.398 | 0.696 | 0.771 | 0.559 | 0.390 | 0.569 | 1 |
| | Q53A | 0.523 | 0.562 | 0.827 | 0.624 | 0.252 | 0.281 | 0.543 | 1 |
| | Y54A | 0.800 | 0.664 | 1.10 | 0.941 | 0.364 | 0.543 | 0.732 | 2 |
| | G55A | 0.468 | 0.498 | 0.920 | 0.485 | 0.271 | 0.209 | 0.487 | 1 |
| | V57A | 0.454 | 0.399 | 0.707 | 0.510 | 0.203 | 0.237 | 0.427 | 1 |
| | N58A | 0.356 | 0.305 | 0.612 | 0.414 | 0.175 | 0.285 | 0.331 | 1 |
| | F59A | 0.593 | 0.395 | 0.872 | 0.534 | 0.341 | 0.363 | 0.465 | 1 |
| | G60A | 0.428 | 0.389 | 0.639 | 0.329 | 0.235 | 0.170 | 0.359 | 1 |
| | G61A | 0.424 | 0.422 | 0.570 | 0.377 | 0.219 | 0.240 | 0.400 | 1 |
| | G62A | 0.467 | 0.499 | 0.694 | 0.490 | 0.265 | 0.286 | 0.479 | 1 |
| | R64A | 0.569 | 0.320 | 1.04 | 0.544 | 0.371 | 0.560 | 0.552 | 1 |
| | D65A | 0.358 | 0.312 | 0.>503 | 0.314 | 0.137 | 0.094 | 0.313 | 1 |
| FRH3 | R71A | 1.40 | 1.35 | 2.68 | 2.26 | 1.44 | 1.26 | 1.420 | 3 |
| | V73A | 0.281 | 0.279 | 0.476 | 0.305 | 0.156 | 0.157 | 0.280 | 1 |
| | Y74A | 0.605 | 0.611 | 0.745 | 0.838 | 0.231 | 0.443 | 0.608 | 1 |
| CDRH3 | G99A | 0.327 | 0.381 | 0.413 | 0.300 | 0.119 | 0.129 | 0.314 | 1 |
| | D100A | 0.461 | 0.452 | 0.575 | 0.375 | 0.167 | 0.160 | 0.414 | 1 |
| | S100AA | 0.353 | 0.467 | 0.577 | 0.431 | 0.158 | 0.186 | 0.392 | 1 |
| | W100CA | 1.35 | 0.756 | 2.13 | 1.57 | 0.488 | 0.701 | 1.053 | 2 |
| FRL1 | Y1A | 0.489 | 0.>502 | 0.>501 | 0.429 | 0.155 | 0.211 | 0.459 | 1 |
| | I2A | 0.461 | 0.402 | 0.761 | 0.446 | 0.180 | 0.255 | 0.424 | 1 |
| CDRL1 | Q27A | 0.302 | 0.324 | 0.574 | 0.341 | 0.114 | 0.168 | 0.313 | 1 |
| | G28A | 0.464 | 0.295 | 0.483 | 0.516 | 0.151 | 0.205 | 0.380 | 1 |
| | V29A | 0.455 | 0.337 | 0.664 | 0.382 | 0.169 | 0.177 | 0.360 | 1 |
| | G30A | 0.432 | 0.368 | 0.956 | 0.500 | 0.196 | 0.281 | 0.400 | 1 |
| | D32A | 0.405 | 0.373 | 0.717 | 0.429 | 0.172 | 0.242 | 0.389 | 1 |
| CDRL3 | V90A | 0.409 | 0.362 | 0.713 | 0.454 | 0.206 | 0.165 | 0.386 | 1 |
| | L91A | 0.354 | 0.230 | 0.733 | 0.312 | 0.150 | 0.110 | 0.271 | 1 |
| | F96A | 0.409 | 0.540 | 0.420 | 0.428 | 0.209 | 0.210 | 0.415 | 1 |

FIG. 6C

| VRC27 Region | VRC27 Variant ID | Neutralization IC$_{50}$ | | | | | | | Median IC$_{50}$ (μg/ml)[a] | Fold Change[b] |
|---|---|---|---|---|---|---|---|---|---|---|
| | | 0439.v5.c1 Clade A | 93TH057 Clade AE | BG1168.01 Clade B | JRCSF.JB Clade B | 0013095-2.11 Clade C | 16936-2.21 Clade C | | | |
| | WT | 0.063 | 0.118 | 0.193 | 0.056 | 0.059 | 0.044 | | 0.061 | 1 |
| FRH1 | N30A | 0.062 | 0.109 | 0.181 | 0.040 | 0.035 | 0.019 | | 0.051 | 1 |
| CDRH1 | I33A | 0.168 | 0.511 | 1.06 | 0.152 | 8.05 | 0.316 | | 0.414 | 7 |
| FRH2 | W47A | 0.304 | >50 | >50 | 1.74 | >50 | >50 | | 50.000 | |
| | W50A | 0.941 | >50 | >50 | >50 | >50 | >50 | | 50.000 | |
| | K52A | 0.038 | 0.161 | 0.153 | 0.175 | 0.150 | 0.011 | | 0.152 | 2 |
| | K53A | 0.032 | 0.175 | 0.133 | 0.162 | 0.167 | 0.013 | | 0.148 | 2 |
| | F54A | 0.125 | >50 | 0.491 | 0.344 | 3.77 | 0.292 | | 0.418 | 7 |
| | G55A | 0.073 | 1.36 | 0.230 | 0.108 | 0.554 | 0.069 | | 0.169 | 3 |
| CDRH2 | V57A | 0.110 | 14.7 | 0.212 | 0.241 | 3.17 | 0.044 | | 0.227 | 4 |
| | N58A | 0.452 | >50 | >50 | 0.346 | >50 | >50 | | 50.000 | |
| | Y59A | 0.086 | 2.95 | 0.393 | 0.270 | 2.11 | 0.163 | | 0.332 | 5 |
| | H61A | 0.038 | 0.161 | 0.>506 | 0.052 | 0.174 | 0.013 | | 0.107 | 2 |
| | Q64A | 0.034 | 0.177 | 0.102 | 0.037 | 0.079 | 0.017 | | 0.058 | 1 |
| | L69A | 0.041 | 0.180 | 0.133 | 0.061 | 0.073 | 0.017 | | 0.067 | 1 |
| | R71A | 0.716 | >50 | >50 | 1.72 | >50 | >50 | | 50.000 | |
| FRH3 | I73A | 0.068 | 0.206 | 0.201 | 0.089 | 0.095 | 0.012 | | 0.092 | 2 |
| | Y74A | 0.045 | 0.371 | 0.266 | 0.071 | 0.127 | 0.017 | | 0.099 | 2 |
| | L97A | 0.053 | 0.100 | 0.111 | 0.086 | 0.087 | 0.013 | | 0.077 | 1 |
| | D99A | 0.064 | 0.410 | 0.184 | 0.053 | 0.031 | 0.012 | | 0.059 | 1 |
| | G100A | 0.069 | 0.201 | 0.177 | 0.041 | 0.079 | 0.017 | | 0.074 | 1 |
| CDRH3 | S100AA | 0.072 | 0.090 | 0.150 | 0.029 | 0.265 | 0.013 | | 0.081 | 1 |
| | S100BA | 0.051 | 0.118 | 0.135 | 0.052 | 0.057 | 0.012 | | 0.055 | 1 |
| | W100CA | 0.845 | >50 | >50 | >50 | >50 | >50 | | 50.000 | |
| FRL1 | I2A | 0.056 | 2.14 | 1.04 | 0.101 | 1.13 | 0.014 | | 0.571 | 9 |
| | Q3A | 0.045 | 0.131 | 0.130 | 0.027 | 0.047 | 0.021 | | 0.046 | 1 |
| | G28A | 0.141 | >50 | 14.8 | 1.16 | 4.48 | 0.039 | | 7.630 | 6 |
| CDRL1 | I29 | 0.086 | 6.43 | 0.559 | 0.211 | 1.04 | | | 0.385 | 11 |
| | G30 | 0.049 | 2.96 | 1.87 | 0.381 | 0.907 | | | 0.644 | 11 |
| | D32 | 0.050 | >50 | 4.69 | 0.484 | 27.3 | | | 2.587 | 42 |
| | V90 | 0.038 | 1.91 | 0.412 | 0.092 | 0.999 | | | 0.252 | 4 |
| CDRL3 | L91 | 0.191 | >50 | >50 | >50 | >50 | 1.42 | | 50.000 | |
| | E96 | 0.334 | 2.47 | 2.53 | 0.193 | 4.72 | 0.584 | | 1.527 | 7 |

FIG. 6D

| VRC27 Region | VRC27 Variant ID | Neutralization $IC_{80}$ 0439.v5.c1 Clade A | 93TH057 Clade AE | BG1168.01 Clade B | JRCSF.JB Clade B | 0013095-2.11 Clade C | 16936-2.21 Clade C | Median $IC_{80}$ (µg/ml)[a] | Fold Change[b] |
|---|---|---|---|---|---|---|---|---|---|
| | WT | 0.278 | 0.427 | 0.678 | 0.295 | 0.198 | 0.213 | 0.287 | |
| FRH1 | N30A | 0.223 | 0.379 | 0.632 | 0.219 | 0.135 | 0.151 | 0.221 | 1 |
| CDRH1 | I33A | 0.617 | 9.28 | 4.47 | 1.76 | >50 | 13.9 | 6.875 | 24 |
| FRH2 | W47A | 1.52 | >50 | >50 | 11.0 | >50 | >50 | 50.000 | 175 |
| CDRH2 | W50A | 8.05 | >50 | >50 | >50 | >50 | >50 | 50.000 | 175 |
| | K52A | 0.267 | 0.684 | 1.02 | 0.886 | 0.852 | 0.164 | 0.768 | 3 |
| | K53A | 0.272 | 0.554 | 0.757 | 0.813 | 0.819 | 0.145 | 0.656 | 2 |
| | F54A | 0.613 | >50 | 2.35 | 1.78 | >50 | 4.27 | 3.310 | 12 |
| | G55A | 0.351 | 20.7 | 1.46 | 0.634 | 12.6 | 0.705 | 1.083 | 4 |
| | V57A | 0.573 | >50 | 1.74 | 9.00 | >50 | 4.60 | 6.800 | 24 |
| | N58A | 2.94 | >50 | >50 | 4.07 | >50 | >50 | 50.000 | 175 |
| | Y59A | 0.379 | >50 | 1.97 | 1.47 | 43.6 | 1.38 | 1.720 | 6 |
| | H61A | 0.236 | 0.706 | 3.98 | 0.357 | 1.29 | 0.326 | 0.532 | 2 |
| | Q64A | 0.216 | 0.637 | 0.454 | 0.226 | 0.353 | 0.110 | 0.290 | 1 |
| FRH3 | L69A | 0.266 | 0.533 | 0.821 | 0.322 | 0.300 | 0.187 | 0.311 | 1 |
| | R71A | 5.04 | >50 | >50 | >50 | >50 | >50 | 50.000 | 175 |
| | I73A | 0.395 | 0.778 | 1.23 | 0.422 | 0.591 | 0.214 | 0.507 | 2 |
| | Y74A | 0.436 | 2.41 | 1.73 | 0.521 | 1.31 | 0.262 | 0.916 | 3 |
| CDRH3 | L97A | 0.299 | 0.324 | 0.638 | 0.301 | 0.286 | 0.188 | 0.300 | 1 |
| | D99A | 0.340 | 2.16 | 1.03 | 0.232 | 0.159 | 0.239 | 0.290 | 1 |
| | G100A | 0.335 | 0.665 | 1.22 | 0.350 | 0.285 | 0.190 | 0.343 | 1 |
| | S100AA | 0.467 | 0.298 | 0.602 | 0.312 | 4.12 | 0.429 | 0.448 | 2 |
| | S100BA | 0.346 | 0.339 | 0.704 | 0.270 | 0.340 | 0.311 | 0.340 | 1 |
| | W100CA | 7.06 | >50 | >50 | >50 | >50 | >50 | 50.000 | 175 |
| FRL1 | I2A | 0.329 | >50 | 8.52 | 1.09 | >50 | 0.581 | 4.805 | 17 |
| | Q3A | 0.267 | 0.455 | 0.687 | 0.189 | 0.177 | 0.087 | 0.228 | 1 |
| CDRL1 | G28A | 0.603 | >50 | >50 | >50 | >50 | 1.41 | 50.000 | 175 |
| | I29 | 0.348 | >50 | 3.66 | 1.07 | 24.2 | 0.808 | 2.365 | 8 |
| | G30 | 0.446 | 34.7 | 13.3 | 15.5 | 7.79 | 0.304 | 10.545 | 37 |
| | D32 | 0.343 | >50 | >50 | 39.4 | >50 | 0.137 | 44.700 | 156 |
| CDRL3 | V90 | 0.293 | 31.0 | 2.06 | 0.644 | 9.97 | 0.449 | 1.352 | 5 |
| | L91 | 1.03 | >50 | >50 | >50 | >50 | >50 | 50.000 | 175 |
| | E96 | 1.04 | >50 | 11.5 | 0.898 | >50 | 3.69 | 7.595 | 27 |

FIG. 6E

| VRC01 Region | VRC01 Variant ID | Neutralization IC$_{50}$ | | | | | | Median IC$_{50}$ (µg/ml)[a] | Fold Change[b] |
|---|---|---|---|---|---|---|---|---|---|
| | | 0439.v5.c1 Clade A | 93TH057 Clade AE | BG1168.01 Clade B | JRCSF.JB Clade B | 0013095-2.11 Clade C | 16936-2.21 Clade C | | |
| | WT | 0.249 | 0.383 | 0.874 | 0.206 | 0.092 | 0.166 | 0.228 | 1 |
| FRH1 | I30A | 0.272 | 0.406 | 3.05 | 0.279 | 0.132 | 0.087 | 0.276 | 1 |
| CDRH1 | T33A | 0.188 | 0.234 | 0.912 | 0.209 | 0.106 | 0.116 | 0.199 | 1 |
| FRH2 | W47A | 0.288 | 0.411 | >50 | 0.558 | 0.347 | 0.311 | 0.379 | 2 |
| | W50A | 0.302 | 0.445 | >50 | 0.275 | 0.206 | 0.302 | 0.302 | 1 |
| | K52A | 0.224 | 0.157 | 1.05 | 0.157 | 0.136 | 0.073 | 0.157 | 1 |
| | R53A | 0.156 | 0.214 | 0.241 | 0.348 | 0.153 | 0.122 | 0.185 | 1 |
| | G54A | 0.249 | 0.334 | 0.489 | 0.395 | 0.198 | 0.214 | 0.292 | 1 |
| | G55A | 0.591 | 1.23 | >50 | 1.08 | 0.441 | 0.856 | 0.968 | 4 |
| CDRH2 | V57A | 0.107 | 0.207 | 0.523 | 0.139 | 0.032 | 0.071 | 0.123 | 1 |
| | N58A | 0.153 | 0.278 | >50 | 0.151 | 0.131 | 0.081 | 0.152 | 1 |
| | Y59A | 0.128 | 0.188 | 0.995 | 0.161 | 0.040 | 0.105 | 0.145 | 1 |
| | R61A | 0.227 | 0.282 | 2.33 | 0.387 | 0.100 | 0.246 | 0.264 | 1 |
| | P62A | 0.096 | 0.134 | 0.424 | 0.119 | 0.063 | 0.090 | 0.108 | 0 |
| | Q64A | 0.161 | 0.216 | 0.887 | 0.119 | 0.126 | 0.066 | 0.144 | 1 |
| | M69A | 0.394 | 0.468 | 1.24 | 0.396 | 0.202 | 0.267 | 0.395 | 2 |
| FRH3 | R71A | 0.754 | 1.41 | >50 | 2.67 | 1.02 | 1.20 | 1.305 | 6 |
| | V73A | 0.389 | 0.809 | >50 | 0.935 | 0.311 | 0.399 | 0.604 | 3 |
| | Y74A | 0.245 | 0.451 | 2.63 | 0.243 | 0.150 | 0.196 | 0.244 | 1 |
| CDRH3 | D99A | 0.136 | 0.220 | 0.930 | 0.103 | 0.060 | 0.078 | 0.120 | 1 |
| | Y100A | 0.344 | 0.325 | >50 | 0.702 | 0.646 | 0.470 | 0.558 | 2 |
| | N100AA | 0.118 | 0.126 | 1.70 | 0.168 | 0.050 | 0.092 | 0.122 | 1 |
| | W100BA | 4.10 | >50 | >50 | >50 | >50 | >50 | 50.000 | 0 |
| FRL1 | V3A | 0.097 | 0.117 | 0.188 | 0.083 | 0.049 | 0.054 | 0.090 | 1 |
| CDRL1 | Q27A | 0.185 | 0.208 | 0.258 | 0.166 | 0.085 | 0.148 | 0.176 | 1 |
| | Y28A | 0.402 | 0.398 | >50 | 0.352 | 0.210 | 0.265 | 0.375 | 2 |
| | S30A | 0.142 | 0.152 | 0.259 | 0.114 | 0.046 | 0.038 | 0.128 | 1 |
| CDRL3 | Y91A | 0.344 | 5.18 | >50 | 5.10 | >50 | 1.06 | 5.140 | 23 |
| | E96A | 0.138 | >50 | >50 | 0.166 | 4.74 | 0.028 | 2.453 | 11 |
| | F97A | 0.087 | 0.129 | 1.13 | 0.082 | 0.045 | 0.029 | 0.085 | 0 |

FIG. 6F

| VRC01 Region | VRC01 Variant ID | Neutralization IC80 | | | | | | Median IC80 (μg/ml)[a] | Fold Change[b] |
|---|---|---|---|---|---|---|---|---|---|
| | | 0439.v5.c1 Clade A | 93TH057 Clade AE | BG1168.01 Clade B | JRCSF.JB Clade B | 0013095-2.11 Clade C | 16936-2.21 Clade C | | |
| | WT | 1.06 | 1.30 | 3.36 | 0.727 | 0.278 | 0.731 | 0.896 | 1 |
| FRH1 | I30A | 1.14 | 1.50 | 29.9 | 1.50 | >50 | 0.960 | 1.320 | 1 |
| CDRH1 | T33A | 0.572 | 0.728 | 5.03 | 0.709 | 0.346 | 0.654 | 0.682 | 1 |
| FRH2 | W47A | 0.917 | 1.32 | >50 | 1.53 | 1.30 | 1.05 | 1.310 | 1 |
| | W50A | 0.760 | 2.09 | >50 | 1.08 | 1.13 | 1.56 | 1.345 | 2 |
| | K52A | 0.474 | 0.517 | 6.28 | 0.751 | 0.628 | 0.426 | 0.573 | 1 |
| | R53A | 0.495 | 0.591 | 0.922 | 1.27 | 0.572 | 0.472 | 0.582 | 1 |
| | G54A | 0.749 | 0.866 | 1.56 | 1.10 | 0.573 | 0.751 | 0.809 | 1 |
| | G55A | 1.48 | 3.62 | >50 | 3.82 | 1.32 | 2.51 | 3.065 | 3 |
| CDRH2 | V57A | 0.309 | 0.625 | 4.88 | 0.847 | 0.166 | 0.281 | 0.467 | 1 |
| | N58A | 0.633 | 1.21 | >50 | 1.08 | 0.564 | 0.534 | 0.857 | 1 |
| | Y59A | 0.389 | 0.605 | >50 | 0.674 | 0.171 | 0.432 | 0.519 | 1 |
| | R61A | 0.721 | 0.910 | 19.6 | >50 | 0.378 | 1.19 | 1.050 | 1 |
| | P62A | 0.402 | 0.535 | 1.79 | 0.474 | 0.231 | 0.450 | 0.462 | 1 |
| | Q64A | 0.738 | 0.758 | 3.53 | 0.617 | 0.407 | 0.510 | 0.678 | 1 |
| | M69A | 1.08 | 1.25 | 5.46 | 1.52 | 0.651 | 1.06 | 1.165 | 1 |
| | R71A | 1.74 | 2.50 | >50 | 8.86 | 3.97 | 4.09 | 4.030 | 5 |
| FRH3 | V73A | 1.13 | 2.67 | >50 | 3.73 | 1.23 | 2.17 | 2.420 | 3 |
| | Y74A | 0.864 | 1.70 | >50 | 1.26 | 0.599 | 1.56 | 1.410 | 2 |
| | D99A | 0.455 | 0.518 | 2.26 | 0.381 | 0.213 | 0.373 | 0.418 | 0 |
| | Y100A | 1.04 | 1.17 | >50 | 2.19 | 2.20 | 1.53 | 1.860 | 2 |
| CDRH3 | N100AA | 0.362 | 0.358 | >50 | 0.399 | 0.270 | 0.344 | 0.360 | 0 |
| | W100BA | 38.6 | >50 | >50 | >50 | >50 | >50 | 50.000 | 56 |
| FRL1 | V3A | 0.361 | 0.337 | 0.551 | 0.299 | 0.181 | 0.242 | 0.318 | 0 |
| | Q27A | 0.555 | 0.541 | 0.949 | 0.540 | 0.283 | 0.515 | 0.541 | 1 |
| CDRL1 | Y28A | 1.21 | 1.29 | >50 | 1.27 | 0.915 | 0.844 | 1.240 | 1 |
| | S30A | 0.354 | 0.473 | 0.921 | 0.423 | 0.181 | 0.316 | 0.389 | 0 |
| | Y91A | 1.19 | 50.8 | >50 | 34.2 | >50 | 7.50 | 36.100 | 40 |
| CDRL3 | E96A | 0.625 | >50 | >50 | 1.88 | >50 | 0.292 | 25.940 | 29 |
| | F97A | 0.279 | 0.452 | 0.357 | 0.357 | 0.198 | 0.168 | 0.318 | 0 |

FIG. 7

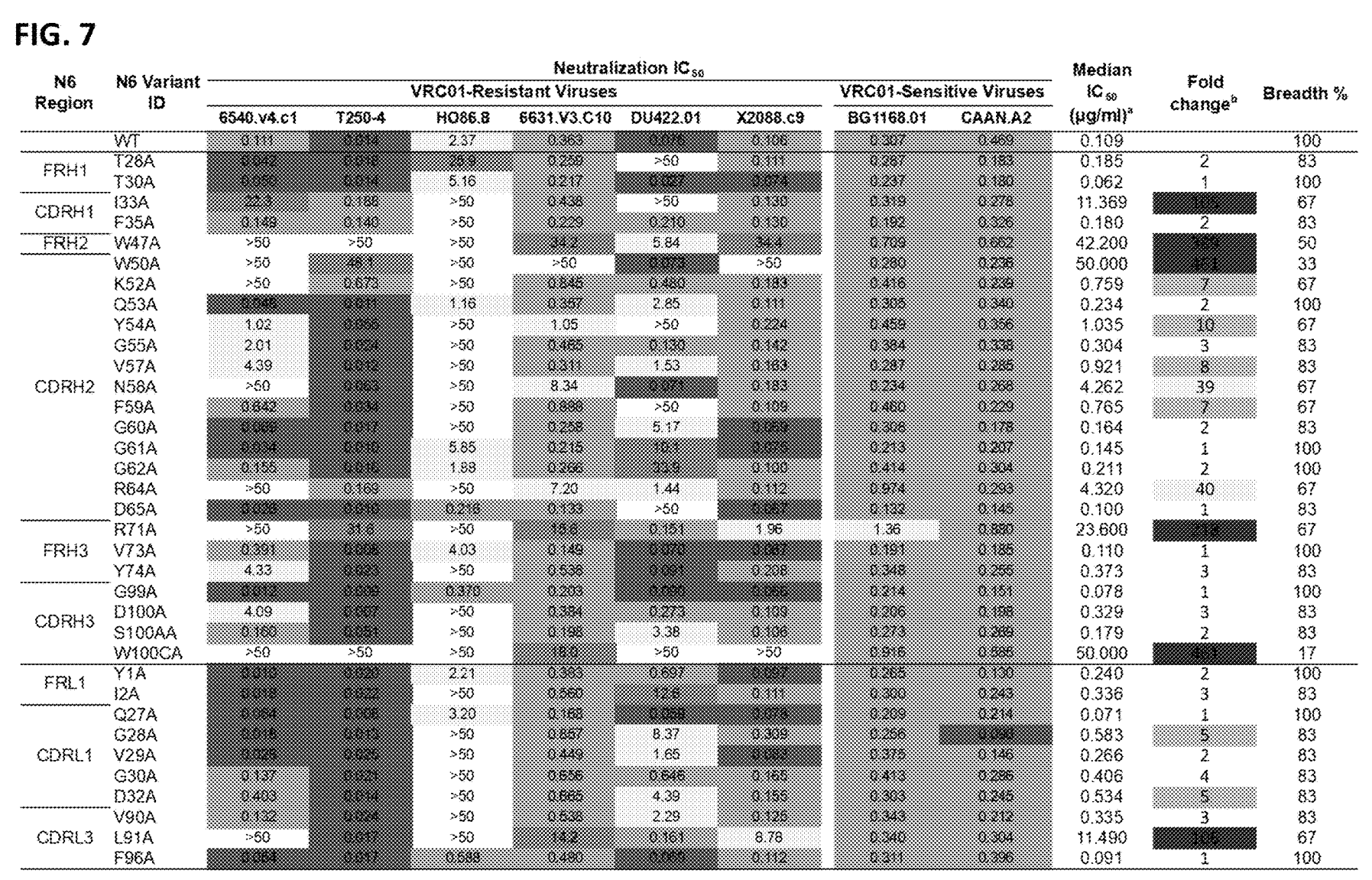

| N6 Region | N6 Variant ID | Neutralization IC50 | | | | | | | | Median IC50 (μg/ml)[a] | Fold change[b] | Breadth % |
|---|---|---|---|---|---|---|---|---|---|---|---|---|
| | | VRC01-Resistant Viruses | | | | | | VRC01-Sensitive Viruses | | | | |
| | | 6540.v4.c1 | T250-4 | HO86.8 | 6631.V3.C10 | DU422.01 | X2088.c9 | BG1168.01 | CAAN.A2 | | | |
| FRH1 | WT | | | 2.37 | 0.363 | | 0.109 | 0.307 | 0.109 | 0.109 | 2 | 100 |
| | T28A | | 0.168 | | 0.255 | >50 | | 0.351 | 0.193 | 0.185 | 1 | 83 |
| | T30A | 2.73 | 0.140 | 5.16 | 0.217 | >50 | 0.130 | 0.319 | 0.180 | 0.062 | 2 | 100 |
|

VRC01 resistant gp120

FIG. 12B

VRC01 resistant gp120

Loop D
Loop V5
Potential steric clash
CDR L3
CDR H2
VRC01 (modelled)

CDR L1
CDR L3
CDR H2 ARP

VRC01 light
VRC01 heavy

Heavy chain

Divergence to IGHV1-2*02 (%)

Light chain

Divergence to IGKV1-33*01 (%)

FIG. 15B

Heavy Chain

| | 1 | 10 | 20 | 30 | 40 | 5052A | 60 | 70 | 8082ABC | 90 | 100ABCDE102 | 110113 |
|---|---|---|---|---|---|---|---|---|---|---|---|---|
| | FR1 | | | CDR1 | FR2 | CDR2 | | FR3 | | | CDR3 | FR4 |
| IGHV1-2*02 | QVQLVQSGAEVKKPGASVKVSCKASGYTFT | | | GYYMH | WVRQAPGQGLEWMG | WINPNSGGTNYAQKFQG | RVTMTRDTSISTAYMELSRLRSDDTAVYYCAR | | | | | |
| I1 | RGH....T......R...ET..... | | | A.IL. | .F............R........ | ..K.KY.AV...HA... | ...L...IYRD....D.G..F... | | | AR DRVYDDSSWQLDP | WGQGTSVIVSS |
| I2 | RGH....T......R...ET..... | | | AHIL. | .F............R........ | ..K.KY.AV...HA... | ...L...IYRD....D.G..F... | | | AR DRVYDDSSWQLDP | WGQGTSVIVSS |
| I3 | RAH....TA.....R...ET..... | | | AHILY | .F............R...V.... | ..K.QY.AV.FGGG.R. | ...L...IYRD...DI.G..F... | | | AR DRSYDDSSWALDA | WGQGITVVVSA |
| I4 | RAH....TAM....R...QT..... | | | AHILF | .F............R...V.... | ..K.QY.AV.FGGG.RD | ...L...IYREI..DIRG.KL... | | | AR DRSYGDSSWALDA | WGQGTTVVVSA |
| I5 | RAH....TAM....R...QT..... | | | A.IL. | .F............R........ | ..K.QY.AV.FGGG.RD | ...L...VYREI..DIRG.KP... | | | AR DRSYGDSSWALDA | WGQGTTVVVSA |
| N6 | SQR....PQ....S..RI.ET..... | | | A.IL. | .F............RS....... | ..K.KF.AV....HS... | ...I.L..IYRE..FLD.TG..F... | | | AR DRSYGDSSWRLDP | WGQGTRVVVSS |
| VRC27 | SQR....PQ.R..S..RI.ET..N | | | A.IL. | .F............RSF...... | ..K.KF.AV....HS... | ...I.L..IYRE..FLD.TG..F... | | | AR DRLYDGSSWRLDP | WGQGTRVVVSS |

Kappa Chain

| | 1 | 10 | 20 | 30 | 40 | 50 | 60 | 70 | 80 | 90 | 100 | 107 |
|---|---|---|---|---|---|---|---|---|---|---|---|---|
| | FR1 | | | CDR1 | FR2 | CDR2 | | FR3 | | | CDR3 | FR4 |
| IGKV1-33*01 | DIQMTQSPSSLSASVGDRVTITC | | | QASQDISNYLN | WYQQKPGKAPKLLIY | DASNLET | GVPSRFSGSGSGTDFTFTISSLQPEDIATYYC | | | | QVL------ES | FGQGTRLEI |
| I1 | Y..V..........V........ | | | ...GVG.D.H | ..............R........ | ...T.A. | .......FH.S........NG...D... | | | | QVL------ES | FGQGTRLEI |
| I2 | Y.HV..........V........ | | | ...GVG.D.H | ..............R........ | ...T.E. | .......FH.S........NG...D... | | | | QVL------ES | FGQGTRLEI |
| I3 | Y.HV..........V........ | | | ...GVGSD.H | ..............R........ | ..H.T.E. | ......T.FH.S........ND...D... | | | | QVL------ES | FGRGSRLDI |
| I4 | Y.HV..........V.....N.. | | | .T.GVGSD.H | .............H.R........ | ..H.SV.D | ......T.FH.S.NL.....ND...AD.. | | | | QVL------QS | FGRGSRLDI |
| I5 | Y.HV..........V.I...N.. | | | .T.GVGSD.H | .............H.R........ | ..H.SV.D | ......T.FH.S.NL.....ND...AD.. | | | | QVL------ES | FGRGSRLDI |
| I6 | Y.HV..........V.I...N.. | | | .T.GVGSD.H | .............H.R........ | ..H.SV.D | ........FH.S.NL.....ND...AD.. | | | | QVL------QF | FGRGSRLHI |
| N6 | Y.HV..........V.I...... | | | .T.GVGSD.H | .............H.R........ | ..HT.SV.D | ........FH.S........D....AD.. | | | | QVL------ES | FGQGTRLEI |
| I7 | Y.HV.........AV........ | | | ...GVGSD.H | ...........R.RP....I..H | ..H.AR.E | ........FH.S........ND...D... | | | | QVL------ES | FGQGTRLEI |
| I8 | Y.HV.........AV........ | | | ...GVGSD.H | ...........R.RP....I..H | ..H.AR.E | ........FH.S........ND...D.F. | | | | QVL------ES | FGQGTRLEI |
| I9 | Y.HV.........AV........ | | | .R.GVGSD.H | ...........R.RP....I..H | ..H.AR.E | ........FH.S........ND...D.F. | | | | QVL------ES | FGQGTRLDI |
| I10 | Y.HV.........AV........ | | | .R..G.GSD.H | ...........R.RP....I..H | ..H.AR.E | ........FH.S........ND...D.V. | | | | QVL------ES | FGQGTRLDI |
| VRC27 | ............AV........ | | | .R..G.GSD.H | ...........R.RP....I..H | ..H.AR.E | .......G..H.S.I.....ND...LD.V. | | | | QVL------ES | FGQGTRLDI |

FIG. 16

| | Virus ID | Clade | IC50 ( µg/ml)* | | | | | | | | |
|---|---|---|---|---|---|---|---|---|---|---|---|
| | | | N6 | Z258 NGS7 | Z258 NGS8 | Z258 NGS2 | Z258 NGS4 | Z258 NGS5 | Z258 NGS1 | Z258 NGS3 | Z258 NGS6 |
| | | | N6 H + N6 K | 2_2014_0017 3626 H mut + 1_2015_0006 5970 L | 2_2014_0017 3626 H mut + 1_2014_0001 9094 L | 2_2014_0017 3626 H mut + N6K | N6H + 1_2015_0006 5970L | N6H + 1_2014_0001 9094 L | 2_2014_0017 3626 H + N6K | N6H + 1_2015_0010 6641 L | N6H + 1_2015_0021 7585 L |
| 1 | 6540.v4.c1 | AC | 0.014 | 0.045 | 0.009 | 0.019 | 0.038 | 0.070 | 0.034 | 0.071 | 0.039 |
| 2 | 6545.V4.C1 | AC | 0.430 | 0.014 | 0.014 | 0.011 | 0.028 | 0.014 | 0.014 | 0.023 | 0.011 |
| 3 | 620345.c1 | AE | 0.338 | 0.280 | 1.87 | 0.397 | 5.19 | >50 | 1.24 | >50 | >50 |
| 4 | 242-14 | AG | 0.256 | 0.362 | 0.947 | 0.332 | 0.736 | 0.897 | 0.573 | 13.5 | >50 |
| 5 | T250-4 | AG | 0.009 | 0.011 | 0.009 | 0.008 | 0.008 | 0.006 | 0.018 | 0.007 | 0.003 |
| 6 | 7165.18 | B | 0.709 | 0.924 | 1.13 | 0.923 | 1.94 | 1.31 | 1.39 | >50 | >50 |
| 7 | HO86.8 | B | 0.445 | 0.112 | 0.003 | 0.225 | 0.034 | >50 | >50 | >50 | 0.178 |
| 8 | 6322.V4.C1 | C | 0.027 | 0.064 | 0.092 | 0.067 | 0.132 | 0.063 | 0.078 | 0.103 | >50 |
| 9 | DU422.01 | C | 0.015 | 0.044 | 0.029 | 0.032 | 0.028 | 0.032 | 0.051 | 0.048 | 0.100 |
| 10 | 6631.V3.C10 | C | 0.065 | 0.073 | 0.047 | 0.035 | 0.082 | 0.077 | 0.121 | 0.082 | 0.092 |
| 11 | TZA125.17 | C | 0.407 | 0.643 | 1.01 | 0.859 | 2.36 | 1.15 | 1.20 | >50 | >50 |
| 12 | CAP210.E8 | C | 12.2 | 6.76 | 27.4 | 23.3 | 28.8 | 24.1 | >50 | >50 | >50 |
| 13 | DU172.17 | C | 0.016 | 0.043 | 0.045 | 0.062 | 0.111 | 0.076 | 0.053 | 0.105 | 2.15 |
| 14 | 3817.v2.c59 | CD | 0.287 | 0.424 | 0.558 | 0.599 | 1.29 | 1.03 | 0.769 | 0.682 | >50 |
| 15 | 57128.vrc15 | D | 5.74 | 2.21 | 2.84 | 2.24 | 5.49 | 2.80 | 2.24 | >50 | >50 |
| 16 | X2088.c9 | G | 0.048 | 0.052 | 0.041 | 0.064 | 0.067 | 9.61 | 0.251 | 0.051 | 0.100 |
| 17 | T278-50 | AG | >50 | >50 | >50 | >50 | >50 | >50 | >50 | >50 | >50 |
| 18 | BL01.DG | B | >50 | >50 | >50 | >50 | >50 | >50 | >50 | >50 | >50 |
| 19 | 6471.V1.C16 | C | >50 | >50 | >50 | >50 | >50 | >50 | >50 | >50 | >50 |
| 20 | TV1.29 | C | >50 | 5.45 | 7.11 | 18.5 | 26.9 | 1.63 | >50 | >50 | >50 |
| Geometric Mean IC50 (µg/ml) | | | 0.510 | 0.446 | 0.435 | 0.495 | 0.786 | 1.189 | 1.026 | 2.330 | 3.590 |
| Median IC50 (µg/ml) | | | 0.373 | 0.321 | 0.753 | 0.364 | 1.015 | 1.227 | 0.984 | 31.765 | 50.000 |
| Breadth | | | 80% | 85% | 85% | 85% | 85% | 75% | 70% | 50% | 40% |

Calculate the resistant viruses with a value of 50

FIG. 17

| Antibody | IC50 (μg/ml) | | | | | | | Median IC50 (μg/ml) | Fold change | Breadth (%) |
|---|---|---|---|---|---|---|---|---|---|---|
| | VRC01-Resistant Viruses | | | | | | VRC01-Sensitive Viruses | | | |
| | 6540.v4.c1 | T250-4 | HO86.8 | 631.V3.C1 | DU422.01 | X2088.c9 | BG1168.01 | CAAN.A2 | | | |
| I1 | 5.23 | >25 | >25 | >25 | >25 | >25 | 0.191 | 0.529 | 50.00 | 565 | 17 |
| I2 | 19.1 | >25 | >25 | >25 | >25 | 24.8 | 0.175 | 0.389 | 50.00 | 266 | 33 |
| I3 | 0.054 | 0.019 | >25 | 0.117 | 1.14 | 0.036 | 0.115 | 0.242 | 0.086 | 5 | 83 |
| I4 | 0.018 | 0.017 | 0.098 | 0.041 | 0.051 | 0.041 | 0.077 | 0.203 | 0.039 | 2 | 100 |
| N6 | 0.011 | 0.014 | 0.445 | 0.095 | 0.020 | 0.015 | 0.031 | 0.096 | 0.018 | 1 | 100 |

FIG. 18

```
                          1         10        20        30             40          5052A  57
                          |         |         |         |              |           | ||   |
Heavy Chain   _____FR1_____    CDR1_   _____FR2_____    _CDR2____
   IGHV1-2*02 QVQLVQSGAEVKKPGASVKVSCKASGYTFT            GYYMH   WVRQAPGQGLEWMG     WINPNSGGT
          N6  RAHLVQSGTAMKKPGASVRVSCQTSGYTFT            AHILF   WFRQAPGRGLEWVG     WIKPQYGAV
2_2014_00173626_H    RAHLVQSGTAMKKPGASVRVSCQTSGYTFT     AHILF   WFRQAPGRGLEWVG     WIKPQYGAV
2_2014_00173626_H Mt RAHLVQSGTAMKKPGASVRVSCQTSGYTFT     AHILF   WFRQAPGRGLEWVG     WIKPQYGAV 60        70       8082ABC         90       100ABCDE102    110113
                           |         |        | ||||          |        |||||| |       |  |
Heavy Chain   _CDR2____    _____FR3_____    ___CDR3_____  FR4(HJ5*01)
   IGHV1-2*02 NYAQKFQG     RVTMTRDTSISTAYMELSRLRSDDTAVYYCAR             AYCGGDCYNWFDS  WGQGTLVTVSS
          N6  NFGGGFRD     RVTLTRDVYREIAYMDIRGLKPDDTAVYYCAR             DRSYGDSSWALDA  WGQGTTVVVSA
2_2014_00173626_H   NFGGGFRD  RVTLTRDIYREIAYMDIRGLKLDDTAVYYCAR          DRSYGDSSWALDA  WGQGTTVVVS
2_2014_00173626_HMt NFGGGFRD  RVTLTRDIYREIAYMDIRGLKLDDTAVYYCAR          DRSYGDSSWALDA  WGQGTTVVVSA 1         10        20        30             40          5052
                          |         |         |         |              |           | |
Kappa Chain   _____FR1_____    _CDR1_____     ____FR2_____    _CDR2___
   IGKV1-33*01 DIQMTQSPSSLSASVGDRVTITC                  QASQDISNYLN    WYQQKPGKAPKLLIY     DASNLET
          N6   YIHVTQSPSSLSVSIGDRVTINC                  QTSQGVSDLH     WYQHKPGRAPKLLIH     HTSSVED
1_2015_00106641_L YIHVTQSPSSLSVSIGDRVTINC               QTSQGVSDLH     WYQHKPGRDPKLLIR     HTTSVED
1_2015_00065970_L YIHVTQSPSSLSVSIGDRVTINC               QTSQGVSDLH     WYQHKPGRAPKLLIH     HASSVDD
1_2014_00019094_L YIHVTQSPSSLSVSIGDRVTINC               QTSQGVSDLH     WYQHKPGRAPKLLIH     HASSVED
1_2015_00217585_L YIHVTQSPSSLSVSIGDRVTINC               QTSQGFGRDLH    WYQHKPGRAPKLLIH     HAPYVDD 60        70       80         90        100       107
                           |         |        |          |         |         |
Kappa Chain   _____FR3_____    ___CDR3___  FR4(KJ5*01)
   IGKV1-33*01 GVPSRFSGSGSGTDFTFTISSLQPEDIATYYC              QQYDNLPIT   FGQGTRLEIK
          N6   GVPSRFSGSGFHTSFNLTISDLQADDIATYYC              QVL-----QF  FGRGSRLHIK
1_2015_00106641_L GVPSRVSGSGFHTSFNLTISDLQADDIATYYC           QVL-----QF  FGRGSRLHIK
1_2015_00065970_L GVPSRFSGSGFHTSFNLTINDLQADDIATYYC           QVL-----QF  FGRGSRLHIK
1_2014_00019094_L GVPSRFSGSTFHTSFNLTINDLQADDIGTYYC           QVL-----SF  FGRGSRLDTK
1_2015_00217585_L GVPSRFSGSGFHTSFNLTINDLQADDIATYYC           QVL-----QF  FGRGSRLHIK
```

NEUTRALIZING ANTIBODIES TO GP120 AND THEIR USE

CROSS REFERENCE TO RELATED APPLICATIONS

This is a continuation of U.S. patent application Ser. No. 17/358,522, filed on Jun. 25, 2021, now abandoned, which is a continuation of U.S. patent application Ser. No. 16/786,267, filed Feb. 10, 2020, now abandoned, which is a continuation of U.S. patent application Ser. No. 15/559,791, filed Sep. 19, 2017, issued as U.S. Pat. No. 10,562,960, which is the U.S. National Stage of International Application No. PCT/US2016/023145, filed Mar. 18, 2016, which claims the benefit of U.S. Provisional Application No. 62/136,228, filed Mar. 20, 2015, and U.S. Provisional Application No. 62/250,378, filed Nov. 3, 2015. All of the prior applications are incorporated herein by reference.

FIELD OF THE DISCLOSURE

This relates to monoclonal antibodies and antigen binding fragments that specifically bind to gp120 and their use, for example, in methods of treating a subject with HIV-1 infection.

BACKGROUND

Human Immunodeficiency Virus type 1 (HIV-1) infection, and the resulting Acquired Immunodeficiency Syndrome (AIDS), remain threats to global public health, despite extensive efforts to develop anti-HIV-1 therapeutic agents.

An enveloped virus, HIV-1 hides from humoral recognition behind a wide array of protective mechanisms. The major HIV-1 envelope protein (HIV-1 Env) is a glycoprotein of approximately 160 kD (gp160). During infection, proteases of the host cell cleave gp160 into gp120 and gp41. gp41 is an integral membrane protein, while gp120 protrudes from the mature virus. Together gp120 and gp41 make up the HIV-1 envelope spike, which is a target for neutralizing antibodies. Broadly neutralizing antibodies that bind to HIV-1 Env have been identified, including the VRC01 antibody, which specifically binds to the CD4-binding site of gp120 and can neutralize a high percentage of HIV-1 strains. However, there is a need to develop additional neutralizing antibodies for HIV-1 with varying recognition and neutralization profiles for commercial production.

SUMMARY

Isolated monoclonal antibodies and antigen binding fragments thereof that specifically bind to the CD4 binding site on gp120 and neutralize HIV-1 are provided herein. As disclosed herein, a novel antibody termed "N6" neutralized 98% of pseudoviruses in a 181 pseudovirus panel representing a wide variety of HIV-1 strains with an $IC_{50}$<50 μg/ml, and 96% of the pseudoviruses with an $IC_{50}$<1 μg/ml. The median $IC_{50}$ of neutralized viruses was 0.038 μg/ml, among the most potent thus far described. Further, N6 successfully neutralized 16 of 20 pseudoviruses in the panel that are resistant to neutralization by VRC01, the canonical broadly neutralizing CD4 binding site antibody. Accordingly, embodiments of the disclosure include antibodies and antigen binding fragments with the binding specificity of the N6 antibody, as well as variants thereof.

In some embodiments, the antibody or antigen binding fragment comprises a heavy chain variable region ($V_H$) comprising a HCDR1, a HCDR2, and a HCDR3 of the $V_H$ set forth as SEQ ID NO: 1 (N6 $V_H$) and/or a light chain variable region ($V_L$) comprising a LCDR1, a LCDR2, and a LCDR3 of the $V_L$ set forth as SEQ ID NO: 2 (N6 $V_L$). In additional embodiments, the antibody or antigen binding fragment comprises a $V_H$ comprising a HCDR1, a HCDR2, and a HCDR3 of the $V_H$ set forth as SEQ ID NO: 3 (N17 $V_H$) and/or a $V_L$ comprising a LCDR1, a LCDR2, and a LCDR3 of the $V_L$ set forth as SEQ ID NO: 4 (N17 $V_H$). In further embodiments, the antibody or antigen binding fragment comprises a $V_H$ comprising a HCDR1, a HCDR2, and a HCDR3 of the $V_H$ set forth as SEQ ID NO: 5 (F8 $V_H$) and/or a $V_L$ comprising a LCDR1, a LCDR2, and a LCDR3 of the $V_L$ set forth as SEQ ID NO: 6 (F8 $V_H$). The disclosed antibodies and antigen binding fragment can specifically bind to gp120 and neutralize HIV-1

In some embodiments, the antibody or antigen binding fragment comprises a $V_H$ and a $V_L$ comprising the amino acid sequences set forth as SEQ ID NOs: 1 and 2, respectively. In some embodiments, the antibody or antigen binding fragment comprises a $V_H$ and a $V_L$ comprising the amino acid sequences set forth as SEQ ID NOs: 3 and 4, respectively. In some embodiments, the antibody or antigen binding fragment comprises a $V_H$ and a $V_L$ comprising the amino acid sequences set forth as SEQ ID NOs: 5 and 6 respectively.

Also disclosed are compositions including the antibodies and antigen binding fragments, nucleic acids encoding the antibodies and antigen binding fragments, expression vectors comprising the nucleic acids, and isolated host cells that comprise the nucleic acids. In several embodiments, the nucleic acid molecule encoding a disclosed antibody or antigen binding fragment can be a cDNA molecule that encodes the antibody or antigen binding fragment. In additional embodiments, the nucleic acid molecule can be a bicistronic expression construct encoding the $V_H$ and $V_L$ of the antibody or antigen binding fragment.

The disclosed antibodies and antigen binding fragments potently neutralize HIV-1 in an accepted in vitro model of HIV-1 infection. Accordingly, a method is disclosed for treating or inhibiting an HIV-1 infection in a subject. The methods include administering a therapeutically effective amount of one or more of the disclosed antibodies, antigen binding fragments, nucleic acid molecules, vectors, or compositions, to the subject, such as a subject at risk of or having an HIV-1 infection.

The antibodies, antigen binding fragments, nucleic acid molecules, vectors, and compositions disclosed herein can be used for a variety of additional purposes, such as for detecting an HIV-1 infection or diagnosing HIV-1 infection in a subject, or detecting HIV-1 in a sample.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1F show a set of tables and a sequence alignment illustrating the sequence and neutralization activity of the N6 antibody and several variants thereof. (FIG. 1A) Neutralization fingerprints encompassing ten different epitope specificities were used to interrogate the serum specificities of HIV-infected patient Z258. Sera of patients 45 and 127/C, from whom VRC01 and VRC01-like antibodies were isolated, were used as controls. Values predict the fraction of serum neutralization that can be attributed to each antibody specificity. Strong VRC01-like signals were observed in the sera (values >0.3). A panel of 21 HIV-1 strains was used in the neutralization analysis and for computing serum breadth. (FIG. 1B) Amino acid sequences of the variable regions of N6, its variants N17 and F8, and related antibodies VRC01 and VRC27. Residues in bold represent substitutions from the germline sequence. Kabat numbering is used to identify specific residues in the N6 heavy and light chains. Sequences shown include IGHV1-2*02 (SEQ ID NO: 77), N6 $V_H$ (SEQ ID NO: 1), N17 $V_H$ (SEQ ID NO: 3), F8 $V_H$ (SEQ ID NO: 5, VRC01 $V_H$ (SEQ ID NO: 73), VRC27 $V_H$ (SEQ ID NO: 75), IGHV1-2*02 (SEQ ID NO: 78), N6 $V_L$ (SEQ ID NO: 2), N17 $V_L$ (SEQ ID NO: 4), F8 $V_L$ (SEQ ID NO: 6), VRC01 $V_L$ (SEQ ID NO: 74), and VRC27 $V_L$ (SEQ ID NO: 76). (FIG. 1C) Germline genes of N6 heavy and light chain variable regions. (FIG. 1D) Neutralizing potency and breadth of antibodies against a panel of 181-isolate Env-pseudovirus panel. Data show the number of tested viruses, the percentage of viruses neutralized, the geometric mean and median $IC_{50}$ for viruses neutralized with an $IC_{50}$<50 μg/ml. (FIG. 1E) Breadth-potency curves of neutralization by antibodies against 181-pseudovirus panel. Solid line shows the median $IC_{50}$ of all viruses including those with $IC_{50}$>50 mg/ml, which were assigned a value of 50. Dash line shows the median $IC_{50}$ of sensitive viruses only. Numbers on top of the dot plots represent the percentage of viruses resistant to neutralization. (FIG. 1F) Neutralization characteristics of the N6 antibody, as well as several N6 variants for a panel of 20 HIV-1 pseudoviruses representing a variety of HIV-1 strains that are resistant to VRC01. The variants include Variant 1 (N6 $V_H$+F8 $V_L$), Variant 2 (N6 $V_H$+N17 $V_L$), Variant 3 (N17 $V_H$+F8 $V_L$), Variant 4 (N17 $V_H$+N6 $V_L$), Variant 5 (F8 $V_H$+N6 $V_L$), and Variant 6 ((F8 $V_H$+N17 $V_L$).

FIG. 2 is a table showing the neutralization profile of N6, VRC01, 3BNC117 and VRC07-523-LS against 20 VRC01-resistant pseudoviruses. Values are shown in μg/ml.

FIGS. 3A-3C are a set of graphs and tables showing N6 autoreactivity properties. (FIG. 3A) Reactivity of N6 with HEP-2 epithelial cells. VRC07-G54W, VRC07-523-LS and 4E10 were used as positive controls. VRC01-LS was used as a negative control. Antibody concentration was 25 μg/ml. All pictures are shown at 400× magnification. (FIG. 3B) ELISA binding of N6 to cardiolipin. Controls are as in FIG. 3A. (FIG. 3C) Reactivity of N6 with autoantigens was detected by the Luminex assay. 4E10 was used as a positive control. Synagis, an anti-RSV monoclonal antibody, was used as a negative control. SSA, Sjogren's syndrome antigen A; SSB, Sjogren syndrome antigen B; Sm, Smith antigen; RNP, ribonucleoprotein; Scl 70, scleroderma 70; Jol, antigen; CentrB, centromere B.

FIGS. 4A-4E are a set of graphs and a table illustrating binding specificity of N6 for gp120. (FIG. 4A) ELISA binding of N6 to gp120$^{YU2}$ in competition with CD4Ig-biotin, VRC01-biotin and VRC-PG04-biotin. B12, VRC01 and CD4-Ig were used as positive controls and 2G12 was used as a negative control. (FIG. 4B) ELISA binding of N6 to gp120$^{BaL}$, RSC3 and their CD4 binding site knockout mutants gp120$^{BaL}$D368R and RSC3 Δ371I P363N. (FIG. 4C) N6 and the N6 Variant-1 bind to gp140 foldon (a soluble, trimeric gp140 linked to a foldon domain) and gp120, but not gp41 or MPER peptide. (FIG. 4D) Binding of N6 to alanine scanning mutants in the context of monomeric gp120$^{JRCSF}$ by ELISA. Amino acid numbering of mutants is based on HIV-1 HXB2 sequence. Binding affinities to captured gp120s were measured based on the antibody concentration at half-maximal binding. 2G12 was used as a control to measure the amount of captured gp120 to standardized the effect of each mutation on antibody binding. (FIG. 4E) Neutralization of a panel of gp120$^{JRCSF}$ alanine mutant pseudoviruses. Neutralization fold change was calculated by $IC_{50}$ of JRCSF mutant/$IC_{50}$ of JRCSF WT.

FIGS. 5A-5F are a set of tables providing results illustrating the neutralization mechanism of N6. (FIGS. 5A and 5B) N6-resistant viruses and Z258 autologous viruses neutralization profile. Amino acid sequences of loop D, CD4 BLP and β23-V5 region of N6- and VRC01-sensitive viruses HXB2, JRCSF and 93TH057, several N6-sensitive but VRC01-resistant viruses, and N6- and VRC01-resistant viruses are shown. Sequence variation of gp120 displayed by N6-resistant viruses and Z258 autologous viruses compared to reference sequences are listed in bold. Sequence numbering is based on HXB2. (FIGS. 5C-5D) Neutralization by N6 of N6-resistant viruses and Z258 autologous viruses and their mutants with reverse mutations in loop D, CD4 BLP and β23-V5 region. CD4Ig and CD4 binding site antibodies, VRC01, 3BNC117, VRC-PG04, 12A21 and VRC27, were used as positive controls and 2G12 was used as a negative control. Sequence variation of gp120 displayed by N6-resistant viruses and Z258 autologous viruses compared to reference sequences are shown. (FIGS. 5E-5F) Neutralization of N6 to N6-resistant viruses and Z258 autologous viruses with reverse mutations in loop D. Reverse mutation in loop D were highlighted in bold and underline.

FIGS. 6A-6F are a set of tables showing $IC_{50}$ and IC80 values from pseudovirus neutralization assays for alanine-scanning variants N6 (FIGS. 6A-6B), VRC27 (FIGS. 6C-6D), and VRC01 (FIGS. 6E-6F) against six VRC01-sensitive viruses. Neutralization values are shown in μg/ml. Fold change is defined as $IC_{50}$ of antibody mutant/$IC_{50}$ of antibody WT.

FIG. 7 is a table showing $IC_{50}$ values from pseudovirus neutralization assays using N6 alanine variants against six VRC01-resistant viruses and two VRC01-sensitive viruses. Neutralization values are shown in μg/ml. Median $IC_{50}$ is calculated based on VRC01-resistant viruses. Neutralization values are shown in μg/ml. Fold change is defined as $IC_{50}$ of antibody mutant/$IC_{50}$ of antibody WT.

FIGS. 8A-8C are a set of tables illustrating HIV-1 neutralization and binding by N6 antibody and variants thereof. (FIG. 8A) Neutralization of cross-complemented antibodies, including the heavy and light chains of the N6, VRC01, VRC27 and 12A21 antibodies. Neutralization fold change was calculated by $IC_{50}$ of original antibody/$IC_{50}$ of antibody combination. Median $IC_{50}$ is based on all tested viruses, including those resistant viruses, which were assigned a value of 50. (FIGS. 8B-8C) Neutralization by antibody mutants with substitutions of various contact residues of N6 with those of VRC01, VRC27 or N6 variant N17. N6 and VRC01 were used as controls. Median $IC_{50}$ is calculated based on all VRC01-resistant viruses. For those $IC_{50}$>50, a value of 50 were assigned. Neutralization fold change was calculated by $IC_{50}$ of antibody mutant/$IC_{50}$ of antibody WT.

FIG. 11 shows that like other VRC01-class antibodies, N6 also uses the flexible GxG motif in LCDR1 to avoid clashes with loop D.

Figure 12A:
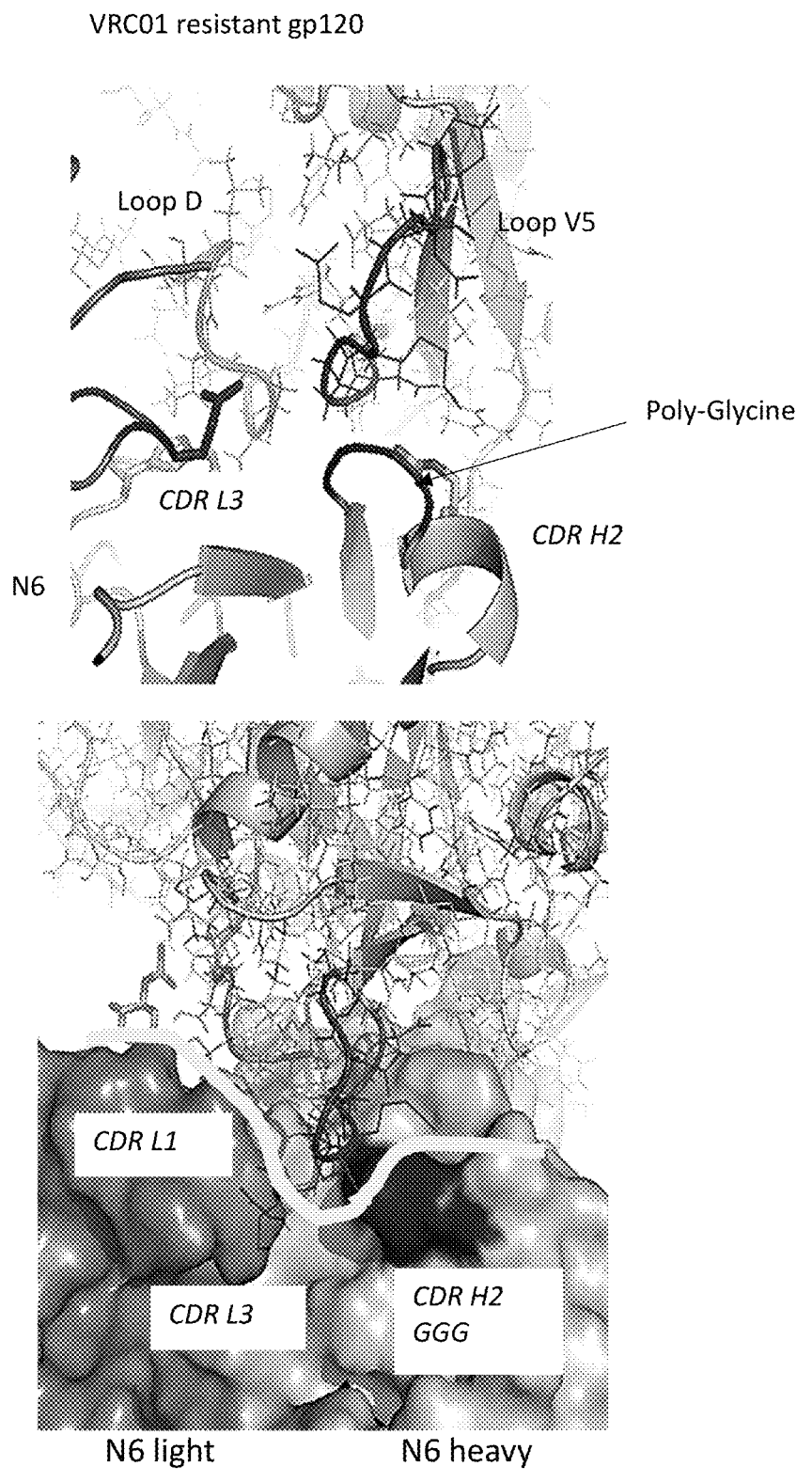

FIGS. 12A and 12B are a set of diagrams illustrating that the N6 HCDR2 and LCDR3 contribute to the tolerance of variation at gp120 V5 observed for N6.

FIGS. 14, 15A, and 15B are a set of graphs and a table illustrating development of N6 within the VRC27-lineage in donor Z258. (FIG. 14) Heavy and light chains Identity-divergency plots from donor Z258 samples in 2012, 2014 and 2015. Sequences are plotted as a function of sequence identity to the N6 (top) and VRC27 (bottom) and of sequence divergence from heavy chain IGHV1-2*02 (left) or light chain IGKV1-33*01 (right) germline V genes. (FIG. 15A) Paired phylogenetic tree of N6 lineage. Phylogenetic tree of heavy chain is based on the sequence identity in CDR H3 to that of N6, VRC27 F8 or N17. Phylogenetic tree of light chain is based on the reads deriving form IGKV1-33*01 and the 5 amino acid-CDRL3 signature of VRC01-class antibodies. (FIG. 15B) Amino acid sequences of variable region of NGS inferred intermediates compared to N6. Residues in lighter grey represent substitutions from the I1 sequences of heavy and light chains. Kabat numbering is used to identify specific residues in the N6 heavy and light chains. Sequences shown include IGHV1-2*02 (SEQ ID NO: 77), I1 $V_H$ (SEQ ID NO: 79), I2 $V_H$ (SEQ ID NO: 80), I3 $V_H$ (SEQ ID NO: 81), I4 $V_H$ (SEQ ID NO: 82), N6 $V_H$ (SEQ ID NO: 1), I5 $V_H$ (SEQ ID NO: 83), VRC27 $V_H$ (SEQ ID NO: 75), IGHV1-2*02 (SEQ ID NO: 78), I1 $V_L$ (SEQ ID NO: 84), I2 $V_L$ (SEQ ID NO: 85), I3 $V_L$ (SEQ ID NO: 86), I4 $V_L$ (SEQ ID NO: 87), I5 $V_L$ (SEQ ID NO: 88), I6 $V_L$ (SEQ ID NO: 89), N6 $V_L$ (SEQ ID NO: 2), I7 $V_L$ (SEQ ID NO: 90), I8 $V_L$ (SEQ ID NO: 91), I9 $V_L$ (SEQ ID NO: 92), I10 $V_L$ (SEQ ID NO: 93), and VRC27 $V_L$ (SEQ ID NO: 76).

FIGS. 16 and 17 are tables of neutralization of VRC01-resistant pseudoviruses by various combinations of N6-like heavy and light chains derived by NGS sequencing from 2014 and 2015 time-points (FIG. 16, variant sequences shown in FIG. 18) or imputed precursors of N6 (FIG. 17, variant sequences shown in FIG. 15B).

FIG. 18 shows an alignment of variant N6 heavy and light chain sequences. The following heavy chain sequences are shown: IGHV1-2*02 (SEQ ID NO: 77), N6 (SEQ ID NO: 1), 2_2014_00173626_H (SEQ ID NO: 112), and 2_2014_00173626_H Mt (SEQ ID NO: 115). The following Kappa chain sequences are shown: IGKV1-33*01 (SEQ ID NO: 78), N6 (SEQ ID NO: 2), 1_2015_00106641_L (SEQ ID NO: 104), 1_2015_00065970_L Mt (SEQ ID NO: 106), 1_2014_00019094_L (SEQ ID NO: 108), and 1_2015_00217585_L (SEQ ID NO: 110).

SEQUENCES

Figure 1E:
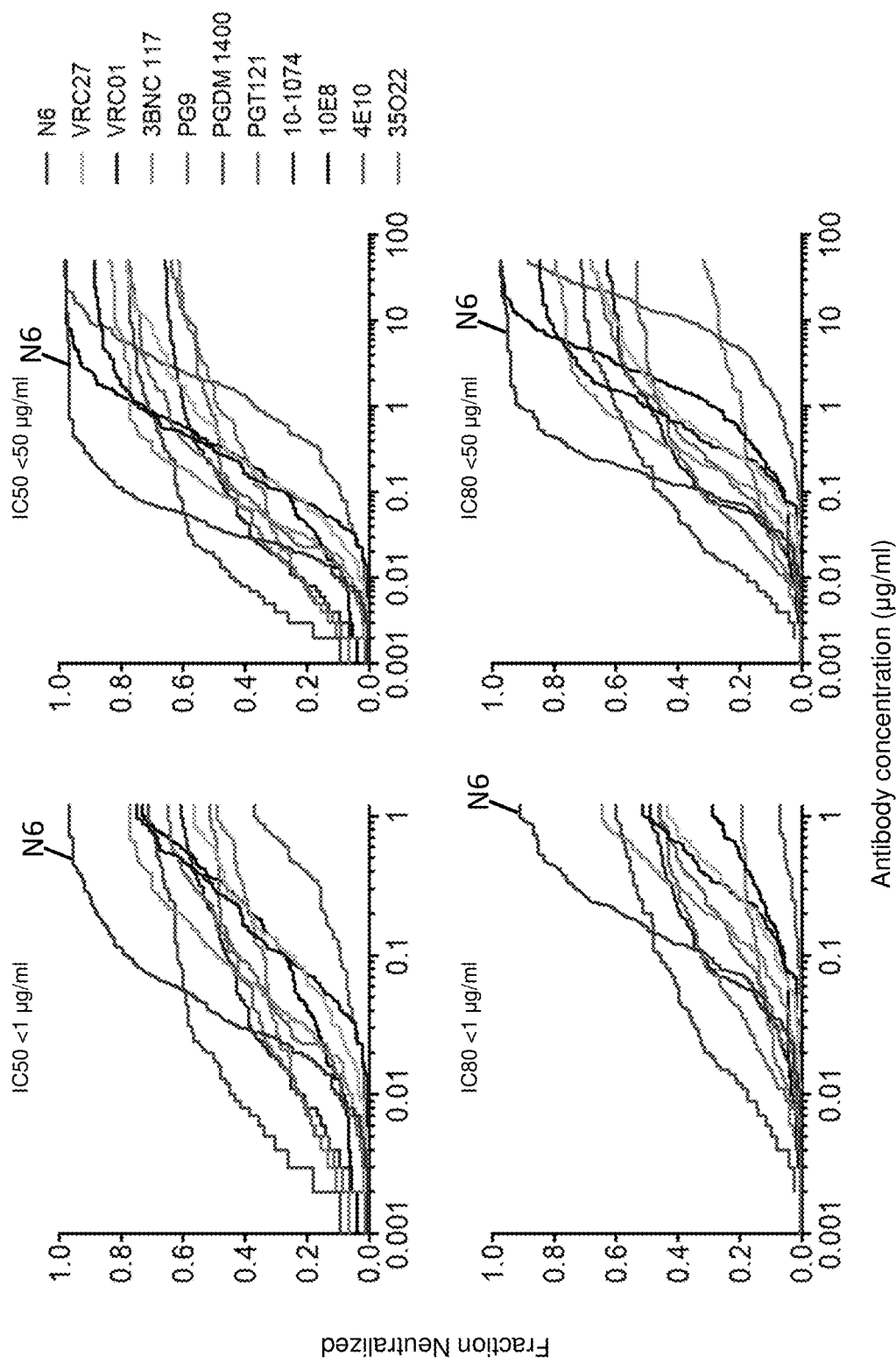

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~115 KB), which was created on Jun. 30, 2022, and which is incorporated by reference herein. In the accompanying sequence listing:

```
SEQ ID NO: 1 is the amino acid sequence of the V_H of the N6 mAb.
RAHLVQSGTAMKKPGASVRVSCQTSGYTFTAHILFWFRQAPGRGLEWVGWIKPQYGAVNFGGG

FRDRVTLTRDVYREIAYMDIRGLKPDDTAVYYCARDRSYGDSSWALDAWGQGTTVVVSA

SEQ ID NO: 2 is the amino acid sequence of the V_L of the N6 mAb.
YIHVTQSPSSLSVSIGDRVTINCQTSQGVGSDLHWYQHKPGRAPKLLIHHTSSVEDGVPSRFS

GSGFHTSFNLTISDLQADDIATYYCQVLQFFGRGSRLHIK

SEQ ID NO: 3 is the amino acid sequence of the V_H of the N17 mAb.
RAHLVQSGTAVKRPGASVRVSCETSGYTFTAHILYWFRQAPGRGLEWVGWIKPQYGAVNFGGGF

RGRVTLTRDIYRDTAYMDISGLRFDDTAVYYCARDRSYDDSSWALDAWGQGTTVVVSA

SEQ ID NO: 4 is the amino acid sequence of the V_L of the N17 mAb.
YIHVTQSPSSLSVSAGDRVTINCQTSQGVGRDLHWYQHKPGRAPKLLIRHASSVEDGVPSRFSG

TGFHTSFNLTINDLQSDDIATYYCQVLESFGRGSRLDFK

SEQ ID NO: 5 is the amino acid sequence of the V_H of the F8 mAb.
QVQLVQSGTAMKKPGASVRVSCQTSGYTFTAHILFWFRQAPGRGLEWVGWIKPQYGAVNFGGG

FRDRVTLTRDIYREIAYMDIRGLKLDDTAVYYCARDRSYGDSSWALDAWGQGTTVVASA

SEQ ID NO: 6 is the amino acid sequence of the V_L of the F8 mAb.
YIHVTQSPSSLSVSIGDRVTINCQTSQGVGSDLHWYQHKPGRAPKLLIHHASSVEDGVPSRFS

GSGFHTSFNLTINDLQADDIATYYCQVLQFFGRGSRLHIK

SEQ ID NOs: 7-18 are amino acid sequences of the kabat CDRs of
the N6, N17, and F8 antibodies.

SEQ ID NOs: 19-24 are consensus amino acid sequences of the kabat
CDRs of the N6, N17, and F8 antibodies.
```

-continued

SEQ ID NOs: 25-34 are amino acid sequences relating to chimeric antigen receptors.

SEQ ID NO: 35 is the amino acid sequence of HIV-1 Env from the HXB2 strain of HIV-1.

SEQ ID NO: 36 is an exemplary nucleic acid sequence encoding the $V_H$ of the N6 mAb.
CGAGCGCACCTGGTACAATCAGGGACTGCGATGAAGAAACCGGGGGCCTCAGTAAGAGTCTCCTGCCAGACCTCTGGA

TACACCTTTACCGCCCACATATTATTTTGGTTCCGACAGGCCCCCGGGCGAGGACTTGAGTGGGTGGGGTGGATCAAG

CCACAATATGGGGCCGTGAATTTTGGTGGTGGTTTTCGGGACAGGGTCACATTGACTCGAGACGTATATAGAGAGATT

GCGTACATGGACATCAGAGGCCTTAAACCTGACGACACGGCCGTCTATTACTGTGCGAGAGACCGTTCCTATGGCGAC

TCCTCTTGGGCCTTAGATGCCTGGGGACAGGGAACGACGGTCGTCGTCTCCGCG

SEQ ID NO: 37 is an exemplary nucleic acid sequence encoding the $V_L$ of the N6 mAb.
TACATCCACGTGACCCAGTCTCCGTCCTCCCTGTCTGTGTCTATTGGAGACAGAGTCACCATCAATTGCCAGACGAGT

CAGGGTGTTGGCAGTGACCTACATTGGTATCAACACAAACCGGGGAGAGCCCCTAAACTCTTGATCCACCATACCTCT

TCTGTGGAAGACGGTGTCCCCTCAAGATTCAGCGGCTCTGGATTTCACACATCTTTTAATCTGACCATCAGCGACCTA

CAGGCTGACGACATTGCCACATATTACTGTCAAGTTTTACAATTTTTCGGCCGAGGGAGTCGACTCCATATTAAA

SEQ ID NO: 38 is an exemplary nucleic acid sequence encoding the $V_H$ of the N17 mAb.
CGAGCGCACCTGGTACAATCAGGGACTGCGGTGAAGAGACCGGGGGCCTCAGTAAGGGTCTCCTGCGAGACTTCTGGA

TACACCTTTACCGCCCACATATTATACTGGTTCCGACAGGCCCCCGGGCGAGGGCTTGAGTGGGTGGGGTGGATCAAG

CCACAATACGGTGCCGTGAACTTTGGGGGTGGTTTTCGGGGCAGGGTCACATTGACGCGAGACATATATAGAGATACT

GCATATATGGACATCAGTGGCCTGAGATTTGACGACACGGCCGTCTACTATTGTGCGAGAGACCGTTCTTATGACGAC

TCTTCTTGGGCCTTAGATGCCTGGGGCCAGGGAACGACGGTCGTCGTCTCCGCG

SEQ ID NO: 39 is an exemplary nucleic acid sequence encoding the $V_L$ of the N17 mAb.
TACATCCACGTGACCCAGTCTCCGTCCTCCCTGTCTGTGTCTGCTGGGGACAGAGTCACCATCAATTGCCAGACGAGT

CAGGGTGTTGGCCGTGACCTACATTGGTATCAACACAAACCGGGGAGAGCCCCTAAACTCCTGATCCGCCACGCCTCT

TCTGTGGAGGACGGTGTCCCGTCAAGATTCAGTGGCACTGGATTTCACACATCTTTTAATTTGACCATCAACGACCTG

CAGTCTGACGACATTGCCACATATTACTGTCAGGTGTTAGAATCTTTCGGCCGAGGGAGTCGACTGGATTTTAAA

SEQ ID NO: 40 is an exemplary nucleic acid sequence encoding the $V_H$ of the F8 mAb.
CAGGTGCAGCTGGTACAATCAGGGACTGCGATGAAGAAACCGGGGGCCTCAGTAAGGGTCTCCTGCCAGACTTCTGGA

TACACCTTTACCGCCCACATATTATTTTGGTTCCGACAGGCCCCCGGGCGAGGGCTTGAGTGGGTGGGATGGATCAAG

CCACAATACGGGGCCGTGAATTTTGGTGGTGGTTTTCGGGACAGGGTCACATTGACTCGAGACATATATAGAGAGATT

GCATACATGGACATCAGAGGCCTTAAACTTGACGACACGGCCGTCTATTACTGTGCGAGAGACCGTTCCTATGGCGAC

TCCTCTTGGGCCTTAGATGCCTGGGGACAGGGAACGACGGTCGTCGCCTCCGCG

SEQ ID NO: 41 is an exemplary nucleic acid sequence encoding the $V_L$ of the F8 mAb.
TACATCCACGTGACCCAGTCTCCGTCCTCCCTGTCTGTGTCTATTGGAGACAGAGTCACCATCAATTGCCAGACGAGT

CAGGGTGTTGGCAGTGACCTACATTGGTATCAACACAAACCGGGGAGAGCCCCTAAACTCTTGATCCACCATGCCTCT

TCTGTGGAGGACGGTGTCCCGTCAAGATTCAGTGGCTCTGGATTTCACACATCTTTTAATCTGACCATCAACGACCTA

CAGGCTGACGACATTGCCACATATTACTGTCAGGTTTTACAATTTTTCGGCCGAGGGAGTCGACTCCATATTAAA

SEQ ID NOs: 42-64 are the amino acid sequence of modified antibody heavy and light chain variable regions.

SEQ ID NOs: 65-71 are oligonucleotide primers.

SEQ ID NO: 72 is a peptide sequence.

SEQ ID NO: 73 is the VRC01 $V_H$.
QVQLVQSGGQMKKPGESMRISCRASGYEFIDCTLNWIRLAPGKRPEWMGWLKPRGGAVNYA

RPLQGRVTMTRDVYSDTAFLELRSLTVDDTAVYFCTRGKNCDYNWDFEHWGRGTPVIVSS

SEQ ID NO: 74 is the VRC01 V$_L$.
EIVLTQSPGTLSLSPGETAIISCRTSQYGSLAWYQQRPGQAPRLVIYSGSTRAAGIPDRFS

GSRWGPDYNLTISNLESGDFGVYYCQQYEFFGQGTKVQVDIKR

SEQ ID NO: 75 is the VRC27 V$_H$.
QRLVQSGPQVRKPGSSVRISCETSGYTFNAYILHWFRQAPGRSFEWMGWIKPKFGAVNYAH

SFQGRITLTRDIYRETAFLDLTGLRFDDTAVYYCARDRLYDGSSWRLDPWGQGTRVVVSS

SEQ ID NO: 76 is the VRC27 V$_L$.
FALMTQSPATLAVSVGDRVTITCRASQGIGSDLHWYQQKPGRPPKILIHHASAREEGVPSR

FGGSGSHTSFIFTINDLQLDDVATYYCQVLESFGQGTRLDIN

SEQ ID NO: 77 is the IGHV1-2*02 sequence.
QVQLVQSGAEVKKPGASVKVSCKASGYTFTGYYMHWVRQAPGQGLEWMGWINPNSGGTNYA

QKFQGRVTMTRDTSISTAYMELSRLRSDDTAVYYCARAYCGGDCYNWFDSWGQGTLVTVSS

SEQ ID NO: 78 is the IGKV1-33*01 sequence.
DIQMTQSPSSLSASVGDRVTITCQASQDISNYLNWYQQKPGKAPKLLIYDASNLETGVPSR

FSGSGSGTDFTFTISSLQPEDIATYYCQQYDNLPITFGQGTRLEIK

SEQ ID NOs: 79-93 are amino acid sequences of N6 V$_H$ and V$_L$ variants.

SEQ ID NO: 94 is an exemplary heavy chain sequence including the N6 V$_H$.
RAHLVQSGTAMKKPGASVRVSCQTSGYTFTAHILFWFRQAPGRGLEWVGWIKPQYGAVNFGGGFRDRVTLTRDVYREI

AYMDIRGLKPDDTAVYYCARDRSYGDSSWALDAWGQGTTVVVSAASTKGPSVFPLAPSSKSTSGGTAALGCLVKDYFP

EPVTVSWNSGALTSGVHTFPAVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHNAKTKPREEQYNSTYRWSVLT

VLHQDWLNGKEYKCKVSNKALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 95 is an exemplary nucleic acid sequence encoding a heavy chain including the N6 V$_H$.
CGAGCGCACCTGGTACAATCAGGGACTGCGATGAAGAAACCGGGGGCCTCAGTAAGAGTCTCCTGCCAGACCTCTGGA

TACACCTTTACCGCCCACATATTATTTTGGTTCCGACAGGCCCCCGGGCGAGGACTTGAGTGGGTGGGGTGGATCAAG

CCACAATATGGGGCCGTGAATTTTGGTGGTGGTTTTCGGGACAGGGTCACATTGACTCGAGACGTATATAGAGAGATT

GCGTACATGGACATCAGAGGCCTTAAACCTGACGACACGGCCGTCTATTACTGTGCGAGAGACCGTTCCTATGGCGAC

TCCTCTTGGGCCTTAGATGCCTGGGGACAGGGAACGACGGTCGTCGTCTCCGCGGCGTCGACCAAGGGCCCATCGGTC

TTCCCCCTGGCACCCTCCTCCAAGAGCACCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGAAT

CACAAGCCCAGCAACACCAAGGTGGACAAGAAAGTTGAGCCCAAATCTTGTGACAAAACTCACACATGCCCACCGTGC

CCAGCACCTGAACTCCTGGGGGGACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCTCACC

GTCCTGCACCAGGACTGGCTGAATGGCAAGGAGTACAAGTGCAAGGTCTCCAACAAAGCCCTCCCAGCCCCCATCGAG

AAAACCATCTCCAAAGCCAAAGGGCAGCCCCGAGAACCACAGGTGTACACCCTGCCCCCATCCCGGGATGAGCTGACC

AAGAACCAGGTCAGCCTGACCTGCCTGGTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGATGCATGAGGCTCTGCACAACCACTACACG

CAGAAGAGCCTCTCCCTGTCTCCGGGTAAA

SEQ ID NO: 96 is an exemplary light chain sequence including the N6 $V_L$.
YIHVTQSPSSLSVSIGDRVTINCQTSQGVGSDLHWYQHKPGRAPKLLIHHTSSVEDGVPSRFSGSGFHTSFNLTISDL

QADDIATYYCQVLQFFGRGSRLHIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

SEQ ID NO: 97 is an exemplary nucleic acid sequence encoding a light chain including the N6 $V_H$.
TACATCCACGTGACCCAGTCTCCGTCCTCCCTGTCTGTGTCTATTGGAGACAGAGTCACCATCAATTGCCAGACGAGT

CAGGGTGTTGGCAGTGACCTACATTGGTATCAACACAAACCGGGGAGAGCCCCTAAACTCTTGATCCACCATACCTCT

TCTGTGGAAGACGGTGTCCCCTCAAGATTCAGCGGCTCTGGATTTCACACATCTTTTAATCTGACCATCAGCGACCTA

CAGGCTGACGACATTGCCCACATATTACTGTCAAGTTTTACAATTTTTCGGCCGAGGGAGTCGACTCCATATTAAACGT

ACGGTGGCTGCACCATCTGTCTTCATCTTCCCGCCATCTGATGAGCAGTTGAAATCTGGAACTGCCTCTGTTGTGTGC

CTGCTGAATAACTTCTACCCCAGAGAAGCCAAAGTGCAGTGGAAGGTGGACAACGCCCTGCAGAGCGGAAACAGCCAG

GAAAGCGTGACAGAGCAGGATTCCAAGGATTCCACATACAGCCTGAGCAGCACACTGACACTGTCCAAGGCCGACTAC

GAGAAGCACAAGGTGTACGCCTGCGAAGTGACACACCAGGGACTGTCCTCCCCTGTGACAAAGAGCTTCAACAGAGGA

GAATGC

SEQ ID NO: 98 is the heavy chain sequence including the N6 $V_H$ as isolated from the human donor, which include polymorphism compared to SEQ ID NO: 94.
RAHLVQSGTAMKKPGASVRVSCQTSGYTFTAHILFWFRQAPGRGLEWVGWIKPQYGAVNFGGGFRDRVTLTRDVYREI

AYMDIRGLKPDDTAVYYCARDRSYGDSSWALDAWGQGTTVVVSAASTKGPSVFPLAPSSKSTSGGTAALGCLVKDYFP

EPVTVSWNSGALTSGVHTFPAVLQSSGLYSLSSVVTVPSSSLGTQTYICNVNHKPSNTKVDKRVEPKSCDKTHTCPPC

PAPELLGGPSVFLFPPKPKDTLMISRTPEVTCVVVDVSHEDPEVKFNWYVDGVEVHNAKTKPREEQYNSTYRWSVLT

VLHQDWLNGEEYKCKVSNKALPAPIEKTISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 99 is the sequence of the nucleic acid molecule encoding the N6 $V_H$ as isolated from the human donor.
CGAGCGCACCTGGTACAATCAGGGACTGCGATGAAGAAACCGGGGGCCTCAGTAAGAGTCTCCTGCCAGACCTCTGGA

TACACCTTTACCGCCCACATATTATTTTGGTTCCGACAGGCCCCCGGGCGAGGACTTGAGTGGGTGGGGTGGATCAAG

CCACAATATGGGGCCGTGAATTTTGGTGGTGGTTTTCGGGACAGGGTCACATTGACTCGAGACGTATATAGAGAGATT

GCGTACATGGACATCAGAGGCCTTAAACCTGACGACACGCCGTCTATTACTGTGCGAGAGACCGTTCCTATGGCGAC

TCCTCTTGGGCCTTAGATGCCTGGGGACAGGGAACGACGGTCGTCGTCTCCGCGGCCTCCACCAAGGGCCCATCGGTC

TTCCCCCTGGCACCCTCCTCCAAGAGCACCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGAAT

CACAAGCCCAGCAACACCAAGGTGGACAAGAGAGTTGAGCCCAAATCTTGTGACAAAACTCACACATGCCCACCGTGC

CCAGCACCTGAACTCCTGGGGGGACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCTCACC

GTCCTGCACCAGGACTGGCTGAATGGCGAGGAGTACAAGTGCAAGGTCTCCAACAAAGCCCTCCCAGCCCCCATCGAG

AAAACCATCTCCAAAGCCAAAGGGCAGCCCCGAGAACCACAGGTGTACACCCTGCCCCCATCCCGGGAGGAGATGACC

AAGAACCAGGTCAGCCTGACCTGCCTTGTCAAAGGCTTCTATCCCAGCGACATCGCCGTGGAGTGGGAGAGCAATGGG

CAGCCGGAGAACAACTACAAGACCACGCCTCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGATGCATGAGGCTCTGCACAACCACTACACG

CAGAAGAGCCTCTCCCTGTCTCCGGGTAAA

SEQ ID NO: 100 is an exemplary nucleotide sequence encoding the N6 I1 $V_H$ intermediate.
CGAGGGCACTTGGTGCAGTCAGGGACTGAGGTGAAGAAACCGGGGGCCTCAGTGAGAGTCTCCTGCGAGACTTCTGGA

TACACCTTCACCGCCTACATTTTACATTGGTTCCGACAGGCCCCCGGACGAGGGCTTGAGTGGATGGGGTGGATCAAG

CCAAAATATGGAGCCGTCAATTATGCTCATGCATTTCAGGGCAGGGTCACCCTGACCAGAGACATATATAGAGACACT

GCATACATGGACTTGAGTGGCCTAAGATTCGACGACACGGCCGTCTATTACTGTGCGAGAGATCGCGTTTATGACGAT

TCGTCTTGGCAATTGGATCCCTGGGGCCAGGGAACTTCGGTCATCGTCTCCTCA

SEQ ID NO: 101 is an exemplary nucleotide sequence encoding the N6 I2 $V_H$ intermediate.
CGAGGGCACTTGGTGCAGTCAGGGACTGAGGTGAAGAAACCGGGGGCCTCAGTGAGAGTCTCCTGCGAGACTTCTGGA

TACACCTTCACCGCCCACATTTTACATTGGTTCCGACAGGCCCCCGGACGAGGGCTTGAGTGGATGGGGTGGATCAAG

CCAAAATATGGAGCCGTCAATTATGCTCATGCATTTCAGGGCAGGGTCACCCTGACCAGAGACATATATAGAGACACT

GCATACATGGACTTGAGTGGCCTAAGATTCGACGACACGGCCGTCTATTACTGTGCGAGAGATCGCGTTTATGACGAT

TCGTCTTGGCAATTGGATCCCTGGGGCCAGGGAACTTCGGTCATCGTCTCCTCA

SEQ ID NO: 102 is an exemplary nucleotide sequence encoding the N6 I3 $V_H$ intermediate.
CGAGCGCACTTGGTGCAGTCAGGGACTGCGGTGAAGAAACCGGGGGCCTCAGTGAGAGTCTCCTGCGAGACTTCTGGA

TACACCTTCACCGCCCACATTTTATATTGGTTCCGACAGGCCCCCGGACGAGGGCTTGAGTGGGTGGGGTGGATCAAG

CCACAATATGGGGCCGTGAATTTTGGTGGTGGTTTTCGGGGCAGGGTCACCCTGACCAGAGACATATATAGAGACACT

GCATACATGGACATCAGTGGCCTAAGATTCGACGACACGGCCGTCTATTACTGTGCGAGAGATCGCTCCTATGACGAC

TCCTCTTGGGCCTTAGATGCCTGGGGACAGGGAACGACGGTCGTCGTCTCCGCG

SEQ ID NO: 103 is an exemplary nucleotide sequence encoding the N6 I4 $V_H$ intermediate.
CGAGCGCACCTGGTACAATCAGGGACTGCGATGAAGAAACCGGGGGCCTCAGTAAGAGTCTCCTGCCAGACCTCTGGA

TACACCTTTACCGCCCACATATTATTTTGGTTCCGACAGGCCCCCGGGCGAGGACTTGAGTGGGTGGGGTGGATCAAG

CCACAATATGGGGCCGTGAATTTTGGTGGTGGTTTTCGGGACAGGGTCACATTGACTCGAGACATATATAGAGATT

GCGTACATGGACATCAGAGGCCTTAAACTTGACGACACGGCCGTCTATTACTGTGCGAGAGACCGTTCCTATGGCGAC

TCCTCTTGGGCCTTAGATGCCTGGGGACAGGGAACGACGGTCGTCGTCTCCGCG

SEQ ID NO: 104 is the amino acid sequence of the 1_2015_00106641_L $V_L$.
YIHVTQSPSSLSVSIGDRVTINCQTSQGVGSDLHWYQHKPGRDPKLLIRHTTSVEDGVPSRVSGSGFHT

SFNLTISDLQADDIATYYCQVLQFFGRGSRLHIK

SEQ ID NO: 105 is an exemplary DNA sequence encoding 1_2015_00106641_L $V_L$.
TACATCCACGTGACCCAGTCTCCGTCCTCCCTGTCTGTGTCTATTGGAGACAGAGTCACCATCAATTGCCAGACGAGT

CAGGGTGTTGGCAGTGACCTACATTGGTATCAACACAAACCGGGGAGAGACCCTAAACTCTTGATCCGCCATACCACT

TCTGTGGAAGACGGTGTCCCCTCAAGAGTCAGCGGCTCTGGATTTCACACATCTTTTAATCTGACCATCAGCGACCTA

CAGGCTGACGACATTGCCACATATTACTGTCAAGTTTTACAATTTTTCGGCCGAGGGAGTCGACTCCATATTAAA

SEQ ID NO: 106 is the amino acid sequence of the 1_2015_00065970_L $V_L$.
YIHVTQSPSSLSVSIGDRVTINCQTSQGVGSDLHWYQHKPGRAPKLLIHHASSVDDGVPSRFSGSGFHTSFNLTINDL

QADDIATYYCQVLQFFGRGSRLHIK

SEQ ID NO: 107 is an exemplary DNA sequence encoding 1_2015_00065970_L $V_L$.
TACATCCACGTGACCCAGTCTCCGTCCTCCCTGTCTGTGTCTATTGGAGACAGGGTCACCATCAATTGCCAGACGAGT

CAGGGTGTTGGCAGTGACCTACATTGGTATCAACACAAGCCGGGGAGAGCCCCTAAACTCTTGATTCATCATGCCTCT

TCTGTGGACGACGGTGTCCCGTCAAGATTCAGTGGCTCTGGATTTCACACATCTTTTAATCTGACCATCAACGACCTA

CAGGCTGACGACATTGCCACATATTACTGTCAGGTTTTACAATTTTTCGGCCGAGGGAGTCGACTCCATATTAAA

SEQ ID NO: 108 is the amino acid sequence of the 1_2014_00019094_L $V_L$.
YIHVTQSPSSLSVSIGDRVTINCQTSQGVGSDLHWYQHKPGRAPKLLIHHASSVEDGVPSRFSGTGFHTSFNLTINDL

QADDIGTYYCQVLQSFGRGSRLDTK

SEQ ID NO: 109 is an exemplary DNA sequence encoding 1_2014_00019094_L V$_L$.
TACATCCACGTGACCCAGTCTCCGTCCTCCCTGTCTGTGTCTATAGGGGACAGAGTCACCATCAATTGCCAGACGAGT

CAGGGTGTTGGCAGTGACCTACATTGGTATCAACACAAACCGGGGAGAGCCCCTAAACTCCTGATCCACCATGCCTCT

TCTGTGGAGGACGGTGTCCCGTCAAGATTCAGTGGCACTGGATTTCACACATCTTTTAATTTGACCATCAACGACCTG

CAGGCTGACGACATTGGCACTTATTACTGTCAGGTGTTACAATCTTTCGGCCGAGGGAGTCGACTGGATACTAAA

SEQ ID NO: 110 is the amino acid sequence of the 1_2015_00217585_L V$_L$.
YIHVTQSPSSLSVSIGDRVTINCQTSQGFGRDLHWYQHKPGRAPKLLIHHAPYVDDGVPSRFSGSGFHTSFNLTINDL

QADDIATYYCQVLQFFGRGSRLHIK

SEQ ID NO: 111 is an exemplary DNA sequence encoding 1_2015_00217585_L V$_L$.
TACATCCACGTGACCCAGTCTCCGTCCTCCCTGTCTGTGTCTATTGGAGACAGGGTCACCATCAATTGCCAGACGAGT

CAGGGTTTTGGCAGGGACCTACATTGGTATCAACACAAGCCGGGGAGAGCCCCTAAACTCTTGATTCATCATGCCCCT

TATGTGGACGACGGTGTCCCTTCAAGATTCAGTGGCTCTGGATTTCACACATCTTTTAATCTGACCATCAACGACCTA

CAGGCTGACGACATTGCCACATATTACTGTCAGGTTTTACAATTTTTCGGCCGAGGGAGTCGACTCCATATTAAA

SEQ ID NO: 112 is the amino acid sequence of the 2_2014_00173626_H V$_H$.
RAHLVQSGTAMKKPGASVRVSCQTSGYTFTAHILFWFRQAPGRGLEWVGWIKPQYGAVNFGGGFRDRVTLTRDIYREI

AYMDIRGLKLDDTAVYYCARDRSYGDSSWALDAWGQGTTVVVS

SEQ ID NO: 113 is an exemplary DNA sequence encoding 2_2014_00173626_H V$_H$.
CGAGCGCACCTGGTACAATCAGGGACTGCGATGAAGAAACCGGGGGCCTCAGTAAGGGTCTCCTGCCAGACTTCTGGA

TACACCTTTACCGCCCACATATTATTTTGGTTCCGACAGGCCCCCGGGCGAGGGCTGGAGTGGGTGGGATGGATCAAG

CCACAATACGGGGCCGTGAATTTTGGTGGTGGTTTTCGGGACAGGGTCACATTGACTCGAGACATATATAGAGAGATT

GCATACATGGACATCAGAGGCCTTAAACTTGACGACACGGCCGTCTATTACTGTGCGAGAGACCGTTCCTATGGCGAC

TCCTCTTGGGCCTTAGATGCCTGGGGACAGGGAACGACGGTCGTCGTCTCC

SEQ ID NO: 114 is the amino acid sequence of the 2_2014_00173626_Hmut V$_H$.
RAHLVQSGTAMKKPGASVRVSCQTSGYTFTAHILFWFRQAPGRGLEWVGWIKPQYGAVNFGGGFRDRVTLTRDIYREI

AYMDIRGLKLDDTAVYYCARDRSYGDSSWALDAWGQGTTVVVSA

SEQ ID NO: 115 is an exemplary DNA sequence encoding 2_2014_00173626_Hmut V$_H$.
CGAGCGCACCTGGTACAATCAGGGACTGCGATGAAGAAACCGGGGGCCTCAGTAAGGGTCTCCTGCCAGACTTCTGGA

TACACCTTTACCGCCCACATATTATTTTGGTTCCGACAGGCCCCCGGGCGAGGGCTGGAGTGGGTGGGATGGATCAAG

CCACAATACGGGGCCGTGAATTTTGGTGGTGGTTTTCGGGACAGGGTCACATTGACTCGAGACATATATAGAGAGATT

GCATACATGGACATCAGAGGCCTTAAACTTGACGACACGGCCGTCTATTACTGTGCGAGAGACCGTTCCTATGGCGAC

TCCTCTTGGGCCTTAGATGCCTGGGGACAGGGAACGACGGTCGTCGTCTCCGCG

DETAILED DESCRIPTION

I. SUMMARY OF TERMS

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in a protein with a different amino acid.

Anti-retroviral agent: An agent that specifically inhibits a retrovirus from replicating or infecting cells. Non-limiting examples of antiretroviral drugs include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon).

Anti-retroviral therapy (ART): A therapeutic treatment for HIV-1 infection involving administration of at least one anti-retroviral agents (e.g., one, two, three or four anti-retroviral agents) to an HIV-1 infected individual. One example of an ART regimen includes treatment with a combination of tenofovir, emtricitabine and efavirenz. In some examples, ART includes Highly Active Anti-Retroviral Therapy (HAART). One example of a HAART regimen includes treatment with a combination of tenofovir, emtricitabine and efavirenz.

Antibody: An immunoglobulin, antigen-binding fragment, or derivative thereof, that specifically binds and recognizes an analyte (antigen) such as HIV-1 gp120. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, IL); Kuby, J., *Immunology*, $3^{rd}$ Ed., W.H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., page 91 (2007).) In several embodiments, the $V_H$ and $V_L$ combine to specifically bind the antigen. In additional embodiments, only the $V_H$ is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). Any of the disclosed antibodies can include a heterologous constant domain. For example the antibody can include constant domain that is different from a native constant domain, such as a constant domain including one or more modifications (such as the "LS" mutations) to increase half-life.

References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, MD, 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions which have substantially no effect on antigen binding or other immunoglobulin functions. (See, for example, Harlow & Lane, *Antibodies, A Laboratory Manual*, $2^{nd}$ ed. Cold Spring Harbor Publications, New York (2013).)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel*. $1^{st}$ Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008)

Antibody or antigen binding fragment that neutralizes HIV-1: An antibody or antigen binding fragment that specifically binds to HIV-1 Env (for example, that binds gp120) in such a way as to inhibit a biological function associated with HIV-1 Env (such as binding to its target receptor). In several embodiments, an antibody or antigen binding fragment that neutralizes HIV-1 reduces the infectious titer of HIV-1.

Broadly neutralizing antibodies to HIV-1 are distinct from other antibodies to HIV-1 in that they neutralize a high percentage of the many types of HIV-1 in circulation. In some embodiments, broadly neutralizing antibodies to HIV-1 are distinct from other antibodies to HIV-1 in that they neutralize a high percentage (such as at least 90%, at least 95%, at least 96%, at least 97%, at least 98%, at least 99%) of the many types of HIV-1 in circulation. Non-limiting examples of HIV-1 broadly neutralizing antibodies include N6, 2G12, PGT122, VRC01, and 35O22.

Antibody self-reactivity or autoreactivity: A property of an antibody, whereby the antibody reacts with self-epitopes, which are epitopes of proteins and/or lipids that are produced by the subject. An antibody that does not have self-reactivity does not substantially bind to epitopes or lipids present on the membrane of a cell from a subject. Methods of determining if an antibody reacts with self epitopes are known to the person of ordinary skill in the art. In one example, antibody self reactivity is evaluated using HEp-2 cell staining, a cardiolipin binding assay, or an anti-nuclear antigen (ANA) assay. The anti-ANA assay can include an anti-ANA LUMINEX® assay or an ANA cell-staining assay, for example. In several embodiments, a disclosed antibody is not self-reactive (or autoreactive), or is minimally self-reactive. In one non-limiting example, a disclosed antibody does not have self reactivity above background levels, for example, as measured using an anti-ANA LUMINEX® assay or an ANA cell-staining assay.

Biological sample: A sample obtained from a subject. Biological samples include all clinical samples useful for detection of disease or infection (for example, HIV-1 infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having an HIV-1 infection.

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), or combinations thereof. A bispecific antibody can include one or more constant domains, but does not necessarily include a constant domain.

CD3 (Cluster of differentiation 3 T-cell Co-receptor): A specific protein complex including at least four polypeptide chains, which are non-covalently associated with the T-cell receptors on the surface of T-cells. The four polypeptide chains include two CD3-epsilon chains, a CD3-delta chain and a CD3-gamma chain. CD3 is present on both helper T cells and cytotoxic T cells.

CD4: Cluster of differentiation factor 4 polypeptide; a T-cell surface protein that mediates interaction with the MHC class II molecule. CD4 also serves as the primary receptor site for HIV-1 on T-cells during HIV-1 infection. CD4 is known to bind to gp120 from HIV-1. The known sequence of the CD4 precursor has a hydrophobic signal peptide, an extracellular region of approximately 370 amino acids, a highly hydrophobic stretch with significant identity to the membrane-spanning domain of the class II MHC beta chain, and a highly charged intracellular sequence of 40 resides (Maddon, *Cell* 42:93, 1985).

Chimeric Antigen Receptor (CAR): An engineered T cell receptor having an extracellular antibody-derived targeting domain (such as an scFv) joined to one or more intracellular signaling domains of a T cell receptor. A "chimeric antigen receptor T cell" is a T cell expressing a CAR, and has antigen specificity determined by the antibody-derived targeting domain of the CAR. Methods of making CARs are available (see, e.g., Park et al., *Trends Biotechnol.*, 29:550-557, 2011; Grupp et al., N Engl J Med., 368:1509-1518, 2013; Han et al., J. Hematol Oncol., 6:47, 2013; PCT Pubs. WO2012/079000, WO2013/059593; and U.S. Pub. 2012/0213783, each of which is incorporated by reference herein in its entirety.)

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, Antibodies, *A Laboratory Manual*, 2$^{nd}$ ed. Cold Spring Harbor Publications, New York (2013), for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography Immunological binding properties of selected antibodies may be quantified using methods well known in the art.

Conjugate: A complex of two molecules linked together, for example, linked together by a covalent bond. In one embodiment, an antibody is linked to an effector molecule; for example, an antibody that specifically binds to HIV-1 Env covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to interact with a target protein. For example, in some embodiments, an HIV-specific antibody can include up to 1, 2, 3, 4, 5, 6, 7, 8, 9, or up to 10 conservative substitutions compared to a reference antibody sequence and retain specific binding activity for HIV-1 antigen, and/or HIV-1 neutralization activity. The term conservative variation also includes the use of a substituted amino acid in place of an unsubstituted parent amino acid.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the HIV-specific antibody, such as the ability to specifically bind to gp120. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as sample obtained from a healthy patient not infected with HIV-1. In other embodiments, the control is a positive control, such as a tissue sample obtained from a patient diagnosed with HIV-1 infection. In still other embodiments, the control is a historical control or standard reference value or range of values (such as a previously tested control sample, such as a group of HIV-1 patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Degenerate variant: In the context of the present disclosure, a "degenerate variant" refers to a polynucleotide encoding a protein (for example, an antibody that specifically binds gp120 or a variable region thereof) that includes a sequence that is degenerate as a result of the genetic code. There are twenty natural amino acids, most of which are specified by more than one codon. Therefore, all degenerate nucleotide sequences are included as long as the amino acid sequence of the antibody that binds gp120 encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, 4$^{th}$ ed, Cold Spring Harbor, New York, 2012) and Ausubel et al. (In Current Protocols in Molecular Biology, John Wiley & Sons, New York, through supplement 104, 2013).

Detecting: To identify the existence, presence, or fact of something. General methods of detecting are known to the skilled artisan and may be supplemented with the protocols and reagents disclosed herein. For example, included herein are methods of detecting a cell that expresses gp120 in a subject.

Effector molecule: A molecule intended to have or produce a desired effect; for example, a desired effect on a cell to which the effector molecule is targeted. Effector molecules can include, for example, polypeptides and small molecules. In one non-limiting example, the effector molecule is a toxin. The skilled artisan will understand that some effector molecules may have or produce more than one desired effect.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on gp120.

Expression: Transcription or translation of a nucleic acid sequence. For example, an encoding nucleic acid sequence (such as a gene) can be expressed when its DNA is transcribed into an RNA or RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc polypeptide: The polypeptide including the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region includes immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to include residues C226 or P230 to its carboxyl-terminus, wherein the numbering is according to the EU index as in Kabat. For IgA, the Fc region includes immunoglobulin domains Calpha2 and Calpha3 (Cα2 and Cα3) and the lower part of the hinge between Calpha1 (Cα1) and Cα2.

HIV-1 Envelope protein (Env): The HIV-1 envelope protein is initially synthesized as a precursor protein of 845-870 amino acids in size, designated gp160. Individual gp160 polypeptides form a homotrimer and undergo glycosylation within the Golgi apparatus as well as processing to remove the signal peptide, and cleavage by a cellular protease between approximately positions 511/512 to generate separate gp120 and gp41 polypeptide chains, which remain associated as gp120/gp41 protomers within the homotrimer. The ectodomain (that is, the extracellular portion) of the HIV-1 Env trimer undergoes several structural rearrangements from a prefusion mature (cleaved) closed conformation that evades antibody recognition, through intermediate conformations that bind to receptors CD4 and co-receptor (either CCR5 or CXCR4), to a postfusion conformation.

The numbering used in the disclosed HIV-1 Env proteins and fragments thereof is relative to the HXB2 numbering scheme as set forth in *Numbering Positions in HIV Relative to HXB2CG* Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, NM, which is incorporated by reference herein in its entirety.

HIV-1 gp120: A polypeptide that is part of the HIV-1 Env protein. Mature gp120 includes approximately HIV-1 Env residues 31-511, contains most of the external, surface-exposed, domains of the HIV-1 Env trimer, and it is gp120 which binds both to cellular CD4 receptors and to cellular chemokine receptors (such as CCR5). A mature gp120 polypeptide is an extracellular polypeptide that interacts with the gp41 ectodomain to form an HIV-1 Env protomer that trimerizes to form the HIV-1 Env trimer.

HIV-1 gp140: A recombinant HIV-1 Env polypeptide including gp120 and the gp41 ectodomain, but not the gp41 transmembrane or cytosolic domains. HIV-1 gp140 polypeptides can trimerize to form a soluble HIV-1 Env ectodomain trimer.

HIV-1 gp41: A polypeptide that is part of the HIV-1 Env protein. Mature gp41 includes approximately HIV-1 Env residues 512-860, and includes cytosolic-, transmembrane-, and ecto-domains. The gp41 ectodomain (including approximately HIV-1 Env residues 512-644) can interact with gp120 to form an HIV-1 Env protomer that trimerizes to form the HIV-1 Env trimer.

Human Immunodeficiency Virus type 1 (HIV-1): A retrovirus that causes immunosuppression in humans (HIV-1 disease), and leads to a disease complex known as the acquired immunodeficiency syndrome (AIDS). "HIV-1 disease" refers to a well-recognized constellation of signs and symptoms (including the development of opportunistic infections) in persons who are infected by an HIV-1 virus, as determined by antibody or western blot studies. Laboratory findings associated with this disease include a progressive decline in T cells. Related viruses that are used as animal models include simian immunodeficiency virus (SIV) and feline immunodeficiency virus (FIV). Treatment of HIV-1 with HAART has been effective in reducing the viral burden and ameliorating the effects of HIV-1 infection in infected individuals.

HXB2 numbering system: A reference numbering system for HIV-1 protein and nucleic acid sequences, using HIV-1 HXB2 strain sequences as a reference for all other HIV-1 strain sequences. The person of ordinary skill in the art is familiar with the HXB2 numbering system, and this system is set forth in "Numbering Positions in HIV Relative to HXB2CG," Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex., which is incorporated by reference herein in its entirety. HXB2 is also known as: HXBc2, for HXB clone 2; HXB2R, in the Los Alamos HIV database, with the R for revised, as it was slightly revised relative to the original HXB2 sequence; and HXB2CG in GENBANK™, for HXB2 complete genome. The numbering used in gp120 polypeptides disclosed herein is relative to the HXB2 numbering scheme. For reference, the amino acid sequence of HIV-1 Env of HXB2 is set forth below:

(SEQ ID NO: 35; GENBANK ® Accession No. K03455, incorporated by reference
herein as present in the database on Mar. 15, 2015)
MRVKEKYQHLWRWGWRWGTMLLGMLMICSATEKLWVTVYYGVPVWKEATTTLFCASDAKAYDTEVHNVWATHAC

VPTDPNPQEVVLVNVTENFNMWKNDMVEQMHEDIISLWDQSLKPCVKLTPLCVSLKCTDLKNDTNTNSSSGRMI

MEKGEIKNCSFNISTSIRGKVQKEYAFFYKLDIIPIDNDTTSYKLTSCNTSVITQACPKVSFEPIPIHYCAPAG

FAILKCNNKTFNGTGPCTNVSTVQCTHGIRPVVSTQLLLNGSLAEEEVVIRSVNFTDNAKTIIVQLNTSVEINC

TRPNNNTRKRIRIQRGPGRAFVTIGKIGNMRQAHCNISRAKWNNTLKQIASKLREQFGNNKTIIFKQSSGGDPE

IVTHSFNCGGEFFYCNSTQLFNSTWFNSTWSTEGSNNTEGSDTITLPCRIKQIINMWQKVGKAMYAPPISGQIR

CSSNITGLLLTRDGGNSNNESEIFRPGGGDMRDNWRSELYKYKVVKIEPLGVAPTKAKRRVVQREKRAVGIGAL

FLGFLGAAGSTMGAASMTLTVQARQLLSGIVQQQNNLLRAIEAQQHLLQLTVWGIKQLQARILAVERYLKDQQL

LGIWGCSGKLICTTAVPWNASWSNKSLEQIWNHTTWMEWDREINNYTSLIHSLIEESQNQQEKNEQELLELDKW

ASLWNWFNITNWLWYIKLFIMIVGGLVGLRIVFAVLSIVNRVRQGYSPLSFQTHLPTPRGPDRPEGIEEEGGER

DRDRSIRLVNGSLALIWDDLRSLCLFSYHRLRDLLLIVTRIVELLGRRGWEALKYWWNLLQYWSQELKNSAVSL

LNATAIAVAEGTDRVIEVVQGACRAIRHIPRRIRQGLERILL.

IgA: A polypeptide belonging to the class of antibodies that are substantially encoded by a recognized immunoglobulin alpha gene. In humans, this class or isotype comprises $IgA_1$ and $IgA_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$. In mice, this class comprises $IgG_1$, $IgG_{2a}$, $IgG_{2b}$, $IgG_3$.

Immune complex: The binding of antibody or antigen binding fragment (such as a scFv) to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Linker: A bi-functional molecule that can be used to link two molecules into one contiguous molecule, for example, to link an effector molecule to an antibody. In some embodiments, the provided conjugates include a linker between the effector molecule or detectable marker and an antibody. In some cases, a linker is a peptide within an antigen binding fragment (such as an Fv fragment) which serves to indirectly bond the $V_H$ and $V_L$. Non-limiting examples of peptide linkers include glycine linkers and glycine-serine linkers.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The nucleotides can be ribonucleotides, deoxyribonucleotides, or modified forms of either nucleotide. The term includes single- and double-stranded forms of DNA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Science, 22th ed.*, Pharmaceutical Press, London, UK (2012), describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as non-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Polypeptide modifications: polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

Specifically bind: When referring to an antibody or antigen binding fragment, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an antigen present on the surface of a pathogen, for example HIV-1 Env) and does not bind in a significant amount to other proteins or polysaccharides present in the sample or subject. Specific binding can be determined by methods known in the art. With reference to an antibody-antigen complex, specific binding of the antigen and antibody has a $K_d$ of less than about $10^{-7}$ Molar, such as less than about $10^{-8}$ Molar, $10^{-9}$, or even less than about $10^{-10}$ Molar.

$K_d$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

The antibodies disclosed herein specifically bind to a defined target (or multiple targets, in the case of a bispecific antibody). Thus, an antibody that specifically binds to an epitope on gp120 is an antibody that binds substantially to gp120, including cells or tissue expressing gp120, substrate to which the gp120 is attached, or gp120 in a biological specimen. It is, of course, recognized that a certain degree of non-specific interaction may occur between an antibody or conjugate including an antibody (such as an antibody that specifically binds gp120 or conjugate including such antibody) and a non-target (such as a cell that does not express gp120). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, $2^{nd}$ ed., Cold Spring Harbor Publications, New York (2013), for a description of immunoassay formats and conditions that can be used to determine specific immunoreactivity.

Subject: Living multi-cellular vertebrate organisms, a category that includes human and non-human mammals. In an example, a subject is a human. In a particular example, the subject is a newborn infant. In an additional example, a subject is selected that is in need of inhibiting of an HIV-1 infection. For example, the subject is either uninfected and at risk of HIV-1 infection or is infected in need of treatment.

Therapeutically effective amount: The amount of agent, such as a disclosed gp120 specific antibody or antigen binding fragment that is sufficient to prevent, treat (including prophylaxis), reduce and/or ameliorate the symptoms or underlying causes of a disorder or disease, such as HIV-1 infection. In some embodiments, a therapeutically effective amount is sufficient to reduce or eliminate a symptom of HIV-1 infection, such as AIDS. For instance, this can be the amount necessary to inhibit or prevent HIV-1 replication or to measurably alter outward symptoms of the HIV-1 infection. Ideally, a therapeutically effective amount provides a therapeutic effect without causing a substantial cytotoxic effect in the subject.

In some embodiments, administration of a therapeutically effective amount of a disclosed antibody or antigen binding fragment that binds to gp120 can reduce or inhibit an HIV-1 infection (for example, as measured by infection of cells, or by number or percentage of subjects infected by HIV-1, or by an increase in the survival time of infected subjects) by a desired amount, for example by at least 10%, at least 20%, at least 50%, at least 60%, at least 70%, at least 80%, at least 90%, at least 95%, at least 98%, or even at least 100% (elimination or prevention of detectable HIV-1 infection), as compared to a suitable control.

Several preparations disclosed herein are administered in therapeutically effective amounts. A therapeutically effective amount of an antibody or antigen binding fragment that specifically binds gp120 that is administered to a subject will vary depending upon a number of factors associated with that subject, for example the overall health and/or weight of the subject. A therapeutically effective amount can be determined by varying the dosage and measuring the resulting therapeutic response, such as, for example, a reduction in viral titer. Therapeutically effective amounts also can be determined through various in vitro, in vivo or in situ immunoassays.

A therapeutically effective amount encompasses a fractional dose that contributes in combination with previous or subsequent administrations to attaining a therapeutic response. For example, a therapeutically effective amount of an agent can be administered in a single dose, or in several doses, for example daily, during a course of treatment lasting several days or weeks. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Transformed: A transformed cell is a cell into which a nucleic acid molecule has been introduced by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Treating or preventing a disease: Inhibiting the full development of a disease or condition, for example, in a subject who is at risk of or has an HIV-1 infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease for the purpose of reducing the risk of developing pathology.

Vector: Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. In some embodiments, a viral vector is provided that comprises one or more nucleic acid molecules encoding a disclosed antibody or antigen binding fragment that specifically binds to HIV-1 gp120 and neutralizes HIV-1. In some embodiments, the viral vector can be an adeno-associated virus (AAV) vector. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

VRC01-class antibody, heavy chain or light chain: A class of antibodies that bind to the CD4 binding site on gp120 and can neutralize HIV-1, as well as heavy and light chains thereof. The prototypical member of the VRC01-class of antibodies—VRC01—can neutralize over 90% of circulating HIV-1 isolates with an average 50% inhibitory concentration ($IC_{50}$) of ~0.3 µg/ml. Despite overall sequence differences between VRC01-class antibodies, antibody-gp120 co-crystal structures revealed VRC01-class recognition of gp120 to be consistent across the class. Indeed, three-dimensional structure analysis of HIV-1 gp120 from different HIV-1 clades in complexes with different VRC01-class antibodies from multiple donors show that the VRC01-class antibodies share striking similarity in physical structure, and revealed several antibody features that contribute to gp120 binding and HIV-1 neutralization. The substantial structural and ontogenetic characterization of VRC01-class of antibodies allows recognition of the members of this class by interrogation of antibody sequence.

For example, the $V_H$ of a VRC01-class antibody has a VH1-2 germline origin, wherein the VRC01-class $V_H$ encoding sequence is from 20-35% (such as 25-30%) divergent from the corresponding germline gene sequence. The VRC01-class $V_H$ includes a tryptophan residue at kabat position 50 ($V_H$ $Trp_{50}$), an asparagine residue at kabat position 58 ($V_H$ $Asn_{58}$), and an arginine residue at kabat position 71 ($V_H$ $Arg_{71}$). These residues form specific interactions with amino acids on gp120 that contribute to the VRC01-class specificity and neutralization properties. When a VRC01-class antibody is bound to gp120, $V_H$ $Trp_{50}$ forms a hydrogen bond with gp120 $Asn_{280}$, $V_H$ $Asp_{58}$ forms hydrogen bonds with gp120 $Arg_{456}$ and $Gly_{458}$, $V_H$ $Arg_{71}$ forms salt bridges with gp120 $Asp_{368}$, and $V_H$ $Trp100B$ forms a hydrogen bond with gp120 $Asn_{279}$.

Further, the $V_L$ of a VRC01-class antibody has an IGKV1-33, IGKV3-11, IGKV3-15, IGKV3-20, IGLV2-14 germline origin, wherein the VRC01-class $V_L$ encoding sequence is from 15-35% (such as 25-30%) divergent from the corresponding germline gene sequence. The VRC01-class $V_L$ includes either a LCDR1 (kabat positioning) with a 2-6 amino acid deletion, or a LCDR1 with glycine residues at kabat positions 28 and 30. The deletion or the presence of the glycine residues provides flexibility that allows the LCDR1 to avoid structural clash with the D loop of gp120 when the antibody is bound to the CD4 binding site. Further, the VRC01-class $V_L$ includes an LCDR3 that is five amino acids in length (according to kabat positioning) and includes a hydrophobic residue (such as leucine or tyrosine) at kabat position 91, deletion of kabat positions 92-95, and a glutamate or glutamine residue at kabat position 96. The hydrophobic residue at position 91 packs against the backbone of gp120 loop D, and the glutamate or glutamine residue at kabat position 96 interacts with a conserved electropositive region on the base of the gp120 V5 domain.

Non-limiting examples of antibodies that fall within the VRC01-class include the VRC01, VRC03, VRC07, VRC07-523, VRC13, 3BCN117, 12A12, 12A21, VRC-PG04, NIH45-46, VRC23, VRC-CH30, VRC-CH31, and VRC-PG20 antibodies. Description, characterization, and productions of these antibodies, as well as the VRC01-class of antibodies is available and familiar to the person of ordinary skill in the art (see, e.g., Diskin et al., *Science*, 334(6060): 1289-93, 2011; Kwong and Mascola, *Immunity*, 37, 412-425, 2012; Li et al., *J. Virol.*, 85, 8954-8967, 2011; Rudicell et al., *J. Virol.*, 88, 12669-12682, 2012; Scheid et al., *Science*, 333(6049):1633-1637, 2011; West et al., *PNAS*, 109:E2083-2090, 2012; Wu et al., *Science*, 329(5993):856-861, 2010; Wu et al., *Science*, 333(6049):1593-1602, 2011; Zhou et al., *Immunity*, 39:245-258, 2013; Georgiev et al., *Science*, 340:751-756, 2013; Zhu et al., *PNAS*, 110, E4088-E4097, 2013; and WIPO Pub. Nos. WO 2012/158948, WO2011038290, WO2012154312, WO2013142324, and WO2013016468, each of which is incorporated by reference herein in its entirety).

II. DESCRIPTION OF SEVERAL EMBODIMENTS

Isolated monoclonal antibodies and antigen binding fragments that specifically bind an epitope on gp120 are provided. The antibodies and antigen binding fragments can be fully human. In several embodiments, the antibodies and antigen binding fragments can be used to neutralize HIV-1. Also disclosed herein are compositions including the antibodies and antigen binding fragments and a pharmaceutically acceptable carrier. Nucleic acids encoding the antibodies or antigen binding fragments, expression vectors (such as adeno-associated virus (AAV) viral vectors) including these nucleic acids are also provided.

The antibodies, antigen binding fragments, nucleic acid molecules, host cells, and compositions can be used for research, diagnostic and therapeutic purposes. For example, the monoclonal antibodies and antigen binding fragments can be used to diagnose or treat a subject with an HIV-1 infection, or can be administered prophylactically to prevent HIV-1 infection in a subject. In some embodiments, the antibodies can be used to determine HIV-1 titer in a subject.

A. Antibodies and Antigen Binding Fragments

This disclosure provides the novel N6, N17, or F8 antibodies and variants thereof (including antigen binding fragments). Epitope mapping and competition binding studies show that the disclosed antibodies and antigen binding fragments specifically bind HIV-1 Env at an epitope that overlaps with the CD4-binding site on gp120.

The disclosed antibodies and antigen binding fragments are surprisingly effective for neutralization of HIV-1. For example, as discussed in Example 1, the N6 antibody neutralized 98% of HIV-1 pseudoviruses in a standardized neutralization assay with an $IC_{50}$ of less than 50 µg/ml, and 96% of the pseudoviruses with an $IC_{50}$ value of less than 1 µg/ml. Further, the N6 antibody neutralized numerous HIV-1 viral strains that are resistant to VRC01 antibody.

In some embodiments, the antibodies and antigen binding fragments include a $V_H$ and a $V_L$ and specifically bind to gp120 and neutralize HIV-1. In several embodiments, the antibodies and antigen binding fragments include a $V_H$ comprising a heavy chain complementarity determining region (HCDR)1, a HCDR2 and a HCDR3, and a light chain comprising a light chain complementarity determining region (LCDR) 1, a LCDR2, and a LCDR3 and specifically bind to gp120 and neutralize HIV-1. In some embodiments, the antibody or antigen binding fragment includes a $V_H$ comprising one or more (i.e., one, two, or all three) HCDRs from one of the N6, N17, or F8 antibodies. In some embodiments, the antibody or antigen binding fragment includes a $V_L$ comprising one or more (i.e., one, two, or all three) LCDRs from one of the N6, N17, or F8 antibodies. In several embodiments, the antibody or antigen binding fragment includes a $V_H$ and a $V_L$ including the HCDR1, the HCDR2, and the HCDR3, the LCDR1, the LCDR2, and the LCDR3, respectively, of one of the N6, N17, or F8 antibodies, and specifically binds to gp120 and neutralize HIV-1.

The discussion of monoclonal antibodies below refers to monoclonal antibodies that include a $V_H$ and a $V_L$ including CDRs with reference to the Kabat numbering scheme (unless the context indicates otherwise). The person of ordinary skill in the art will understand that various CDR numbering schemes (such as the Kabat, Chothia, or IMGT numbering schemes) can be used to determine CDR positions. The amino acid sequence and the CDR positions of the heavy and light chains of the N6, N17, or F8 antibodies according to the Kabat numbering scheme are shown in Table 1.

TABLE 1

Kabat CDR sequences of N6 and variant antibodies.

N6 $V_H$

| $V_H$ | SEQ ID NO: 1 positions | CDR protein sequence | CDR SEQ ID NO |
|---|---|---|---|
| HCDR1 | 31-35 | AHILF | 7 |
| HCDR2 | 50-66 | WIKPQYGAVNFGGG-FRD | 8 |
| HCDR3 | 99-111 | DRSYGDSSWALDA | 9 |

N6 $V_L$

| $V_L$ | SEQ ID NO: 2 positions | A.A. Sequence | CDR SEQ ID NO |
|---|---|---|---|
| LCDR1 | 24-34 | QTSQGVGSDLH | 10 |
| LCDR2 | 50-56 | HTSSVED | 11 |
| LCDR3 | 89-93 | QVLQF | 12 |

N17 $V_H$

| $V_H$ | SEQ ID NO: 3 positions | CDR protein sequence | CDR SEQ ID NO |
|---|---|---|---|
| HCDR1 | 31-35 | AHILY | 13 |
| HCDR2 | 50-66 | WIKPQYGAVNFGGG-FRG | 14 |
| HCDR3 | 99-111 | DRSYDDSSWALDA | 15 |

N17 $V_L$

| $V_L$ | SEQ ID NO: 4 positions | A.A. Sequence | CDR SEQ ID NO |
|---|---|---|---|
| LCDR1 | 24-34 | QTSQGVGRDLH | 16 |
| LCDR2 | 50-56 | HASSVED | 17 |
| LCDR3 | 89-93 | QVLES | 18 |

F8 $V_H$

| $V_H$ | SEQ ID NO: 5 positions | CDR protein sequence | CDR SEQ ID NO |
|---|---|---|---|
| HCDR1 | 31-35 | AHILF | 7 |
| HCDR2 | 50-66 | WIKPQYGAVNFGGG-FRD | 8 |
| HCDR3 | 99-111 | DRSYGDSSWALDA | 9 |

TABLE 1-continued

Kabat CDR sequences of N6 and variant antibodies.

F8 $V_L$

| $V_L$ | SEQ ID NO: 6 positions | A.A. Sequence | CDR SEQ ID NO |
|---|---|---|---|
| LCDR1 | 24-34 | QTSQGVGSDLH | 10 |
| LCDR2 | 50-56 | HASSVED | 17 |
| LCDR3 | 89-93 | QVLQF | 18 |

N6

In some embodiments, the antibody or antigen binding fragment can be based on or derived from the N6 antibody, and can specifically bind to gp120 and neutralize HIV-1. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT or kabat), of the N6 antibody, and can specifically bind to gp120 and neutralize HIV-1.

In some embodiments, the antibody or antigen binding fragment can comprise a $V_H$ comprising the HCDR1, the HCDR2, and the HCDR3 of the N6 $V_H$ as set forth in Table 1, and can specifically bind to gp120 and neutralize HIV-1. In some embodiments, the antibody or antigen binding fragment can comprise a $V_L$ comprising the LCDR1, the LCDR2, and the LCDR3 of the N6 $V_L$ as set forth in Table 1, and can specifically bind to gp120 and neutralize HIV-1. In some embodiments, the antibody or antigen binding fragment can comprise a $V_H$ and a $V_L$ comprising the HCDR1, the HCDR2, the HCDR3, the LCDR1, the LCDR2, and the LCDR3 of the N6 $V_H$ and $V_L$ as set forth in Table 1, and can specifically bind to gp120 and neutralize HIV-1.

In some embodiments, the antibody or antigen binding fragment includes at least one CDR (such as an HCDR3) with a sequence that has at least 90% (such as at least 95%, at least 96%, at least 97%, at least 98%, at least 99%, or even 100%) sequence identity to any one of the heavy or light chain CDRs of the N6 $V_H$ or $V_L$ as shown in Table 1, and can specifically bind to gp120 and neutralize HIV-1. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 31-35, 50-66, and 99-111, respectively, of SEQ ID NO: 1, and can specifically bind to gp120 and neutralize HIV-1. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-34, 50-56, and 89-93, respectively, of SEQ ID NO: 2, and can specifically bind to bind to gp120 and neutralize HIV-1. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 31-35, 50-66, and 99-111, respectively, of SEQ ID NO: 1, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-34, 50-56, and 89-93, respectively, of SEQ ID NO: 2, and can specifically bind to gp120 and neutralize HIV-1.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 1, and can specifically bind to gp120 and neutralize HIV-1. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 2, and can specifically bind to gp120 and neutralize HIV-1. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 1 and 2, respectively, and can specifically bind to gp120 and neutralize HIV-1.

In additional embodiments, the antibody or antigen binding fragment includes a $V_H$ comprising the amino acid sequence set forth as one of SEQ ID NO: 1, and can specifically bind to gp120 and neutralize HIV-1. In more embodiments, the antibody or antigen binding fragment includes a $V_L$ comprising the amino acid sequence set forth as SEQ ID NO: 2, and can specifically bind to gp120 and neutralize HIV-1. In some embodiments, the antibody or antigen binding fragment includes a $V_H$ and a $V_L$ comprising the amino acid sequences set forth as SEQ ID NOs: 1 and 2, respectively, and can specifically bind to gp120 and neutralize HIV-1.

N17

In some embodiments, the antibody or antigen binding fragment can be based on or derived from the N17 antibody, and can specifically bind to gp120 and neutralize HIV-1. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT or kabat), of the N17 antibody, and can specifically bind to gp120 and neutralize HIV-1.

In some embodiments, the antibody or antigen binding fragment can comprise a $V_H$ comprising the HCDR1, the HCDR2, and the HCDR3 of the N17 $V_H$ as set forth in Table 1, and can specifically bind to gp120 and neutralize HIV-1. In some embodiments, the antibody or antigen binding fragment can comprise a $V_L$ comprising the LCDR1, the LCDR2, and the LCDR3 of the N17 $V_L$ as set forth in Table 1, and can specifically bind to gp120 and neutralize HIV-1. In some embodiments, the antibody or antigen binding fragment can comprise a $V_H$ and a $V_L$ comprising the HCDR1, the HCDR2, the HCDR3, the LCDR1, the LCDR2, and the LCDR3 of the N17 $V_H$ and $V_L$ as set forth in Table 1, and can specifically bind to gp120 and neutralize HIV-1.

In some embodiments, the antibody or antigen binding fragment includes at least one CDR (such as an HCDR3) with a sequence that has at least 90% (such as at least 95%, at least 96%, at least 97%, at least 98%, at least 99%, or even 100%) sequence identity to any one of the heavy or light chain CDRs of the N17 $V_H$ or $V_L$ as shown in Table 1, and can specifically bind to gp120 and neutralize HIV-1. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 31-35, 50-66, and 99-111, respectively, of SEQ ID NO: 3, and can specifically bind to gp120 and neutralize HIV-1. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-34, 50-56, and 89-93, respectively, of SEQ ID NO: 4, and can specifically bind to bind to gp120 and neutralize HIV-1. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 31-35, 50-66, and 99-111, respectively, of SEQ ID NO: 3, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-34, 50-56, and 89-93, respectively, of SEQ ID NO: 4, and can specifically bind to gp120 and neutralize HIV-1.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 3, and can specifically bind to gp120 and neutralize HIV-1. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 4, and can specifically bind to gp120 and neutralize HIV-1. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 3 and 4, respectively, and can specifically bind to gp120 and neutralize HIV-1.

In additional embodiments, the antibody or antigen binding fragment includes a $V_H$ comprising the amino acid sequence set forth as one of SEQ ID NO: 3, and can specifically bind to gp120 and neutralize HIV-1. In more embodiments, the antibody or antigen binding fragment includes a $V_L$ comprising the amino acid sequence set forth as SEQ ID NO: 4, and can specifically bind to gp120 and neutralize HIV-1. In some embodiments, the antibody or antigen binding fragment includes a $V_H$ and a $V_L$ comprising the amino acid sequences set forth as SEQ ID NOs: 3 and 4, respectively, and can specifically bind to gp120 and neutralize HIV-1.

F8

In some embodiments, the antibody or antigen binding fragment can be based on or derived from the F8 antibody, and can specifically bind to gp120 and neutralize HIV-1. For example, the antibody or antigen binding fragment can comprise a $V_H$ and a $V_L$ comprising the HCDR1, the HCDR2, and the HCDR3, and the LCDR1, the LCDR2, and the LCDR3, respectively (for example, according to IMGT or kabat), of the F8 antibody, and can specifically bind to gp120 and neutralize HIV-1.

In some embodiments, the antibody or antigen binding fragment can comprise a $V_H$ comprising the HCDR1, the HCDR2, and the HCDR3 of the F8 $V_H$ as set forth in Table 1, and can specifically bind to gp120 and neutralize HIV-1.

In some embodiments, the antibody or antigen binding fragment can comprise a $V_L$ comprising the LCDR1, the LCDR2, and the LCDR3 of the F8 $V_L$ as set forth in Table 1, and can specifically bind to gp120 and neutralize HIV-1. In some embodiments, the antibody or antigen binding fragment can comprise a $V_H$ and a $V_L$ comprising the HCDR1, the HCDR2, the HCDR3, the LCDR1, the LCDR2, and the LCDR3 of the F8 $V_H$ and $V_L$ as set forth in Table 1, and can specifically bind to gp120 and neutralize HIV-1.

In some embodiments, the antibody or antigen binding fragment includes at least one CDR (such as an HCDR3) with a sequence that has at least 90% (such as at least 95%, at least 96%, at least 97%, at least 98%, at least 99%, or even 100%) sequence identity to any one of the heavy or light chain CDRs of the F8 $V_H$ or $V_L$ as shown in Table 1, and can specifically bind to gp120 and neutralize HIV-1. In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 31-35, 50-66, and 99-111, respectively, of SEQ ID NO: 5, and can specifically bind to gp120 and neutralize HIV-1. In some embodiments, the antibody or antigen binding fragment includes a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-34, 50-56, and 89-93, respectively, of SEQ ID NO: 6, and can specifically bind to bind to gp120 and neutralize HIV-1. In additional embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 31-35, 50-66, and 99-111, respectively, of SEQ ID NO: 5, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 24-34, 50-56, and 89-93, respectively, of SEQ ID NO: 6, and can specifically bind to gp120 and neutralize HIV-1.

In some embodiments, the antibody or antigen binding fragment includes a $V_H$ comprising an amino acid sequence at least 90% (such as at least 95%, at least 96%, at least 97%, at least 98%, or at least 99%) identical to the amino acid sequence set forth as SEQ ID NO: 5, and can specifically bind to gp120 and neutralize HIV-1. In more embodiments, the antibody or antigen binding fragment includes a $V_L$ comprising an amino acid sequence at least 90% (such as at least 95%, at least 96%, at least 97%, at least 98%, or at least 99%) identical to the amino acid sequence set forth as SEQ ID NO: 6, and can specifically bind to gp120 and neutralize HIV-1. In additional embodiments, the antibody or antigen binding fragment includes a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 5 and 6, respectively, and can specifically bind to gp120 and neutralize HIV-1.

In additional embodiments, the antibody or antigen binding fragment includes a $V_H$ comprising the amino acid sequence set forth as one of SEQ ID NO: 5, and can specifically bind to gp120 and neutralize HIV-1. In more embodiments, the antibody or antigen binding fragment includes a $V_L$ comprising the amino acid sequence set forth as SEQ ID NO: 6, and can specifically bind to gp120 and neutralize HIV-1. In some embodiments, the antibody or antigen binding fragment includes a $V_H$ and a $V_L$ comprising the amino acid sequences set forth as SEQ ID NOs: 5 and 6, respectively, and can specifically bind to gp120 and neutralize HIV-1.

Additional N6 Variants

Additional variants of the N6 $V_H$ and $V_L$ were identified by next generation sequencing studies. The heavy and light chain sequences of these variant sequences are shown in FIG. 18 and include the 2_2014_00173626_H and 2_2014_00173626_Hmut $V_H$ sequences, and the 1_2015_00106641_L, 1_2015_00065970_L, 1_2014_00019094_L, and 1_2015_00217585_L $V_L$ sequences. In several embodiments, the $V_H$ and $V_L$ sequences, or the CDR sequences, of these antibodies can be "mixed and matched" to form an antibody that specifically binds to gp120 and neutralizes HIV.

In some embodiments, the antibody or antigen binding fragment can comprise a $V_H$ comprising the HCDR1, the HCDR2, and the HCDR3 of the 2_2014_00173626_H (SEQ ID NO: 112) $V_H$ as set forth in FIG. 18, and the LCDR1, the LCDR2, and the LCDR3 of the 1_2015_00106641_L (SEQ ID NO: 104) $V_L$ as set forth in FIG. 18, and can specifically bind to gp120 and neutralize HIV-1. In some embodiments, the antibody or antigen binding fragment can comprise a $V_H$ comprising the HCDR1, the HCDR2, and the HCDR3 of the 2_2014_00173626_H (SEQ ID NO: 112) $V_H$ as set forth in FIG. 18, and the LCDR1, the LCDR2, and the LCDR3 of the 1_2015_00065970_L (SEQ ID NO: 106) $V_L$ as set forth in FIG. 18, and can specifically bind to gp120 and neutralize HIV-1. In some embodiments, the antibody or antigen binding fragment can comprise a $V_H$ comprising the HCDR1, the HCDR2, and the HCDR3 of the 2_2014_00173626_H (SEQ ID NO: 112) $V_H$ as set forth in FIG. 18, and the LCDR1, the LCDR2, and the LCDR3 of the 1_2014_00019094_L (SEQ ID NO: 108) $V_L$ as set forth in FIG. 18, and can specifically bind to gp120 and neutralize HIV-1. In some embodiments, the antibody or antigen binding fragment can comprise a $V_H$ comprising the HCDR1, the HCDR2, and the HCDR3 of the 2_2014_00173626_H (SEQ ID NO: 112) $V_H$ as set forth in FIG. 18, and the LCDR1, the LCDR2, and the LCDR3 of the 1_2015_00217585_L (SEQ ID NO: 110) $V_L$ as set forth in FIG. 18, and can specifically bind to gp120 and neutralize HIV-1.

In some embodiments, the antibody or antigen binding fragment can comprise the 2_2014_00173626_H (SEQ ID NO: 112) $V_H$ as set forth in FIG. 18, and the 1_2015_00106641_L (SEQ ID NO: 104) $V_L$ as set forth in FIG. 18, and can specifically bind to gp120 and neutralize HIV-1. In some embodiments, the antibody or antigen binding fragment can comprise the 2_2014_00173626_H (SEQ ID NO: 112) $V_H$ as set forth in FIG. 18, and the 1_2015_00065970_L (SEQ ID NO: 106) $V_L$ as set forth in FIG. 18, and can specifically bind to gp120 and neutralize HIV-1. In some embodiments, the antibody or antigen binding fragment can comprise the 2_2014_00173626_H (SEQ ID NO: 112) $V_H$ as set forth in FIG. 18, and the 1_2014_00019094_L (SEQ ID NO: 108) $V_L$ as set forth in FIG. 18, and can specifically bind to gp120 and neutralize HIV-1. In some embodiments, the antibody or antigen binding fragment can comprise the 2_2014_00173626_H (SEQ ID NO: 112) $V_H$ as set forth in FIG. 18, and the 1_2015_00217585_L (SEQ ID NO: 110) $V_L$ as set forth in FIG. 18, and can specifically bind to gp120 and neutralize HIV-1.

In some embodiments, the antibody or antigen binding fragment can comprise a $V_H$ comprising an amino acid sequence at least 90% (such as at least 95%, at least 96%, at least 97%, at least 98%, or at least 99%) identical to the sequence of the 2_2014_00173626_H (SEQ ID NO: 112) $V_H$ as set forth in FIG. 18, and a $V_L$ comprising an amino acid sequence at least 90% (such as at least 95%, at least 96%, at least 97%, at least 98%, or at least 99%) identical to the sequence of the 1_2015_00106641_L (SEQ ID NO: 104) $V_L$ as set forth in FIG. 18, and can specifically bind to gp120 and neutralize HIV-1. In some embodiments, the antibody or antigen binding fragment can comprise a $V_H$ comprising an amino acid sequence at least 90% (such as at least 95%, at least 96%, at least 97%, at least 98%, or at least 99%) identical to the sequence of the 2_2014_00173626_H (SEQ ID NO: 112) $V_H$ as set forth in FIG. 18, and a $V_L$ comprising an amino acid sequence at least 90% (such as at least 95%, at least 96%, at least 97%, at least 98%, or at least 99%) identical to the sequence of the 1_2015_00065970_L (SEQ ID NO: 106) $V_L$ as set forth in FIG. 18, and can specifically bind to gp120 and neutralize HIV-1. In some embodiments, the antibody or antigen binding fragment can comprise a $V_H$ comprising an amino acid sequence at least 90% (such as at least 95%, at least 96%, at least 97%, at least 98%, or at least 99%) identical to the sequence of the 2_2014_00173626_H (SEQ ID NO: 112) $V_H$ as set forth in FIG. 18, and a $V_L$ comprising an amino acid sequence at least 90% (such as at least 95%, at least 96%, at least 97%, at least 98%, or at least 99%) identical to the sequence of the 1_2014_00019094_L (SEQ ID NO: 108) $V_L$ as set forth in FIG. 18, and can specifically bind to gp120 and neutralize HIV-1. In some embodiments, the antibody or antigen binding fragment can comprise a $V_H$ comprising an amino acid sequence at least 90% (such as at least 95%, at least 96%, at least 97%, at least 98%, or at least 99%) identical to the sequence of the 2_2014_00173626_H (SEQ ID NO: 112) $V_H$ as set forth in FIG. 18, and a $V_L$ comprising an amino acid sequence at least 90% (such as at least 95%, at least 96%, at least 97%, at least 98%, or at least 99%) identical to the sequence of the 1_2015_00217585_L (SEQ ID NO: 110) $V_L$ as set forth in FIG. 18, and can specifically bind to gp120 and neutralize HIV-1.

In some embodiments, the antibody or antigen binding fragment can comprise a $V_H$ comprising the HCDR1, the HCDR2, and the HCDR3 of the 2_2014_00173626_Hmut (SEQ ID NO: 114) $V_H$ as set forth in FIG. 18, and the LCDR1, the LCDR2, and the LCDR3 of the 1_2015_00106641_L (SEQ ID NO: 104) $V_L$ as set forth in FIG. 18, and can specifically bind to gp120 and neutralize HIV-1. In some embodiments, the antibody or antigen binding fragment can comprise a $V_H$ comprising the HCDR1, the HCDR2, and the HCDR3 of the 2_2014_00173626_Hmut (SEQ ID NO: 114) $V_H$ as set forth in FIG. 18, and the LCDR1, the LCDR2, and the LCDR3 of the 1_2015_00065970_L (SEQ ID NO: 106) $V_L$ as set forth in FIG. 18, and can specifically bind to gp120 and neutralize HIV-1. In some embodiments, the antibody or antigen binding fragment can comprise a $V_H$ comprising the HCDR1, the HCDR2, and the HCDR3 of the 2_2014_00173626_Hmut (SEQ ID NO: 114) $V_H$ as set forth in FIG. 18, and the LCDR1, the LCDR2, and the LCDR3 of the 1_2014_00019094_L (SEQ ID NO: 108) $V_L$ as set forth in FIG. 18, and can specifically bind to gp120 and neutralize HIV-1. In some embodiments, the antibody or antigen binding fragment can comprise a $V_H$ comprising the HCDR1, the HCDR2, and the HCDR3 of the 2_2014_00173626_Hmut (SEQ ID NO: 114) $V_H$ as set forth in FIG. 18, and the LCDR1, the LCDR2, and the LCDR3 of the 1_2015_00217585_L (SEQ ID NO: 110) $V_L$ as set forth in FIG. 18, and can specifically bind to gp120 and neutralize HIV-1.

In some embodiments, the antibody or antigen binding fragment can comprise the 2_2014_00173626_Hmut (SEQ ID NO: 114) $V_H$ as set forth in FIG. 18, and the 1_2015_00106641_L (SEQ ID NO: 104) $V_L$ as set forth in FIG. 18, and can specifically bind to gp120 and neutralize HIV-1. In some embodiments, the antibody or antigen binding fragment can comprise the 2_2014_00173626_Hmut (SEQ ID NO: 114) $V_H$ as set forth in FIG. 18, and the 1_2015_00065970_L (SEQ ID NO: 106) $V_L$ as set forth in FIG. 18, and can specifically bind to gp120 and neutralize HIV-1. In some embodiments, the antibody or antigen binding fragment can comprise the 2_2014_00173626_Hmut (SEQ ID NO: 114) $V_H$ as set forth in FIG. 18, and the 1_2014_00019094_L (SEQ ID NO: 108) $V_L$ as set forth in FIG. 18, and can specifically bind to gp120 and neutralize HIV-1. In some embodiments, the antibody or antigen binding fragment can comprise the 2_2014_00173626_Hmut (SEQ ID NO: 114) $V_H$ as set forth in FIG. 18, and the 1_2015_00217585_L (SEQ ID NO: 110) $V_L$ as set forth in FIG. 18, and can specifically bind to gp120 and neutralize HIV-1.

In some embodiments, the antibody or antigen binding fragment can comprise a $V_H$ comprising an amino acid sequence at least 90% (such as at least 95%, at least 96%, at least 97%, at least 98%, or at least 99%) identical to the sequence of the 2_2014_00173626_Hmut (SEQ ID NO: 114) $V_H$ as set forth in FIG. 18, and a $V_L$ comprising an amino acid sequence at least 90% (such as at least 95%, at least 96%, at least 97%, at least 98%, or at least 99%) identical to the sequence of the 1_2015_00106641_L (SEQ ID NO: 104) $V_L$ as set forth in FIG. 18, and can specifically bind to gp120 and neutralize HIV-1. In some embodiments, the antibody or antigen binding fragment can comprise a $V_H$ comprising an amino acid sequence at least 90% (such as at least 95%, at least 96%, at least 97%, at least 98%, or at least 99%) identical to the sequence of the 2_2014_00173626_Hmut (SEQ ID NO: 114) $V_H$ as set forth in FIG. 18, and a $V_L$ comprising an amino acid sequence at least 90% (such as at least 95%, at least 96%, at least 97%, at least 98%, or at least 99%) identical to the sequence of the 1_2015_00065970_L (SEQ ID NO: 106) $V_L$ as set forth in FIG. 18, and can specifically bind to gp120 and neutralize HIV-1. In some embodiments, the antibody or antigen binding fragment can comprise a $V_H$ comprising an amino acid sequence at least 90% (such as at least 95%, at least 96%, at least 97%, at least 98%, or at least 99%) identical to the sequence of the 2_2014_00173626_Hmut (SEQ ID NO: 114) $V_H$ as set forth in FIG. 18, and a $V_L$ comprising an amino acid sequence at least 90% (such as at least 95%, at least 96%, at least 97%, at least 98%, or at least 99%) identical to the sequence of the 1_2014_00019094_L (SEQ ID NO: 108) $V_L$ as set forth in FIG. 18, and can specifically bind to gp120 and neutralize HIV-1. In some embodiments, the antibody or antigen binding fragment can comprise a $V_H$ comprising an amino acid sequence at least 90% (such as at least 95%, at least 96%, at least 97%, at least 98%, or at least 99%) identical to the sequence of the 2_2014_00173626_Hmut (SEQ ID NO: 114) $V_H$ as set forth in FIG. 18, and a $V_L$ comprising an amino acid sequence at least 90% (such as at least 95%, at least 96%, at least 97%, at least 98%, or at least 99%) identical to the sequence of the 1_2015_00217585_L (SEQ ID NO: 110) $V_L$ as set forth in FIG. 18, and can specifically bind to gp120 and neutralize HIV-1.

1. Additional Description of Antibodies and Antigen Binding Fragments

The N6, N17, or F8 antibodies are clonal variants of each other, and include similar heavy and light chain CDRs that derive from the same heavy and light chain germline genes. Accordingly, the CDR sequences of these antibodies can be used to generate consensus CDR sequences for a genus of antibodies and antigen binding fragments that specifically bind to gp120 and neutralize HIV-1. In some embodiments, the antibody or antigen binding fragment includes a $V_H$ including a HCDR1, a HCDR2, and/or a HCDR3 including the amino acid sequence of SEQ ID NO: 19 (AHILX$_1$, wherein X$_1$ is F or Y), SEQ ID NO: 20 (WIKPQYGAVNFGGG-FRX$_1$, wherein X$_1$ is D or G), and/or SEQ ID NO: 21 (ARDRSYX$_1$DSSWALDAW, wherein X$_1$ is G or D), respectively. In some embodiments, the antibody antigen binding fragment includes a $V_L$ including a LCDR1, a LCDR2, and/or a LCDR3 including the amino acid sequence of SEQ ID NO: 22 (QTSQGVGX$_1$DLH, wherein X$_1$ is G or S), SEQ ID NO: 23 (HX$_1$SSVED, wherein X$_1$ is A or T), and/or SEQ ID NO: 24 (QVLX$_1$X$_2$F, wherein X$_1$ is E or Q, and X2 is S or F), respectively. In some embodiments, the antibody antigen binding fragment includes a $V_H$ including a HCDR1, a HCDR2, and/or a HCDR3 including the amino acid sequence of SEQ ID NO: 19, SEQ ID NO: 20, and SEQ ID NO: 21, respectively, and further includes a $V_L$ including a LCDR1, a LCDR2, and/or a LCDR3 including the amino acid sequence of SEQ ID NO: 22, SEQ ID NO: 23, and SEQ ID NO: 24, respectively.

In some embodiments, the $V_H$ and $V_L$ segments of the disclosed antibodies can be "mixed and matched," in which different pairs of the $V_L$ and $V_H$ segments are combined and screened for binding to gp120 to select $V_L/V_H$ pair combinations of interest.

In yet another embodiment, the antibody or antigen binding fragment includes a HCDR1 with the amino acid sequence of one of SEQ ID NOs: 7, 13, or 19, a HCDR2 with the amino acid sequence of one of SEQ ID NOs: 8, 14, or 20, and a HCDR3 with the amino acid sequence of one of SEQ ID NOs: 9, 15, or 21. In yet another embodiment, the antibody or antigen binding fragment includes a LCDR1 with the amino acid sequence of one of SEQ ID NOs: 10, 16, or 22, a LCDR2 with the amino acid sequence of one of SEQ ID NOs: 11, 17, or 23, and a LCDR3 with the amino acid sequence of one of SEQ ID NOs: 12, 18, or 24. In more embodiments, the antibody or antigen binding fragment includes a HCDR1 with the amino acid sequence of one of SEQ ID NOs: 7, 13, or 19, a HCDR2 with the amino acid sequence of one of SEQ ID NOs: 8, 14, or 20, a HCDR3 with the amino acid sequence of one of SEQ ID NOs: 9, 15, or 21, a LCDR1 with the amino acid sequence of one of SEQ ID NOs: 10, 16, or 22, a LCDR2 with the amino acid sequence of one of SEQ ID NOs: 11, 17, or 23, and a LCDR3 with the amino acid sequence of one of SEQ ID NOs: 12, 18, or 23.

In some embodiment, the antibody or antibody fragment includes at least one CDR with a sequence that has at least 95% sequence identity to any one of SEQ ID NOs: 7-18, wherein the antibody specifically binds to gp120 and neutralizes HIV-1 infection. In additional embodiments, the antibody or antigen binding fragment includes a $V_H$ including a HCDR1, a HCDR2, and HCDR3 including amino acid sequences at least 90% (such as at least 95%, at least 96%, at least 97%, at least 98%, or at least 99%) identical to amino acids 31-35, 50-66, and/or 99-111, respectively, of one of SEQ ID NOs: 1, 3, or 5. In some embodiments, the antibody or antigen binding fragment includes a $V_L$ including a LCDR1, a LCDR2, and a LCDR3 including amino acid sequences at least 90% (such as at least 95%, at least 96%, at least 97%, at least 98%, or at least 99%) identical to amino acids 24-34, 50-56, and/or 89-93, respectively, of one of SEQ ID NOs: 2, 4, or 6.

The structural studies provided herein illustrate several features of the N6 antibody interaction with gp120, including (1) a tyrosine residue at kabat position 54 of the N6 $V_H$ (located in the HCDR2), (2) three glycine residues at kabat positions 61-63 of the N6 $V_H$ (also located in the HCDR2), (3) a glycine residue at kabat position 28 of the N6 $V_L$ (located in the LCDR1), (4) a GXG motif at kabat positions 28-30 of the N6 $V_L$ (also located in the LCDR1), and (5) a five residue LCDR3. As illustrated in FIG. 1, these features are conserved across the N6, N17, or F8 antibodies. In some embodiments, the disclosed antibodies including the CDRs of the N6, N17, or F8 antibodies (or variants thereof) can further include one or more of features (1)-(5) listed above (such as features (1) and (2); (1) and (3); (1) and (4); (1) and (5); (2) and (3); (2) and (4); (2) and (5); (3) and (4); (3) and (5); (4) and (5); (1), (2), and (3); (1), (2), and (4); (1), (2), and (5); (1), (3), and (4); (1), (3), and (5); (1), (4), and (5); (2), (3), and (4); (2), (3), and (5); (2), (4), and (5); (3), (4), and (5); (1), (2), (3), and (4); (1), (2), (3), and (5); (1), (3), (4), and (5); (2), (3), (4), and (5); or (1), (2), (3), (4), and (5)) and specifically bind to gp120 and neutralize HIV-1.

Further, due to the similarity of the N6, N17, or F8 antibodies with certain known VRC01-class antibodies, the indicated features (1)-(5) listed above (such as features (1) and (2); (1) and (3); (1) and (4); (1) and (5); (2) and (3); (2) and (4); (2) and (5); (3) and (4); (3) and (5); (4) and (5); (1), (2), and (3); (1), (2), and (4); (1), (2), and (5); (1), (3), and (4); (1), (3), and (5); (1), (4), and (5); (2), (3), and (4); (2), (3), and (5); (2), (4), and (5); (3), (4), and (5); (1), (2), (3), and (4); (1), (2), (3), and (5); (1), (3), (4), and (5); (2), (3), (4), and (5); or (1), (2), (3), (4), and (5)) can be included on VRC01-class antibodies to increase the breadth and potency with which these antibodies specifically bind to gp120 and neutralize HIV-1. Non-limiting examples of VRC01-class antibodies that can be modified to include one or more of the features (1)-(5) include the VRC01, VRC03, VRC07, VRC07-523, 3BCN117, 12A12, 12A21, VRC-PG04, NIH45-46, VRC18, VRC23, VRC27, VRC-CH30, VRC-CH31, VRC-PG04, and VRC-PG20 antibodies.

The antibody or antigen binding fragment can be a human antibody or fragment thereof. Chimeric antibodies are also provided. The antibody or antigen binding fragment can include any suitable framework region, such as (but not limited to) a human framework region. Human framework regions, and mutations that can be made in a human antibody framework regions, are known in the art (see, for example, in U.S. Pat. No. 5,585,089, which is incorporated herein by reference). Alternatively, a heterologous framework region, such as, but not limited to a mouse or monkey framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.)

The antibody can be of any isotype. The antibody can be, for example, an IgM or an IgG antibody, such as IgG$_1$, IgG$_2$, IgG$_3$, or IgG$_4$. The class of an antibody that specifically binds gp120 can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. A nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds gp120, that was originally IgG may be class switched to an IgM. Class switching can be used to convert one IgG subclass to another, such as from $IgG_1$ to $IgG_2$, $IgG_3$, or $IgG_4$.

In some examples, the disclosed antibodies are oligomers of antibodies, such as dimers, trimers, tetramers, pentamers, hexamers, septamers, octomers and so on.

(a) Binding Affinity

In several embodiments, the antibody or antigen binding fragment can specifically bind gp120 with an affinity (e.g., measured by $K_d$) of no more than $1.0 \times 10^{-8}$ M, no more than $5.0 \times 10^{-8}$ M, no more than $1.0 \times 10^{-9}$ M, no more than $5.0 \times 10^{-9}$ M, no more than $1.0 \times 10^{-10}$ M, no more than $5.0 \times 10^{-10}$ M, or no more than $1.0 \times 10^{-11}$ M. $K_d$ can be measured, for example, by a radiolabeled antigen binding assay (RIA) performed with the Fab version of an antibody of interest and its antigen using known methods. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

In another assay, $K_d$ can be measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

(b) Neutralization

In some embodiments, the antibody or antigen binding fragment can also be distinguished by neutralization breadth. In some embodiments, the antibody or antigen binding fragment can neutralize at least 70% (such as at least 75%, at least 80%, at least 85%, least 90%, or at least 95%) of the HIV-1 isolates included in a standardized panel of HIV-1 pseudoviruses (including, e.g., gp120 from Clade A isolates KER2018, RW020.2, Q168.a2, Q769.d22, and Q769.h5, Clade B isolates JRFL.JB, BaL.01, YU2.DG, PVO.04, TRO.11, CAAN.A2, TRJO.58, THRO.18, BG1168.1, and 6101.1, and Clade C isolates ZA012.29, DU156.12, DU422.01, ZM106.9, and ZM55.28a) with an $IC_{50}$ of less than 50 µg/ml. Exemplary pseudovirus neutralization assays and panels of HIV-1 pseudovirus are described for example, in Li et al., *J Virol* 79, 10108-10125, 2005, incorporated by reference herein. In some embodiments, a disclosed antibody or antigen binding fragment specifically binds to the CD4 binding site of gp120 and can neutralize neutralizes at least 50% of the HIV-1 isolates listed in FIG. 2B (namely, the 6540.v4.c1, 620345.c1, T278-50, 6322.V4.C1, DU422.01, X2088.c9, 6545.V4.C1, 242-14, T250-4, 7165.18, BL01.DG, HO86.8, 6471.V1.C16, 6631.V3.C10, TVI.29, TZA125.17, CAP210.E8, DU172.17) with an inhibitory concentration ($IC_{50}$) of <50 µg/ml. The person of ordinary skill in the art is familiar with methods of measuring neutralization breadth and potency, for example such methods include the single-round HIV-1 Env-pseudoviruses infection of TZM-b1 cells (see, e.g., Li et al., *J Virol* 79, 10108-10125, 2005, incorporated by reference herein; see also, PCT Pub. No. WO2011/038290, incorporated by reference herein).

An additional methods to assay for neutralization activity includes a single-cycle infection assay as described in Martin et al. (2003) *Nature Biotechnology* 21:71-76. In this assay, the level of viral activity is measured via a selectable marker whose activity is reflective of the amount of viable virus in the sample, and the $IC_{50}$ is determined. In other assays, acute infection can be monitored in the PM1 cell line or in primary cells (normal PBMC). In this assay, the level of viral activity can be monitored by determining the p24 concentrations using ELISA. See, for example, Martin et al. (2003) *Nature Biotechnology* 21:71-76.

(c) Multispecific Antibodies

In some embodiments, the antibody or antigen binding fragment is included on a multispecific antibody, such as a bi-specific antibody. Such multispecific antibodies can be produced by known methods, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

In some embodiments, the antibody or antigen binding fragment is included on a bispecific antibody that that specifically binds to gp120 and further specifically binds to CD3. Examples of CD3 binding domains that can be included on the bispecific antibody or antigen binding fragment are known and include those disclosed in PCT Pub. No. WO2013/163427, which is incorporated by reference herein in its entirety.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack, *J. Immunol.*, 158:3965-3970, 1997; Mack, *PNAS*, 92:7021-7025, 1995; Kufer, *Cancer Immunol. Immunother.*, 45:193-197, 1997; Loffler, *Blood*, 95:2098-2103, 2000; and Bruhl, *J. Immunol.*, 166:2420-2426, 2001. Production of bispecific Fab-scFv ("bibody") molecules are described, for example, in Schoonjans et al. (*J. Immunol.* 165:7050-57, 2000) and Willems et al. (J Chromatogr B Analyt Technol Biomed Life Sci. 786:161-76, 2003). For bibodies, a scFv molecule can be fused to one of the VL-CL (L) or VH-CH1 chains, e.g., to produce a bibody one scFv is fused to the C-term of a Fab chain.

(d) Fragments

Antigen binding fragments are encompassed by the present disclosure, such as Fab, F(ab')2, and Fv which include a heavy chain and $V_L$ and specifically bind gp120. These antibody fragments retain the ability to selectively bind with the antigen and are "antigen-binding" fragments. Non-limiting examples of such fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the $V_H$ and $V_L$ expressed as two chains; and (5) Single chain antibody (such as scFv), defined as a genetically engineered molecule containing the $V_H$ and the $V_L$ linked by a suitable polypeptide linker as a genetically fused single chain molecule (see, e.g., Ahmad et al., Clin. Dev. Immunol., 2012, doi:10.1155/2012/980250; Marbry, IDrugs, 13:543-549, 2010). The intramolecular orientation of the $V_H$-domain and the $V_L$-domain in a scFv, is not decisive for the provided antibodies (e.g., for the provided multispecific antibodies). Thus, scFvs with both possible arrangements ($V_H$-domain-linker domain-$V_L$-domain; $V_L$-domain-linker domain-$V_H$-domain) may be used.

(6) A dimer of a single chain antibody (scFV$_2$), defined as a dimer of a scFV. This has also been termed a "miniantibody."

Methods of making these fragments are known in the art (see for example, Harlow and Lane, *Antibodies: A Laboratory Manual*, 2$^{nd}$, Cold Spring Harbor Laboratory, New York, 2013).

In some embodiments, the antigen binding fragment can be an Fv antibody, which is typically about 25 kDa and contain a complete antigen-binding site with three CDRs per each heavy chain and each light chain. To produce Fv antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the $V_H$ and the $V_L$ are chemically linked by disulfide bonds. In an additional example, the Fv fragments include $V_H$ and $V_L$ chains connected by a peptide linker. These single-chain antigen binding proteins (scFv) can be prepared by constructing a nucleic acid molecule encoding the $V_H$ and $V_L$ domains connected by an oligonucleotide. The nucleic acid molecule is inserted into an expression vector, which is subsequently introduced into a host cell such as a mammalian cell. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., Bio/Technology 11:1271, 1993; Ahmad et al., *Clin. Dev. Immunol.*, 2012, doi:10.1155/2012/980250; Marbry, *IDrugs*, 13:543-549, 2010). Dimers of a single chain antibody (scFV$_2$), are also contemplated.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem.*

J. 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Antigen binding single $V_H$ domains, called domain antibodies (dAb), have also been identified from a library of murine $V_H$ genes amplified from genomic DNA of immunized mice (Ward et al. *Nature* 341:544-546, 1989). Human single immunoglobulin variable domain polypeptides capable of binding antigen with high affinity have also been described (see, for example, PCT Publication Nos. WO 2005/035572 and WO 2003/002609). The CDRs disclosed herein can also be included in a dAb.

In some embodiments, one or more of the heavy and/or light chain complementarity determining regions (CDRs) from a disclosed antibody (such as the N6, N17, or F8 antibody) is expressed on the surface of another protein, such as a scaffold protein. The expression of domains of antibodies on the surface of a scaffolding protein are known in the art (see e.g., Liu et al., *J. Virology* 85(17): 8467-8476, 2011). Such expression creates a chimeric protein that retains the binding for gp120. In some specific embodiments, one or more of the heavy chain CDRs is grafted onto a scaffold protein, such as one or more of heavy chain CDR1, CDR2, and/or CDR3. One or more CDRs can also be included in a diabody or another type of single chain antibody molecule.

(e) Additional Antibodies that Bind to the N6, N17, or F8 Epitope on Gp120.

Also included are antibodies that bind to the same epitope on gp120 to which the N6, N17, or F8 antibody binds. Antibodies that bind to such an epitope can be identified based on their ability to cross-compete (for example, to competitively inhibit the binding of, in a statistically significant manner) with the N6, N17, or F8 antibodies provided herein in gp120 binding assays (such as those described in the Examples). An antibody "competes" for binding when the competing antibody inhibits gp120 binding of the N6, N17, or F8 antibody by more than 50%, in the presence of competing antibody concentrations higher than $10^6 \times K_d$ of the competing antibody. In a certain embodiment, the antibody that binds to the same epitope on gp120 as the N6, N17, or F8 antibody is a human monoclonal antibody. Such human monoclonal antibodies can be prepared and isolated as described herein.

Human antibodies that bind to the same epitope on gp120 to which the N6, N17, or F8 antibody binds can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Such antibodies may be prepared, for example, by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies that bind to the same epitope on gp120 to which the N6, N17, or F8 antibody binds can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4): 265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3): 185-91 (2005). Human antibodies may also be generated by isolating Fv clone variable domain sequences selected from human-derived phage display libraries. Such variable domain sequences may then be combined with a desired human constant domain.

Antibodies and antigen binding fragments that specifically bind to the same epitope on gp120 as N6, N17, or F8 can also be isolated by screening combinatorial libraries for antibodies with the desired binding characteristics. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

(f) Additional Description of Antibody Variants

In some embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants having one or more amino acid substitutions are provided. Sites of interest for substitutional mutagenesis include the CDRs and the framework regions. Amino acid substitutions may be introduced into an antibody of interest and the products screened for a desired activity, e.g., retained/improved antigen binding, increased HIV-1 neutralization breadth or potency, decreased immunogenicity, or improved ADCC or CDC.

The variants typically retain amino acid residues necessary for correct folding and stabilizing between the $V_H$ and the $V_L$ regions, and will retain the charge characteristics of the residues in order to preserve the low pI and low toxicity of the molecules. In some embodiments, amino acid substitutions can be made in the $V_H$ and the $V_L$ regions to increase yield.

In some embodiments, the $V_H$ of the antibody can comprise up to 10 (such as up to 1, up to 2, up to 3, up to 4, up to 5, up to 6, up to 7, up to 8, or up to 9) amino acid substitutions (such as conservative amino acid substitutions) compared to the $V_H$ amino acid sequence set forth as one of SEQ ID NOs: 1, 3, or 5, and can specifically bind to gp120 and neutralize HIV-1. In some embodiments, the $V_L$ of the antibody can comprise up to 10 (such as up to 1, up to 2, up to 3, up to 4, up to 5, up to 6, up to 7, up to 8, or up to 9) amino acid substitutions (such as conservative amino acid substitutions) compared to the $V_L$ amino acid sequence set forth as one of SEQ ID NOs: 2, 4, or 6, and can specifically bind to gp120 and neutralize HIV-1.

In some embodiments, the antibody or antigen binding fragment can include up to 10 (such as up to 1, up to 2, up to 3, up to 4, up to 5, up to 6, up to 7, up to 8, or up to 9) amino acid substitutions (such as conservative amino acid substitutions) in the framework region of the $V_H$ of the antibody or the framework region of the $V_L$ of the antibody compared to a known framework region, or compared to the framework regions of the N6, N17, or F8 antibody, and can specifically bind to gp120 and neutralize HIV-1.

In some embodiments, the antibody or antigen binding fragment can comprise up to 10 amino acid substitutions (such as conservative amino acid substitutions) in the HCDR1, the HCDR2, the HCDR3, the LCDR1, the LCDR2, and the LCDR3, compared to the corresponding native CDR sequences of one of the N6, N17, or F8 antibodies (e.g., as set forth in Table 1), and can specifically bind to gp120 and neutralize HIV-1.

In some embodiments, the amino acid sequences of the HCDR1, the HCDR2, the HCDR3, the LCDR1, the LCDR2, and the LCDR3 of the antibody or antigen binding fragment can, in aggregate, together comprise up to 10 amino acid substitutions (such as up to 8, up to 6, up to 5, up to 4, or up to 2 amino acid substitutions) compared to the corresponding CDR sequences of an N6 antibody comprising the $V_H$ and $V_L$ set forth as SEQ ID NOs: 1 and 2, respectively, and can specifically bind to gp120 and neutralize HIV-1. In some such embodiments, the antibody or antigen binding fragment can comprise no more than one amino acid substitution in each CDR compared to the corresponding CDR sequences of an N6 antibody comprising the $V_H$ and $V_L$ set forth as SEQ ID NOs: 1 and 2, respectively, and can specifically bind to gp120 and neutralize HIV-1. In some embodiments, the amino acid substitutions can be conservative amino acid substitutions.

In some embodiments, the amino acid sequences of the HCDR1, the HCDR2, the HCDR3, the LCDR1, the LCDR2, and the LCDR3 of the antibody or antigen binding fragment can, in aggregate, together comprise up to 10 amino acid substitutions (such as up to 8, up to 6, up to 5, up to 4, or up to 2 amino acid substitutions) compared to the corresponding CDR sequences of an antibody comprising the $V_H$ and $V_L$ set forth as SEQ ID NOs: 114 and 104, respectively, and can specifically bind to gp120 and neutralize HIV-1. In some such embodiments, the antibody or antigen binding fragment can comprise no more than one amino acid substitution in each CDR compared to the corresponding CDR sequences of an N6 antibody comprising the $V_H$ and $V_L$ set forth as SEQ ID NOs: 114 and 104, respectively, and can specifically bind to gp120 and neutralize HIV-1. In some embodiments, the amino acid substitutions can be conservative amino acid substitutions.

In some embodiments, the amino acid sequences of the HCDR1, the HCDR2, the HCDR3, the LCDR1, the LCDR2, and the LCDR3 of the antibody or antigen binding fragment can, in aggregate, together comprise up to 10 amino acid substitutions (such as up to 8, up to 6, up to 5, up to 4, or up to 2 amino acid substitutions) compared to the corresponding CDR sequences of an antibody comprising the $V_H$ and $V_L$ set forth as SEQ ID NOs: 114 and 106, respectively, and can specifically bind to gp120 and neutralize HIV-1. In some such embodiments, the antibody or antigen binding fragment can comprise no more than one amino acid substitution in each CDR compared to the corresponding CDR sequences of an N6 antibody comprising the $V_H$ and $V_L$ set forth as SEQ ID NOs: 114 and 106, respectively, and can specifically bind to gp120 and neutralize HIV-1. In some embodiments, the amino acid substitutions can be conservative amino acid substitutions.

In some embodiments, the amino acid sequences of the HCDR1, the HCDR2, the HCDR3, the LCDR1, the LCDR2, and the LCDR3 of the antibody or antigen binding fragment can, in aggregate, together comprise up to 10 amino acid substitutions (such as up to 8, up to 6, up to 5, up to 4, or up to 2 amino acid substitutions) compared to the corresponding CDR sequences of an antibody comprising the $V_H$ and $V_L$ set forth as SEQ ID NOs: 114 and 106, respectively, and can specifically bind to gp120 and neutralize HIV-1. In some such embodiments, the antibody or antigen binding fragment can comprise no more than one amino acid substitution in each CDR compared to the corresponding CDR sequences of an N6 antibody comprising the $V_H$ and $V_L$ set forth as SEQ ID NOs: 114 and 108, respectively, and can specifically bind to gp120 and neutralize HIV-1. In some embodiments, the amino acid substitutions can be conservative amino acid substitutions.

In some embodiments, the amino acid sequences of the HCDR1, the HCDR2, the HCDR3, the LCDR1, the LCDR2, and the LCDR3 of the antibody or antigen binding fragment can, in aggregate, together comprise up to 10 amino acid substitutions (such as up to 8, up to 6, up to 5, up to 4, or up to 2 amino acid substitutions) compared to the corresponding CDR sequences of an antibody comprising the $V_H$ and $V_L$ set forth as SEQ ID NOs: 114 and 106, respectively, and can specifically bind to gp120 and neutralize HIV-1. In some such embodiments, the antibody or antigen binding fragment can comprise no more than one amino acid substitution in each CDR compared to the corresponding CDR sequences of an N6 antibody comprising the $V_H$ and $V_L$ set forth as SEQ ID NOs: 114 and 110, respectively, and can specifically bind to gp120 and neutralize HIV-1. In some embodiments, the amino acid substitutions can be conservative amino acid substitutions.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In certain embodiments of the variant $V_H$ and $V_L$ sequences provided above, each CDR either is unaltered, or contains no more than one, two or three amino acid substitutions.

To increase binding affinity of the antibody, the $V_L$ and $V_H$ segments can be randomly mutated, such as within HCDR3 region or the LCDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the HCDR3 or LCDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR regions. These randomly mutated $V_H$ and $V_L$ segments can be tested to determine the binding affinity for gp120. In particular examples, the $V_H$ amino acid sequence is one of SEQ ID NOs: 1, 3, or 5. In other examples, the $V_L$ amino acid sequence is one of SEQ ID NOs: 2, 4, or 6. Methods of in vitro affinity maturation are known (see, e.g., Chowdhury, *Methods Mol. Biol.* 207:179-196 (2008)), and Hoogenboom et al. in *Methods in Molecular Biology* 178:1-37 (O'Brien et al., ed., Human Press, Totowa, N.J., (2001).)

In certain embodiments, an antibody or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec 13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In several embodiments, the constant region of the antibody includes one or more amino acid substitutions to optimize in vivo half-life of the antibody. The serum half-life of IgG Abs is regulated by the neonatal Fc receptor (FcRn). Thus, in several embodiments, the antibody includes an amino acid substitution that increases binding to the FcRn. Several such substitutions are known to the person of ordinary skill in the art, such as substitutions at IgG constant regions T250Q and M428L (see, e.g., Hinton et al., *J Immunol.*, 176:346-356, 2006); M428L and N434S (the "LS" mutation, see, e.g., Zalevsky, et al., *Nature Biotechnology*, 28:157-159, 2010); N434A (see, e.g., Petkova et al., *Int. Immunol.*, 18:1759-1769, 2006); T307A, E380A, and N434A (see, e.g., Petkova et al., *Int. Immunol.*, 18:1759-1769, 2006); and M252Y, S254T, and T256E (see, e.g., Dall'Acqua et al., *J. Biol. Chem.*, 281:23514-23524, 2006). The disclosed antibodies and antigen binding fragments can be linked to a Fc polypeptide including any of the substitutions listed above, for example, the Fc polypeptide can include the M428L and N434S substitutions.

In some embodiments, the constant region of the antibody includes one of more amino acid substitutions to optimize antibody-dependent cell-mediated cytotoxicity (ADCC). ADCC is mediated primarily through a set of closely related Fcγ receptors. In some embodiments, the antibody includes one or more amino acid substitutions that increase binding to FcγRIIIa. Several such substitutions are known to the person of ordinary skill in the art, such as substitutions at IgG constant regions S239D and I332E (see, e.g., Lazar et al., *Proc. Natl., Acad. Sci. U.S.A.*, 103:4005-4010, 2006); and S239D, A330L, and I332E (see, e.g., Lazar et al., *Proc. Natl., Acad. Sci. U.S.A.*, 103:4005-4010, 2006).

Combinations of the above substitutions are also included, to generate an IgG constant region with increased binding to FcRn and FcγRIIIa. The combinations increase antibody half-life and ADCC. For example, such combination include antibodies with the following amino acid substitution in the Fc region: (1) S239D/I332E and T250Q/M428L; (2) S239D/I332E and M428L/N434S; (3) S239D/I332E and N434A; (4) S239D/I332E and T307A/E380A/N434A; (5) S239D/I332E and M252Y/S254T/T256E; (6) S239D/A330L/I332E and 250Q/M428L; (7) S239D/A330L/I332E and M428L/N434S; (8) S239D/A330L/I332E and N434A; (9) S239D/A330L/I332E and T307A/E380A/N434A; or (10) S239D/A330L/I332E and M252Y/S254T/T256E. In some examples, the antibodies, or an antigen binding fragment thereof is modified such that it is directly cytotoxic to infected cells, or uses natural defenses such as complement, antibody dependent cellular cytotoxicity (ADCC), or phagocytosis by macrophages.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The antibody or antigen binding fragment can be derivatized or linked to another molecule (such as another peptide or protein). In general, the antibody or antigen binding fragment is derivatized such that the binding to gp120 is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

B. Conjugates

The antibodies and antigen binding fragments that specifically bind to an epitope on gp120 can be conjugated to an agent, such as an effector molecule or detectable marker, using any number of means known to those of skill in the art. Both covalent and noncovalent attachment means may be used. One of skill in the art will appreciate that various effector molecules and detectable markers can be used, including (but not limited to) toxins and radioactive agents such as $^{125}$I, $^{32}$P, $^{14}$C, $^{3}$H and $^{35}$S and other labels, target moieties and ligands, etc. The choice of a particular effector molecule or detectable marker depends on the particular target molecule or cell, and the desired biological effect.

The choice of a particular effector molecule or detectable marker depends on the particular target molecule or cell, and the desired biological effect. Thus, for example, the effector molecule can be a cytotoxin that is used to bring about the death of a particular target cell (such as an HIV-1 infected cell). In other embodiments, the effector molecule can be a cytokine, such as IL-15; conjugates including the cytokine can be used, e.g., to stimulate immune cells locally.

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, IL. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In view of the large number of methods that have been reported for attaching a variety of radiodiagnostic compounds, radiotherapeutic compounds, labels (such as enzymes or fluorescent molecules), toxins, and other agents to antibodies one skilled in the art will be able to determine a suitable method for attaching a given agent to an antibody or antigen binding fragment or other polypeptide. For example, the antibody or antigen binding fragment can be conjugated with effector molecules such as small molecular weight drugs such as Monomethyl Auristatin E (MMAE), Monomethyl Auristatin F (MMAF), maytansine, maytansine derivatives, including the derivative of maytansine known as DM1 (also known as mertansine), or other agents to make an antibody drug conjugate (ADC). In several embodiments, conjugates of an antibody or antigen binding fragment and one or more small molecule toxins, such as a calicheamicin, maytansinoids, dolastatins, auristatins, a trichothecene, and CC1065, and the derivatives of these toxins that have toxin activity, are provided.

The antibody or antigen binding fragment can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

The antibody or antigen binding fragment can also be conjugated with a radiolabeled amino acid. The radiolabel may be used for both diagnostic and therapeutic purposes. For instance, the radiolabel may be used to detect gp120 and gp120 expressing cells by x-ray, emission spectra, or other diagnostic techniques. Examples of labels for polypeptides include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The average number of effector molecule or detectable marker moieties per antibody or antigen binding fragment in a conjugate can range, for example, from 1 to 20 moieties per antibody or antigen binding fragment. In certain embodiments, the average number of effector molecule or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments.

C. Chimeric Antigen Receptors (CARs)

Also disclosed herein are chimeric antigen receptor (CARs) that are artificially constructed chimeric proteins including an extracellular antigen binding domain (e.g., single chain variable fragment (scFv)) that specifically binds to gp120, linked to a transmembrane domain, linked to one or more intracellular T-cell signaling domains. Characteristics of the disclosed CARs include their ability to redirect T-cell specificity and reactivity towards gp120 expressing cells in a non-MHC-restricted manner. The non-MHC-restricted gp120 recognition gives T cells expressing a disclosed CAR the ability to recognize antigen independent of antigen processing.

The intracellular T cell signaling domains can include, for example, a T cell receptor signaling domain, a T cell costimulatory signaling domain, or both. The T cell receptor signaling domain refers to a portion of the CAR comprising the intracellular domain of a T cell receptor, such as the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Region

Several embodiments provide a CAR including an antigen binding domain that specifically binds to gp120 as disclosed herein (see, e.g., section II.A). For example, the antigen binding domain can be a scFv including the $V_H$ and the $V_L$ of any of the antibodies or antigen binding fragments thereof disclosed in section II.A.

In some embodiments, the antigen binding domain can include a $V_H$ and a $V_L$ including the HCDR1, HCDR2, and HCDR3, and LCDR1, LCDR2, and LCDR3 of the $V_H$ and $V_L$, respectively, of one of the N6, N17, or F8 antibodies (e.g., as set forth in Table 1).

In some embodiments, the antigen binding domain includes a $V_H$ and a $V_L$ including the amino acid sequences set forth as SEQ ID NOs: 1 and 2, respectively; SEQ ID NOs: 3 and 4, respectively; or SEQ ID NOs: 5 and 6, respectively. In several embodiments, the antigen binding domain can be a scFv. In some embodiments, the scFv includes a $V_H$ and a $V_L$ joined by a peptide linker, such as a linker including the amino acid sequence set forth as GGGGSGGGGSGGGGS (SEQ ID NO: 25).

The CAR can include a signal peptide sequence, e.g., N-terminal to the antigen binding domain. The signal peptide sequence may comprise any suitable signal peptide sequence. In an embodiment, the signal peptide sequence is a human granulocyte-macrophage colony-stimulating factor (GM-CSF) receptor sequence, such as an amino acid sequence including or consisting of LLVTSLLLCEL-PHPAFLLIPDT SEQ ID NO: 26. While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

Between the antigen binding domain and the transmembrane domain of the CAR, there may be a spacer domain, which includes a polypeptide sequence. The spacer domain may comprise up to 300 amino acids, preferably 10 to 100 amino acids and most preferably 25 to 50 amino acids. In some embodiments, the spacer domain can include an immunoglobulin domain, such as a human immunoglobulin sequence. In an embodiment, the immunoglobulin domain comprises an immunoglobulin CH2 and CH3 immunoglobulin G (IgG1) domain sequence (CH2CH3). In this regard, the spacer domain can include an immunoglobulin domain comprising or consisting of the amino acid sequence set forth as SEQ ID NO: 27:

```
EPKSCDKTHTCPPCPAPELLGGPSVFLFPPKPKDTLMISRTPEVT

CVVVDVSHEDPEVKFNWYVDGVEVHNAKTKPREEQYNSTYRVVSV

LTVLHQDWLNGKEYKCKVSNKALPAPIEKTISKAKGQPREPQVYT

LPPSRDELTKNQVSLTCLVKGFYPSDIAVEWESNGQPENNYKTTP

PVLDSDGSFFLYSKLTVDKSRWQQGNVFSCSVMHEALHNHYTQKS

LSLSPGKKDPK
```

Without being bound to a particular theory, it is believed that the CH2CH3 domain extends the antigen binding domain of the CAR away from the membrane of CAR-expressing cells and may more accurately mimic the size and domain structure of a native TCR.

2. Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used.

The transmembrane domain may be derived either from a natural or from a synthetic source. Where the source is natural, the domain may be derived from any membrane-bound or transmembrane protein. Exemplary transmembrane domains for use in the disclosed CARs can include at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD154. Alternatively the transmembrane domain may be synthetic, in which case it will comprise predominantly hydrophobic residues such as leucine and valine. In several embodiments, a triplet of phenylalanine, tryptophan and valine will be found at each end of a synthetic transmembrane domain.

Optionally, a short oligo- or polypeptide linker, preferably between 2 and 10 amino acids in length may form the linkage between the transmembrane domain and the intracellular T cell signaling domain and/or T cell costimulatory domain of the CAR. A exemplary linker sequence includes one or more glycine-serine doublets.

In some embodiments, the transmembrane domain comprises the transmembrane domain of a T cell receptor, such as a CD8 transmembrane domain. Thus, the CAR can include a CD8 transmembrane domain including or consisting of SEQ ID NO: 28:

```
TTTPAPRPPTPAPTIASQPLSLRPEACRPAAGGAVHTRGLDFAC

DIYIWAPLAGTCGVLLLSLVITLYC
```

In another embodiment, the transmembrane domain comprises the transmembrane domain of a T cell costimulatory molecule, such as CD137 or CD28. Thus, the CAR can include a CD28 transmembrane domain including or consisting of SEQ ID NO: 29:

```
IEVMYPPPYLDNEKSNGTIIHVKGKHLCPSPLFPGPSKPFWVLVV

VGGVLACYSLLVTVAFIIFWVR
```

3. Intracellular Region

The intracellular region of the CAR includes one or more intracellular T cell signaling domains responsible for activation of at least one of the normal effector functions of a T cell in which the CAR is expressed or placed in. Exemplary T cell signaling domains are provided herein, and are known to the person of ordinary skill in the art.

While an entire intracellular T cell signaling domain can be employed in a CAR, in many cases it is not necessary to use the entire chain. To the extent that a truncated portion of the intracellular T cell signaling domain is used, such truncated portion may be used in place of the intact chain as long as it transduces the relevant T cell effector function signal.

Examples of intracellular T cell signaling domains for use in the CAR include the cytoplasmic sequences of the T cell receptor (TCR) and co-stimulatory molecules that act in concert to initiate signal transduction following antigen receptor engagement, as well as any derivative or variant of these sequences and any synthetic sequence that has the same functional capability.

T cell receptor signaling domains regulate primary activation of the T cell receptor complex either in a stimulatory way, or in an inhibitory way. The disclosed CARs can include primary cytoplasmic signaling sequences that act in a stimulatory manner, which may contain signaling motifs that are known as immunoreceptor tyrosine-based activation motifs or ITAMs. Examples of ITAM containing primary cytoplasmic signaling sequences that can be included in a disclosed CAR include those from CD3 zeta, FcR gamma, FcR beta, CD3 gamma, CD3 delta, CD3 epsilon, CDS, CD22, CD79a, CD79b, and CD66d proteins. In several embodiments, the cytoplasmic signaling molecule in the CAR includes an intracellular T cell signaling domain from CD3 zeta.

The intracellular region of the CAR can include the ITAM containing primary cytoplasmic signaling domain (such as CD3-zeta) by itself or combined with any other desired cytoplasmic domain(s) useful in the context of a CAR. For example, the cytoplasmic domain of the CAR can include a CD3 zeta chain portion and an intracellular costimulatory signaling domain. The costimulatory signaling domain refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40 (CD134), CD30, CD40, PD-1, ICOS, lymphocyte function-associated antigen 1 (LFA-1), CD2, CD7, LIGHT, NKG2C, and B7-H3. An additional example of a signaling domain that can be included in a disclosed CARs is a Tumor necrosis factor receptor superfamily member 18 (TNFRSF18; also known as glucocorticoid-induced TNFR-related protein, GITR) signaling domain.

In some embodiments, the CAR can include a CD3 zeta signaling domain, a CD8 signaling domain, a CD28 signaling domain, a CD137 signaling domain or a combination of two or more thereof. In one embodiment, the cytoplasmic domain includes the signaling domain of CD3-zeta and the signaling domain of CD28. In another embodiment, the cytoplasmic domain includes the signaling domain of CD3 zeta and the signaling domain of CD137. In yet another embodiment, the cytoplasmic domain includes the signaling domain of CD3-zeta and the signaling domain of CD28 and CD137. The order of the one or more T cell signaling domains on the CAR can be varied as needed by the person of ordinary skill in the art. Exemplary amino acid sequences for such T cell signaling domains are provided. For example, the CD3 zeta signaling domain can include or consist of the amino acid sequence set forth as SEQ ID NO: 30 (RVKFSR-SADAPAYQQGQNQLYNELNLGRREEYDVLDKRR-GRDPEMGGKPRRKNPQEGLYNELQKDKMAEAYSE IGMKGERRRGKGHDGLYQGLSTATKDTY-DALHMQALPPR), the CD8 signaling domain can include or consist of the amino acid sequence set forth as SEQ ID NO: 31 (FVPVFLPAKPTTTPAPRPPTPAPTIA-SQPLSLRPEACRPAAGGAVHTRGLDFACDIYI-WAPLAGTCGVLLLSL VITLYCNHRNR), the CD28 signaling domain can include or consist of the amino acid sequence set forth as SEQ ID NO: 32 (SKRSRLLHSDYMNMTPRRPGPTRKHYQPYAPPRD-FAAYRS), the CD137 signaling domain can include or consist of the amino acid sequences set forth as SEQ ID NO: 33 (KRGRKKLLYIFKQPFMRPVQTTQEEDGCSCR FPEEEEGGCEL) or SEQ ID NO: 34 (RFSVVKRGRKKL-LYIFKQPFMRPVQTTQEEDGCSCRFPEEEEGGCEL).

The cytoplasmic signaling sequences within the cytoplasmic signaling portion of the CAR of the invention may be linked to each other in a random or specified order. Optionally, a short polypeptide linker, preferably between 2 and 10 amino acids in length may form the linkage. A glycine-serine doublet provides a particularly suitable linker. Further, between the signaling domain and the transmembrane domain of the CAR, there may be a spacer domain, which includes a polypeptide sequence. The spacer domain may comprise up to 300 amino acids, preferably 10 to 100 amino acids and most preferably 25 to 50 amino acids.

4. Additional Description of CARs

Also provided are functional portions of the CARs described herein. The term "functional portion" when used in reference to a CAR refers to any part or fragment of the CAR, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The CAR or functional portion thereof, can include additional amino acids at the amino or carboxy terminus, or at both termini, which additional amino acids are not found in the amino acid sequence of the parent CAR. Desirably, the additional amino acids do not interfere with the biological function of the CAR or functional portion, e.g., recognize target cells, detect cancer, treat or prevent cancer, etc. More desirably, the additional amino acids enhance the biological activity, as compared to the biological activity of the parent CAR.

Also provided are functional variants of the CARs described herein, which have substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 85%, about 90%, about 91%, about 92%, about 93%, about 94%, about 95%, about 96%), about 97%, about 98%, about 99% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, oc-aminocycloheptane carboxylic acid, -(2-amino-2-norbornane)-carboxylic acid, γ-diaminobutyric acid, α,β-diaminopropionic acid, homophenylalanine, and α-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

Methods of generating chimeric antigen receptors, T cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.*, 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety.) For example, a nucleic acid molecule encoding a disclosed chimeric antigen binding receptor can be included in an expression vector (such as a lentiviral vector) for expression in a host cell, such as a T cell, to make the disclosed CAR. In some embodiments, methods of using the chimeric antigen receptor include isolating T cells from a subject, transforming the T cells with an expression vector (such as a lentiviral vector) encoding the chimeric antigen receptor, and administering the engineered T cells expressing the chimeric antigen receptor to the subject for treatment, for example for treatment of a tumor in the subject.

D. Polynucleotides and Expression

Nucleic acids molecules (for example, cDNA molecules) encoding the amino acid sequences of antibodies, antigen binding fragments, CARs and conjugates that specifically bind gp120 are provided. Nucleic acids encoding these molecules can readily be produced by one of skill in the art, using the amino acid sequences provided herein (such as the CDR sequences and $V_H$ and $V_L$ sequences), sequences available in the art (such as framework or constant region sequences), and the genetic code. In several embodiments, a nucleic acid molecules can encode the $V_H$, the $V_L$, or both the $V_H$ and $V_L$ (for example in a bicistronic expression vector) of a disclosed antibody or antigen binding fragment. In several embodiments, the nucleic acid molecules can be expressed in a host cell (such as a mammalian cell) to produce a disclosed antibody or antigen binding fragment.

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

In a non-limiting example, an isolated nucleic acid molecule encodes the $V_H$ of a disclosed antibody or antigen binding fragment and includes the nucleic acid sequence set forth as any one of SEQ ID NOs: 36, 38, or 40. In a non-limiting example, an isolated nucleic acid molecule encodes the $V_L$ of a disclosed antibody or antigen binding fragment and includes the nucleic acid sequence set forth as any one of SEQ ID NOs: 37, 39, or 41. In a non-limiting example, an isolated nucleic acid molecule encodes the $V_H$ and $V_L$ of a disclosed antibody or antigen binding fragment and includes the nucleic acid sequences set forth as any one of SEQ ID NOs: 36 and 37, respectively, 38 and 39, respectively, or 40 and 41, respectively. In a non-limiting example, an isolated nucleic acid molecule encodes the $V_H$ and $V_L$ of a disclosed antibody or antigen binding fragment and includes the nucleic acid sequences set forth as any one of SEQ ID NOs: 113 and 105, respectively, 113 and 107, respectively, 113 and 109, respectively, 113 and 111, respectively, 114 and 105, respectively, 114 and 107, respectively, 114 and 109, respectively, 114 and 111, respectively.

Nucleic acid sequences encoding the of antibodies, antigen binding fragments, CARs and conjugates that specifically bind gp120 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques, and instructions sufficient to direct persons of skill through many cloning exercises are known (see, e.g, Sambrook et al. (Molecular Cloning: A Laboratory Manual, 4th ed, Cold Spring Harbor, New York, 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (Carlsbad, CA), and Applied Biosystems (Foster City, CA), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In some embodiments, the nucleic acid molecule encodes a CAR as provided herein for expression in a T cell to generate a chimeric antigen receptor T cell. The nucleic acid molecule encoding the chimeric antigen binding receptor can be included in a vector (such as a lentiviral vector) for expression in a host cell, such as a T cell. Exemplary cells include a T cell, a Natural Killer (NK) cell, a cytotoxic T lymphocyte (CTL), and a regulatory T cell. Methods of generating nucleic acid molecules encoding chimeric antigen receptors and T cells including such receptors are known in the art (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.*, 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety.)

The nucleic acid molecules can be expressed in a recombinantly engineered cell such as bacteria, plant, yeast, insect and mammalian cells. The antibodies, antigen binding fragments, and conjugates can be expressed as individual $V_H$ and/or $V_L$ chain (linked to an effector molecule or detectable marker as needed), or can be expressed as a fusion protein. Methods of expressing and purifying antibodies and antigen binding fragments are known and further described herein (see, e.g., Al-Rubeai (ed), *Antibody Expression and Production*, Springer Press, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990; Kontermann and Dubel (Ed) Antibody Engineering, Vols. 1-2, $2^{nd}$ Ed., Springer Press, 2010; Harlow and Lane, *Antibodies: A Laboratory Manual*, $2^{nd}$, Cold Spring Harbor Laboratory, New York, 2013). Optionally, a cleavage site can be included in a linker, such as a furin cleavage site.

The nucleic acid encoding a $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 2010/093979, incorporated herein by reference. In one example, the immunoadhesin is an $IgG_1$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to gp120 and another antigen, such as, but not limited to CD3. The encoded $V_H$ and $V_L$ optionally can include a furin cleavage site between the $V_H$ and $V_L$ domains.

Those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibodies, antigen binding fragments, CARs or conjugates can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the antibodies and antigen binding fragments described herein can be achieved by operably linking the DNA or cDNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this can include a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antigen biding fragment, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

For purposes of producing a recombinant CAR, the host cell may be a mammalian cell. The host cell may be a human cell. In some embodiments, the host cell may be a peripheral blood lymphocyte (PBL) or a peripheral blood mononuclear cell (PBMC), or a T cell. The T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), tumor infiltrating cells, memory T cells, naive T cells, and the like. The T cell may be a CD8$^+$ T cell or a CD4$^+$ T cell.

Also provided is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the antibodies, antigen binding fragments, and conjugates can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin.

Methods for expression of the antibodies, antigen binding fragments, and conjugates, and/or refolding to an appropriate active form, from mammalian cells, and bacteria such as *E. coli* have been described and are well-known and are applicable to the antibodies disclosed herein. See, e.g., Harlow and Lane, *Antibodies: A Laboratory Manual*, 2$^{nd}$, Cold Spring Harbor Laboratory, New York, 2013, Simpson ed., Basic methods in Protein Purification and Analysis: A laboratory Manual, Cold Harbor Press, 2008, and Ward et al., *Nature* 341:544, 1989.

In addition to recombinant methods, the antibodies, antigen binding fragments, and/or conjugates can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis, 2nd ed.*, Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

E. Methods and Compositions

1. Therapeutic Methods

Methods are disclosed herein for the prevention or treatment of an HIV-1 infection. Prevention can include inhibition of infection with HIV-1. The methods include contacting a cell with a therapeutically effective amount of a disclosed antibody, antigen binding fragment, conjugate, CAR or T cell expressing a CAR that specifically binds gp120, or a nucleic acid encoding such an antibody, antigen binding fragment, conjugate, or CAR. The method can also include administering to a subject a therapeutically effective amount of a disclosed antibody, antigen binding fragment, conjugate, CAR or T cell expressing a CAR that specifically binds gp120, or a nucleic acid encoding such an antibody, antigen binding fragment, conjugate, or CAR, to a subject. In some examples, the antibody, antigen binding fragment, conjugate, CAR, T cell expressing a CAR, or nucleic acid molecule, can be used pre-exposure (for example, to prevent or inhibit HIV-1 infection). In some examples, the antibody, antigen binding fragment, conjugate, CAR, T cell expressing a CAR, or nucleic acid molecule, can be used in post-exposure prophylaxis. In some examples, the antibody, antigen binding fragment, conjugate, or nucleic acid molecule, can be used to eliminate or reduce the viral reservoir of HIV-1 in a subject. For example a therapeutically effective amount of an antibody, antigen binding fragment, conjugate, CAR, T cell expressing a CAR, or nucleic acid molecule, can be administered to a subject with HIV-1, such as a subject being treated with anti-viral therapy. In some examples the antibody, antigen binding fragment, conjugate, or nucleic acid molecule is modified such that it is directly cytotoxic to infected cells (e.g., by conjugation to a toxin), or uses natural defenses such as complement, antibody dependent cellular cytotoxicity (ADCC), or phagocytosis by macrophages.

HIV-1 infection does not need to be completely eliminated for the method to be effective. For example, a method can decrease HIV-1 infection by a desired amount, for example by at least 10%, at least 20%, at least 50%, at least 60%, at least 70%, at least 80%, at least 90%, at least 95%, at least 98%, or even at least 100% (elimination of detectable HIV-1 infected cells), as compared to HIV-1 infection in the absence of the treatment. In some embodiments, the cell is also contacted with a therapeutically effective amount of an additional agent, such as anti-viral agent. The cell can be in vivo or in vitro. The methods can include administration of one on more additional agents known in the art. In additional embodiments, HIV-1 replication can be reduced or inhibited by similar methods. HIV-1 replication does not need to be completely eliminated for the method to be effective. For example, a method can decrease HIV-1 replication by a desired amount, for example by at least 10%, at least 20%, at least 50%, at least 60%, at least 70%, at least 80%, at least 90%, at least 95%, at least 98%, or even at least 100% (elimination of detectable HIV-1), as compared to HIV-1 replication in the absence of the treatment.

In one embodiment, administration of a disclosed antibody, antigen binding fragment, conjugate, CAR, T cell expressing a CAR, or nucleic acid molecule, results in a reduction in the establishment of HIV-1 infection and/or reducing subsequent HIV-1 disease progression in a subject. A reduction in the establishment of HIV-1 infection and/or a reduction in subsequent HIV-1 disease progression encompass any statistically significant reduction in HIV-1 activity. In some embodiments, methods are disclosed for treating a subject with an HIV-1 infection. These methods include administering to the subject a therapeutically effective amount of a disclosed antibody, antigen binding fragment, conjugate, CAR, T cell expressing a CAR, or nucleic acid molecule, thereby preventing or treating the HIV-1 infection.

Studies have shown that the rate of HIV-1 transmission from mother to infant is reduced significantly when zidovudine is administered to HIV-infected women during pregnancy and delivery and to the offspring after birth (Connor et al., 1994 *Pediatr Infect Dis J* 14: 536-541). Several studies of mother-to-infant transmission of HIV-1 have demonstrated a correlation between the maternal virus load at delivery and risk of HIV-1 transmission to the child. The present disclosure provides antibodies, antigen binding fragments, conjugates, CAR, T cell expressing a CAR, and nucleic acid molecule that are of use in decreasing HIV-transmission from mother to infant. Thus, in some examples, a therapeutically effective amount of a gp120-specific antibody or antigen binding fragment thereof or nucleic acid encoding such antibodies or antibody antigen binding fragments, is administered in order to prevent transmission of HIV-1, or decrease the risk of transmission of HIV-1, from a mother to an infant. In some examples, a therapeutically effective amount of the antibody, or an antigen binding fragment or nucleic acid encoding such antibodies or antigen binding fragment, is administered to mother and/or to the child at childbirth. In other examples, a therapeutically effective amount of the antibody, antigen binding fragment, or nucleic acid encoding the antibody or antigen binding fragment is administered to the mother and/or infant prior to breast feeding in order to prevent viral transmission to the infant or decrease the risk of viral transmission to the infant. In some embodiments, both a therapeutically effective amount of the antibody, antigen binding fragment, or nucleic acid encoding the antibody or antigen binding fragment and a therapeutically effective amount of another agent, such as zidovudine, is administered to the mother and/or infant.

For any application, the antibody, antigen binding fragment, conjugate, CAR, T cell expressing a CAR, or nucleic acid molecule can be combined with anti-retroviral therapy. Antiretroviral drugs are broadly classified by the phase of the retrovirus life-cycle that the drug inhibits. The disclosed antibodies can be administered in conjunction with nucleoside analog reverse-transcriptase inhibitors (such as zidovudine, didanosine, zalcitabine, stavudine, lamivudine, abacavir, emtricitabine, entecavir, and apricitabine), nucleotide reverse transcriptase inhibitors (such as tenofovir and adefovir), non-nucleoside reverse transcriptase inhibitors (such as efavirenz, nevirapine, delavirdine, etravirine, and rilpivirine), protease inhibitors (such as saquinavir, ritonavir, indinavir, nelfinavir, amprenavir, lopinavir, fosamprenavir, atazanavir, tipranavir, and darunavir), entry or fusion inhibitors (such as maraviroc and enfuvirtide), maturation inhibitors, (such as bevirimat and vivecon), or a broad spectrum inhibitors, such as natural antivirals. In some examples, a disclosed antibody or active fragment thereof or nucleic acids encoding such is administered in conjunction with IL-15, or conjugated to IL-15.

Studies have shown that cocktails of HIV-1 neutralizing antibodies that target different epitopes of gp120 can treat macaques chronically infected with SHIV (Shingai et al., Nature, 503, 277-280, 2013; and Barouch et al., Nature, 503, 224-228, 2013). Accordingly, in some examples, a subject is further administered one or more additional antibodies that bind HIV-1 Env (e.g., that bind to gp120 or gp41), and that can neutralize HIV-1. The additional antibodies can be administrated before, during, or after administration of the novel antibodies disclosed herein (e.g., the N6, N17, or F8 antibody). In some embodiments, the additional antibody can be an antibody that specifically binds to an epitope on HIV-1 Env such as the CD4 binding site (e.g., b12, 3BNC117, VRC01 or VRC07 antibody), the membrane-proximal external region (e.g., 10E8 antibody), the V1N2 domain (e.g., PG9 antibody, CAP256-VRC26), or the V3 loop (e.g., 10-1074, PGT 121, or PGT128 antibody), or those that bind both gp120 and gp41 subunits (eg. 35022, PGT151, or 8ANC195). Antibodies that specifically bind to these regions and neutralizing HIV-1 infection are known to the person of ordinary skill in the art. Non-limiting examples can be found, for example, in PCT Pub. No. WO 2011/038290, WO/2013/086533, WO/2013/090644, WO/2012/158948, which are incorporated herein by reference in their entirety.

In some examples, a subject is administered the DNA encoding the antibody or antigen binding fragments thereof, to provide in vivo antibody production, for example using the cellular machinery of the subject. Immunization by nucleic acid constructs is well known in the art and taught, for example, in U.S. Pat. Nos. 5,643,578, and 5,593,972 and 5,817,637. 5,880,103 describes several methods of delivery of nucleic acids encoding to an organism. One approach to administration of nucleic acids is direct administration with plasmid DNA, such as with a mammalian expression plasmid. The nucleotide sequence encoding the disclosed antibody, or antigen binding fragments thereof, can be placed under the control of a promoter to increase expression. The methods include liposomal delivery of the nucleic acids. Such methods can be applied to the production of an antibody, or antigen binding fragments thereof, by one of ordinary skill in the art. In some embodiments, a disclosed antibody or antigen binding fragment is expressed in a subject using the pVRC8400 vector (described in Barouch et al., J. Virol, 79, 8828-8834, 2005, which is incorporated by reference herein).

The nucleic acid molecules encoding the disclosed antibodies (such as N6 antibody) or antigen binding fragments can be included in a viral vector, for example for expression of the antibody or antigen binding fragment in a host cell, or a subject (such as a subject with or at risk of HIV-1 infection). A number of viral vectors have been constructed, that can be used to express the disclosed antibodies or antigen binding fragments, such as a retroviral vector, an adenoviral vector, or an adeno-associated virus (AAV) vector. In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

In several embodiments, a subject (such as a human subject with or at risk of HIV-1 infection) can be administered a therapeutically effective amount of an adeno-associated virus (AAV) viral vector that includes one or more nucleic acid molecules encoding a disclosed antibody or antigen binding fragment (such as N6 antibody). The AAV viral vector is designed for expression of the nucleic acid molecules encoding a disclosed antibody or antigen binding fragment, and administration of the therapeutically effective amount of the AAV viral vector to the subject leads to expression of a therapeutically effective amount of the antibody or antigen binding fragment in the subject. Non-limiting examples of AAV viral vectors that can be used to express a disclosed antibody or antigen binding fragment in a subject include those provided in Johnson et al ("Vector-mediated gene transfer engenders long-lived neutralizing activity and protection against SIV infection in monkeys," *Nat. Med.*, 15(8):901-906, 2009) and Gardner et al. ("AAV-expressed eCD4-Ig provides durable protection from multiple SHIV challenges," *Nature*, 519(7541): 87-91, 2015), each of which is incorporated by reference herein in its entirety.

In one embodiment, a nucleic acid encoding a disclosed antibody, or antigen binding fragments thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

2. Dosages

A therapeutically effective amount of a gp120-specific antibody, antigen binding fragment, conjugate, CAR, T cell expressing a CAR, or nucleic acid molecule encoding such molecules, will depend upon the severity of the disease and/or infection and the general state of the patient's health. A therapeutically effective amount is that which provides either subjective relief of a symptom(s) or an objectively identifiable improvement as noted by the clinician or other qualified observer. The gp120-specific antibody, antigen binding fragment, conjugate, CAR, T cell expressing a CAR, or nucleic acid molecule encoding such molecules, can be administered in conjunction with another therapeutic agent, either simultaneously or sequentially.

Single or multiple administrations of a composition including a disclosed gp120-specific antibody, antigen binding fragment, conjugate, CAR, T cell expressing a CAR, or nucleic acid molecule encoding such molecules, can be administered depending on the dosage and frequency as required and tolerated by the patient. Compositions including the gp120-specific antibody, antigen binding fragment, conjugate, CAR, T cell expressing a CAR, or nucleic acid molecule encoding such molecules, should provide a sufficient quantity of at least one of the gp120-specific antibody, antigen binding fragment, conjugate, CAR, T cell expressing a CAR, or nucleic acid molecule encoding such molecules to effectively treat the patient. The dosage can be administered once, but may be applied periodically until either a therapeutic result is achieved or until side effects warrant discontinuation of therapy. In one example, a dose of the antibody or antigen binding fragment is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The therapeutically effective dose can be determined from cell culture assays and animal studies.

In certain embodiments, the antibody or antigen binding fragment that specifically binds gp120, or conjugate thereof, or a nucleic acid molecule or vector encoding such a molecule, or a composition including such molecules, is administered at a dose in the range of from about 5 or 10 nmol/kg to about 300 nmol/kg, or from about 20 nmol/kg to about 200 nmol/kg, or at a dose of about 5, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg, or at a dose of about 5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 1000 µg/kg, or about 1, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. In some embodiments, the antibody or antigen binding fragment can be administered to a subject at a dose of from about 0.5 to about 40 mg/kg, such as about 1 to about 30, about 1 to about 20, about 1 to about 15, about 1 to about 10, about 1 to about 5, about 1 to about 3, about 0.5 to about 40 mg/kg, such as about 0.5 to about 30, about 0.5 to about 20, about 0.5 to about 15, about 0.5 to about 10, about 0.5 to about 5, about 0.5 to about 3, about 3 to about 7, about 8 to about 12, about 15 to about 25, about 18 to about 22, about 28 to about 32, about 10 to about 20, about 5 to about 15, or about 20 to about 40 mg/kg. The doses described herein can be administered according to the dosing frequency/frequency of administration described herein, including without limitation daily, 2 or 3 times per week, weekly, every 2 weeks, every 3 weeks, monthly, every other month, etc.

In some embodiments, a disclosed therapeutic agent may be administered intravenously, subcutaneously or by another mode daily or multiple times per week for a period of time, followed by a period of no treatment, then the cycle is repeated. In some embodiments, the initial period of treatment (e.g., administration of the therapeutic agent daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the therapeutic agent is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

3. Modes of Administration

The gp120-specific antibody, antigen binding fragment, conjugate, CAR, T cell expressing a CAR, or nucleic acid molecule encoding such molecules, or a composition including such molecules, as well as additional agents, can be administered to subjects in various ways, including local and systemic administration, such as, e.g., by injection subcutaneously, intravenously, intra-arterially, intraperitoneally, intramuscularly, intradermally, or intrathecally. In an embodiment, a therapeutic agent is administered by a single subcutaneous, intravenous, intra-arterial, intraperitoneal, intramuscular, intradermal or intrathecal injection once a day. The therapeutic agent can also be administered by direct injection at or near the site of disease.

The gp120-specific antibody, antigen binding fragment, conjugate, or nucleic acid molecule encoding such molecules, or a composition including such molecules may also be administered orally in the form of microspheres, microcapsules, liposomes (uncharged or charged (e.g., cationic)), polymeric microparticles (e.g., polyamides, polylactide, polyglycolide, poly(lactide-glycolide)), microemulsions, and the like.

A further method of administration is by osmotic pump (e.g., an Alzet pump) or mini-pump (e.g., an Alzet mini-osmotic pump), which allows for controlled, continuous and/or slow-release delivery of the therapeutic agent or pharmaceutical composition over a pre-determined period. The osmotic pump or mini-pump can be implanted subcutaneously, or near a target site.

It will be apparent to one skilled in the art that the gp120-specific antibody, antigen binding fragment, conjugate, or nucleic acid molecule encoding such molecules, or a composition including such molecules can also be administered by other modes. Determination of the most effective mode of administration is within the skill of the skilled artisan. The gp120-specific antibody, antigen binding fragment, conjugate, or nucleic acid molecule encoding such molecules, or a composition including such molecules can be administered as pharmaceutical formulations suitable for, e.g., oral (including buccal and sub-lingual), rectal, nasal, topical, pulmonary, vaginal or parenteral (including intramuscular, intraarterial, intrathecal, subcutaneous and intravenous) administration, or in a form suitable for administration by inhalation or insufflation. Depending on the intended mode of administration, the pharmaceutical formulations can be in the form of solid, semi-solid or liquid dosage forms, such as tablets, suppositories, pills, capsules, powders, liquids, suspensions, emulsions, creams, ointments, lotions, and the like. The formulations can be provided in unit dosage form suitable for single administration of a precise dosage. The formulations comprise an effective amount of a therapeutic agent, and one or more pharmaceutically acceptable excipients, carriers and/or diluents, and optionally one or more other biologically active agents.

4. Compositions

Compositions are provided that include one or more of the gp120-specific antibody, antigen binding fragment, conjugate, CAR, T cell expressing a CAR, or nucleic acid molecule encoding such molecules, that are disclosed herein in a carrier. The compositions are useful, for example, for example, for the treatment or detection of an HIV-1 infection. The compositions can be prepared in unit dosage forms for administration to a subject. The amount and timing of administration are at the discretion of the treating physician to achieve the desired purposes. The gp120-specific antibody, antigen binding fragment, conjugate, CAR, T cell expressing a CAR, or nucleic acid molecule encoding such molecules can be formulated for systemic or local administration. In one example, the gp120-specific antibody, antigen binding fragment, conjugate, CAR, T cell expressing a CAR, or nucleic acid molecule encoding such molecules, is formulated for parenteral administration, such as intravenous administration.

In some embodiments, the compositions comprise an antibody, antigen binding fragment, or conjugate thereof, in at least 70% (such as at least 75%, at least 80%, at least 85%, at least 90%, at least 95%, at least 96%, at least 97%, at least 98% or at least 99% purity. In certain embodiments, the compositions contain less than 10% (such as less than 5%, less than 4%, less than 3%, less than 2%, less than 1%, less than 0.5%, or even less) of macromolecular contaminants, such as other mammalian (e.g., human) proteins.

The compositions for administration can include a solution of the gp120-specific antibody, antigen binding fragment, conjugate, CAR, T cell expressing a CAR, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions will be known or apparent to those skilled in the art and are described in more detail in such publications as *Remington's Pharmaceutical Science*, *22th ed.*, Pharmaceutical Press, London, UK (2012). In some embodiments, the composition can be a liquid formulation including one or more antibodies, antigen binding fragments (such as an antibody or antigen binding fragment that specifically binds to gp120), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, or an antigen binding fragment thereof or a conjugate or a nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antigen binding fragments, can then be added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies, antigen binding fragments, conjugates, or a nucleic acid encoding such molecules, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

5. Methods of Detection and Diagnosis

Methods are also provided for the detection of the expression of gp120 in vitro or in vivo. In one example, expression of gp120 is detected in a biological sample, and can be used to detect HIV-1 infection as the presence of HIV-1 in a sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection can include contacting a cell or sample, or administering to a subject, an antibody or antigen binding fragment that specifically binds to gp120, or conjugate there of (e.g. a conjugate including a detectable marker) under conditions sufficient to form an immune complex, and detecting the immune complex (e.g., by detecting a detectable marker conjugated to the antibody or antigen binding fragment.

In several embodiments, a method is provided for detecting AIDS and/or an HIV-1 infection in a subject. The disclosure provides a method for detecting HIV-1 in a biological sample, wherein the method includes contacting a biological sample from a subject with a disclosed antibody or antigen binding fragment under conditions sufficient for formation of an immune complex, and detecting the immune complex, to detect the gp120 in the biological sample. In one example, detection of gp120 in the sample confirms a diagnosis of AIDS and/or an HIV-1 infection in the subject.

In some embodiments, the disclosed antibodies or antigen binding fragments thereof are used to test vaccines. For example to test if a vaccine composition including gp120 assumes a conformation including the N6, N17, or F8 epitope. Thus provided herein is a method for testing a vaccine, wherein the method includes contacting a sample containing the vaccine, such as a gp120 immunogen, with a disclosed antibody or antigen binding fragment under conditions sufficient for formation of an immune complex, and detecting the immune complex, to detect the vaccine with an HIV-1 immunogen including the N6, N17, or F8 epitope in the sample. In one example, the detection of the immune complex in the sample indicates that vaccine component, such as a HIV-1 Env immunogen assumes a conformation capable of binding the antibody or antigen binding fragment.

In one embodiment, the antibody or antigen binding fragment is directly labeled with a detectable marker. In another embodiment, the antibody that binds HIV-1 Env (the first antibody) is unlabeled and a second antibody or other molecule that can bind the antibody that binds the first antibody is utilized for detection. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody, antigen binding fragment or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

F. Kits

Kits are also provided. For example, kits for treating a subject with an HIV-1 infection, or for detecting gp120 in a sample or in a subject. The kits will typically include a disclosed gp120-specific antibody, antigen binding fragment, conjugate, CAR, T cell expressing a CAR, or nucleic acid molecule encoding such molecules, or compositions including such molecules. More than one of the disclosed gp120-specific antibody, antigen binding fragment, conjugate, CAR, T cell expressing a CAR, or nucleic acid molecule encoding such molecules, or compositions including such molecules can be included in the kit.

In one embodiment, the kit is a diagnostic kit and includes an immunoassay. Although the details of the immunoassays may vary with the particular format employed, the method of detecting gp120 in a biological sample generally includes the steps of contacting the biological sample with an antibody which specifically reacts, under conditions sufficient to form an immune complex, to gp120. The antibody is allowed to specifically bind under immunologically reactive conditions to form an immune complex, and the presence of the immune complex (bound antibody) is detected directly or indirectly.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, or compositions. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of the antibodies, antigen binding fragments, conjugates, nucleic acid molecules, or compositions included in the kit. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

III. EXAMPLES

The following examples are provided to illustrate particular features of certain embodiments, but the scope of the claims should not be limited to those features exemplified.

Example 1

Broad and Potent HIV-1 Neutralization by a Human Antibody that Binds the CD4 Binding Site This example illustrates the isolation and characterization of the N6 antibody, and several variants thereof. N6 antibody is a broad and extremely potent gp120-specific mAb, which binds to the CD4 binding site of HIV-1 Env on gp120. N6 neutralized 98% of pseudoviruses in a 181 pseudovirus panel representing a wide variety of HIV-1 strains with an $IC_{50}<50$ µg/ml. The median $IC_{50}$ of neutralized viruses was 0.038 µg/ml, among the most potent thus far described. Further, N6 successfully neutralized 16 of 20 pseudoviruses in the panel that are resistant to neutralization by VRC01, the canonical broadly neutralizing CD4 binding site antibody.

Introduction

Among the most broad of HIV-1 neutralizing antibodies are members of a group that bind the CD4 binding site. Several such antibodies that have been isolated from patients, most of which have been extensively characterized with regard to structure and function. Most of these antibodies share remarkably similar characteristics with regard to their $V_H$ usage and mode of binding, and for this reason have been designated "VRC01-class." Although these antibodies are among the most broad, some less broad antibodies to other areas of Env are 10- to 20-fold more potent, such as those that target the N332 glycan or V1V2. In addition, approximately 12% of isolates are resistant to VRC01-class antibodies.

This example provides a new monoclonal CD4 binding site antibody, named N6, that achieves both potency and remarkable breadth. N6 is a member of the VRC01-class yet neutralizes the vast majority of VRC01-resistant isolates very potently. Neutralization, structure, and mutagenesis data are provided that indicate that these activities are mediated through novel interactions between multiple domains of N6 and HIV-1 Env. This mechanism involves avoidance of steric clashes that are the major mechanism of resistance to VRC01-class antibodies. In addition, it involves a unique and critical interaction between the CDRH3 of N6 and a highly conserved stretch of loop D of HIV-1 Env. The potency and breadth of N6, and its lack of autoreactivity, make it a highly desirable antibody for use in prophylaxis or therapy.

Results

N6 Isolation and Neutralizing Properties

Assays were performed to understand the specificities that underlie the broad and potently neutralizing serum of patient Z258. Serum from this patient was potent and broad based upon neutralization of 20 HIV-1 Env pseudoviruses (FIG. 1A). The potency, breadth, and pattern of neutralization were similar to that of patient 45, from whom the well-known CD4-binding site antibody VRC01 was cloned. In addition, based upon the neutralization fingerprint (Georgiev et al., *Science*, 340, 751-756, 2013) (FIG. 1A) this patient's serum suggested that a CD4 binding site antibody was a dominant specificity. To determine the specificities that mediate HIV-specific neutralization in this patient, a technique to isolate monoclonal antibodies of interest from peripheral blood B cells without prior knowledge of the target specificity was applied (Huang et al., *Nat. Protoc.*, 8, 1907-1915, 2013). Peripheral blood IgM⁻, IgA⁻, IgD⁻ memory B cells of Z258 were sorted and expanded. The supernatants of B cell microcultures were then screened for neutralizing activity and IgG genes from wells with neutralizing activity were cloned and re-expressed. Three clonal family variants of an antibody with neutralizing activity were found, among which the antibody named N6 (isolated as an IgG1 mAb) was the most potent and broad (FIG. 1B). The identified antibodies, and corresponding sequence identifiers are as follows:

| Antibody | $V_H$ protein SEQ ID | $V_H$ CDR SEQ ID | $V_L$ protein SEQ ID | $V_L$ CDR SEQ ID | $V_H$ DNA SEQ ID | $V_L$ DNA SEQ ID |
|---|---|---|---|---|---|---|
| N6 | 1 | 7, 8, 9 | 2 | 10, 11, 12 | 36 | 37 |
| N17 | 3 | 13, 14, 15 | 4 | 16, 17, 18 | 38 | 39 |
| F8 | 5 | 7, 8, 9 | 6 | 10, 17, 18 | 40 | 41 |

Consistent with many other HIV-specific broadly neutralizing monoclonal antibodies, N6 was highly somatically mutated, in both heavy (31%) and light chains (25%). The N6 antibody sequence also contained features that were consistent with a VRC01-class antibody (Zhou et al., Science, 329, 811-817, 2010) such as a heavy chain derived from VH1-2*02 germline gene, and a light chain CDR3 (LCDR3) composed of 5 amino acids (FIG. 1B and FIG. 1C). Although they derive from the same ancestor B cell, N6 was quite distinct from VRC27 and differed at the amino acid level of the heavy chain by 38%.

To compare the neutralization breadth and potency of N6 with other broadly neutralizing anti-HIV-1 antibodies, N6 was tested against a 181-pseudovirus panel in parallel with VRC01, 3BNC117, VRC27, PG9, PGDM1400, PGT121, 10-1074, 10E8, 4E10, and 35022. As shown in FIGS. 1D and 1E, N6 neutralized 98% of the 181 pseudoviruses at an $IC_{50}$<50 μg/ml. Although the breadth of many antibodies sharply declines at less than 1 μg/ml, at this level N6 still neutralized 96% of the tested isolates. The median $IC_{50}$ was 0.038 μg/ml, which is among the most potent thus far described.

Additionally, cross-complemented antibodies including the heavy and light chains of the N6, F8 antibodies were generated and tested for HIV-1 neutralization (FIG. 1F). The chimeric antibodies included Variant 1 (N6 $V_H$+F8 $V_L$), Variant 2 (N6 $V_H$+N17 $V_L$), Variant 3 (N17 $V_H$+F8 $V_L$), Variant 4 (N17 $V_H$ N6 $V_L$), Variant 5 (F8 $V_H$+N6 $V_L$), and Variant 6 ((F8 $V_H$+N17 $V_L$). As illustrated in FIG. 1F, all of the chimeric antibodies tested neutralized HIV-1 in the pseudovirus assay.

A striking result was that N6 neutralized many isolates that were highly resistant to VRC01. When the activity against a 20-virus panel made up of VRC01-resistant isolates was examined and compared with activity of other members of the VRC01-class (VRC01, VRC07-523-LS and 3BNC117), N6 neutralized 16 of 20 isolates (FIG. 2). It is perhaps more remarkable that it neutralizes these isolates very potently. This suggested that N6 might have a novel mode of recognition that operates across diverse Envs that permits it to avoid resistance common to other members of the VRC01-class of antibodies.

Autoreactivity or polyreactivity is a property of several HIV-specific antibodies that could limit their use in therapies or prophylaxis. However, N6 did not bind Hep-2 epithelial cells (FIG. 3A), nor did it bind cardiolipin (FIG. 3B) or a panel of autoantigens (FIG. 3C), suggesting that autoreactivity may not limit the potential use of N6 in HIV-1 prophylaxis, treatment and prevention.

Figure 4A:
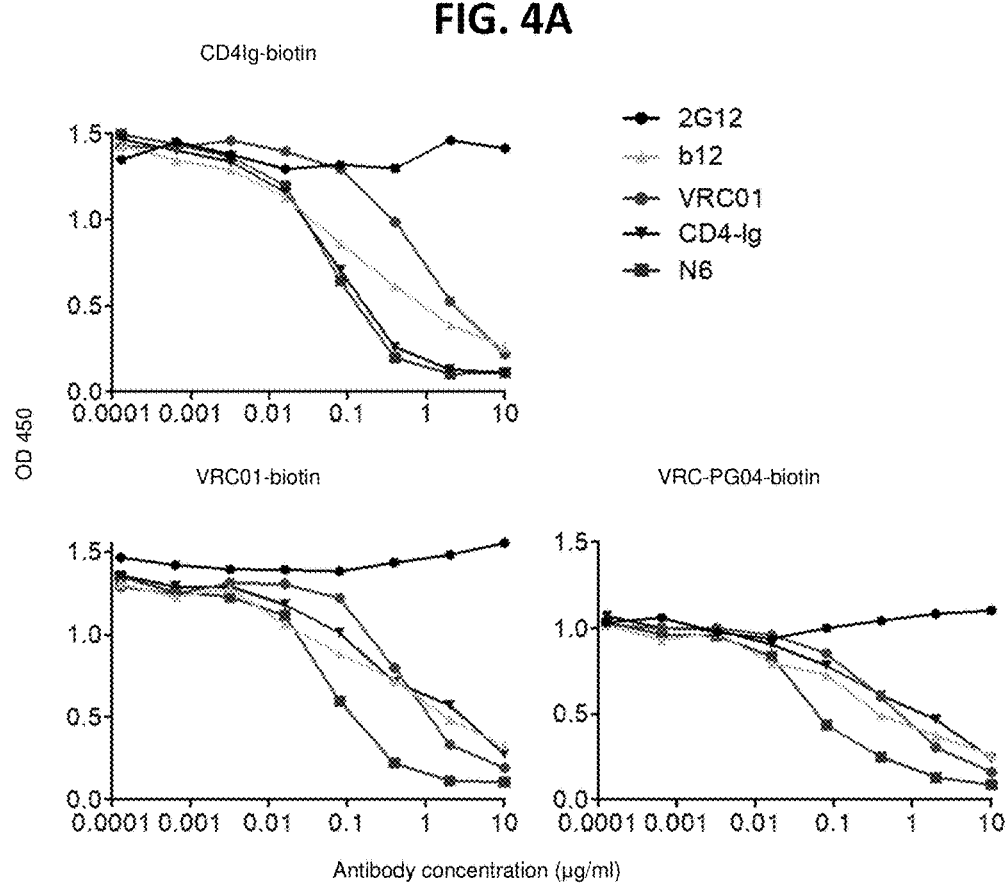
Figure 4B:
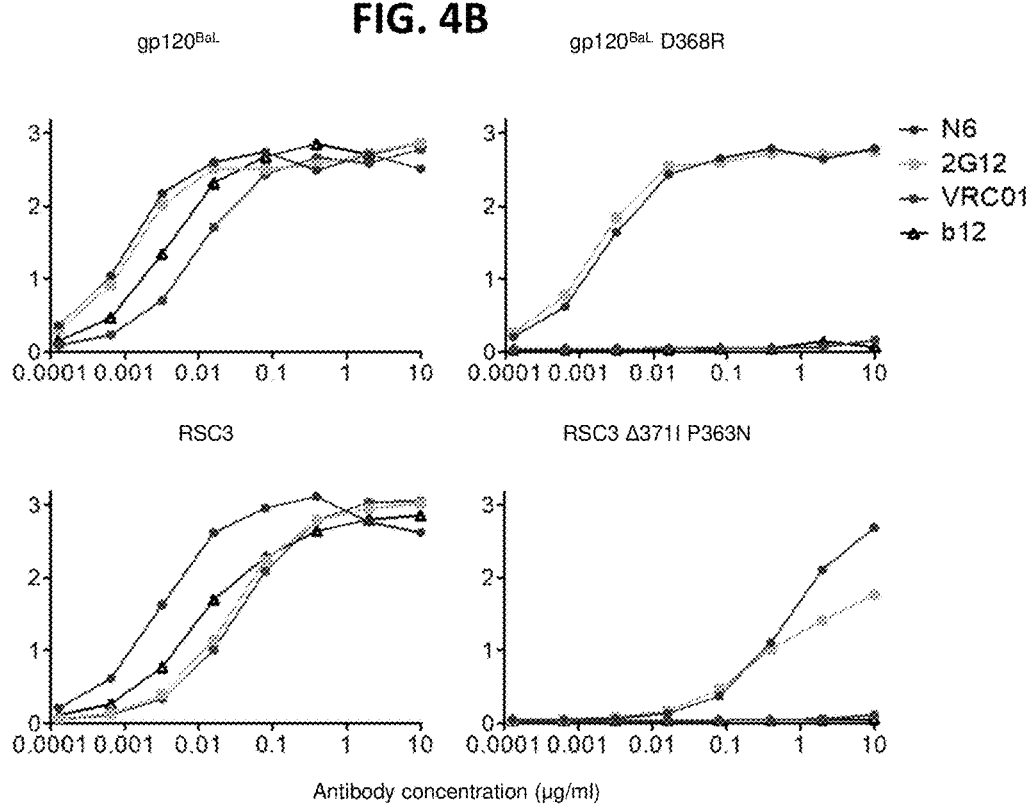
Figure 4C:
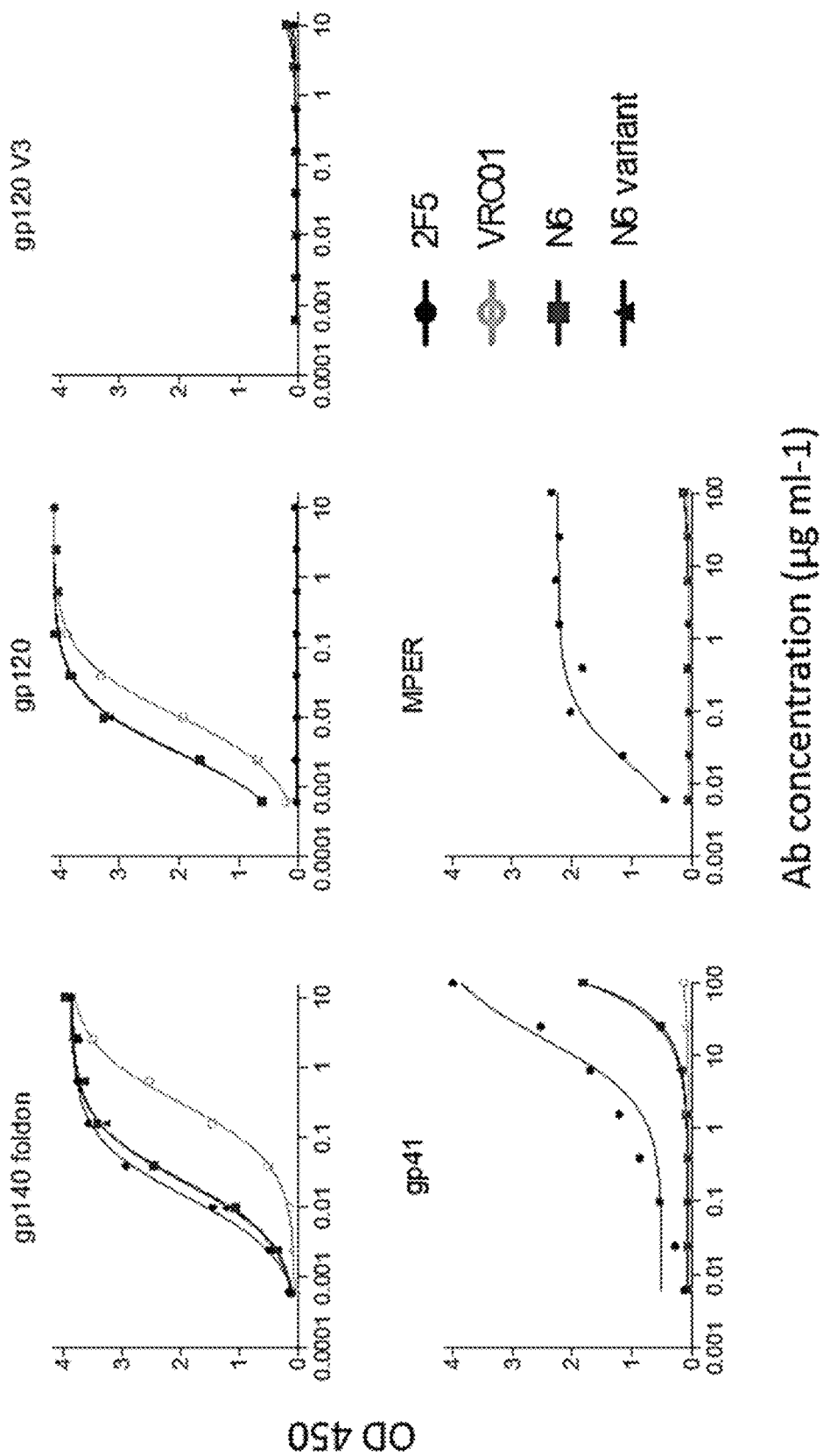
Figure 9:
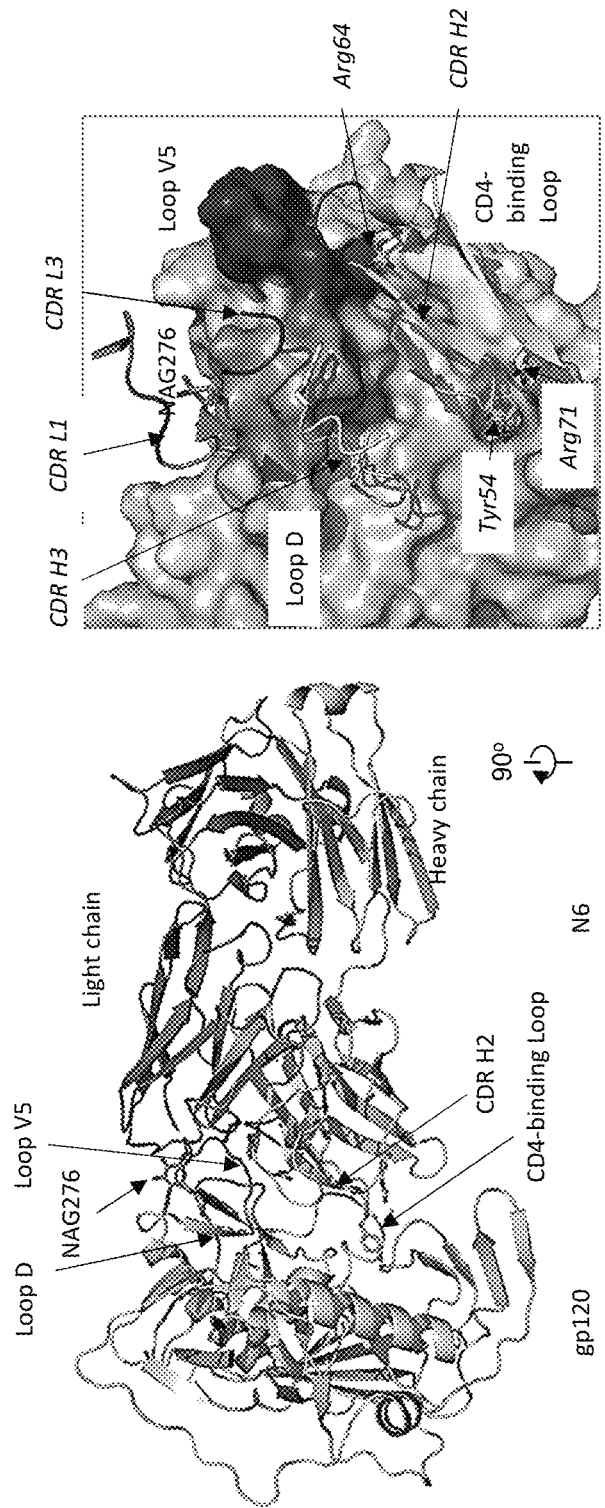
FIG. 9 shows a set of diagrams illustrating the three dimensional structure of N6 antibody in complex with gp120, and that N6 is a VRC01-class antibody with CDR H2 interacting with the CD4-binding loop on HIV-1 gp120 and a 5-amino acids signature LCDR3.
Figure 10:
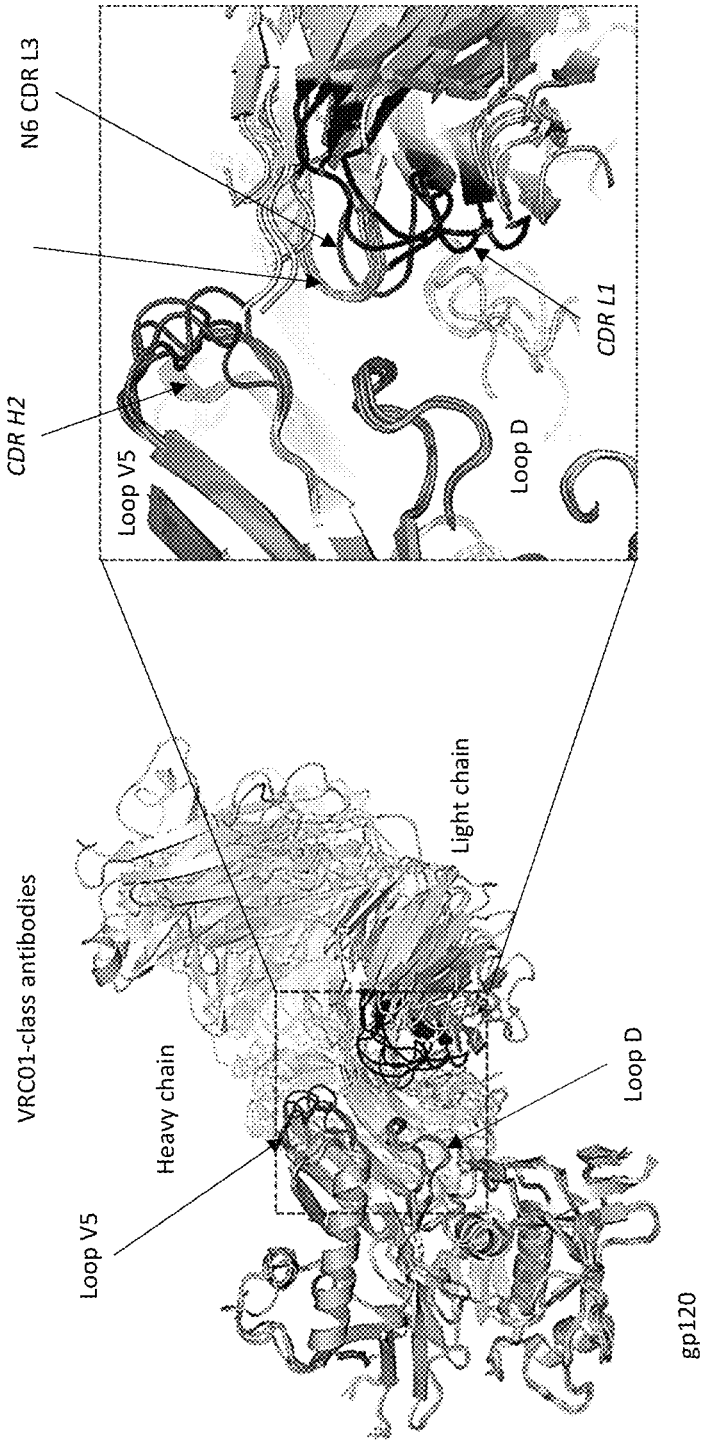
FIGS. 10 and 11 show that when superposed on HIV-1 gp120, the light chain of N6 assumes a different orientation relative to that of other VRC01 class antibodies, and this orientation allows N6 light chain to avoid potential clashes with HIV-1 gp120 V5 and loop D.
Figure 11:
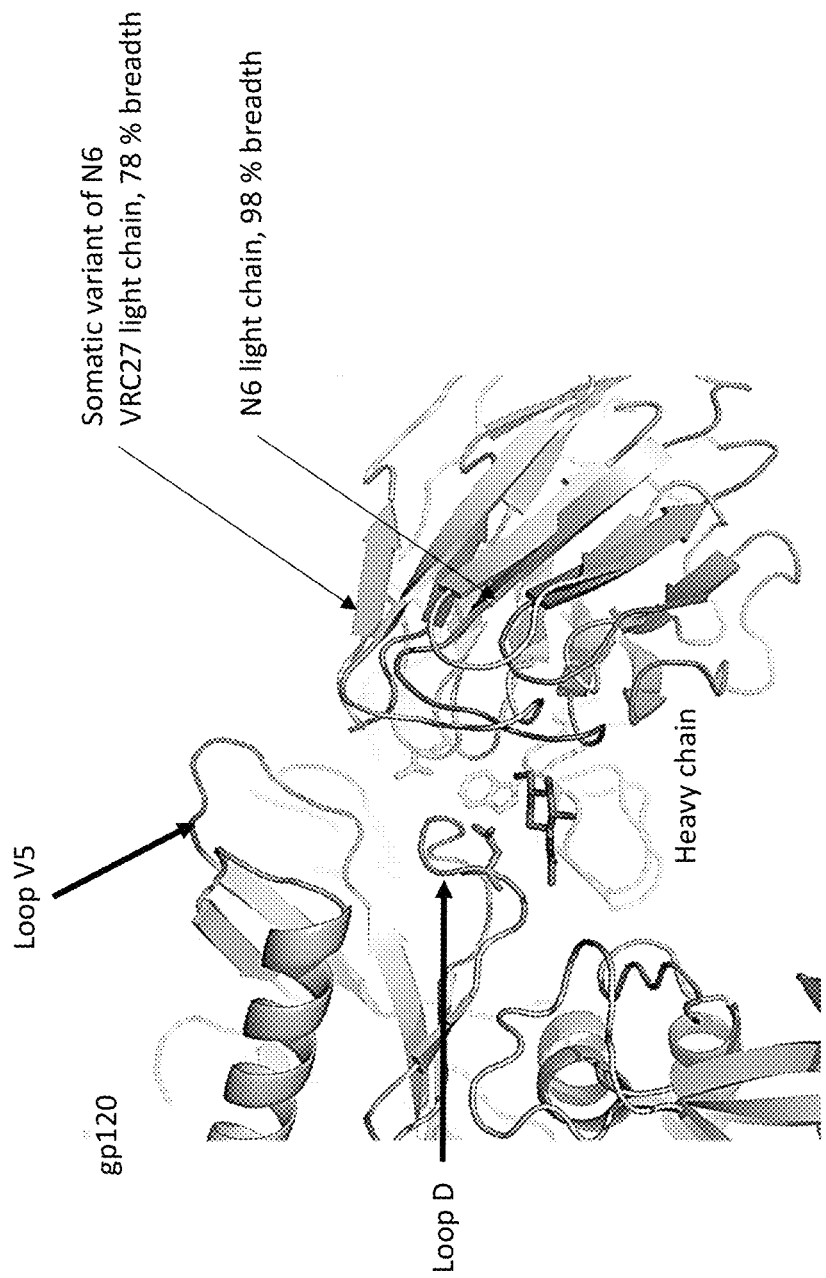
Figure 13:
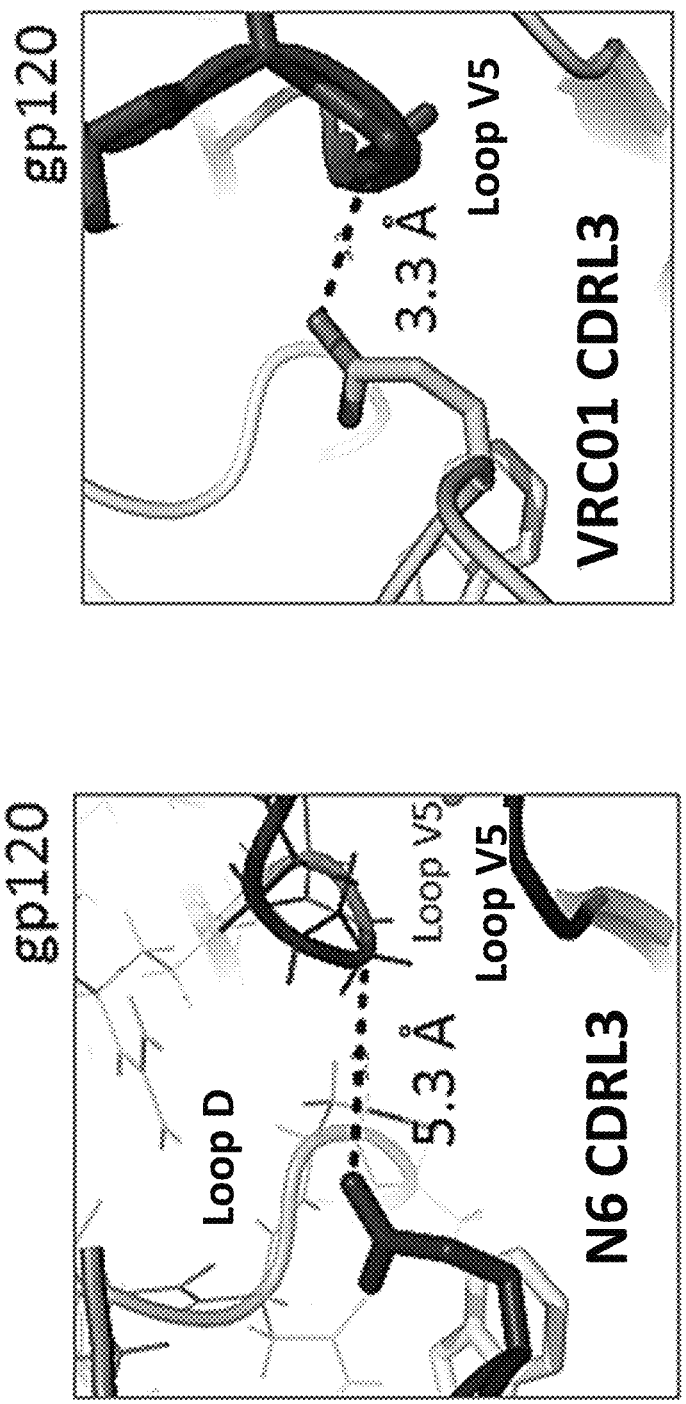
FIG. 13 shows that N6 LCDR3 Gln96 engages Loop V5 indirectly to accommodate variations in V5, and shows that VRC01 LCDR3 Gln96 engages Loop V5 with a hydrogen bond and is sensitive to a bulkier side chain in V5.

To understand the binding specificity of N6 its ability to compete with other antibodies or bind gp120 mutants by ELISA was examined. Consistent with a VRC01-class antibody, N6 competed with biotinylated CD4Ig, and CD4 binding site antibodies, to bind gp120 (FIG. 4A). For the competition binding assays, like b12, VRC01, and CD-Ig (which are known to bind to the CD4 binding site on gp120), N6 and Variant 1 (N6 heavy chain in combination with F8 kappa chain) competed for binding to gp120 (FIG. 4A). As shown in FIG. 4B, binding of the N6 and Variant 1 (N6 heavy chain in combination with F8 kappa chain) antibodies to BaL gp120, RSC3, and RSC3Δ371I P363N was similar to that of the CD4 binding site antibodies VRC01 and b12. However, unlike VRC01 and b12, N6 and Variant 1 (N6 heavy chain in combination with F8 kappa chain) maintained binding to BaL gp120 D368R. It is interesting to note that the D368R mutant is used to gate out non-CD4 binding site antibodies in probe based sorting strategies. Therefore N6 was likely eliminated from analysis in prior efforts to recover CD4 binding site antibodies. To further confirm that the N6 and Variant 1 (N6 heavy chain in combination with F8 kappa chain) antibodies bind to the CD4 binding site, the binding of N6 to gp120 was assayed by ELIZA (FIG. 4C). As shown in FIG. 4C, N6 and the N6 Variant-1 specifically bound to trimeric gp140 (gp140 foldon) and monomeric gp120, but did not bind to gp120 V3 domain, gp41, or MPER peptide.

N6 Binding Specificity

To more precisely map the epitope of N6 on HIV-1 gp120, the binding of N6 to alanine scanning mutants in the context of monomeric gp120$^{JRCSF}$ was tested by ELISA. Based upon prior structural analyses and viral mutagenesis, members of the VRC01 antibody class are known to contact gp120 in three main areas; loop D, the CD4 binding loop (CD4 BLP), and β23-V5 region. Mutations at residues in loop D, CD4 BLP or β23-V5 region of JRCSF resulted in decreased N6-mediated gp120 binding (FIG. 4D), consistent with other CD4 binding site antibodies. Overall, differences between N6 binding and other VRC01-class antibodies were not observed in this context. However, the conformation of monomeric gp120 tested in an ELISA format may not accurately reflect the interaction between N6 and the intact functional trimer. To better assess this interaction, a panel of JRCSF Env pseudovirus alanine scanning mutants was used to examine the neutralization potency of N6 in comparison with other CD4 binding site antibodies and 2G12 as a negative control. As shown in FIG. 4E, a single mutation in loop D of JRCSF, such as D279A or K282A, resulted in resistance to neutralization by most CD4 binding site mAbs, consistent with prior results (Li et al., J. Virol., 85, 8954-8967, 2011; Lynch et al., J. Virol., 89, 4201-4213, 2015). In contrast, single mutations in loop D, CD4 BLP or β23-V5 region of JRCSF showed no resistance to neutralization by N6. These results, in addition to the binding to RSC mutants described above (FIG. 4B), suggested that N6 might bind to the CD4 binding site through a novel mode of recognition.

N6 Epitope

Figure 5B:
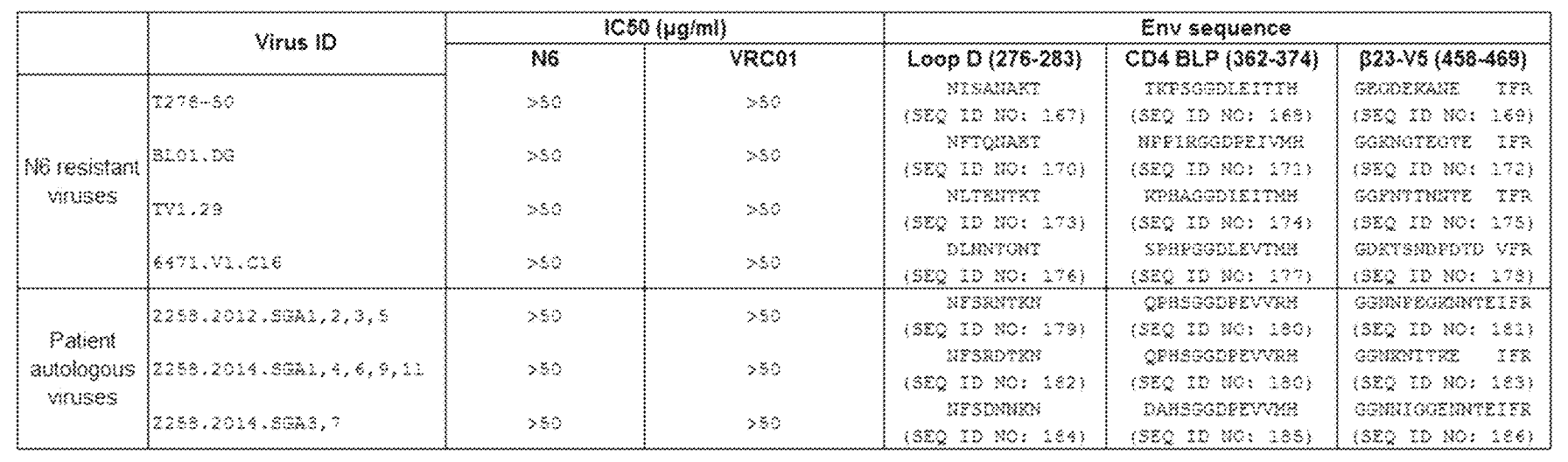

In prior work resistance to VRC01-class antibodies has typically been mediated by mutations in known contact areas in loop D, the CD4 BLP, or β23-V5 of gp120 (Lynch et al., J Virol 89, 4201-4213, 2015). Of 181 tested viruses, only 4 were highly resistant to N6 with $IC_{50}$>50 μg/ml and 2 were less sensitive to N6 with $IC_{50}$>5 μg/ml (FIG. 5A). Each of the resistant viruses have mutations in loop D (residues 276-283), CD4 BLP (residues 362-374) and β23-V5 region (residues 458-469) relative to the reference virus sequences HXB2, JFCSF and 93TH057. However, sequences of N6-sensitive viruses and resistant viruses within 20 VRC01-resistant virus panel have no clear pattern (FIG. 5A). In addition, we made full-length clones of Env from plasma viruses of the patient Z258, from whom N6 was isolated. In prior work it has been observed that autologous viruses typically are resistant to the contemporaneous serologic response, and can provide information regarding mechanisms of resistance[46,50-55]. Consistent with these prior observations, eleven pseudoviruses expressing these autologous Envs were also resistant to N6-mediated neutralization (FIG. 5A). Analysis of the autologous Env sequences revealed that their sequences also had mutations in loop D, CD4 BLP and β23-V5 region relative to the reference virus sequences (FIG. 5A). To determine the relative contributions of these mutations to resistance to N6, the loop D, CD4 BLP and β23-V5 regions of T278-50, BL01 and TV1.29 were reverse mutated, and autologous virus Z258.2012.SGA5 pseudoviruses, to a sensitive viral sequence HIV$^{JRCSF}$ (FIGS. 5B-5C). Replacing β23-V5 with sequences from HIV$^{JRCSF}$ increased the sensitivity to N6 by 3-5-fold in two pseudoviruses, T278-50 and TV1.29, but not in BL01 and Z258.2012.SGA5. Replacement of the CD4 BLP with sequences from HIV$^{JRCSF}$ caused no increase in N6 sensitivity. Only when sequences from HIV$^{JRCSF}$ were introduced into loop D did all the pseudoviruses become highly sensitive to neutralization by N6. In contrast to N6, reverse mutations in loop D, CD4 BLP and β23-V5 region were required for full sensitivity of the CD4 binding site antibodies, VRC01, 3BNC117, VRC-PG04, 12A12 and VRC27. The binding of N6 to reverse mutants of T278-50, BL01, TV1.29 and autologous virus Z258.2012.SGA5 was also tested by ELISA. Similarly, reverse mutations at residues in loop D resulted in strong N6-mediated gp120 binding, while reverse mutations in loop D, CD4 BLP and β23-V5 region were required for binding of the CD4 binding site antibodies. To confirm the mutations in loop D are essential for N6 resistance, the sequence of loop D, CD4 BLP or β23-V5 region of JRCSF was inserted into the autologous virus Z258.2012, SGA5 sequence. Substitution of the JRCSF loop D sequence by the loop D of Z258.2012.SGA5 dramatically decreased the neutralization sensitivity of N6 by 11-fold, while CD4 BLP and β23-V5 swap showed a 3-fold difference or no significant difference, respectively. To investigate which residues in loop D might play an important role in N6 escape, we replaced each residue that differed in resistant viruses with the corresponding residue from HIV$^{JRCSF}$. Reverse mutations of positions 281, 282 and 283 showed little or no increase in N6 sensitivity. Only when the conserved residue Asp from HIV$^{JRCSF}$ was introduced into position 279 did most of the pseudoviruses become sensitive to neutralization by N6 (FIGS. 5D-5E). It is likely that resistance to N6 by these viruses is mediated by bulky side chains of residues at position 279 in TV1.29, BL01 and the Z258 autologous virus that cause a direct clash with the CDRH3 of N6. These results suggest that resistance to N6 neutralization requires mutations in loop D. However, unlike other CD4 binding site antibodies, N6 tolerates escape mutations in CD4 BLP and β23-V5 region, including those that may cause a steric clash with the CDRH2 and CDRL3 of other VRC01-class antibodies.

N6 Paratope

To understand the paratope of N6, a panel of N6 alanine scanning mutants was produced to examine the neutralization potency of N6 to six VRC01-sensitive viruses. VRC01 and VRC27 and their alanine scanning mutants were also used as controls. Several changes made a greater than 5-fold decrease in average neutralization potency for VRC01 and VRC27 (FIGS. 6C-6F). The Trp100b$_{VRC01}$ and Trp100c$_{VRC27}$ alanine mutations within the CDRH3 had large effects presumably due to disruptions of interactions with Asp279$_{gp120}$. In addition, several residues in Trp47, Trp50, Asn58 and Arg71 of the VRC27 heavy chain and Gly28 and Ile91 of the VRC27 light chain also had large effects (FIGS. 6E-6F). Remarkably, no such effect was observed in alanine point mutations of N6 (FIGS. 6A-6B). Thus N6 was able to tolerate single mutations across the length of the heavy and light chains presumably because there was sufficient energy spread across the remaining contacts to mediate binding.

The neutralization potency of N6 alanine scanning mutants to six VRC01-resistant viruses, which contain mutations in the loop D, CD4 BLP and V5 loop, was also examined. Residues in Ile33, Trp47, Trp50, Arg71 and Trp 100c of the N6 heavy chain and Ile91 of the N6 light chain also had large effects on decrease of neutralization potency (FIG. 7). Because the above residues are also appeared in VRC27 antibody, it is not sufficient to explain why N6 has superior neutralization activity than VRC27.

Figure 8A:
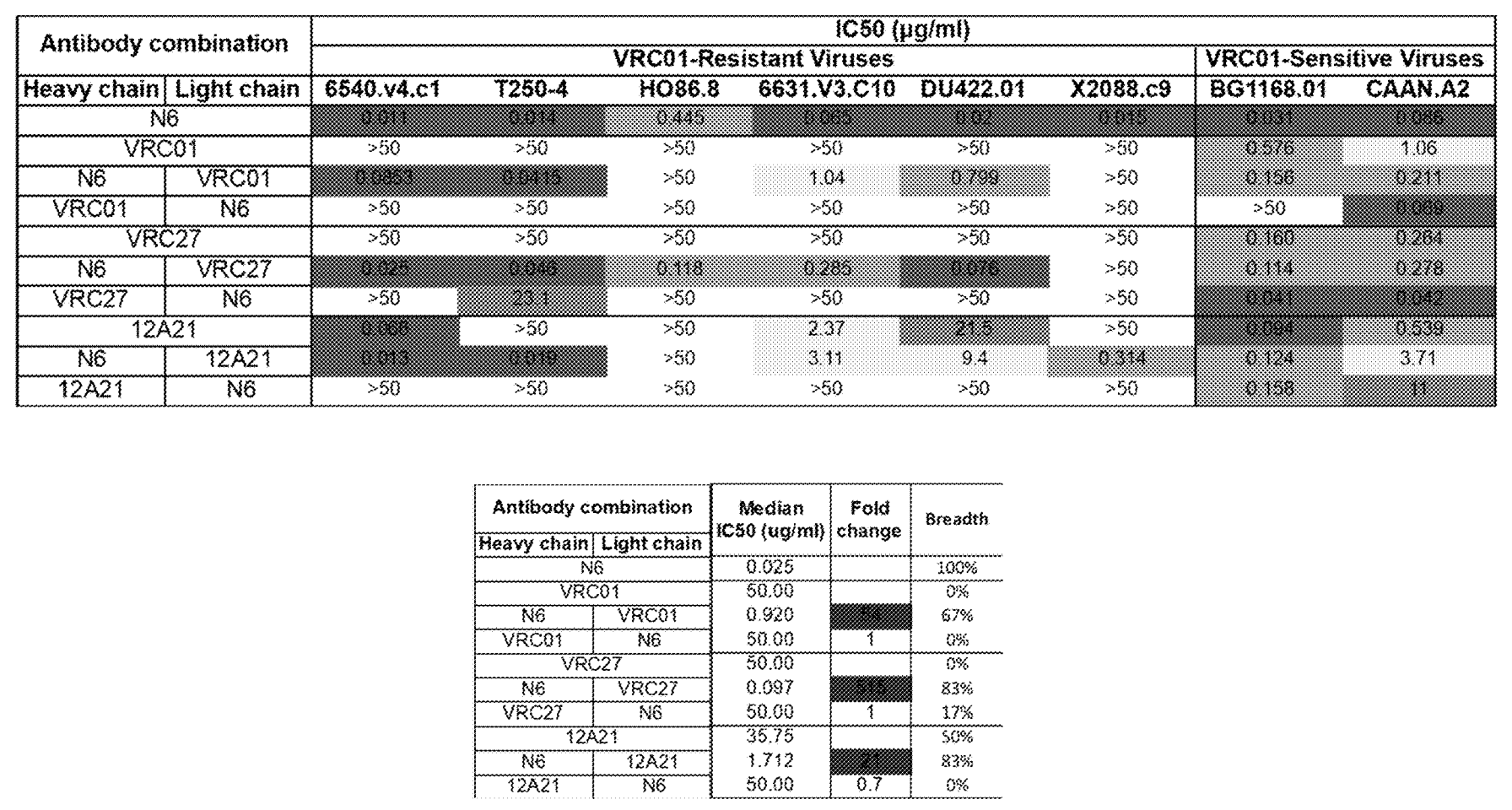

Next, the regions of the N6 heavy chain or light chain that play an essential role in its neutralization breadth and potency were interrogated. First, the heavy and light chains of N6 were exchanged with other CD4 binding site neutralizing antibodies VRC01, VRC27 and 12A21, and their neutralizing activities against six VRC01-resistant and two VRC01-sensitive pseudoviruses were assayed. As shown in FIG. 8A, the combination of N6 heavy chain and VRC01, VRC27 or 12A21 light chain increased the antibody neutralizing potency and breadth relative to VRC01, VRC27 or 12A21, respectively. However, combination of N6 light chain and VRC01, VRC27 or 12A21 heavy chain showed no change in breadth. This result is potentially consistent with the structural data that suggest that the ability of N6 to bind VRC01-resistant viruses, although mediated through light chain orientation, is primarily mediated by the conformation adopted by the heavy chain.

Figure 8B:
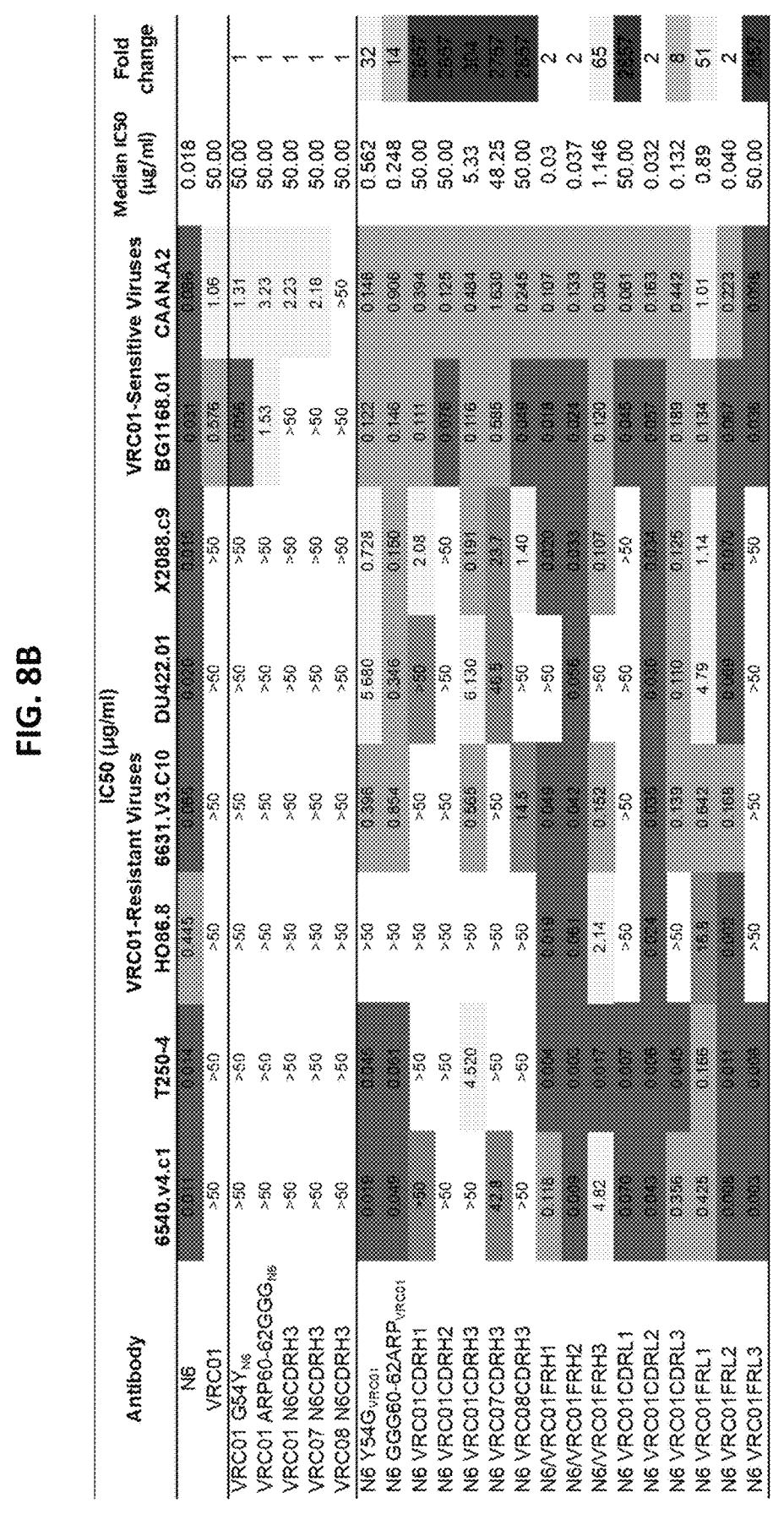

In the N6, Tyr54$_{HC}$ and GlyGlyGly60-62$_{HC}$ within the CDRH2, and the CDRH3 are key areas of interaction with gp120 based on the crystal structure analyses. However substituting these residues into the corresponding regions of VRC01) did not increase its breadth or potency (FIG. 8B). The N6 CDRH3 was also substituted into other VRC01-class antibodies, such as VRC07 and VRC08 and observed no increase in breadth or potency (FIG. 8B). This suggested that these features individually do not confer increased activity to other members of the VRC01 class against resistant viruses.

Whether the activity of N6 against resistant viruses is diminished by mutating the FR and CDRs of N6 to those of other members of the VRC01-class was next examined (FIGS. 8B and BC). Substitution of the Tyr54$_{N6}$ with Gly54$_{VRC01}$, and GlyGlyGly60-62$_{N6}$ with corresponding residues of AlaArgPro60-62$_{VRC01}$ in CDRH2 each gave 32 and 14-fold decrease in neutralization. However, the largest decrease in the activity against these viruses was caused by the substitutions of the N6 CDRH1, CDRH2 and CDRH3 and framework region (FR) FRH3 with those of VRC01, that caused a 2857, 2857, 304 and 60-fold decrease in neutralization activity, respectively. Also N6 CDRH3 was replaced with those of VRC01-like antibodies, such as VRC07 and VRC08. A 2757 and 2857-fold decrease in neutralization activity was observed, respectively. In addition, these antibodies lost neutralization activities against most of VRC01-resistant viruses. This was not due to a large disruption of function by the substitutions given the neutralization of sensitive isolates was unchanged. Substitutions of N6 light chain CDRL1 and FRL3 with those of VRC01 also dramatically decreased the antibody neutralizing activities by 2857-fold. CDRL3 and FRL1 substitutions had a more modest impact.

To further understand the domains of N6 responsible for its breadth and potency, each region of N6 was substituted with those from genetically and structurally similar, but less broad and potent antibodies from the same VRC01-class.

Figure 8C:
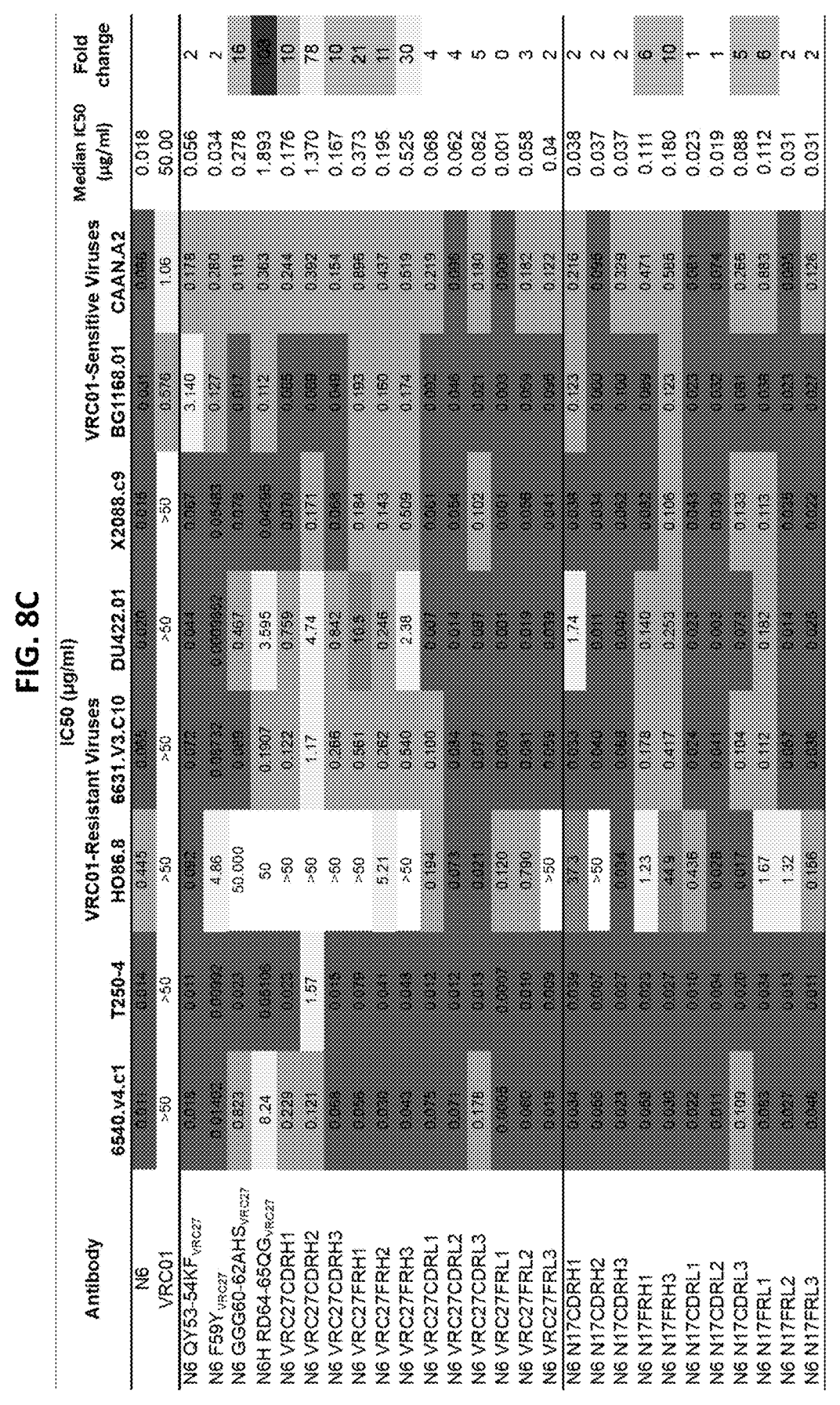

VRC27 is a clonal relative isolated from the same donor, with only five residues that differ from N6 in the CDRH3. However, the neutralizing activity of VRC27 is less than that of VRC01 with a median $IC_{50}$ of 0.217 μg/ml, 78% breadth, and it does not neutralize VRC01-resistant viruses. Substitution of the N6 CDRH3 with that of VRC27 (N6 VRC27 CDRH3) caused a 10-fold decrease in neutralization of VRC01-resistant viruses (FIG. 8). This might be expected given that the CDRH3 of these two antibodies are quite similar. However, substitution of the CDRH2 and CDRH1 of N6 with that of VRC27 led to 78 and 10-fold drop in neutralization. Substitution of the ArgAsp64-65$_{N6}$ with corresponding residues of GlnGly64-65$_{VRC27}$ in CDRH2 gave 108-fold decrease in neutralization. Somewhat surprisingly, substitutions of FRH1, 2, and 3 caused 21, 11 and 30-fold decrease in neutralization (FIG. 8).

N17 is another clonal variant closely related to N6 but with less activity against VRC01-resistant viruses. The N17 heavy chain has the same CDRH1, CDRH2, CDRH3 and FRH2 as N6, but differs at several residues within FRH1 and FRH3. Its light chain is also different from N6 in each FR and CDR. As shown in FIG. 8, substitution of the FRH1 and FRH3 of N6 with the corresponding residues from N17 caused 5- and 7-fold decrease in potency. There was no change in potency observed with substitutions in all FRL and CDRLs. These results suggest that in addition to the N6 CDRH1, CDRH2 and CDRH3, the FRH1 and FRH3 also contribute to the potency of N6 against VRC01-resistant viruses.

Taken together, the heavy and light chain swaps, structural analyses, and mutagenesis suggest that binding by N6 is mediated by multiple contacts spread across the heavy chain CDR and FRs. N6 maintains its most critical contacts within loop D through interactions with the heavy and light chain. However, N6 is able to tolerate mutations within the CD4BLP and β23-V5 regions that introduce residues with bulky side chains that sterically clash with other VRC01-class antibodies. This property is conferred by a unique orientation of the light chain that is dictated by the overall conformation of the heavy chain. It is this property that results in the remarkable ability of N6 to avoid the major mechanisms of resistance to the VRC01 class of antibodies.

Amino acid sequences of the modified antibody heavy and light chain variable regions disclosed above are provided as follows:

```
                                        (SEQ ID NO: 42)
VRC01 G54Y_HC
QVQLVQSGGQMKKPGESMRISCRASGYEFIDCTLNWIRLAPGKRP

EWMGWLKPRYGAVNYARPLQGRVTMTRDVYSDTAFLELRSLTVDD

TAVYFCTRGKNCDYNWDFEHWGRGTPVIVSS (SEQ ID NO: 43)
VRC01 ARP60-62GGG_HC
QVQLVQSGGQMKKPGESMRISCRASGYEFIDCTLNWIRLAPGKRPE

WMGWLKPRGGAVNYGGGLQGRVTMTRDVYSDTAFLELRSLTVDDTA

VYFCTRGKNCDYNWDFEHWGRGTPVIVSS (SEQ ID NO: 44)
VRC01 N6CDRH3
QVQLVQSGGQMKKPGESMRISCRASGYEFIDCTLNWIRLAPGKRPE

WMGWLKPRGGAVNYARPLQGRVTMTRDVYSDTAFLELRSLTVDDTA

VYFCARDRSYGDSSWALDAWGRGTPVIVSS (SEQ ID NO: 45)
VRC07 N6CDRH3
QVRLSQSGGQMKKPGDSMRISCRASGYEFINCPINWIRLAPGKRPE

WMGWMKPRHGAVSYARQLQGRVTMTRDMYSETAFLELRSLTSDDTA

VYFCARDRSYGDSSWALDAWGQGTPVTVSS (SEQ ID NO: 46)
VRC08 N6CDRH3
QVQLVQSGTQMKEPGASVTISCVTSGYEFVEILINWVRQVPGRGLE

WMGWMNPRGGGVNYARQFQGKVTMTRDVYRDTAYLTLSGLTSGDTA

KYFCARDRSYGDSSWALDAWGQGTLVIVSP (SEQ ID NO: 47)
N6 Y54G_HC
RAHLVQSGTAMKKPGASVRVSCQTSGYTFTAHILFWFRQAPGRGLE

WVGWIKPQGGAVNFGGGFRDRVTLTRDVYREIAYMDIRGLKPDDTA

VYYCARDRSYGDSSWALDAWGQGTTVVVSA (SEQ ID NO: 48)
N6 GGG60-62ARP_HC
RAHLVQSGTAMKKPGASVRVSCQTSGYTFTAHILFWFRQAPGRGLE

WVGWIKPQYGAVNFARPFRDRVTLTRDVYREIAYMDIRGLKPDDTA

VYYCARDRSYGDSSWALDAWGQGTTVVVSA (SEQ ID NO: 49)
N6 VRC07CDRH3
RAHLVQSGTAMKKPGASVRVSCQTSGYTFTAHILFWFRQAPGRGLE

WVGWIKPQYGAVNFGGGFRDRVTLTRDVYREIAYMDIRGLKPDDTA

VYYCARGKYCTARDYYNWALDAWGQGTTVVVSA (SEQ ID NO: 50)
N6 VRC08CDRH3
RAHLVQSGTAMKKPGASVRVSCQTSGYTFTAHILFWFRQAPGRGLE

WVGWIKPQYGAVNFGGGFRDRVTLTRDVYREIAYMDIRGLKPDDTA

VYYCARGRSCCGGRRHCNGADCFNWALDAWGQGTTVVVSA (SEQ ID NO: 51)
N6 VRC27CDRH2
RAHLVQSGTAMKKPGASVRVSCQTSGYTFTAHILFWFRQAPGRGLE

WVGWIKPKFGAVNYAHSFQGRVTLTRDVYREIAYMDIRGLKPDDTA

VYYCARDRSYGDSSWALDAWGQGTTVVVSA (SEQ ID NO: 52)
N6 VRC27CDRH3
RAHLVQSGTAMKKPGASVRVSCQTSGYTFTAHILFWFRQAPGRGLE

WVGWIKPQYGAVNFGGGFRDRVTLTRDVYREIAYMDIRGLKPDDTA

VYYCARDRLYDGSSWRLDPWGQGTTVVVSA (SEQ ID NO: 53)
N6 VRC27FRH1
SQRLVQSGPQVRKPGSSVRISCETSGYTFNAHILFWFRQAPGRGLE

WVGWIKPQYGAVNFGGGFRDRVTLTRDVYREIAYMDIRGLKPDDTA

VYYCARDRSYGDSSWALDAWGQGTTVVVSA (SEQ ID NO: 54)
N6 VRC27FRH2
RAHLVQSGTAMKKPGASVRVSCQTSGYTFTAHILFWFRQAPGRSFE

WMGWIKPQYGAVNFGGGFRDRVTLTRDVYREIAYMDIRGLKPDDTA

VYYCARDRSYGDSSWALDAWGQGTTVVVSA
```

-continued

N6 VRC27FRH3 (SEQ ID NO: 55)
RAHLVQSGTAMKKPGASVRVSCQTSGYTFTAHILFWFRQAPGRGLE

WVGWIKPQYGAVNFGGGFRDRITLTRDIYRETAFLDLTGLRFDDTA

VYYCARDRSYGDSSWALDAWGQGTTVVVSA

N6 N17FRH1 (SEQ ID NO: 56)
RAHLVQSGTAVKRPGASVRVSCETSGYTFTAHILFWFRQAPGRGLE

WVGWIKPQYGAVNFGGGFRDRVTLTRDVYREIAYMDIRGLKPDDTA

VYYCARDRSYGDSSWALDAWGQGTTVVVSA

N6 N17FRH3 (SEQ ID NO: 57)
RAHLVQSGTAMKKPGASVRVSCQTSGYTFTAHILFWFRQAPGRGLE

WVGWIKPQYGAVNFGGGFRDRVTLTRDIYRDTAYMDISGLRFDDTA

VYYCARDRSYGDSSWALDAWGQGTTVVVSA

N6 N17FRL1 (SEQ ID NO: 58)
YIHVTQSPSSLSVSAGDRVTINCQTSQGVGSDLHWYQHKPGRAPKL

LIHHTSSVEDGVPSRFSGSGFHTSFNLTISDLQADDIATYYCQVLQ

FFGRGSRLHIK

N6 N17FRL2 (SEQ ID NO: 59)
YIHVTQSPSSLSVSIGDRVTINCQTSQGVGSDLHWYQHKPGRAPKL

LIRHTSSVEDGVPSRFSGSGFHTSFNLTISDLQADDIATYYCQVLQ

FFGRGSRLHIK

N6 N17FRL3 (SEQ ID NO: 60)
YIHVTQSPSSLSVSIGDRVTINCQTSQGVGSDLHWYQHKPGRAPKL

LIHHTSSVEDGVPSRFSGTGFHTSFNLTINDLQSDDIATYYCQVLQ

FFGRGSRLHIK

N6 N17FRL4 (SEQ ID NO: 61)
YIHVTQSPSSLSVSIGDRVTINCQTSQGVGSDLHWYQHKPGRAPKL

LIHHTSSVEDGVPSRFSGSGFHTSFNLTISDLQADDIATYYCQVLQ

FFGRGSRLDFK

N6 N17CDRL1 (SEQ ID NO: 62)
YIHVTQSPSSLSVSIGDRVTINCQTSQGVGRDLHWYQHKPGRAPKL

LIHHTSSVEDGVPSRFSGSGFHTSFNLTISDLQADDIATYYCQVLQ

FFGRGSRLHIK

N6 N17CDRL2 (SEQ ID NO: 63)
YIHVTQSPSSLSVSIGDRVTINCQTSQGVGSDLHWYQHKPGRAPKL

LIHHASSVEDGVPSRFSGSGFHTSFNLTISDLQADDIATYYCQVLQ

FFGRGSRLHIK

N6 N17CDRL3 (SEQ ID NO: 64)
YIHVTQSPSSLSVSIGDRVTINCQTSQGVGSDLHWYQHKPGRAPKL

LIHHTSSVEDGVPSRFSGSGFHTSFNLTISDLQADDIATYYCQVLE

SFGRGSRLHIK

Crystal Structure of N6 in Complex with Gp120

To define the structural mechanisms by which N6 might mediate such potency and breadth, structural analysis of the antigen-binding fragment of N6 (Fab) in complex with HIV gp120 proteins from strains with different sensitivity to VRC01-class antibodies was performed (see FIGS. 9-13). These include clade AE 93TH057, a strain sensitive to most VRC01-class antibodies; DU172, a strain resistant to VRC01, but sensitive to several other VRC01-class antibodies, including N6; and X2088, a strain only sensitive to N6.

Analysis of the structures revealed that N6 had several features in common with other members of the VRC01 class of antibodies. These include contacts between the CDRH3 and loop D, although these contacts were more extensive than those of VRC01. N6 also had contacts between the CDRH2 and the CD4 BLP, salt bridges between $Arg71_{HC}$ and $Asp368_{gp120}$ N6 also had a pocket-filling $Tyr54_{HC}$, which mimics the interaction of $Phe43_{CD4}$ with gp120, a feature also found in some of the VRC01-class antibodies, such as VRC27 (also isolated from patient Z258), VRC-PG20, and 12A21, which contain a Phe54, or VRC03 which has a Trp54. The light chain is IGKV1-33-derived, similar to some other antibodies such as 12A21. In common with some other VRC01-class antibodies, N6 also contains the flexible GlyXGly motif (aa 28-30) within the CDRL1 that permits it to avoid steric clashes with loop D. Although the N6 CDRH3 has a different conformation from VRC01, the CDR H3 Trp100c (Kabat numbering ref) has a similar position to VRC01 Trp100b which interacts with the $Asp279_{gp120}$.

N6 was also found to have several structural features that were distinct from other VRC01-class antibodies. For example, the N6 heavy chain contains a polyglycine 60-62 that is not found in any other isolated CD4 binding site antibodies. Also the N6 light chain has a unique orientation in that it was rotated such that the CDRL3 was further away from β23-V5 compared to VRC01. Addition of residues with large side chains into this domain is a previously described mechanism of resistance to VRC01-class antibodies. The greater distance between CDRL3 and this area may permit N6 to better tolerate such changes in V5 compared to other VRC01-class antibodies. Consistent with this interpretation, the structure of the co-crystal of the N6-X2088.c9$_{gp120}$ revealed that the rotation of the N6 light chain accommodated the extra residues between the alpha 2 helix and the CD4BLP of this Env that protrude in the direction of the light chain and likely clash with other antibodies of this type. It is important to note that the unique orientation of the N6 light chain was not due to special features of the light chain, or heavy and light chain interface, given these overlapped with those of VRC27. Rather it remains possible that the binding mode or orientation of the N6 heavy chain permitted this rotation of the light chain. Overall, N6 has a unique light chain orientation compared to other VRC01-class antibodies in that it permits the light chain to avoid potential clashes with β23-V5 and loop D.

N6 Developmental Pathway

In order to understand how N6 developed such outstanding potency and breadth compared to other VRC01-class antibodies, next-generation sequencing (NGS) of peripheral blood memory B cells from donor Z258 at three time points (2012, 2014, and 2015) was performed to identify additional lineage members. Briefly, B cell receptor cDNA was prepared from each time point and sequenced using Illumina MiSeq, with an average sequencing depth of ~40×. Lineage-related heavy chain transcripts were identified based on sequence identity in CDRH3 to that of N6, VRC27, F8, or N17. Related light chain transcripts were identified as reads deriving from IGKV1-33 and using the five amino acid CDRL3 signature of the VRC01-class (Zhou et al. Immunity 39, 245-258, 2013). After removing duplicates and transcripts containing stop codons or out-of-frame junctions, the remaining reads were clustered to account for sequencing error. Finally, the clustered sequences were manually curated to yield final sets of heavy and light chain lineage members for each time point.

Figure 14:
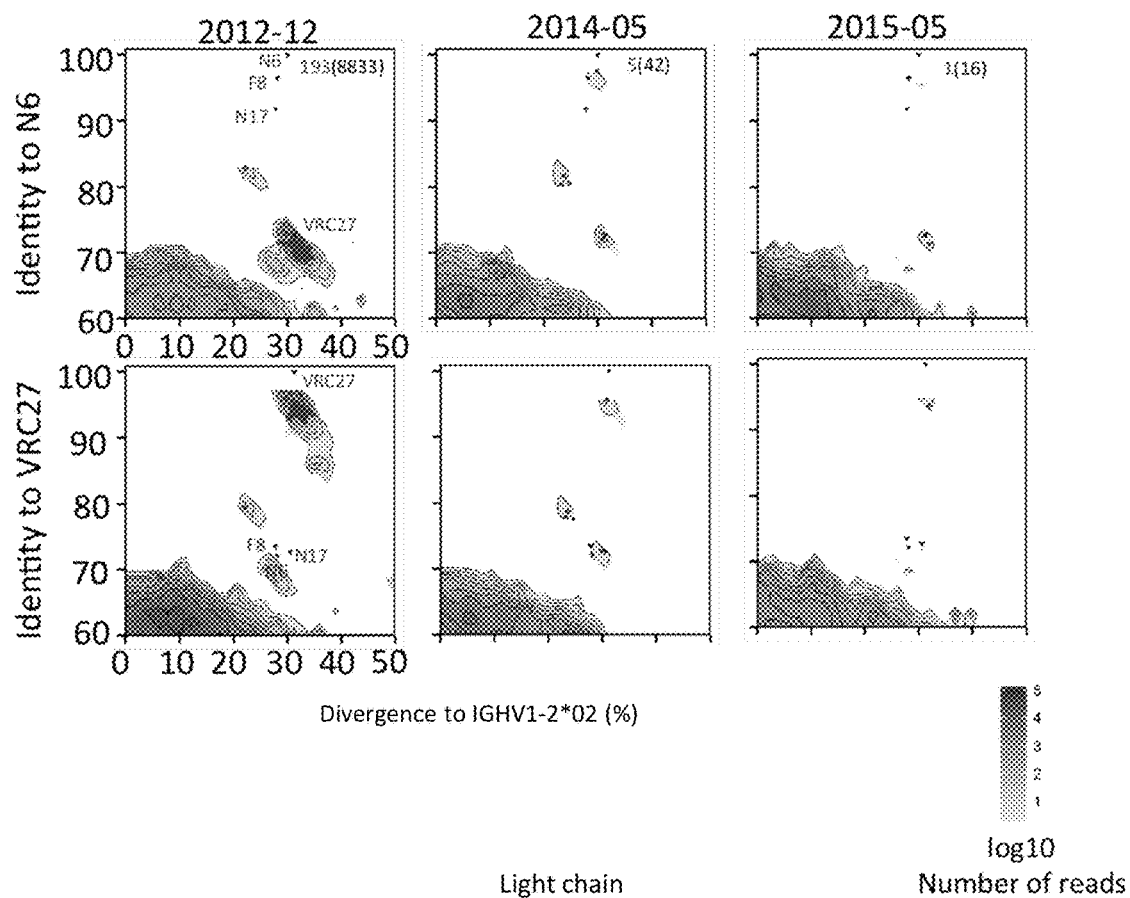
Figure 14:
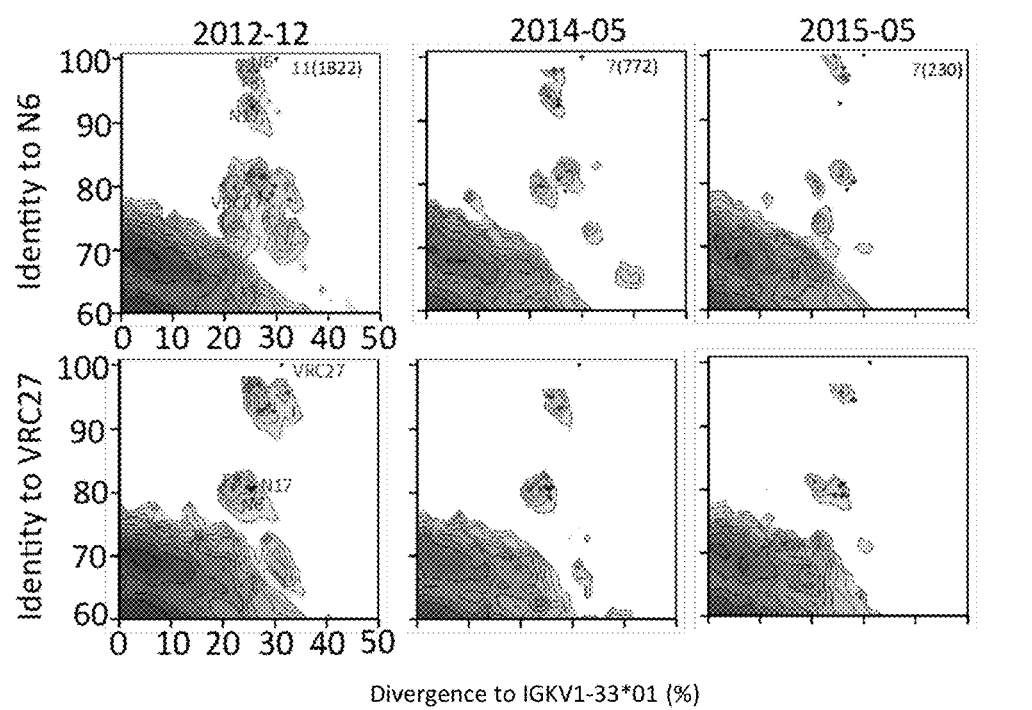

The curated transcripts of both heavy and light chains showed high levels of somatic hypermutation (>20%), with more transcripts highly similar to VRC27 than N6 (FIG. 14). Nonetheless, heavy chain transcripts showing less somatic mutation (~23%) than either N6 or VRC27 were observed at the 2012 and 2014 time points. Similarly, some light chain transcripts with ~20% somatic hypermutation, compared to ~25% for N6 and VRC27 light were also observed. More lineage-related transcripts were observed from the 2012 time point than 2014 or 2015, likely because more B cells were used for the NGS experiment. N6-like light chain transcripts were observed at all three time points (FIG. 14), but no heavy chain transcripts with high similarity to N6 were observed in the 2012 or 2015 data. While the vast majority of curated heavy chain sequences are closely related to VRC27 in the phylogenetic tree (FIG. 15) it is likely that this does not reflect a biological expansion of the VRC27 clade relative to the N6 clade. This diversity may instead have been artificially generated by low sequence quality in the overlap between forward and reverse MiSeq reads.

Figure 15A:
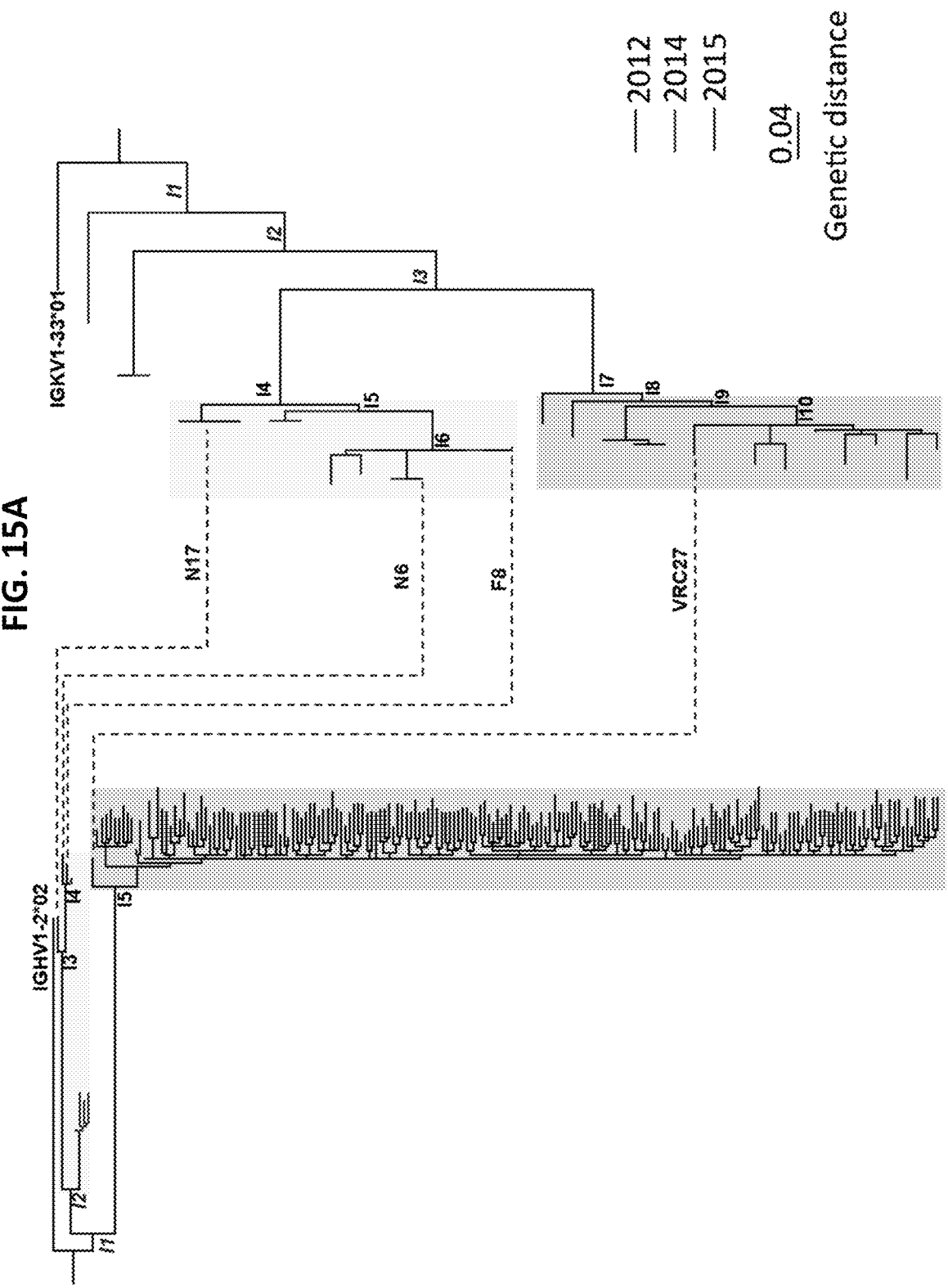

To investigate the phylogenetic structure of the lineage, maximum likelihood trees were constructed for heavy chain and light chain (FIG. 15). The phylogenetic trees consistently showed that N6 and VRC27 formed two highly divergent groups. Nonetheless, in addition to using the same genetic elements, both groups have similar heavy chain and light chain junctions, as well as sharing 15 and 14 mutations in the heavy and light chains respectively, confirming that they represent two clades of a single clonal lineage.

The phylogenetic tree further showed that the two clades diverged early in lineage development. Although 3 transcripts from the 2014 time point fall between the N6 and VRC27 branches (FIG. 15), the analysis did not retrieve a sufficient number of early lineage-member sequences to define the point at which the two clades diverged. It appears that the heavy chain GlyGlyGly60-62$_{N6}$ motif and RD63-64$_{N6}$ motif appeared after the two and three clades, respectively. In the light chain, the GlyXGly motif in CDRL1 appeared before the divergence of the two clades, while Gln96 in CDRL3 appeared late in the development of the N6 clade.

We paired phylogenetic tree of N6 lineage and cloned the Z258 heavy and light chain transcripts related to N6. Two heavy chains were derived from 2015 and four light chains were derived from 2014 and 2015. We found three out of eight pairing antibodies had similar potency with N6 (FIG. 16). Interestingly, all three antibodies could neutralize N6-resistant virus TV1.29, suggesting patient Z258 was developing antibodies with greater breadth in during this time period.

Discussion

These results have several important implications for efforts to stimulate a broadly neutralizing antibody response and efforts to utilize bNAbs in prophylaxis or therapies. Of those antibodies being considered for clinical development there has been a general trend that they are either extremely broad (such as 10E8 or VRC01) or extremely potent and less broad (PGT121, PGDM1400). However, the discovery of the N6 antibody demonstrates that this new VRC01-class antibody can mediate both extraordinary breadth and potency even against isolates traditionally resistant to antibodies in this class. Sequence analysis of resistant isolates, mutagenesis, and structural data each confirm that N6 has many of the features and contacts that are characteristic of the VRC01 class. However, it is able to achieve its breadth and potency well above other VRC01-class antibodies through a complex combination of changes in multiple domains within both heavy and light chains.

The increase in potency, compared to other VRC01-class antibodies, is largely mediated through a series of contacts between the heavy chain and gp120. An exchange of heavy and light chains of N6 with those of other VRC01-class antibodies indicated that the activity of N6 is largely mediated through heavy chain interactions. This occurs primarily through contacts at the CDRH2, CDRH3, and Tyr54$_{N6Heavy}$. Although substituting any one of these sequences into other VRC01-class antibodies did not confer increased activity, mutating each of these reduced the activity of N6. However, the most dominant of these interactions occurred between the CDR H3 of N6 and loop D. This degree of dependence on the CDRH3-loop D interaction is surprising given that previously described VRC01-class antibodies that utilize VH1-2*02 were found to be largely dependent on CDR H2 interactions[43]. It is perhaps this interaction, along with those with the CDRH2 and Y54$_{N6}$, that in combination give N6 its additional potency compared to other antibodies of the VRC01 class.

It is particularly interesting to note that through natural selection in vivo, N6 has features that have been engineered into other antibodies to increase potency or breadth, or reduce the possibility of antibody escape. Although the naturally occurring VH1-2*02-derived VRC01-class antibodies thus far described mimic the interaction of CD4 with gp120, the vast majority do not fill a hydrophobic pocket on gp120 typically filled by Phe43$_{CD4}$. Substitutions of hydrophobic residues for Gly54 in the antibodies NIH45-46[58] and VRC07[59] have resulted in large increases in potency and some increases in breadth. The N6 antibody, through natural selection in vivo, has a Tyr54$_{N6}$ that binds in this pocket and contributes to the potency of N6. In addition, the light chains of both VRC07 and NIH 45-46 have been engineered to avoid steric clashes with the β-23 V5 loop[49,59,60]. These same steric clashes are avoided by the N6 antibody through changes in the light chain orientation that permit it to tolerate bulky side chains within the β-23 V5 domain. However, many of these engineered changes in VRC01-class antibodies that led to improvements in potency and breadth have come at a cost of increased autoreactivity ([59] and reviewed in [61]). Although natural autoreactive antibodies can occur, especially among bNabs[62]; surprisingly autoreactivity for the N6 antibody was not observed. Expansion of B cells expressing clonal relatives of N6 with strong autoreactivity were likely selected against in vivo. These data indicate that the development of the both breadth and potency in antibodies such as N6 is not necessarily accompanied by autoreactivity.

The N6 antibody has several characteristics that make it a desirable candidate for use in prophylaxis and therapy. The lack of autoreactivity suggests that N6 will have a longer half-life in vivo compared to other antibodies that are reactive in such assays. The potency of N6 may further increase the durability of a prophylactic or therapeutic benefit in the case of passive administration because less antibody is required to persist to mediate an effect. This effect might be further extended by introducing mutations into N6 that are able to extend its half-life in vivo. In addition to its potency, use of an antibody with this breadth might dramatically limit the likelihood of transmission when used in prophylaxis or selection of escape mutations in the setting of therapy.

The rare occurrence of N6 resistance mutations may suggest that such mutations come at a high fitness cost that represents a barrier to the selection of resistant mutants. The Z258 autologous virus contained rare changes in the loop D sequence at positions $279_{gp120}$ and $281_{gp120}$. Resistance to N6 appears to require that these positions of loop D be mutated. Changes at these positions have been observed in patients or humanized mice in response to VRC01-class antibody selection[50,60]. The autologous virus of patient 45, from whom VRC01 and NIH45-46 were cloned, contained $Asp279Glu_{gp120}$ and $Ala281His_{gp120}$ mutations. In this case the $Ala281His_{gp120}$ restored viral fitness in isolates containing $Asp279Glu_{gp120}$. In one recent effort to engineer VRC01-like antibodies to constrain viral escape an engineered NIH45-46 antibody was given as therapy to $HIV^{YU-2}$-infected humanized mice. This therapy selected for an $Ala281Thr_{gp120}$ mutant that resulted in reduced viral fitness, potentially through introduction of a glycan at $Asn279_{gp120}$ by generating the Asn-X-Thr/Ser glycosylation sequon. The impact of individual mutations on the conformation and replicative fitness of the Z258 autologousvirus are yet to be defined. However, these changes only occur in <0.01% of 5132 viruses in a large database (www.hiv.lanl.gov), suggesting such mutations are likely strongly disfavored. Thus, in addition to its potency and breadth, the N6 antibody may be particularly effective for therapeutic use due to the viral fitness costs associated with generating N6-resistance.

Experimental Procedures

Study patients. The plasma and peripheral blood mononuclear cells (PBMCs) were selected from the HIV-1-infected patients enrolled in the National Institutes of Health under a clinical protocol approved by the Investigational Review Board in the National Institute of Allergy and Infectious Diseases (NIAID-IRB). All participants signed informed consent approved by the NIAID-IRB. The criteria for enrolment were as follows: having a detectable viral load, a stable CD4 T-cell count above 400 cells/μl, being diagnosed with HIV-1 infection for at least 4 years, and off antiretroviral treatment for at least 5 years. Donor Z258 was selected for B-cell sorting and antibody generation because his serum neutralizing activity is among the most potent and broad in the cohort. At the time of leukapheresis, he had been infected with HIV-1 for 21 years, with CD4 T-cell counts of 733 cells/μl, plasma HIV-1 RNA values of 996 copies/ml and was not on antiretroviral treatment.

Memory B-cell staining, sorting and antibody cloning. Staining and single-cell sorting of memory B cells were performed following a detailed protocol recently published (Huang et al., *Nat. Protoc.,* 8, 1907-1915, 2013). Briefly, a total of 75,000 $CD19\pm IgA^{-}IgD^{-}IgM^{-}$ memory B cells were sorted and re-suspended in medium with IL-2, IL-21 and irradiated 3T3-msCD40L feeder cells, and seeded into 384-well microtitre plates at a density of 4 cells per well. After 13 days of incubation, supernatants from each well were screened for neutralization activity using a high-throughput micro-neutralization assay against $HIV\text{-}1^{MN.3}$ and $HIV\text{-}1^{Bal.26}$. From the wells that scored positive in both the $HIV\text{-}1_{MN.3}$ and $HIV\text{-}1^{Bal.26}$ neutralization assay the variable region of the heavy chain and the light chain of the immunoglobulin gene were amplified by RT-PCR and re-expressed as described previously (Tiller et al., *J. Immunol. Methods,* 329, 112-124, 2008; Georgiev et al., *Science,* 340: 751-756, 2013). The full-length IgG was purified using a recombinant protein-A column (GE Healthcare).

Generation of pseudoviruses. HIV-1 Env pseudoviruses were generated by co-transfection of 293T cells with an Env-deficient backbone (pSG3ΔEnv) and a second plasmid that expressed HIV-1 Env at a ratio of 2:1. 72 h after transfection, supernatants containing pseudoviruses were harvested and frozen at −80° C. until further use. JRCSF mutants were produced by altering the JRCSF Env plasmid with QuikChange Lightning site-directed mutagenesis kit according to the manufacturer's protocol (Agilent).

Neutralization assays. Neutralization activity of monoclonal antibodies or serum was measured using single-round HIV-1 Env-pseudovirus infection of TZM-b1 cells as described previously (Li et al., *J. Virol.,* 79, 10108-10125, 2005. Heat-inactivated patient serum or monoclonal antibody (mAb) was serially diluted five-fold with Dulbecco's modified Eagle medium 10% FCS (Gibco), and 10 μl of serum or mAb was incubated with 40 μl of pseudovirus in a 96-well plate at 37° C. for 30 min. TZM-b1 cells were then added and plates were incubated for 48 h. Assays were then developed with a luciferase assay system (Promega, Finnboda Varvsväg, Sweden), and the relative light units (RLU) were read on a luminometer (Perkin Elmer).

Binding assays. $HIV^{BAL26}$ gp120 monomers, gp120 Resurfaced Stabilized Cores (RSC3) and their CD4 knockout mutants gp120D368R and RSC3 Δ371I P363N at 2 μg/ml were coated on 96-well plates overnight at 4° C. Plates were blocked with BLOTTO buffer (PBS, 1% FBS, 5% non-fat milk) for 1 h at room temperature, followed by incubation with antibody serially diluted in disruption buffer (PBS, 5% FBS, 2% BSA, 1% Tween-20) for 1 h at room temperature. 1:10,000 dilution of horseradish peroxidase (HRP)-conjugated goat anti-human IgG antibody was added for 1 h at room temperature. Plates were washed between each step with 0.2% Tween 20 in PBS. Plates were developed using 3,3',5,5'-tetramethylbenzidine (TMB) (Sigma-Aldrich) and read at 450 nm.

Cross-competition ELISA. Cross-competition ELISA was performed following the method published previously (Wu et al., *Science,* 329, 856-861, 2010). $HIV_{YU2}$ gp120 at 2 μg/ml was coated on 96-well plates overnight at 4° C. Plates were blocked with B3T buffer (PBS, 3.3% FBS, 2% BSA, 0.07% Tween-20, 0.02% thimerosal, 150 mM NaCl, 50 mM Tris-HCl, and 1 mM EDTA) for 1 h at 37° C. 50 μl of serially diluted non-biotinylated competitor antibodies was added to the plate in B3T buffer, followed by addition of 50 μl of biotinylated antibody or CD4-Ig at a fixed concentration: 250 ng/ml of VRC01-biotin, 5 μg/ml of VRC23-biotin, 1 μg/ml of VRC-PG04-biotin or 150 ng/ml of CD4-Ig-biotin. Plates were incubated for 1 h at 37° C. 1:200 dilution of HRP-conjugated streptavidin (BD) was added and incubated for 30 min at room temperature. Plates were washed between each step with 0.2% Tween-20 in PBS. Plates were developed using TMB and read at 450 nm.

Viral capture ELISA. The relative binding capacity of monomeric gp120 and N6 was determined by a gp120 capture enzyme-linked immunosorbent assay (ELISA) as previously described (Moore et al., *J. Virol.,* 69, 101-109, 1995). 100 μl of anti-gp120 D7324 (Aalto Bioreagent, Dublin, Ireland) at 1 μg/ml in PBS was coated on 96-well plates overnight at 4° C. JRCSF pseudovirus stocks treated with Triton X-100 (0.5%) were added and incubated for 2 h at 37° C. Plates were blocked with B3T buffer for 1 h at 37° C., followed by incubation with antibody serially diluted in B3T buffer for 1 h at 37° C. 1:10,000 dilution of horseradish peroxidase (HRP)-conjugated goat anti-human IgG antibody (Jackson ImmunoResearch Laboratories) was added for 1 h at 37° C. Plates were washed between each step with 0.2% Tween-20 in PBS, developed using TMB and read at 450 nm.

Autoreactivity assays. Reactivity to HIV-1 negative human epithelial (HEp-2) cells was determined by indirect immunofluorescence on slides using Evans Blue as a counterstain and FITC-conjugated goat anti-human IgG (Zeus Scientific) (Haynes et al., Science, 308, 1906-1908, 2005). Slides were photographed on a Nikon Optiphot fluorescence microscope. Kodachrome slides were taken of each monoclonal antibody binding to HEp-2 cells at a 10-s exposure, and the slides scanned into digital format. The Luminex AtheNA Multi-Lyte ANA test (Wampole Laboratories) was used to test for monoclonal antibody reactivity to SSA/Ro, SS-B/La, Sm, ribonucleoprotein (RNP), Jo-1, double-stranded DNA, centromere B, and histone and was performed as per the manufacturer's specifications and as previously described (Haynes et al., Science, 308, 1906-1908, 2005). Monoclonal antibody concentrations assayed were 50 µg/ml. 10 µl of each concentration was incubated with the luminex fluorescent beads and the test performed per the manufacturer's specifications.

Viral RNA extraction and cDNA synthesis. Viral RNA extraction and cDNA synthesis were performed as described previously (Wu et al., J. Virol., 86, 5844-5856, 2012). In brief, Viral RNA of patient Z258 was extracted from 280 µl of serum sample from two different time points using the QIAamp viral RNA mini kit (Qiagen) and eluted in 50 µl of elution buffer. The first-strand cDNA synthesis was carried out using the SuperScript III reverse transcriptase (Invitrogen Life Technologies). The final 100 ul reaction volume was composed of 50 µl viral RNA, 5 µl of a deoxynucleoside triphosphate (dNTP) mixture (each at 10 mM), 1.25 antisense primer envB3out (5'-TTGCTACTTGTGATTGCTC-CATGT-3', SEQ ID NO: 65) at 20 µM, 20 µl 5× first-strand buffer, 5 µl dithiothreitol at 100 mM, 5 µl RNaseOUT and 5 µl SuperScript III reverse transcriptase. RNA, primers, and dNTPs were heated at 65° C. for 5 min and then chilled on ice for 1 min, and then the entire reaction mixture was incubated at 50° C. for 60 min, followed by 55° C. for an additional 60 min. Finally, the reaction was heat inactivated at 70° C. for 15 min and then treated with 1 µl RNase H at 37° C. for 20 min. The resulting cDNA was used immediately for PCR or frozen at 80° C. to await further analysis.

SGA. The nested PCR of HIV-1 env SGA was described previously (Wu et al., J. Virol., 86, 5844-5856, 2012). Briefly, the cDNA was serially diluted and distributed in replicates of 12 PCR reactions in ThermoGrid 96-well plates (Denville Scientific) to identify a dilution where PCR-positive wells constituted about 30% of the total number of reactions. At this dilution, most of the wells contain amplicons derived from a single cDNA molecule. Additional PCR amplifications were performed using this dilution in full 96-well plates. PCR amplification was carried out using the Platinum Taq High Fidelity PCR system (Invitrogen Life Technologies). The final 20 µl reaction volume was composed of 2 µl 10× buffer, 0.8 µl MgSO$_4$, 0.4 µl dNTP mixture (each at 10 mM), 0.2 µl each primer at 20 µM, 0.1 µl Platinum Taq High Fidelity polymerase, and 1 µl template DNA. The primers for the first-round PCR were envB5out (5'-TAGAGCCCTGGAAGCATCCAGGAAG-3', SEQ ID NO: 66) and envB3out (5'-TTGCTACTTGTGATTGCTC-CATGT-3', SEQ ID NO: 67). The primers for the second-round PCR were envB5 in (5'-CACCTTAGGCATCTCC-TATGGCAGGAAGAAG-3', SEQ ID NO: 68) and envB3 in (5'-GTCTCGAGATACTGCTCCCACCC-3', SEQ ID NO: 69). The cycler parameters were 94° C. for 2 min, followed by 35 cycles of 94° C. for 15 s, 55° C. for 30 s, and 68° C. for 4 min and by a final extension of 68° C. for 10 min. The product of the first-round PCR (1 µl) was subsequently used as the template in the second-round PCR under the same conditions but with a total of 45 cycles. The amplicons were inspected on a precast 1% agarose gel (Embi Tec). All PCR procedures were carried out in a designated PCR clean hood using procedural safeguards against sample contamination.

DNA sequencing. Amplicons were directly sequenced by BigDye Terminator chemistry by ACGT, Inc. (Wheeling, IL). Both DNA strands were sequenced using partially overlapping fragments. Individual sequence fragments for each amplicon were assembled and edited using Sequencher 5.0 (Gene Codes, Ann Arbor, MI). All chromatograms were inspected for sites of mixed bases (double peaks), which would be evidence of priming from more than one template or the introduction of PCR error in early cycles. Any sequence with evidence of double peaks was excluded from further analysis.

Donor Z258 information. Donor Z258 was selected for B-cell sorting and antibody generation because his serum neutralizing activity is among the most potent and broad in our cohort. At the time of leukapheresis, he had been infected with HIV-1 for 21 years, with CD4 T-cell counts of 733 cells/□l, plasma HIV-1 RNA values of 996 copies/ml and was not on antiretroviral treatment.

Cloning of donor Z258 HIV-1 env genes. Representative env sequences from donor Z258 were selected for cloning. The second-round env PCR products containing full-length rev and env genes were amplified using Herculase II Fusion DNA Polymerase (Agilent Technologies), primers HIV RevS (CACCATGGCAGGAAGAAG, SEQ ID NO: 70) and envB3 in (5'-GTCTCGAGATACTGCTCCCACCC-3', SEQ ID NO: 71) with the same conditions of the second-round PCR as described above. PCR amplicons were gel-purified and ligated into the expression vector pcDNA3.1D (Invitrogen Life Technologies) under the control of the T7 promoter. Followed by transfection into TOP10 Chemically Competent E. coli (Invitrogen Life Technologies), each rev and env expression plasmid was maxiprepped (Qiagen), and its sequence was verified. Of a total of seven env sequences cloned from donor Z258, seven (100%) were functional in mediating virus entry.

Statistical analysis. The correlations of neutralization potencies between N6 and VRC01, 10E8, PGT121 or PG9 antibodies against 181 pseudoviruses were evaluated by the Spearman test.

Next Generation Sequencing (NGS) of the PBMC Memory B Cells:

NGS data processing. The 2×300 raw reads were assembled to single end transcripts using USEARCH[75]. Transcripts containing more than 10 sequencing errors estimated using Usearch were excluded. Then the transcripts were processed using our in-house implemented bioinformatics pipeline[76]. Briefly, transcripts shorter than 300 nucleotides were removed. BLAST (http://www.ncbi.nlm-.nih.gov/blast/) was used to assign germline V, D, and J genes to each transcript with customized parameters. Sequences other than the V(D)J region of a transcript were removed and transcripts containing frame-shift or stop codon were excluded. The sequence identities of each transcript to germline V gene, N6, F8, N17, and VRC27 were calculated using ClustalO[77] and were shown in 2D heatmaps plotted using ggplot2 in R.

Identification of N6 lineage related transcripts from NGS. To find lineage related heavy chain transcripts, we used ClustalO77 to calculate the sequence identity of CDR3 of each transcript in each dataset to that of N6, F8, N17, and VRC27. Transcripts with germline V gene assignment to IGHV1-2, sequence identity of CDR3 higher than 60% to N6, F8, N17, or VRC27, and the length of CDR3 in the range of 10-20 amino acids, were sieved for further analyses. To remove PCR duplicates and transcripts containing sequencing errors, two steps of clustering were performed using USEARCH. The transcripts were firstly clustered at 100% sequence identity and the transcripts were ranked by sequencing coverage. Then the transcripts with high coverage were used as seeds or centers for the second step of clustering at 97% sequence identity. One representative sequence was selected from each cluster containing more than one transcripts and a curated unique dataset was then generated for each time point. We then manually removed non-related transcripts from the curated dataset.

To find lineage related light chain transcripts, we first identified transcripts containing the CDR3 signatures (X-X-[AFILMYWV, SEQ ID NO: 72]-[EQ]X) of the VRC01 class 57. Two steps of clustering were then performed to remove PCR duplicates and transcripts containing sequencing errors (See heavy chain data processing). Finally, a curated unique light chain dataset was generated for each time point and non-related transcripts were manually removed.

Phylogenetic analyses and inference of intermediates. The lineage related transcripts of heavy and light chains were aligned separately using Muscle and manually adjusted. Maximum likelihood phylogenetic trees for heavy and light chains were constructed using MEGA678. The GTR+G+I substitution model, selected using MEGA6 as the best overall model for fitting to the sequence datasets 78, was used to estimate genetic distance. Five categories were used when modeling rate heterogeneity by Γ distribution. The phylogenetic trees of heavy and light chains were rooted using IGHV1-2*02 and IGKV1-33*01 respectively. The rooted phylogenetic trees and aligned sequences were input into MEGA6 to infer intermediates using the maximum likelihood method 78.

J. Virol., 86, 5844-5856, 2012.

Example 2

Detecting HIV-1 in a Sample or a Subject Using a Gp120-Specific Antibody

This example describes the use of HIV-1 monoclonal neutralizing antibodies specific to gp120 for the detection of HIV-1 in a sample or a subject. This example further describes the use of these antibodies to confirm the diagnosis of HIV-1 infection in a subject.

A biological sample, such as a blood sample, is obtained from the patient diagnosed with, undergoing screening for, or suspected of having an HIV-1 infection. A blood sample taken from a patient who is not infected is used as a control, although a standard result can also be used as a control. An ELISA is performed to detect the presence of gp120 in the blood sample. Proteins present in the blood samples (the patient sample and control sample) are immobilized on a solid support, such as a 96-well plate, according to methods well known in the art (see, for example, Robinson et al., Lancet 362:1612-1616, 2003, incorporated herein by reference). Following immobilization, HIV-1 monoclonal neutralizing antibodies specific to gp120 that are directly labeled with a fluorescent marker are applied to the protein-immobilized plate. The plate is washed in an appropriate buffer, such as PBS, to remove any unbound antibody and to minimize non-specific binding of antibody. Fluorescence can be detected using a fluorometric plate reader according to standard methods. An increase in fluorescence intensity of the patient sample, relative to the control sample, indicates the gp120 antibody specifically bound proteins from the blood sample, thus detecting the presence of gp120 protein in the sample. Detection of gp120 protein in the patient sample indicates the patient has an HIV-1 infection, or confirms diagnosis of HIV-1 infection in the subject.

Example 3

Treatment of HIV-1 Using a Monoclonal Antibody Specific for Gp120

This example describes a particular method that can be used to treat HIV-1 infection in a human subject by administration of one or more gp120-specific human neutralizing mAbs. Although particular methods, dosages, and modes of administrations are provided, one skilled in the art will appreciate that variations can be made without substantially affecting the treatment.

Based upon the teaching disclosed herein, HIV-1 infection can be treated by administering a therapeutically effective amount of one or more of the neutralizing mAbs described herein, thereby reducing or eliminating HIV-1 infection.
Screening Subjects In particular examples, the subject is first screened to determine if they have an HIV-1 infection. Examples of methods that can be used to screen for HIV-1 infection include a combination of measuring a subject's CD4+ T cell count and the level of HIV-1 virus in serum blood levels. Additional methods using the gp120-specific mAbs described herein can also be used to screen for HIV-1 infection.

In some examples, HIV-1 testing consists of initial screening with an enzyme-linked immunosorbent assay (ELISA) to detect antibodies to HIV-1. Specimens with a nonreactive result from the initial ELISA are considered HIV-1-negative unless new exposure to an infected partner or partner of unknown HIV-1 status has occurred. Specimens with a reactive ELISA result are retested in duplicate. If the result of either duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered HIV-positive and indicative of HIV-1 infection. Specimens that are repeatedly ELISA-reactive occasionally provide an indeterminate Western blot result, which may be either an incomplete antibody response to HIV-1 in an infected person, or nonspecific reactions in an uninfected person. IFA can be used to confirm infection in these ambiguous cases. In some instances, a second specimen will be collected more than a month later and retested for subjects with indeterminate Western blot results. In additional examples, nucleic acid testing (e.g., viral RNA or proviral DNA amplification method) can also help diagnosis in certain situations.

The detection of HIV-1 in a subject's blood is indicative that the subject is infected with HIV-1 and is a candidate for receiving the therapeutic compositions disclosed herein. Moreover, detection of a CD4+ T cell count below 350 per microliter, such as 200 cells per microliter, is also indicative that the subject is likely to have an HIV-1 infection.

Pre-screening is not required prior to administration of the therapeutic compositions disclosed herein.

Pre-Treatment of Subjects

In particular examples, the subject is treated prior to administration of a therapeutic agent that includes one or more antiretroviral therapies known to those of skill in the art. However, such pre-treatment is not always required, and can be determined by a skilled clinician.

Administration of Therapeutic Compositions

Following subject selection, a therapeutically effective dose of a gp120-specific neutralizing mAb described herein (such as the N6 antibody) is administered to the subject (such as an adult human or a newborn infant either at risk for contracting HIV-1 or known to be infected with HIV-1). Additional agents, such as anti-viral agents, can also be administered to the subject simultaneously or prior to or following administration of the disclosed agents. Administration can be achieved by any method known in the art, such as oral administration, inhalation, intravenous, intramuscular, intraperitoneal, or subcutaneous.

The amount of the composition administered to prevent, reduce, inhibit, and/or treat HIV-1 or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., HIV-1) in a subject without causing a substantial cytotoxic effect in the subject. An effective amount can be readily determined by one skilled in the art, for example using routine trials establishing dose response curves. As such, these compositions may be formulated with an inert diluent or with a pharmaceutically acceptable carrier.

In one specific example, antibodies are administered at 5 mg per kg every two weeks or 10 mg per kg every two weeks depending upon the particular stage of HIV-1. In an example, the antibodies are administered continuously. In another example, antibodies or antibody fragments are administered at 50 µg per kg given twice a week for 2 to 3 weeks.

Administration of the therapeutic compositions can be taken long term (for example over a period of months or years).

Assessment

Following the administration of one or more therapies, subjects with HIV-1 can be monitored for reductions in HIV-1 levels, increases in a subject's CD4+ T cell count, or reductions in one or more clinical symptoms associated with HIV-1 disease. In particular examples, subjects are analyzed one or more times, starting 7 days following treatment. Subjects can be monitored using any method known in the art. For example, biological samples from the subject, including blood, can be obtained and alterations in HIV-1 or CD4+ T cell levels evaluated.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in HIV-1 infection, HIV-1 replication or combination thereof. A partial response may also be an increase in CD4+ T cell count such as at least 350 T cells per microliter.

It will be apparent that the precise details of the methods or compositions described may be varied or modified without departing from the spirit of the described embodiments. We claim all such modifications and variations that fall within the scope and spirit of the claims below.

The invention claimed is:

1. An isolated monoclonal antibody, comprising
a heavy chain variable region ($V_H$) comprising the amino acid sequence of SEQ ID NO: 1;
a light chain variable region ($V_L$) comprising the amino acid sequence of SEQ ID NO: 2; and
an IgG constant domain comprising M428L and N434S mutations, wherein the antibody binds to CD4 binding site on HIV-1 gp120.

2. The isolated monoclonal antibody of claim 1, wherein the isolated monoclonal antibody specifically binds to HIV-1 gp120 and neutralizes HIV-1.

3. The isolated monoclonal antibody of claim 1, wherein the isolated monoclonal antibody neutralizes at least 50% of the following HIV-1 isolates: 6540.v4.c1, 620345.c1, T278-50, 6322.V4.C1, DU422.01, X2088.c9, 6545.V4.C1, 242-14, T250-4, 7165.18, BL01.DG, HO86.8, 6471.V1.C16, 6631.V3.C10, TVI.29, TZA125.17, CAP210.E8, and DU172.17, with an inhibitory concentration ($IC_{50}$) of <50 µg/ml.

4. A method of treating an HIV-1 infection in a subject, comprising administering to the subject a therapeutically effective amount of the isolated monoclonal antibody of claim 1, thereby treating the HIV-1 infection.

5. The method of claim 4, further comprising administering to the subject an additional antibody, an additional antigen binding fragment, or a nucleic acid encoding the additional antibody or additional antigen binding fragment, wherein the additional antibody or additional antigen binding fragment specifically binds to HIV-1 Env and neutralizes HIV-1 infection.

6. The method of claim 4, wherein the subject is a human subject.

7. The method of claim 6, wherein the subject is a pregnant female.

8. The method of claim 7, further comprising administering to the subject an effective amount of an anti-retroviral therapy.

9. The method of claim 8, wherein the anti-retroviral therapy is a nucleoside analog reverse-transcriptase inhibitor, a nucleotide reverse transcriptase-inhibitor, a non-nucleoside reverse transcriptase inhibitor, a protease inhibitor, a viral entry or fusion inhibitor, a maturation inhibitor, or IL-15.

10. A pharmaceutical composition for use in treating an HIV-1 infection, comprising:
a therapeutically effective amount of the isolated monoclonal antibody of claim 1; and
a pharmaceutically acceptable carrier.

11. The pharmaceutical composition of claim 10, wherein the pharmaceutical composition is sterile and/or is in unit dosage form or a multiple thereof.

* * * * *

SEQUENCE LISTING

```
<160> NUMBER OF SEQ ID NOS: 199

<210> SEQ ID NO 1
<211> LENGTH: 122
<212> TYPE: PRT
<213> ORGANISM: homo sapiens

<400> SEQUENCE: 1

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120
```

```
<210> SEQ ID NO 2
<211> LENGTH: 103
<212> TYPE: PRT
<213> ORGANISM: homo sapiens

<400> SEQUENCE: 2

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100

<210> SEQ ID NO 3
<211> LENGTH: 122
<212> TYPE: PRT
<213> ORGANISM: homo sapiens

<400> SEQUENCE: 3

Arg Ala His Leu Val Gln Ser Gly Thr Ala Val Lys Arg Pro Gly Ala
1               5                   10                  15

Ser Val Arg Val Ser Cys Glu Thr Ser Gly Tyr Thr Phe Thr Ala His
            20                  25                  30

Ile Leu Tyr Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Gly Arg Val Thr Leu Thr Arg Asp Ile Tyr Arg Asp Thr Ala Tyr
65                  70                  75                  80

Met Asp Ile Ser Gly Leu Arg Phe Asp Asp Thr Ala Val Tyr Tyr Cys
                85                  90                  95

Ala Arg Asp Arg Ser Tyr Asp Ser Ser Trp Ala Leu Asp Ala Trp
            100                 105                 110

Gly Gln Gly Thr Thr Val Val Val Ser Ala
        115                 120

<210> SEQ ID NO 4
<211> LENGTH: 103
<212> TYPE: PRT
<213> ORGANISM: homo sapiens

<400> SEQUENCE: 4

Tyr Ile His Val Thr Gln Ser Pro Ser Ser Leu Ser Val Ser Ala Gly
1               5                   10                  15

Asp Arg Val Thr Ile Asn Cys Gln Thr Ser Gln Gly Val Gly Arg Asp
            20                  25                  30

Leu His Trp Tyr Gln His Lys Pro Gly Arg Ala Pro Lys Leu Leu Ile
        35                  40                  45

Arg His Ala Ser Ser Val Glu Asp Gly Val Pro Ser Arg Phe Ser Gly
50                  55                  60
```

```
Thr Gly Phe His Thr Ser Phe Asn Leu Thr Ile Asn Asp Leu Gln Ser
65                  70                  75                  80

Asp Asp Ile Ala Thr Tyr Tyr Cys Gln Val Leu Glu Ser Phe Gly Arg
                85                  90                  95

Gly Ser Arg Leu Asp Phe Lys
            100
```

<210> SEQ ID NO 5
<211> LENGTH: 122
<212> TYPE: PRT
<213> ORGANISM: homo sapiens

<400> SEQUENCE: 5

```
Gln Val Gln Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
                20                  25                  30

Ile Leu Phe Trp Phe Arg Gln Ala Pro Gly Arg Gly Leu Glu Trp Val
            35                  40                  45

Gly Trp Ile Lys Pro Gln Tyr Gly Ala Val Asn Phe Gly Gly Gly Phe
        50                  55                  60

Arg Asp Arg Val Thr Leu Thr Arg Asp Ile Tyr Arg Glu Ile Ala Tyr
65                  70                  75                  80

Met Asp Ile Arg Gly Leu Lys Leu Asp Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110

Gly Gln Gly Thr Thr Val Val Ala Ser Ala
        115                 120
```

<210> SEQ ID NO 6
<211> LENGTH: 103
<212> TYPE: PRT
<213> ORGANISM: homo sapiens

<400> SEQUENCE: 6

```
Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
                20                  25                  30

Leu His Trp Tyr Gln His Lys Pro Gly Arg Ala Pro Lys Leu Leu Ile
            35                  40                  45

His His Ala Ser Ser Val Glu Asp Gly Val Pro Ser Arg Phe Ser Gly
        50                  55                  60

Ser Gly Phe His Thr Ser Phe Asn Leu Thr Ile Asn Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100
```

<210> SEQ ID NO 7
<211> LENGTH: 5
<212> TYPE: PRT
<213> ORGANISM: homo sapiens

<400> SEQUENCE: 7

Ala His Ile Leu Phe
1               5

<210> SEQ ID NO 8
<211> LENGTH: 17
<212> TYPE: PRT
<213> ORGANISM: homo sapiens

<400> SEQUENCE: 8

Trp Ile Lys Pro Gln Tyr Gly Ala Val Asn Phe Gly Gly Gly Phe Arg
1               5                   10                  15

Asp

<210> SEQ ID NO 9
<211> LENGTH: 13
<212> TYPE: PRT
<213> ORGANISM: homo sapiens

<400> SEQUENCE: 9

Asp Arg Ser Tyr Gly Asp Ser Ser Trp Ala Leu Asp Ala
1               5                   10

<210> SEQ ID NO 10
<211> LENGTH: 11
<212> TYPE: PRT
<213> ORGANISM: homo sapiens

<400> SEQUENCE: 10

Gln Thr Ser Gln Gly Val Gly Ser Asp Leu His
1               5                   10

<210> SEQ ID NO 11
<211> LENGTH: 7
<212> TYPE: PRT
<213> ORGANISM: homo sapiens

<400> SEQUENCE: 11

His Thr Ser Ser Val Glu Asp
1               5

<210> SEQ ID NO 12
<211> LENGTH: 5
<212> TYPE: PRT
<213> ORGANISM: homo sapiens

<400> SEQUENCE: 12

Gln Val Leu Gln Phe
1               5

<210> SEQ ID NO 13
<211> LENGTH: 5
<212> TYPE: PRT
<213> ORGANISM: homo sapiens

<400> SEQUENCE: 13

Ala His Ile Leu Tyr
1               5

<210> SEQ ID NO 14
<211> LENGTH: 17
<212> TYPE: PRT
<213> ORGANISM: homo sapiens

<400> SEQUENCE: 14

```
Trp Ile Lys Pro Gln Tyr Gly Ala Val Asn Phe Gly Gly Gly Phe Arg
1               5                   10                  15
Gly

<210> SEQ ID NO 15
<211> LENGTH: 13
<212> TYPE: PRT
<213> ORGANISM: homo sapiens

<400> SEQUENCE: 15

Asp Arg Ser Tyr Asp Asp Ser Ser Trp Ala Leu Asp Ala
1               5                   10

<210> SEQ ID NO 16
<211> LENGTH: 11
<212> TYPE: PRT
<213> ORGANISM: homo sapiens

<400> SEQUENCE: 16

Gln Thr Ser Gln Gly Val Gly Arg Asp Leu His
1               5                   10

<210> SEQ ID NO 17
<211> LENGTH: 7
<212> TYPE: PRT
<213> ORGANISM: homo sapiens

<400> SEQUENCE: 17

His Ala Ser Ser Val Glu Asp
1               5

<210> SEQ ID NO 18
<211> LENGTH: 5
<212> TYPE: PRT
<213> ORGANISM: homo sapiens

<400> SEQUENCE: 18

Gln Val Leu Glu Ser
1               5

<210> SEQ ID NO 19
<211> LENGTH: 5
<212> TYPE: PRT
<213> ORGANISM: artificial sequence
<220> FEATURE:
<223> OTHER INFORMATION: consensus sequence
<220> FEATURE:
<221> NAME/KEY: MISC_FEATURE
<222> LOCATION: (5)..(5)
<223> OTHER INFORMATION: X is F or Y

<400> SEQUENCE: 19

Ala His Ile Leu Xaa
1               5

<210> SEQ ID NO 20
<211> LENGTH: 17
<212> TYPE: PRT
<213> ORGANISM: artificial sequence
<220> FEATURE:
<223> OTHER INFORMATION: consensus sequence
<220> FEATURE:
<221> NAME/KEY: MISC_FEATURE
<222> LOCATION: (17)..(17)
<223> OTHER INFORMATION: X is D or G

<400> SEQUENCE: 20
```

```
Trp Ile Lys Pro Gln Tyr Gly Ala Val Asn Phe Gly Gly Gly Phe Arg
1               5                   10                  15

Xaa

<210> SEQ ID NO 21
<211> LENGTH: 16
<212> TYPE: PRT
<213> ORGANISM: artificial sequence
<220> FEATURE:
<223> OTHER INFORMATION: consensus sequence
<220> FEATURE:
<221> NAME/KEY: MISC_FEATURE
<222> LOCATION: (7)..(7)
<223> OTHER INFORMATION: X is G or D

<400> SEQUENCE: 21

Ala Arg Asp Arg Ser Tyr Xaa Asp Ser Ser Trp Ala Leu Asp Ala Trp
1               5                   10                  15

<210> SEQ ID NO 22
<211> LENGTH: 11
<212> TYPE: PRT
<213> ORGANISM: artificial sequence
<220> FEATURE:
<223> OTHER INFORMATION: consensus sequence
<220> FEATURE:
<221> NAME/KEY: MISC_FEATURE
<222> LOCATION: (8)..(8)
<223> OTHER INFORMATION: X is G or S

<400> SEQUENCE: 22

Gln Thr Ser Gln Gly Val Gly Xaa Asp Leu His
1               5                   10

<210> SEQ ID NO 23
<211> LENGTH: 7
<212> TYPE: PRT
<213> ORGANISM: artificial sequence
<220> FEATURE:
<223> OTHER INFORMATION: consensus sequence
<220> FEATURE:
<221> NAME/KEY: MISC_FEATURE
<222> LOCATION: (2)..(2)
<223> OTHER INFORMATION: X is A or T

<400> SEQUENCE: 23

His Xaa Ser Ser Val Glu Asp
1               5

<210> SEQ ID NO 24
<211> LENGTH: 6
<212> TYPE: PRT
<213> ORGANISM: artificial sequence
<220> FEATURE:
<223> OTHER INFORMATION: consensus sequence
<220> FEATURE:
<221> NAME/KEY: MISC_FEATURE
<222> LOCATION: (4)..(4)
<223> OTHER INFORMATION: X is E or Q
<220> FEATURE:
<221> NAME/KEY: MISC_FEATURE
<222> LOCATION: (5)..(5)
<223> OTHER INFORMATION: X is S or F

<400> SEQUENCE: 24

Gln Val Leu Xaa Xaa Phe
1               5
```

```
<210> SEQ ID NO 25
<211> LENGTH: 15
<212> TYPE: PRT
<213> ORGANISM: artificial sequence
<220> FEATURE:
<223> OTHER INFORMATION: CAR sequence

<400> SEQUENCE: 25

Gly Gly Gly Gly Ser Gly Gly Gly Ser Gly Gly Gly Gly Ser
1               5                   10                  15

<210> SEQ ID NO 26
<211> LENGTH: 22
<212> TYPE: PRT
<213> ORGANISM: artificial sequence
<220> FEATURE:
<223> OTHER INFORMATION: CAR sequence

<400> SEQUENCE: 26

Leu Leu Val Thr Ser Leu Leu Leu Cys Glu Leu Pro His Pro Ala Phe
1               5                   10                  15

Leu Leu Ile Pro Asp Thr
            20

<210> SEQ ID NO 27
<211> LENGTH: 236
<212> TYPE: PRT
<213> ORGANISM: artificial sequence
<220> FEATURE:
<223> OTHER INFORMATION: CAR sequence

<400> SEQUENCE: 27

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

```
Ser Leu Ser Leu Ser Pro Gly Lys Lys Asp Pro Lys
225                 230                 235
```

<210> SEQ ID NO 28
<211> LENGTH: 69
<212> TYPE: PRT
<213> ORGANISM: artificial sequence
<220> FEATURE:
<223> OTHER INFORMATION: CAR sequence

<400> SEQUENCE: 28

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65
```

<210> SEQ ID NO 29
<211> LENGTH: 67
<212> TYPE: PRT
<213> ORGANISM: artificial sequence
<220> FEATURE:
<223> OTHER INFORMATION: CAR sequence

<400> SEQUENCE: 29

```
Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
        50                  55                  60

Trp Val Arg
65
```

<210> SEQ ID NO 30
<211> LENGTH: 112
<212> TYPE: PRT
<213> ORGANISM: artificial sequence
<220> FEATURE:
<223> OTHER INFORMATION: CAR sequence

<400> SEQUENCE: 30

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80
```

```
Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 31
<211> LENGTH: 84
<212> TYPE: PRT
<213> ORGANISM: artificial sequence
<220> FEATURE:
<223> OTHER INFORMATION: CAR sequence

<400> SEQUENCE: 31

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg
```

<210> SEQ ID NO 32
<211> LENGTH: 40
<212> TYPE: PRT
<213> ORGANISM: artificial sequence
<220> FEATURE:
<223> OTHER INFORMATION: CAR sequence

<400> SEQUENCE: 32

```
Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40
```

<210> SEQ ID NO 33
<211> LENGTH: 42
<212> TYPE: PRT
<213> ORGANISM: artificial sequence
<220> FEATURE:
<223> OTHER INFORMATION: CAR sequence

<400> SEQUENCE: 33

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 34
<211> LENGTH: 47
<212> TYPE: PRT
<213> ORGANISM: artificial sequence
<220> FEATURE:
<223> OTHER INFORMATION: CAR sequence -continued

```
<400> SEQUENCE: 34

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
                20                  25                  30

Cys Ser Cys Arg Phe Pro Glu Glu Glu Gly Gly Cys Glu Leu
            35                  40                  45

<210> SEQ ID NO 35
<211> LENGTH: 856
<212> TYPE: PRT
<213> ORGANISM: human immunodeficiency virus

<400> SEQUENCE: 35

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
                35                  40                  45

Thr Thr Thr Leu Phe Cys Ala Ser Asp Ala Lys Ala Tyr Asp Thr Glu
            50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
                180                 185                 190

Leu Thr Ser Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
            210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
                260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Asn Thr Arg
            290                 295                 300

Lys Arg Ile Arg Ile Gln Arg Gly Pro Gly Arg Ala Phe Val Thr Ile
305                 310                 315                 320
```

-continued

```
Gly Lys Ile Gly Asn Met Arg Gln Ala His Cys Asn Ile Ser Arg Ala
                325                 330                 335
Lys Trp Asn Asn Thr Leu Lys Gln Ile Ala Ser Lys Leu Arg Glu Gln
            340                 345                 350
Phe Gly Asn Asn Lys Thr Ile Ile Phe Lys Gln Ser Ser Gly Gly Asp
        355                 360                 365
Pro Glu Ile Val Thr His Ser Phe Asn Cys Gly Gly Glu Phe Phe Tyr
    370                 375                 380
Cys Asn Ser Thr Gln Leu Phe Asn Ser Thr Trp Phe Asn Ser Thr Trp
385                 390                 395                 400
Ser Thr Glu Gly Ser Asn Asn Thr Glu Gly Ser Asp Thr Ile Thr Leu
                405                 410                 415
Pro Cys Arg Ile Lys Gln Ile Ile Asn Met Trp Gln Lys Val Gly Lys
            420                 425                 430
Ala Met Tyr Ala Pro Pro Ile Ser Gly Gln Ile Arg Cys Ser Ser Asn
        435                 440                 445
Ile Thr Gly Leu Leu Leu Thr Arg Asp Gly Gly Asn Ser Asn Asn Glu
    450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
                485                 490                 495
Ala Pro Thr Lys Ala Lys Arg Arg Val Gln Arg Glu Lys Arg Ala
            500                 505                 510
Val Gly Ile Gly Ala Leu Phe Leu Gly Phe Leu Gly Ala Ala Gly Ser
        515                 520                 525
Thr Met Gly Ala Ala Ser Met Thr Leu Thr Val Gln Ala Arg Gln Leu
    530                 535                 540
Leu Ser Gly Ile Val Gln Gln Gln Asn Asn Leu Leu Arg Ala Ile Glu
545                 550                 555                 560
Ala Gln Gln His Leu Leu Gln Leu Thr Val Trp Gly Ile Lys Gln Leu
                565                 570                 575
Gln Ala Arg Ile Leu Ala Val Glu Arg Tyr Leu Lys Asp Gln Gln Leu
            580                 585                 590
Leu Gly Ile Trp Gly Cys Ser Gly Lys Leu Ile Cys Thr Thr Ala Val
        595                 600                 605
Pro Trp Asn Ala Ser Trp Ser Asn Lys Ser Leu Glu Gln Ile Trp Asn
    610                 615                 620
His Thr Thr Trp Met Glu Trp Asp Arg Glu Ile Asn Asn Tyr Thr Ser
625                 630                 635                 640
Leu Ile His Ser Leu Ile Glu Glu Ser Gln Asn Gln Gln Glu Lys Asn
                645                 650                 655
Glu Gln Glu Leu Leu Glu Leu Asp Lys Trp Ala Ser Leu Trp Asn Trp
            660                 665                 670
Phe Asn Ile Thr Asn Trp Leu Trp Tyr Ile Lys Leu Phe Ile Met Ile
        675                 680                 685
Val Gly Gly Leu Val Gly Leu Arg Ile Val Phe Ala Val Leu Ser Ile
    690                 695                 700
Val Asn Arg Val Arg Gln Gly Tyr Ser Pro Leu Ser Phe Gln Thr His
705                 710                 715                 720
Leu Pro Thr Pro Arg Gly Pro Asp Arg Pro Glu Gly Ile Glu Glu Glu
                725                 730                 735
Gly Gly Glu Arg Asp Arg Asp Arg Ser Ile Arg Leu Val Asn Gly Ser
```

```
                    740                 745                 750
Leu Ala Leu Ile Trp Asp Asp Leu Arg Ser Leu Cys Leu Phe Ser Tyr
                755                 760                 765

His Arg Leu Arg Asp Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
                835                 840                 845

Gln Gly Leu Glu Arg Ile Leu Leu
    850                 855

<210> SEQ ID NO 36
<211> LENGTH: 366
<212> TYPE: DNA
<213> ORGANISM: homo sapiens

<400> SEQUENCE: 36
cgagcgcacc tggtacaatc agggactgcg atgaagaaac cgggggcctc agtaagagtc     60
tcctgccaga cctctggata cacctttacc gcccacatat tattttggtt ccgacaggcc    120
cccgggcgag gacttgagtg ggtggggtgg atcaagccac aatatggggc cgtgaatttt    180
ggtggtggtt ttcgggacag ggtcacattg actcgagacg tatatagaga gattgcgtac    240
atggacatca gaggccttaa acctgacgac acggccgtct attactgtgc gagagaccgt    300
tcctatggcg actcctcttg ggccttagat gcctgggac agggaacgac ggtcgtcgtc    360
tccgcg                                                              366

<210> SEQ ID NO 37
<211> LENGTH: 309
<212> TYPE: DNA
<213> ORGANISM: homo sapiens

<400> SEQUENCE: 37
tacatccacg tgacccagtc tccgtcctcc ctgtctgtgt ctattggaga cagagtcacc     60
atcaattgcc agacgagtca gggtgttggc agtgacctac attggtatca acacaaaccg    120
gggagagccc ctaaactctt gatccaccat acctcttctg tggaagacgg tgtcccctca    180
agattcagcg gctctggatt tcacacatct tttaatctga ccatcagcga cctacaggct    240
gacgacattg ccacatatta ctgtcaagtt ttacaatttt cggccgagg gagtcgactc    300 catattaaa                                                           309

<210> SEQ ID NO 38
<211> LENGTH: 366
<212> TYPE: DNA
<213> ORGANISM: homo sapiens

<400> SEQUENCE: 38
cgagcgcacc tggtacaatc agggactgcg gtgaagagac cgggggcctc agtaagggtc     60
tcctgcgaga cttctggata cacctttacc gcccacatat tatactggtt ccgacaggcc    120
cccgggcgag ggcttgagtg ggtggggtgg atcaagccac aatacggtgc cgtgaacttt    180
```

```
gggggtggtt ttcggggcag ggtcacattg acgcgagaca tatatagaga tactgcatat    240
atggacatca gtggcctgag atttgacgac acggccgtct actattgtgc gagagaccgt    300
tcttatgacg actcttcttg ggccttagat gcctggggcc agggaacgac ggtcgtcgtc    360
tccgcg                                                               366

<210> SEQ ID NO 39
<211> LENGTH: 309
<212> TYPE: DNA
<213> ORGANISM: homo sapiens

<400> SEQUENCE: 39
tacatccacg tgacccagtc tccgtcctcc ctgtctgtgt ctgctgggga cagagtcacc     60
atcaattgcc agacgagtca gggtgttggc cgtgacctac attggtatca acacaaaccg    120
gggagagccc ctaaactcct gatccgccac gcctcttctg tggaggacgg tgtcccgtca    180
agattcagtg gcactggatt tcacacatct tttaatttga ccatcaacga cctgcagtct    240
gacgacattg ccacatatta ctgtcaggtg ttagaatctt tcggccgagg gagtcgactg    300
gatttttaaa                                                           309

<210> SEQ ID NO 40
<211> LENGTH: 366
<212> TYPE: DNA
<213> ORGANISM: homo sapiens

<400> SEQUENCE: 40
caggtgcagc tggtacaatc agggactgcg atgaagaaac cggggggcctc agtaagggtc     60 tcctgccaga cttctggata cacctttacc gcccacatat tattttggtt ccgacaggcc    120
cccgggcgag ggcttgagtg ggtgggatgg atcaagccac aatacggggc cgtgaatttt    180
ggtggtggtt ttcgggacag ggtcacattg actcgagaca tatatagaga gattgcatac    240
atggacatca gaggccttaa acttgacgac acggccgtct attactgtgc gagagaccgt    300
tcctatggcg actcctcttg ggccttagat gcctggggac agggaacgac ggtcgtcgcc    360
tccgcg                                                               366

<210> SEQ ID NO 41
<211> LENGTH: 309
<212> TYPE: DNA
<213> ORGANISM: homo sapiens

<400> SEQUENCE: 41
tacatccacg tgacccagtc tccgtcctcc ctgtctgtgt ctattggaga cagagtcacc     60
atcaattgcc agacgagtca gggtgttggc agtgacctac attggtatca acacaaaccg    120
gggagagccc ctaaactctt gatccaccat gcctcttctg tggaggacgg tgtcccgtca    180
agattcagtg gctctggatt tcacacatct tttaatctga ccatcaacga cctacaggct    240
gacgacattg ccacatatta ctgtcaggtt ttacaatttt tcggccgagg gagtcgactc    300
catattaaa                                                            309

<210> SEQ ID NO 42
<211> LENGTH: 121
<212> TYPE: PRT
<213> ORGANISM: artificial sequence
<220> FEATURE:
<223> OTHER INFORMATION: variant antibody sequence

<400> SEQUENCE: 42
```

```
Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Tyr Gly Ala Val Asn Tyr Ala Arg Pro Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 43
<211> LENGTH: 121
<212> TYPE: PRT
<213> ORGANISM: artificial sequence
<220> FEATURE:
<223> OTHER INFORMATION: variant antibody sequence

<400> SEQUENCE: 43

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Gly Gly Leu
    50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 44
<211> LENGTH: 122
<212> TYPE: PRT
<213> ORGANISM: artificial sequence
<220> FEATURE:
<223> OTHER INFORMATION: variant antibody sequence

<400> SEQUENCE: 44

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
```

-continued

```
                  50                  55                  60
Gln Gly Arg Val Thr Met Thr Arg Asp Val Tyr Ser Asp Thr Ala Phe
 65                  70                  75                  80

Leu Glu Leu Arg Ser Leu Thr Val Asp Thr Ala Val Tyr Phe Cys
                 85                  90                  95

Ala Arg Asp Arg Ser Tyr Gly Asp Ser Ser Trp Ala Leu Asp Ala Trp
                100                 105                 110

Gly Arg Gly Thr Pro Val Ile Val Ser Ser
            115                 120

<210> SEQ ID NO 45
<211> LENGTH: 122
<212> TYPE: PRT
<213> ORGANISM: artificial sequence
<220> FEATURE:
<223> OTHER INFORMATION: variant antibody sequence

<400> SEQUENCE: 45

Gln Val Arg Leu Ser Gln Ser Gly Gly Gln Met Lys Lys Pro Gly Asp
 1               5                  10                  15

Ser Met Arg Ile Ser Cys Arg Ala Ser Gly Tyr Glu Phe Ile Asn Cys
                20                  25                  30

Pro Ile Asn Trp Ile Arg Leu Ala Pro Gly Lys Arg Pro Glu Trp Met
                35                  40                  45

Gly Trp Met Lys Pro Arg His Gly Ala Val Ser Tyr Ala Arg Gln Leu
            50                  55                  60

Gln Gly Arg Val Thr Met Thr Arg Asp Met Tyr Ser Glu Thr Ala Phe
 65                  70                  75                  80

Leu Glu Leu Arg Ser Leu Thr Ser Asp Asp Thr Ala Val Tyr Phe Cys
                 85                  90                  95

Ala Arg Asp Arg Ser Tyr Gly Asp Ser Ser Trp Ala Leu Asp Ala Trp
                100                 105                 110

Gly Gln Gly Thr Pro Val Thr Val Ser Ser
            115                 120

<210> SEQ ID NO 46
<211> LENGTH: 122
<212> TYPE: PRT
<213> ORGANISM: artificial sequence
<220> FEATURE:
<223> OTHER INFORMATION: variant antibody sequence

<400> SEQUENCE: 46

Gln Val Gln Leu Val Gln Ser Gly Thr Gln Met Lys Glu Pro Gly Ala
 1               5                  10                  15

Ser Val Thr Ile Ser Cys Val Thr Ser Gly Tyr Glu Phe Val Glu Ile
                20                  25                  30

Leu Ile Asn Trp Val Arg Gln Val Pro Gly Arg Gly Leu Glu Trp Met
                35                  40                  45

Gly Trp Met Asn Pro Arg Gly Gly Val Asn Tyr Ala Arg Gln Phe
            50                  55                  60

Gln Gly Lys Val Thr Met Thr Arg Asp Val Tyr Arg Asp Thr Ala Tyr
 65                  70                  75                  80

Leu Thr Leu Ser Gly Leu Thr Ser Gly Asp Thr Ala Lys Tyr Phe Cys
                 85                  90                  95

Ala Arg Asp Arg Ser Tyr Gly Asp Ser Ser Trp Ala Leu Asp Ala Trp
                100                 105                 110
```

```
Gly Gln Gly Thr Leu Val Ile Val Ser Pro
        115                 120
```

<210> SEQ ID NO 47
<211> LENGTH: 122
<212> TYPE: PRT
<213> ORGANISM: artificial sequence
<220> FEATURE:
<223> OTHER INFORMATION: variant antibody sequence

<400> SEQUENCE: 47

```
Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Gly Gly Ala Val Asn Phe Gly Gly Gly Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120
```

<210> SEQ ID NO 48
<211> LENGTH: 122
<212> TYPE: PRT
<213> ORGANISM: artificial sequence
<220> FEATURE:
<223> OTHER INFORMATION: variant antibody sequence

<400> SEQUENCE: 48

```
Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Ala Arg Pro Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120
```

<210> SEQ ID NO 49
<211> LENGTH: 125
<212> TYPE: PRT
<213> ORGANISM: artificial sequence
<220> FEATURE:
<223> OTHER INFORMATION: variant antibody sequence -continued

<400> SEQUENCE: 49

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
                85                  90                  95

Ala Arg Gly Lys Tyr Cys Thr Ala Arg Asp Tyr Tyr Asn Trp Ala Leu
            100                 105                 110

Asp Ala Trp Gly Gln Gly Thr Thr Val Val Val Ser Ala
        115                 120                 125

<210> SEQ ID NO 50
<211> LENGTH: 132
<212> TYPE: PRT
<213> ORGANISM: artificial sequence
<220> FEATURE:
<223> OTHER INFORMATION: variant antibody sequence

<400> SEQUENCE: 50

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
                85                  90                  95

Ala Arg Gly Arg Ser Cys Cys Gly Gly Arg Arg His Cys Asn Gly Ala
            100                 105                 110

Asp Cys Phe Asn Trp Ala Leu Asp Ala Trp Gly Gln Gly Thr Thr Val
        115                 120                 125

Val Val Ser Ala
    130

<210> SEQ ID NO 51
<211> LENGTH: 122
<212> TYPE: PRT
<213> ORGANISM: artificial sequence
<220> FEATURE:
<223> OTHER INFORMATION: variant antibody sequence

<400> SEQUENCE: 51

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
            35                  40                  45

Gly Trp Ile Lys Pro Lys Phe Gly Ala Val Asn Tyr Ala His Ser Phe
 50                  55                  60

Gln Gly Arg Val Thr Leu Thr Arg Asp Val Tyr Arg Glu Ile Ala Tyr
 65                  70                  75                  80

Met Asp Ile Arg Gly Leu Lys Pro Asp Asp Thr Ala Val Tyr Tyr Cys
                 85                  90                  95

Ala Arg Asp Arg Ser Tyr Gly Asp Ser Ser Trp Ala Leu Asp Ala Trp
                100                 105                 110

Gly Gln Gly Thr Thr Val Val Val Ser Ala
            115                 120

<210> SEQ ID NO 52
<211> LENGTH: 122
<212> TYPE: PRT
<213> ORGANISM: artificial sequence
<220> FEATURE:
<223> OTHER INFORMATION: variant antibody sequence

<400> SEQUENCE: 52

Arg Ala His Leu Val Gln Ser Gly Thr Ala Met Lys Lys Pro Gly Ala
 1               5                  10                  15

Ser Val Arg Val Ser Cys Gln Thr Ser Gly Tyr Thr Phe Thr Ala His
                 20                  25                  30

Ile Leu Phe Trp Phe Arg Gln Ala Pro Gly Arg Gly Leu Glu Trp Val
            35                  40                  45

Gly Trp Ile Lys Pro Gln Tyr Gly Ala Val Asn Phe Gly Gly Gly Phe
 50                  55                  60

Arg Asp Arg Val Thr Leu Thr Arg Asp Val Tyr Arg Glu Ile Ala Tyr
 65                  70                  75                  80

Met Asp Ile Arg Gly Leu Lys Pro Asp Asp Thr Ala Val Tyr Tyr Cys
                 85                  90                  95

Ala Arg Asp Arg Leu Tyr Asp Gly Ser Ser Trp Arg Leu Asp Pro Trp
                100                 105                 110

Gly Gln Gly Thr Thr Val Val Val Ser Ala
            115                 120

<210> SEQ ID NO 53
<211> LENGTH: 122
<212> TYPE: PRT
<213> ORGANISM: artificial sequence
<220> FEATURE:
<223> OTHER INFORMATION: variant antibody sequence

<400> SEQUENCE: 53

Ser Gln Arg Leu Val Gln Ser Gly Pro Gln Val Arg Lys Pro Gly Ser
 1               5                  10                  15

Ser Val Arg Ile Ser Cys Glu Thr Ser Gly Tyr Thr Phe Asn Ala His
                 20                  25                  30

Ile Leu Phe Trp Phe Arg Gln Ala Pro Gly Arg Gly Leu Glu Trp Val
            35                  40                  45

Gly Trp Ile Lys Pro Gln Tyr Gly Ala Val Asn Phe Gly Gly Gly Phe
 50                  55                  60

Arg Asp Arg Val Thr Leu Thr Arg Asp Val Tyr Arg Glu Ile Ala Tyr
 65                  70                  75                  80

Met Asp Ile Arg Gly Leu Lys Pro Asp Asp Thr Ala Val Tyr Tyr Cys
                 85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120

<210> SEQ ID NO 54
<211> LENGTH: 122
<212> TYPE: PRT
<213> ORGANISM: artificial sequence
<220> FEATURE:
<223> OTHER INFORMATION: variant antibody sequence

<400> SEQUENCE: 54

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Ser Phe Glu Trp Met
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120

<210> SEQ ID NO 55
<211> LENGTH: 122
<212> TYPE: PRT
<213> ORGANISM: artificial sequence
<220> FEATURE:
<223> OTHER INFORMATION: variant antibody sequence

<400> SEQUENCE: 55

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Ile Thr Leu Thr Arg Asp Ile Tyr Arg Glu Thr Ala Phe
65                  70                  75                  80

Leu Asp Leu Thr Gly Leu Arg Phe Asp Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120

<210> SEQ ID NO 56
<211> LENGTH: 122
<212> TYPE: PRT

<213> ORGANISM: artificial sequence
<220> FEATURE:
<223> OTHER INFORMATION: variant antibody sequence

<400> SEQUENCE: 56

Arg Ala His Leu Val Gln Ser Gly Thr Ala Val Lys Arg Pro Gly Ala
1               5                   10                  15

Ser Val Arg Val Ser Cys Glu Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Val Tyr Arg Glu Ile Ala Tyr
65                  70                  75                  80

Met Asp Ile Arg Gly Leu Lys Pro Asp Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120

<210> SEQ ID NO 57
<211> LENGTH: 122
<212> TYPE: PRT
<213> ORGANISM: artificial sequence
<220> FEATURE:
<223> OTHER INFORMATION: variant antibody sequence

<400> SEQUENCE: 57

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Ile Tyr Arg Asp Thr Ala Tyr
65                  70                  75                  80

Met Asp Ile Ser Gly Leu Arg Phe Asp Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120

<210> SEQ ID NO 58
<211> LENGTH: 103
<212> TYPE: PRT
<213> ORGANISM: artificial sequence
<220> FEATURE:
<223> OTHER INFORMATION: variant antibody sequence

<400> SEQUENCE: 58

Tyr Ile His Val Thr Gln Ser Pro Ser Ser Leu Ser Val Ser Ala Gly
1               5                   10                  15

Asp Arg Val Thr Ile Asn Cys Gln Thr Ser Gln Gly Val Gly Ser Asp
            20                  25                  30

```
Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100

<210> SEQ ID NO 59
<211> LENGTH: 103
<212> TYPE: PRT
<213> ORGANISM: artificial sequence
<220> FEATURE:
<223> OTHER INFORMATION: variant antibody sequence

<400> SEQUENCE: 59

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

Arg His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100

<210> SEQ ID NO 60
<211> LENGTH: 103
<212> TYPE: PRT
<213> ORGANISM: artificial sequence
<220> FEATURE:
<223> OTHER INFORMATION: variant antibody sequence

<400> SEQUENCE: 60

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Thr Gly Phe His Thr Ser Phe Asn Leu Thr Ile Asn Asp Leu Gln Ser
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100
```

```
<210> SEQ ID NO 61
<211> LENGTH: 103
<212> TYPE: PRT
<213> ORGANISM: artificial sequence
<220> FEATURE:
<223> OTHER INFORMATION: variant antibody sequence

<400> SEQUENCE: 61

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu Asp Phe Lys
            100

<210> SEQ ID NO 62
<211> LENGTH: 103
<212> TYPE: PRT
<213> ORGANISM: artificial sequence
<220> FEATURE:
<223> OTHER INFORMATION: variant antibody sequence

<400> SEQUENCE: 62

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Arg Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100

<210> SEQ ID NO 63
<211> LENGTH: 103
<212> TYPE: PRT
<213> ORGANISM: artificial sequence
<220> FEATURE:
<223> OTHER INFORMATION: variant antibody sequence

<400> SEQUENCE: 63

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45
```

```
His His Ala Ser Ser Val Glu Asp Gly Val Pro Ser Arg Phe Ser Gly
            50                  55                  60

Ser Gly Phe His Thr Ser Phe Asn Leu Thr Ile Ser Asp Leu Gln Ala
 65                  70                  75                  80

Asp Asp Ile Ala Thr Tyr Tyr Cys Gln Val Leu Gln Phe Phe Gly Arg
                 85                  90                  95

Gly Ser Arg Leu His Ile Lys
            100

<210> SEQ ID NO 64
<211> LENGTH: 103
<212> TYPE: PRT
<213> ORGANISM: artificial sequence
<220> FEATURE:
<223> OTHER INFORMATION: variant antibody sequence

<400> SEQUENCE: 64

Tyr Ile His Val Thr Gln Ser Pro Ser Ser Leu Ser Val Ser Ile Gly
 1               5                  10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
            35                  40                  45

His His Thr Ser Ser Val Glu Asp Gly Val Pro Ser Arg Phe Ser Gly
            50                  55                  60

Ser Gly Phe His Thr Ser Phe Asn Leu Thr Ile Ser Asp Leu Gln Ala
 65                  70                  75                  80

Asp Asp Ile Ala Thr Tyr Tyr Cys Gln Val Leu Glu Ser Phe Gly Arg
                 85                  90                  95

Gly Ser Arg Leu His Ile Lys
            100

<210> SEQ ID NO 65
<211> LENGTH: 24
<212> TYPE: DNA
<213> ORGANISM: artificial sequence
<220> FEATURE:
<223> OTHER INFORMATION: oligonucleotide primer

<400> SEQUENCE: 65
ttgctacttg tgattgctcc atgt                                          24

<210> SEQ ID NO 66
<211> LENGTH: 25
<212> TYPE: DNA
<213> ORGANISM: artificial sequence
<220> FEATURE:
<223> OTHER INFORMATION: oligonucleotide primer

<400> SEQUENCE: 66
tagagccctg gaagcatcca ggaag                                         25

<210> SEQ ID NO 67
<211> LENGTH: 24
<212> TYPE: DNA
<213> ORGANISM: artificial sequence
<220> FEATURE:
<223> OTHER INFORMATION: oligonucleotide primer

<400> SEQUENCE: 67
ttgctacttg tgattgctcc atgt                                          24
```

-continued

<210> SEQ ID NO 68
<211> LENGTH: 31
<212> TYPE: DNA
<213> ORGANISM: artificial sequence
<220> FEATURE:
<223> OTHER INFORMATION: oligonucleotide primer

<400> SEQUENCE: 68
caccttaggc atctcctatg gcaggaagaa g    31

<210> SEQ ID NO 69
<211> LENGTH: 23
<212> TYPE: DNA
<213> ORGANISM: artificial sequence
<220> FEATURE:
<223> OTHER INFORMATION: oligonucleotide primer

<400> SEQUENCE: 69
gtctcgagat actgctccca ccc    23

<210> SEQ ID NO 70
<211> LENGTH: 18
<212> TYPE: DNA
<213> ORGANISM: artificial sequence
<220> FEATURE:
<223> OTHER INFORMATION: oligonucleotide primer

<400> SEQUENCE: 70
caccatggca ggaagaag    18

<210> SEQ ID NO 71
<211> LENGTH: 23
<212> TYPE: DNA
<213> ORGANISM: artificial sequence
<220> FEATURE:
<223> OTHER INFORMATION: oligonucleotide primer

<400> SEQUENCE: 71
gtctcgagat actgctccca ccc    23

<210> SEQ ID NO 72
<211> LENGTH: 8
<212> TYPE: PRT
<213> ORGANISM: artificial sequence
<220> FEATURE:
<223> OTHER INFORMATION: synthetic peptide

<400> SEQUENCE: 72

Ala Phe Ile Leu Met Tyr Trp Val
1               5

<210> SEQ ID NO 73
<211> LENGTH: 121
<212> TYPE: PRT
<213> ORGANISM: homo sapiens

<400> SEQUENCE: 73

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
            20                  25                  30

Thr Leu Asn Trp Ile Arg Leu Ala Pro Gly Lys Arg Pro Glu Trp Met
        35                  40                  45

Gly Trp Leu Lys Pro Arg Gly Gly Ala Val Asn Tyr Ala Arg Pro Leu
            50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                    85                  90                  95

Thr Arg Gly Lys Asn Cys Asp Tyr Asn Trp Asp Phe Glu His Trp Gly
                100                 105                 110

Arg Gly Thr Pro Val Ile Val Ser Ser
            115                 120

<210> SEQ ID NO 74
<211> LENGTH: 104
<212> TYPE: PRT
<213> ORGANISM: homo sapiens

<400> SEQUENCE: 74

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys Arg
            100

<210> SEQ ID NO 75
<211> LENGTH: 121
<212> TYPE: PRT
<213> ORGANISM: homo sapiens

<400> SEQUENCE: 75

Gln Arg Leu Val Gln Ser Gly Pro Gln Val Arg Lys Pro Gly Ser Ser
1               5                   10                  15

Val Arg Ile Ser Cys Glu Thr Ser Gly Tyr Thr Phe Asn Ala Tyr Ile
            20                  25                  30

Leu His Trp Phe Arg Gln Ala Pro Gly Arg Ser Phe Glu Trp Met Gly
        35                  40                  45

Trp Ile Lys Pro Lys Phe Gly Ala Val Asn Tyr Ala His Ser Phe Gln
    50                  55                  60

Gly Arg Ile Thr Leu Thr Arg Asp Ile Tyr Arg Glu Thr Ala Phe Leu
65                  70                  75                  80

Asp Leu Thr Gly Leu Arg Phe Asp Asp Thr Ala Val Tyr Tyr Cys Ala
                85                  90                  95

Arg Asp Arg Leu Tyr Asp Gly Ser Ser Trp Arg Leu Asp Pro Trp Gly
            100                 105                 110

Gln Gly Thr Arg Val Val Val Ser Ser
            115                 120

<210> SEQ ID NO 76
<211> LENGTH: 103

```
<212> TYPE: PRT
<213> ORGANISM: homo sapiens

<400> SEQUENCE: 76

Phe Ala Leu Met Thr Gln Ser Pro Ala Thr Leu Ala Val Ser Val Gly
 1               5                  10                  15

Asp Arg Val Thr Ile Thr Cys Arg Ala Ser Gln Gly Ile Gly Ser Asp
             20                  25                  30

Leu His Trp Tyr Gln Gln Lys Pro Gly Arg Pro Pro Lys Ile Leu Ile
         35                  40                  45

His His Ala Ser Ala Arg Glu Glu Gly Val Pro Ser Arg Phe Gly Gly
     50                  55                  60

Ser Gly Ser His Thr Ser Phe Ile Phe Thr Ile Asn Asp Leu Gln Leu
 65                  70                  75                  80

Asp Asp Val Ala Thr Tyr Tyr Cys Gln Val Leu Glu Ser Phe Gly Gln
                 85                  90                  95

Gly Thr Arg Leu Asp Ile Asn
            100

<210> SEQ ID NO 77
<211> LENGTH: 122
<212> TYPE: PRT
<213> ORGANISM: homo sapiens

<400> SEQUENCE: 77

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ala Tyr Cys Gly Gly Asp Cys Tyr Asn Trp Phe Asp Ser Trp
            100                 105                 110

Gly Gln Gly Thr Leu Val Thr Val Ser Ser
        115                 120

<210> SEQ ID NO 78
<211> LENGTH: 107
<212> TYPE: PRT
<213> ORGANISM: homo sapiens

<400> SEQUENCE: 78

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
```

```
                65                  70                  75                  80
Glu Asp Ile Ala Thr Tyr Tyr Cys Gln Gln Tyr Asp Asn Leu Pro Ile
                    85                  90                  95

Thr Phe Gly Gln Gly Thr Arg Leu Glu Ile Lys
            100                 105

<210> SEQ ID NO 79
<211> LENGTH: 122
<212> TYPE: PRT
<213> ORGANISM: homo sapiens

<400> SEQUENCE: 79

Arg Gly His Leu Val Gln Ser Gly Thr Glu Val Lys Lys Pro Gly Ala
1               5                   10                  15

Ser Val Arg Val Ser Cys Glu Thr Ser Gly Tyr Thr Phe Thr Ala Tyr
                20                  25                  30

Ile Leu His Trp Phe Arg Gln Ala Pro Gly Arg Gly Leu Glu Trp Met
            35                  40                  45

Gly Trp Ile Lys Pro Lys Tyr Gly Ala Val Asn Tyr Ala His Ala Phe
    50                  55                  60

Gln Gly Arg Val Thr Leu Thr Arg Asp Ile Tyr Arg Asp Thr Ala Tyr
65                  70                  75                  80

Met Asp Leu Ser Gly Leu Arg Phe Asp Asp Thr Ala Val Tyr Tyr Cys
                85                  90                  95

Ala Arg Asp Arg Val Tyr Asp Asp Ser Ser Trp Gln Leu Asp Pro Trp
            100                 105                 110

Gly Gln Gly Thr Ser Val Ile Val Ser Ser
        115                 120

<210> SEQ ID NO 80
<211> LENGTH: 121
<212> TYPE: PRT
<213> ORGANISM: homo sapiens

<400> SEQUENCE: 80

Arg Gly His Leu Val Gln Ser Gly Thr Glu Val Lys Lys Pro Gly Ala
1               5                   10                  15

Ser Val Arg Val Ser Cys Glu Thr Ser Gly Tyr Thr Phe Thr Ala His
                20                  25                  30

Ile Leu His Trp Phe Arg Gln Ala Pro Gly Arg Gly Leu Glu Trp Met
            35                  40                  45

Gly Trp Ile Lys Pro Lys Tyr Gly Ala Val Asn Tyr Ala His Ala Phe
    50                  55                  60

Gln Gly Arg Val Thr Leu Thr Arg Asp Ile Tyr Arg Asp Thr Ala Tyr
65                  70                  75                  80

Met Asp Leu Ser Gly Leu Arg Phe Asp Asp Thr Ala Val Tyr Tyr Cys
                85                  90                  95

Ala Arg Asp Arg Val Tyr Asp Asp Ser Ser Trp Gln Leu Asp Pro Trp
            100                 105                 110

Gly Gln Gly Thr Ser Val Ile Val Ser
        115                 120

<210> SEQ ID NO 81
<211> LENGTH: 122
<212> TYPE: PRT
<213> ORGANISM: homo sapiens

<400> SEQUENCE: 81
```

```
Arg Ala His Leu Val Gln Ser Gly Thr Ala Lys Lys Pro Gly Ala
1               5                   10                  15

Ser Val Arg Val Ser Cys Gln Thr Ser Gly Tyr Thr Phe Thr Ala His
            20                  25                  30

Ile Leu Tyr Trp Phe Arg Gln Ala Pro Gly Arg Gly Leu Glu Trp Val
                35                  40                  45

Gly Trp Ile Lys Pro Gln Tyr Gly Ala Val Asn Phe Gly Gly Gly Phe
    50                  55                  60

Arg Gly Arg Val Thr Leu Thr Arg Asp Ile Tyr Arg Asp Thr Ala Tyr
65                  70                  75                  80

Met Asp Ile Ser Gly Leu Arg Phe Asp Asp Thr Ala Val Tyr Tyr Cys
                85                  90                  95

Ala Arg Asp Arg Ser Tyr Asp Asp Ser Ser Trp Ala Leu Asp Ala Trp
                100                 105                 110

Gly Gln Gly Thr Thr Val Val Val Ser Ala
            115                 120
```

<210> SEQ ID NO 82
<211> LENGTH: 122
<212> TYPE: PRT
<213> ORGANISM: homo sapiens

<400> SEQUENCE: 82

```
Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
                35                  40                  45

Gly Trp Ile Lys Pro Gln Tyr Gly Ala Val Asn Phe Gly Gly Gly Phe
    50                  55                  60

Arg Gly Arg Val Thr Leu Thr Arg Asp Val Tyr Arg Glu Ile Ala Tyr
65                  70                  75                  80

Met Asp Ile Arg Gly Leu Lys Leu Asp Asp Thr Ala Val Tyr Tyr Cys
                85                  90                  95

Ala Arg Asp Arg Ser Tyr Gly Asp Ser Ser Trp Ala Leu Asp Ala Trp
                100                 105                 110

Gly Gln Gly Thr Thr Val Val Val Ser Ala
            115                 120
```

<210> SEQ ID NO 83
<211> LENGTH: 122
<212> TYPE: PRT
<213> ORGANISM: homo sapiens

<400> SEQUENCE: 83

```
Ser Gln Arg Leu Val Gln Ser Gly Pro Gln Val Lys Lys Pro Gly Ser
1               5                   10                  15

Ser Val Arg Ile Ser Cys Glu Thr Ser Gly Tyr Thr Phe Thr Ala Tyr
            20                  25                  30

Ile Leu His Trp Phe Arg Gln Ala Pro Gly Arg Ser Leu Glu Trp Met
                35                  40                  45

Gly Trp Ile Lys Pro Lys Phe Gly Ala Val Asn Tyr Ala His Ser Phe
    50                  55                  60

Gln Gly Arg Ile Thr Leu Thr Arg Asp Ile Tyr Arg Glu Ile Ala Phe
65                  70                  75                  80
```

```
Leu Asp Leu Thr Gly Leu Arg Phe Asp Asp Thr Ala Val Tyr Tyr Cys
                85                  90                  95

Ala Arg Asp Arg Leu Tyr Asp Gly Ser Ser Trp Arg Leu Asp Pro Trp
            100                 105                 110

Gly Gln Gly Thr Arg Val Ile Val Ser Ser
            115                 120
```

<210> SEQ ID NO 84
<211> LENGTH: 102
<212> TYPE: PRT
<213> ORGANISM: homo sapiens

<400> SEQUENCE: 84

```
Tyr Ile Gln Val Thr Gln Ser Pro Ser Ser Leu Ser Val Ser Val Gly
1               5                   10                  15

Asp Arg Val Thr Ile Thr Cys Gln Ala Ser Gln Gly Val Gly Asn Asp
            20                  25                  30

Leu His Trp Tyr Gln Gln Lys Pro Gly Arg Ala Pro Lys Leu Leu Ile
        35                  40                  45

Tyr Asp Ala Ser Thr Leu Glu Ala Gly Val Pro Ser Arg Phe Ser Gly
    50                  55                  60

Ser Gly Phe His Thr Ser Phe Thr Phe Thr Ile Asn Gly Leu Gln Pro
65                  70                  75                  80

Asp Asp Ile Ala Thr Tyr Tyr Cys Gln Val Leu Glu Ser Phe Gly Gln
                85                  90                  95

Gly Thr Arg Leu Glu Ile
            100
```

<210> SEQ ID NO 85
<211> LENGTH: 102
<212> TYPE: PRT
<213> ORGANISM: homo sapiens

<400> SEQUENCE: 85

```
Tyr Ile His Val Thr Gln Ser Pro Ser Ser Leu Ser Val Ser Val Gly
1               5                   10                  15

Asp Arg Val Thr Ile Thr Cys Gln Ala Ser Gln Gly Val Gly Asn Asp
            20                  25                  30

Leu His Trp Tyr Gln Gln Lys Pro Gly Arg Ala Pro Lys Leu Leu Ile
        35                  40                  45

Tyr Asp Ala Ser Thr Leu Glu Glu Gly Val Pro Ser Arg Phe Ser Gly
    50                  55                  60

Thr Gly Phe His Thr Ser Phe Thr Phe Thr Ile Asn Gly Leu Gln Pro
65                  70                  75                  80

Asp Asp Ile Ala Thr Tyr Tyr Cys Gln Val Leu Glu Ser Phe Gly Gln
                85                  90                  95

Gly Thr Arg Leu Glu Ile
            100
```

<210> SEQ ID NO 86
<211> LENGTH: 102
<212> TYPE: PRT
<213> ORGANISM: homo sapiens

<400> SEQUENCE: 86

```
Tyr Ile His Val Thr Gln Ser Pro Ser Ser Leu Ser Val Ser Val Gly
1               5                   10                  15
```

Asp Arg Val Thr Ile Thr Cys Gln Ala Ser Gln Gly Val Gly Ser Asp
                    20                  25                  30

Leu His Trp Tyr Gln Gln Lys Pro Gly Arg Ala Pro Lys Leu Leu Ile
                35                  40                  45

His His Ala Ser Thr Leu Glu Glu Gly Val Pro Ser Arg Phe Ser Gly
            50                  55                  60

Thr Gly Phe His Thr Ser Phe Thr Phe Thr Ile Asn Asp Leu Gln Pro
65                  70                  75                  80

Asp Asp Ile Ala Thr Tyr Tyr Cys Gln Val Leu Glu Ser Phe Gly Gln
                85                  90                  95

Gly Thr Arg Leu Glu Ile
            100

<210> SEQ ID NO 87
<211> LENGTH: 102
<212> TYPE: PRT
<213> ORGANISM: homo sapiens

<400> SEQUENCE: 87

Tyr Ile His Val Thr Gln Ser Pro Ser Ser Leu Ser Val Ser Val Gly
1               5                   10                  15

Asp Arg Val Thr Ile Asn Cys Gln Thr Ser Gln Gly Val Gly Ser Asp
                20                  25                  30

Leu His Trp Tyr Gln His Lys Pro Gly Arg Ala Pro Lys Leu Leu Ile
                35                  40                  45

His His Ala Ser Ser Val Glu Asp Gly Val Pro Ser Arg Phe Ser Gly
            50                  55                  60

Thr Gly Phe His Thr Ser Phe Asn Leu Thr Ile Asn Asp Leu Gln Ala
65                  70                  75                  80

Asp Asp Ile Ala Thr Tyr Tyr Cys Gln Val Leu Glu Ser Phe Gly Arg
                85                  90                  95

Gly Ser Arg Leu Asp Ile
            100

<210> SEQ ID NO 88
<211> LENGTH: 102
<212> TYPE: PRT
<213> ORGANISM: homo sapiens

<400> SEQUENCE: 88

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
                20                  25                  30

Leu His Trp Tyr Gln His Lys Pro Gly Arg Ala Pro Lys Leu Leu Ile
                35                  40                  45

His His Ala Ser Ser Val Glu Asp Gly Val Pro Ser Arg Phe Ser Gly
            50                  55                  60

Thr Gly Phe His Thr Ser Phe Asn Leu Thr Ile Asn Asp Leu Gln Ala
65                  70                  75                  80

Asp Asp Ile Ala Thr Tyr Tyr Cys Gln Val Leu Gln Ser Phe Gly Arg
                85                  90                  95

Gly Ser Arg Leu Asp Ile
            100

<210> SEQ ID NO 89
<211> LENGTH: 102

```
<212> TYPE: PRT
<213> ORGANISM: homo sapiens

<400> SEQUENCE: 89

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Ala Ser Ser Val Glu Asp Gly Val Pro Ser Arg Phe Ser Gly
50                  55                  60

Ser Gly Phe His Thr Ser Phe Asn Leu Thr Ile Asn Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile
            100

<210> SEQ ID NO 90
<211> LENGTH: 102
<212> TYPE: PRT
<213> ORGANISM: homo sapiens

<400> SEQUENCE: 90

Tyr Ile His Val Thr Gln Ser Pro Ser Ser Leu Ala Val Ser Val Gly
1               5                   10                  15

Asp Arg Val Thr Ile Thr Cys Gln Ala Ser Gln Gly Val Gly Ser Asp
            20                  25                  30

Leu His Trp Tyr Gln His Lys Arg Gly Arg Pro Pro Lys Ile Leu Ile
        35                  40                  45

His His Ala Ser Ala Arg Glu Glu Gly Val Pro Ser Arg Phe Ser Gly
50                  55                  60

Ser Gly Phe His Thr Ser Phe Thr Phe Thr Ile Asn Asp Leu Gln Pro
65                  70                  75                  80

Asp Asp Ile Ala Thr Tyr Tyr Cys Gln Val Leu Glu Ser Phe Gly Gln
                85                  90                  95

Gly Thr Arg Leu Glu Ile
            100

<210> SEQ ID NO 91
<211> LENGTH: 102
<212> TYPE: PRT
<213> ORGANISM: homo sapiens

<400> SEQUENCE: 91

Tyr Ile His Val Thr Gln Ser Pro Ser Ser Leu Ala Val Ser Val Gly
1               5                   10                  15

Asp Arg Val Thr Ile Thr Cys Gln Ala Ser Gln Gly Val Gly Ser Asp
            20                  25                  30

Leu His Trp Tyr Gln His Lys Arg Gly Arg Pro Pro Lys Ile Leu Ile
        35                  40                  45

His His Ala Ser Ala Arg Glu Glu Gly Val Pro Ser Arg Phe Ser Gly
50                  55                  60

Ser Gly Phe His Thr Ser Phe Thr Phe Thr Ile Asn Asp Leu Gln Pro
65                  70                  75                  80

Asp Asp Phe Ala Thr Tyr Tyr Cys Gln Val Leu Glu Ser Phe Gly Gln
```

```
                     85                  90                  95

Gly Thr Arg Leu Glu Ile
            100

<210> SEQ ID NO 92
<211> LENGTH: 102
<212> TYPE: PRT
<213> ORGANISM: homo sapiens

<400> SEQUENCE: 92

Tyr Ile His Val Thr Gln Ser Pro Ser Ser Leu Ala Val Ser Val Gly
1               5                   10                  15

Asp Arg Val Thr Ile Thr Cys Arg Ala Ser Gln Gly Val Gly Ser Asp
            20                  25                  30

Leu His Trp Tyr Gln His Lys Arg Gly Arg Pro Pro Lys Ile Leu Ile
        35                  40                  45

His His Ala Ser Ala Arg Glu Glu Gly Val Pro Ser Arg Phe Ser Gly
    50                  55                  60

Ser Gly Phe His Thr Ser Phe Thr Phe Thr Ile Asn Asp Leu Gln Pro
65                  70                  75                  80

Asp Asp Phe Ala Thr Tyr Tyr Cys Gln Val Leu Glu Ser Phe Gly Gln
                85                  90                  95

Gly Thr Arg Leu Glu Ile
            100

<210> SEQ ID NO 93
<211> LENGTH: 102
<212> TYPE: PRT
<213> ORGANISM: homo sapiens

<400> SEQUENCE: 93

Tyr Ile His Val Thr Gln Ser Pro Ser Ser Leu Ala Val Ser Val Gly
1               5                   10                  15

Asp Arg Val Thr Ile Thr Cys Arg Ala Ser Gln Gly Ile Gly Ser Asp
            20                  25                  30

Leu His Trp Tyr Gln His Lys Arg Gly Arg Pro Pro Lys Ile Leu Ile
        35                  40                  45

His His Ala Ser Ala Arg Glu Glu Gly Val Pro Ser Arg Phe Ser Gly
    50                  55                  60

Ser Gly Phe His Thr Ser Phe Thr Phe Thr Ile Asn Asp Leu Gln Pro
65                  70                  75                  80

Asp Asp Val Ala Thr Tyr Tyr Cys Gln Val Leu Glu Ser Phe Gly Gln
                85                  90                  95

Gly Thr Arg Leu Asp Ile
            100

<210> SEQ ID NO 94
<211> LENGTH: 452
<212> TYPE: PRT
<213> ORGANISM: artificial sequence
<220> FEATURE:
<223> OTHER INFORMATION: antibody heavy chain

<400> SEQUENCE: 94

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30
```

```
Ile Leu Phe Trp Phe Arg Gln Ala Pro Gly Arg Gly Leu Glu Trp Val
         35                  40                  45

Gly Trp Ile Lys Pro Gln Tyr Gly Ala Val Asn Phe Gly Gly Gly Phe
 50                  55                  60

Arg Asp Arg Val Thr Leu Thr Arg Asp Val Tyr Arg Glu Ile Ala Tyr
 65                  70                  75                  80

Met Asp Ile Arg Gly Leu Lys Pro Asp Thr Ala Val Tyr Tyr Cys
                 85                  90                  95

Ala Arg Asp Arg Ser Tyr Gly Asp Ser Ser Trp Ala Leu Asp Ala Trp
                100                 105                 110

Gly Gln Gly Thr Thr Val Val Val Ser Ala Ala Ser Thr Lys Gly Pro
                115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
        435                 440                 445

Ser Pro Gly Lys
```

<210> SEQ ID NO 95
<211> LENGTH: 1356
<212> TYPE: DNA
<213> ORGANISM: artificial sequence
<220> FEATURE:
<223> OTHER INFORMATION: antibody heavy chain

<400> SEQUENCE: 95

```
cgagcgcacc tggtacaatc agggactgcg atgaagaaac cgggggcctc agtaagagtc      60
tcctgccaga cctctggata cacctttacc gcccacatat tatttggtt ccgacaggcc     120
cccgggcgag gacttgagtg ggtggggtgg atcaagccac aatatgggc cgtgaatttt     180
ggtggtggtt ttcgggacag ggtcacattg actcgagacg tatatagaga gattgcgtac     240
atggacatca gaggccttaa acctgacgac acggccgtct attactgtgc gagagaccgt     300
tcctatggcg actcctcttg ggccttagat gcctggggac agggaacgac ggtcgtcgtc     360
tccgcggcgt cgaccaaggg cccatcggtc ttccccctgg cacctcctc caagagcacc     420
tctgggggca gcgcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagaaagtt     660
gagcccaaat cttgtgacaa aactcacaca tgcccaccgt gcccagcacc tgaactcctg     720
gggggaccgt cagtcttcct cttcccccca aaacccaagg acaccctcat gatctcccgg     780
accctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga caactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga gagcctctc cctgtctccg ggtaaa                                1356
```

<210> SEQ ID NO 96
<211> LENGTH: 210
<212> TYPE: PRT
<213> ORGANISM: homo sapiens

<400> SEQUENCE: 96

```
Tyr Ile His Val Thr Gln Ser Pro Ser Ser Leu Ser Val Ser Ile Gly
 1               5                  10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Thr Ser Ser Val Glu Asp Gly Val Pro Ser Arg Phe Ser Gly
    50                  55                  60

Ser Gly Phe His Thr Ser Phe Asn Leu Thr Ile Ser Asp Leu Gln Ala
```

```
                65                  70                  75                  80
Asp Asp Ile Ala Thr Tyr Tyr Cys Gln Val Leu Gln Phe Phe Gly Arg
                    85                  90                  95

Gly Ser Arg Leu His Ile Lys Arg Thr Val Ala Ala Pro Ser Val Phe
                100                 105                 110

Ile Phe Pro Pro Ser Asp Glu Gln Leu Lys Ser Gly Thr Ala Ser Val
            115                 120                 125

Val Cys Leu Leu Asn Asn Phe Tyr Pro Arg Glu Ala Lys Val Gln Trp
130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
                195                 200                 205

Glu Cys
    210

<210> SEQ ID NO 97
<211> LENGTH: 630
<212> TYPE: DNA
<213> ORGANISM: homo sapiens

<400> SEQUENCE: 97
tacatccacg tgacccagtc tccgtcctcc ctgtctgtgt ctattggaga cagagtcacc      60
atcaattgcc agacgagtca gggtgttggc agtgacctac attggtatca acacaaaccg     120
gggagagccc ctaaactctt gatccaccat acctcttctg tggaagacgg tgtcccctca     180
agattcagcg gctctggatt tcacacatct tttaatctga ccatcagcga cctacaggct     240
gacgacattg ccacatatta ctgtcaagtt ttacaatttt tcggccgagg gagtcgactc     300
catattaaac gtacggtggc tgcaccatct gtcttcatct tcccgccatc tgatgagcag     360
ttgaaatctg gaactgcctc tgttgtgtgc ctgctgaata acttctaccc cagagaagcc     420
aaagtgcagt ggaaggtgga caacgccctg cagagcggaa acagccagga aagcgtgaca     480
gagcaggatt ccaaggattc cacatacagc ctgagcagca cactgacact gtccaaggcc     540
gactacgaga agcacaaggt gtacgcctgc gaagtgacac accagggact gtcctcccct     600
gtgacaaaga gcttcaacag aggagaatgc                                      630

<210> SEQ ID NO 98
<211> LENGTH: 452
<212> TYPE: PRT
<213> ORGANISM: homo sapiens

<400> SEQUENCE: 98

Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60
```

```
Arg Asp Arg Val Thr Leu Thr Arg Asp Val Tyr Arg Glu Ile Ala Tyr
 65                  70                  75                  80

Met Asp Ile Arg Gly Leu Lys Pro Asp Thr Ala Val Tyr Tyr Cys
                 85                  90                  95

Ala Arg Asp Arg Ser Tyr Gly Asp Ser Ser Trp Ala Leu Asp Ala Trp
            100                 105                 110

Gly Gln Gly Thr Thr Val Val Ser Ala Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Glu Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 99
<211> LENGTH: 1356
<212> TYPE: DNA
```

<213> ORGANISM: homo sapiens

<400> SEQUENCE: 99

| | | | | | |
|---|---|---|---|---|---|
| cgagcgcacc | tggtacaatc | agggactgcg | atgaagaaac | cgggggcctc | agtaagagtc | 60 |
| tcctgccaga | cctctggata | cacctttacc | gcccacatat | tattttggtt | ccgacaggcc | 120 |
| cccgggcgag | gacttgagtg | ggtggggtgg | atcaagccac | aatatggggc | cgtgaatttt | 180 |
| ggtggtggtt | ttcgggacag | ggtcacattg | actcgagacg | tatatagaga | gattgcgtac | 240 |
| atggacatca | gaggccttaa | acctgacgac | acggccgtct | attactgtgc | gagagaccgt | 300 |
| tcctatggcg | actcctcttg | ggccttagat | gcctggggac | agggaacgac | ggtcgtcgtc | 360 |
| tccgcggcct | ccaccaaggg | cccatcggtc | ttccccctgg | caccctcctc | caagagcacc | 420 |
| tctgggggca | cagcggccct | gggctgcctg | gtcaaggact | acttccccga | accggtgacg | 480 |
| gtgtcgtgga | actcaggcgc | cctgaccagc | ggcgtgcaca | ccttcccggc | tgtcctacag | 540 |
| tcctcaggac | tctactccct | cagcagcgtg | gtgaccgtgc | cctccagcag | cttgggcacc | 600 |
| cagacctaca | tctgcaacgt | gaatcacaag | cccagcaaca | ccaaggtgga | caagagagtt | 660 |
| gagcccaaat | cttgtgacaa | aactcacaca | tgcccaccgt | gcccagcacc | tgaactcctg | 720 |
| gggggaccgt | cagtcttcct | cttcccccca | aaacccaagg | acaccctcat | gatctcccgg | 780 |
| acccctgagg | tcacatgcgt | ggtggtggac | gtgagccacg | aagaccctga | ggtcaagttc | 840 |
| aactggtacg | tggacggcgt | ggaggtgcat | aatgccaaga | caaagccgcg | ggaggagcag | 900 |
| tacaacagca | cgtaccgtgt | ggtcagcgtc | ctcaccgtcc | tgcaccagga | ctggctgaat | 960 |
| ggcgaggagt | acaagtgcaa | ggtctccaac | aaagccctcc | cagcccccat | cgagaaaacc | 1020 |
| atctccaaag | ccaaagggca | gccccgagaa | ccacaggtgt | acaccctgcc | cccatcccgg | 1080 |
| gaggagatga | ccaagaacca | ggtcagcctg | acctgccttg | tcaaaggctt | ctatcccagc | 1140 |
| gacatcgccg | tggagtggga | gagcaatggg | cagccggaga | acaactacaa | gaccacgcct | 1200 |
| cccgtgctgg | actccgacgg | ctccttcttc | ctctacagca | agctcaccgt | ggacaagagc | 1260 |
| aggtggcagc | aggggaacgt | cttctcatgc | tccgtgatgc | atgaggctct | gcacaaccac | 1320 |
| tacacgcaga | agagcctctc | cctgtctccg | ggtaaa | | | 1356 |

<210> SEQ ID NO 100
<211> LENGTH: 366
<212> TYPE: DNA
<213> ORGANISM: homo sapiens

<400> SEQUENCE: 100

| | | | | | |
|---|---|---|---|---|---|
| cgagggcact | tggtgcagtc | agggactgag | gtgaagaaac | cgggggcctc | agtgagagtc | 60 |
| tcctgcgaga | cttctggata | cacctthacc | gcctacattt | tacattggtt | ccgacaggcc | 120 |
| cccggacgag | ggcttgagtg | gatggggtgg | atcaagccaa | aatatgggagc | cgtcaattat | 180 |
| gctcatgcat | ttcagggcag | ggtcacccсtg | accagagaca | tatatagaga | cactgcatac | 240 |
| atggacttga | gtggcctaag | attcgacgac | acggccgtct | attactgtgc | gagagatcgc | 300 |
| gtttatgacg | attcgtcttg | gcaattggat | ccctgggggcc | agggaacttc | ggtcatcgtc | 360 |
| tcctca | | | | | | 366 |

<210> SEQ ID NO 101
<211> LENGTH: 366
<212> TYPE: DNA
<213> ORGANISM: homo sapiens

<400> SEQUENCE: 101

```
cgagggcact tggtgcagtc agggactgag gtgaagaaac cggggcctc  agtgagagtc    60 tcctgcgaga cttctggata caccttcacc gcccacattt tacattggtt ccgacaggcc   120
cccggacgag ggcttgagtg gatggggtgg atcaagccaa aatatggagc cgtcaattat   180
gctcatgcat ttcagggcag ggtcaccctg accagagaca tatatagaga cactgcatac   240
atggacttga gtggcctaag attcgacgac acggccgtct attactgtgc gagagatcgc   300
gtttatgacg attcgtcttg gcaattggat ccctggggcc agggaacttc ggtcatcgtc   360
tcctca                                                              366

<210> SEQ ID NO 102
<211> LENGTH: 366
<212> TYPE: DNA
<213> ORGANISM: homo sapiens

<400> SEQUENCE: 102
cgagcgcact tggtgcagtc agggactgcg gtgaagaaac cggggcctc  agtgagagtc    60 tcctgcgaga cttctggata caccttcacc gcccacattt tatattggtt ccgacaggcc   120
cccggacgag ggcttgagtg ggtggggtgg atcaagccac aatatggggc cgtgaatttt   180
ggtggtggtt ttcggggcag ggtcaccctg accagagaca tatatagaga cactgcatac   240
atggacatca gtggcctaag attcgacgac acggccgtct attactgtgc gagagatcgc   300
tcctatgacg actcctcttg ggccttagat gcctggggac agggaacgac ggtcgtcgtc   360
tccgcg                                                              366

<210> SEQ ID NO 103
<211> LENGTH: 366
<212> TYPE: DNA
<213> ORGANISM: homo sapiens

<400> SEQUENCE: 103
cgagcgcacc tggtacaatc agggactgcg atgaagaaac cggggcctc  agtaagagtc    60 tcctgccaga cctctggata caccttacc  gcccacatat tattttggtt ccgacaggcc   120
cccgggcgag gacttgagtg ggtgggggtgg atcaagccac aatatggggc cgtgaatttt   180
ggtggtggtt ttcgggacag ggtcacattg actcgagaca tatatagaga gattgcgtac   240
atggacatca gaggccttaa acttgacgac acggccgtct attactgtgc gagagaccgt   300
tcctatggcg actcctcttg ggccttagat gcctggggac agggaacgac ggtcgtcgtc   360
tccgcg                                                              366

<210> SEQ ID NO 104
<211> LENGTH: 103
<212> TYPE: PRT
<213> ORGANISM: homo sapiens

<400> SEQUENCE: 104

Tyr Ile His Val Thr Gln Ser Pro Ser Ser Leu Ser Val Ser Ile Gly
1               5                  10                  15

Asp Arg Val Thr Ile Asn Cys Gln Thr Ser Gln Gly Val Gly Ser Asp
            20                  25                  30

Leu His Trp Tyr Gln His Lys Pro Gly Arg Asp Pro Lys Leu Leu Ile
        35                  40                  45

Arg His Thr Thr Ser Val Glu Asp Gly Val Pro Ser Arg Val Ser Gly
    50                  55                  60
```

Ser Gly Phe His Thr Ser Phe Asn Leu Thr Ile Ser Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100

<210> SEQ ID NO 105
<211> LENGTH: 309
<212> TYPE: DNA
<213> ORGANISM: homo sapiens

<400> SEQUENCE: 105
tacatccacg tgacccagtc tccgtcctcc ctgtctgtgt ctattggaga cagagtcacc    60
atcaattgcc agacgagtca gggtgttggc agtgacctac attggtatca acacaaaccg   120
gggagagacc ctaaactctt gatccgccat accacttctg tggaagacgg tgtcccctca   180
agagtcagcg gctctggatt tcacacatct tttaatctga ccatcagcga cctacaggct   240
gacgacattg ccacatatta ctgtcaagtt ttacaatttt tcggccgagg gagtcgactc   300
catattaaa                                                           309

<210> SEQ ID NO 106
<211> LENGTH: 103
<212> TYPE: PRT
<213> ORGANISM: homo sapiens

<400> SEQUENCE: 106

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Ala Ser Ser Val Asp Asp Gly Val Pro Ser Arg Phe Ser Gly
    50                  55                  60

Ser Gly Phe His Thr Ser Phe Asn Leu Thr Ile Asn Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100

<210> SEQ ID NO 107
<211> LENGTH: 309
<212> TYPE: DNA
<213> ORGANISM: homo sapiens

<400> SEQUENCE: 107
tacatccacg tgacccagtc tccgtcctcc ctgtctgtgt ctattggaga cagggtcacc    60
atcaattgcc agacgagtca gggtgttggc agtgacctac attggtatca acacaagccg   120
gggagagccc ctaaactctt gattcatcat gcctcttctg tggacgacgg tgtcccgtca   180
agattcagtg gctctggatt tcacacatct tttaatctga ccatcaacga cctacaggct   240
gacgacattg ccacatatta ctgtcaggtt ttacaatttt tcggccgagg gagtcgactc   300
catattaaa                                                           309

<210> SEQ ID NO 108
<211> LENGTH: 103
<212> TYPE: PRT
<213> ORGANISM: homo sapiens

<400> SEQUENCE: 108

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Val Gly Ser Asp
            20                  25                  30

Leu His Trp Tyr Gln His Lys Pro Gly Arg Ala Pro Lys Leu Leu Ile
        35                  40                  45

His His Ala Ser Ser Val Glu Asp Gly Val Pro Ser Arg Phe Ser Gly
    50                  55                  60

Thr Gly Phe His Thr Ser Phe Asn Leu Thr Ile Asn Asp Leu Gln Ala
65                  70                  75                  80

Asp Asp Ile Gly Thr Tyr Tyr Cys Gln Val Leu Gln Ser Phe Gly Arg
                85                  90                  95

Gly Ser Arg Leu Asp Thr Lys
            100

<210> SEQ ID NO 109
<211> LENGTH: 309
<212> TYPE: DNA
<213> ORGANISM: homo sapiens

<400> SEQUENCE: 109
tacatccacg tgacccagtc tccgtcctcc ctgtctgtgt ctataggga cagagtcacc      60 atcaattgcc agacgagtca gggtgttggc agtgacctac attggtatca acacaaaccg    120
gggagagccc ctaaactcct gatccaccat gcctcttctg tggaggacgg tgtcccgtca    180
agattcagtg gcactggatt tcacacatct tttaatttga ccatcaacga cctgcaggct    240
gacgacattg gcacttatta ctgtcaggtg ttacaatctt tcggccgagg gagtcgactg    300
gatactaaa                                                             309

<210> SEQ ID NO 110
<211> LENGTH: 103
<212> TYPE: PRT
<213> ORGANISM: homo sapiens

<400> SEQUENCE: 110

Tyr Ile His Val Thr Gln Ser Pro Ser Ser Leu Ser Val Ser Ile Gly
1               5                   10                  15

Asp Arg Val Thr Ile Asn Cys Gln Thr Ser Gln Gly Phe Gly Arg Asp
            20                  25                  30

Leu His Trp Tyr Gln His Lys Pro Gly Arg Ala Pro Lys Leu Leu Ile
        35                  40                  45

His His Ala Pro Tyr Val Asp Asp Gly Val Pro Ser Arg Phe Ser Gly
    50                  55                  60

Ser Gly Phe His Thr Ser Phe Asn Leu Thr Ile Asn Asp Leu Gln Ala
65                  70                  75                  80

Asp Asp Ile Ala Thr Tyr Tyr Cys Gln Val Leu Gln Phe Phe Gly Arg
                85                  90                  95

Gly Ser Arg Leu His Ile Lys
            100

<210> SEQ ID NO 111

<210> SEQ ID NO 112
<211> LENGTH: 309
<212> TYPE: DNA
<213> ORGANISM: homo sapiens

<400> SEQUENCE: 111

```
tacatccacg tgacccagtc tccgtcctcc ctgtctgtgt ctattggaga cagggtcacc    60
atcaattgcc agacgagtca gggttttggc agggacctac attggtatca acacaagccg   120
gggagagccc ctaaactctt gattcatcat gccccttatg tggacgacgg tgtcccttca   180
agattcagtg gctctggatt tcacacatct tttaatctga ccatcaacga cctacaggct   240
gacgacattg ccacatatta ctgtcaggtt ttacaatttt cggccgagg gagtcgactc   300
catattaaa                                                           309
```

<210> SEQ ID NO 112
<211> LENGTH: 121
<212> TYPE: PRT
<213> ORGANISM: homo sapiens

<400> SEQUENCE: 112

```
Arg Ala His Leu Val Gln Ser Gly Thr Ala Met Lys Lys Pro Gly Ala
1               5                   10                  15
Ser Val Arg Val Ser Cys Gln Thr Ser Gly Tyr Thr Phe Thr Ala His
            20                  25                  30
Ile Leu Phe Trp Phe Arg Gln Ala Pro Gly Arg Gly Leu Glu Trp Val
        35                  40                  45
Gly Trp Ile Lys Pro Gln Tyr Gly Ala Val Asn Phe Gly Gly Phe
    50                  55                  60
Arg Asp Arg Val Thr Leu Thr Arg Asp Ile Tyr Arg Glu Ile Ala Tyr
65                  70                  75                  80
Met Asp Ile Arg Gly Leu Lys Leu Asp Asp Thr Ala Val Tyr Tyr Cys
                85                  90                  95
Ala Arg Asp Arg Ser Tyr Gly Asp Ser Ser Trp Ala Leu Asp Ala Trp
            100                 105                 110
Gly Gln Gly Thr Thr Val Val Val Ser
        115                 120
```

<210> SEQ ID NO 113
<211> LENGTH: 363
<212> TYPE: DNA
<213> ORGANISM: homo sapiens

<400> SEQUENCE: 113

```
cgagcgcacc tggtacaatc agggactgcg atgaagaaac cggggggcctc agtaagggtc    60
tcctgccaga cttctggata caccttta cc gcccacatat tattttggtt ccgacaggcc   120
cccgggcgag ggctggagtg ggtgggatgg atcaagccac aatacgggc cgtgaatttt   180
ggtggtggtt ttcgggacag ggtcacattg actcgagaca tatatagaga gattgcatac   240
atggacatca gaggccttaa acttgacgac acggccgtct attactgtgc gagagaccgt   300
tcctatggcg actcctcttg ggccttagat gcctggggac agggaacgac ggtcgtcgtc   360
tcc                                                                  363
```

<210> SEQ ID NO 114
<211> LENGTH: 122
<212> TYPE: PRT
<213> ORGANISM: homo sapiens

<400> SEQUENCE: 114

```
Arg Ala His Leu Val Gln Ser Gly Thr Ala Met Lys Lys Pro Gly Ala
1               5                   10                  15

Ser Val Arg Val Ser Cys Gln Thr Ser Gly Tyr Thr Phe Thr Ala His
            20                  25                  30

Ile Leu Phe Trp Phe Arg Gln Ala Pro Gly Arg Gly Leu Glu Trp Val
        35                  40                  45

Gly Trp Ile Lys Pro Gln Tyr Gly Ala Val Asn Phe Gly Gly Gly Phe
    50                  55                  60

Arg Asp Arg Val Thr Leu Thr Arg Asp Ile Tyr Arg Glu Ile Ala Tyr
65                  70                  75                  80

Met Asp Ile Arg Gly Leu Lys Leu Asp Asp Thr Ala Val Tyr Tyr Cys
                85                  90                  95

Ala Arg Asp Arg Ser Tyr Gly Asp Ser Ser Trp Ala Leu Asp Ala Trp
            100                 105                 110

Gly Gln Gly Thr Thr Val Val Val Ser Ala
        115                 120
```

<210> SEQ ID NO 115
<211> LENGTH: 366
<212> TYPE: DNA
<213> ORGANISM: homo sapiens

<400> SEQUENCE: 115

```
cgagcgcacc tggtacaatc agggactgcg atgaagaaac cgggggcctc agtaagggtc        60
tcctgccaga cttctggata cacctttacc gcccacatat tattttggtt ccgacaggcc       120
cccgggcgag ggctggagtg ggtgggatgg atcaagccac aatacggggc cgtgaatttt       180
ggtggtggtt ttcgggacag ggtcacattg actcgagaca tatatagaga gattgcatac       240
atggacatca gaggccttaa acttgacgac acggccgtct attactgtgc gagagaccgt       300
tcctatggcg actcctcttg ggccttagat gcctggggac agggaacgac ggtcgtcgtc       360
tccgcg                                                                 366
```

<210> SEQ ID NO 116
<211> LENGTH: 8
<212> TYPE: PRT
<213> ORGANISM: human immunodeficiency virus

<400> SEQUENCE: 116

```
Asn Phe Thr Asp Asn Ala Lys Thr
1               5
```

<210> SEQ ID NO 117
<211> LENGTH: 13
<212> TYPE: PRT
<213> ORGANISM: human immunodeficiency virus

<400> SEQUENCE: 117

```
Lys Gln Ser Ser Gly Gly Asp Pro Glu Ile Val Thr His
1               5                   10
```

<210> SEQ ID NO 118
<211> LENGTH: 12
<212> TYPE: PRT
<213> ORGANISM: human immunodeficiency virus

<400> SEQUENCE: 118

```
Gly Gly Asn Ser Asn Asn Glu Ser Glu Ile Phe Arg
1               5                   10
```

```
<210> SEQ ID NO 119
<211> LENGTH: 13
<212> TYPE: PRT
<213> ORGANISM: human immunodeficiency virus

<400> SEQUENCE: 119

Thr His Ser Ser Gly Gly Asp Pro Glu Ile Val Met His
1               5                   10

<210> SEQ ID NO 120
<211> LENGTH: 12
<212> TYPE: PRT
<213> ORGANISM: human immunodeficiency virus

<400> SEQUENCE: 120

Gly Gly Lys Asn Glu Ser Glu Ile Glu Ile Phe Arg
1               5                   10

<210> SEQ ID NO 121
<211> LENGTH: 8
<212> TYPE: PRT
<213> ORGANISM: human immunodeficiency virus

<400> SEQUENCE: 121

Asn Leu Thr Asn Asn Ala Lys Thr
1               5

<210> SEQ ID NO 122
<211> LENGTH: 13
<212> TYPE: PRT
<213> ORGANISM: human immunodeficiency virus

<400> SEQUENCE: 122

Gln Pro Pro Ser Gly Gly Asp Leu Glu Ile Thr Met His
1               5                   10

<210> SEQ ID NO 123
<211> LENGTH: 12
<212> TYPE: PRT
<213> ORGANISM: human immunodeficiency virus

<400> SEQUENCE: 123

Gly Gly Ala Asn Asn Thr Ser Asn Glu Thr Phe Arg
1               5                   10

<210> SEQ ID NO 124
<211> LENGTH: 8
<212> TYPE: PRT
<213> ORGANISM: human immunodeficiency virus

<400> SEQUENCE: 124

His Ile Gly Asn Ser Ala Lys Asn
1               5

<210> SEQ ID NO 125
<211> LENGTH: 13
<212> TYPE: PRT
<213> ORGANISM: human immunodeficiency virus

<400> SEQUENCE: 125

Lys Asn Ser Ser Gly Gly Asp Ile Glu Ile Thr Thr His
1               5                   10
```

```
<210> SEQ ID NO 126
<211> LENGTH: 12
<212> TYPE: PRT
<213> ORGANISM: human immunodeficiency virus

<400> SEQUENCE: 126

Tyr Gly Asn Asn Asn Ser Asp Asn Glu Ile Phe Arg
1               5                   10

<210> SEQ ID NO 127
<211> LENGTH: 8
<212> TYPE: PRT
<213> ORGANISM: human immunodeficiency virus

<400> SEQUENCE: 127

His Ile Glu Asn Asn Ala Lys Asn
1               5

<210> SEQ ID NO 128
<211> LENGTH: 12
<212> TYPE: PRT
<213> ORGANISM: human immunodeficiency virus

<400> SEQUENCE: 128

Tyr Gly Asn Ser Ser Ser Asp Asn Glu Thr Phe Arg
1               5                   10

<210> SEQ ID NO 129
<211> LENGTH: 8
<212> TYPE: PRT
<213> ORGANISM: human immunodeficiency virus

<400> SEQUENCE: 129

Asp Ile Thr Lys Asn Thr Lys Thr
1               5

<210> SEQ ID NO 130
<211> LENGTH: 13
<212> TYPE: PRT
<213> ORGANISM: human immunodeficiency virus

<400> SEQUENCE: 130

Gln Pro Pro Ser Gly Gly Asp Leu Glu Val Thr Thr His
1               5                   10

<210> SEQ ID NO 131
<211> LENGTH: 13
<212> TYPE: PRT
<213> ORGANISM: human immunodeficiency virus

<400> SEQUENCE: 131

Gly Asp Gly Gly Pro Thr Ala Asp Asn Glu Thr Phe Arg
1               5                   10

<210> SEQ ID NO 132
<211> LENGTH: 8
<212> TYPE: PRT
<213> ORGANISM: human immunodeficiency virus

<400> SEQUENCE: 132

Asn Ile Ser Asn Asn Gly Lys Thr
1               5

<210> SEQ ID NO 133
<211> LENGTH: 13
```

```
<212> TYPE: PRT
<213> ORGANISM: human immunodeficiency virus

<400> SEQUENCE: 133

Thr Asn His Ser Gly Gly Asp Leu Glu Val Thr Thr His
1               5                   10

<210> SEQ ID NO 134
<211> LENGTH: 11
<212> TYPE: PRT
<213> ORGANISM: human immunodeficiency virus

<400> SEQUENCE: 134

Gly Pro Asn Ser Thr Gln Asn Glu Thr Phe Arg
1               5                   10

<210> SEQ ID NO 135
<211> LENGTH: 8
<212> TYPE: PRT
<213> ORGANISM: human immunodeficiency virus

<400> SEQUENCE: 135

Asn Thr Ile Asp Asn Ala Lys Thr
1               5

<210> SEQ ID NO 136
<211> LENGTH: 13
<212> TYPE: PRT
<213> ORGANISM: human immunodeficiency virus

<400> SEQUENCE: 136

Glu Lys His Ser Gly Gly Asp Leu Glu Val Ile Thr His
1               5                   10

<210> SEQ ID NO 137
<211> LENGTH: 14
<212> TYPE: PRT
<213> ORGANISM: human immunodeficiency virus

<400> SEQUENCE: 137

Gly Gly Glu Asn Arg Thr Asp Asn Gly Thr Glu Ile Phe Arg
1               5                   10

<210> SEQ ID NO 138
<211> LENGTH: 8
<212> TYPE: PRT
<213> ORGANISM: human immunodeficiency virus

<400> SEQUENCE: 138

Asn Phe Thr Asp Asn Val Lys Thr
1               5

<210> SEQ ID NO 139
<211> LENGTH: 13
<212> TYPE: PRT
<213> ORGANISM: human immunodeficiency virus

<400> SEQUENCE: 139

Met Gln His Ser Gly Gly Asp Pro Glu Ile Val Thr His
1               5                   10

<210> SEQ ID NO 140
<211> LENGTH: 13
<212> TYPE: PRT
<213> ORGANISM: human immunodeficiency virus
```

<400> SEQUENCE: 140

Gly Gly Glu Asn Arg Thr Asp Gly Thr Glu Ile Phe Arg
1               5                   10

<210> SEQ ID NO 141
<211> LENGTH: 8
<212> TYPE: PRT
<213> ORGANISM: human immunodeficiency virus

<400> SEQUENCE: 141

Asn Phe Thr Lys Asn Glu Lys Thr
1               5

<210> SEQ ID NO 142
<211> LENGTH: 13
<212> TYPE: PRT
<213> ORGANISM: human immunodeficiency virus

<400> SEQUENCE: 142

Asn Gln Ser Thr Gly Gly Asp Pro Glu Thr Ala Met Phe
1               5                   10

<210> SEQ ID NO 143
<211> LENGTH: 12
<212> TYPE: PRT
<213> ORGANISM: human immunodeficiency virus

<400> SEQUENCE: 143

Gly Asp Lys Asn Asn Lys Ser Thr Glu Val Phe Arg
1               5                   10

<210> SEQ ID NO 144
<211> LENGTH: 8
<212> TYPE: PRT
<213> ORGANISM: human immunodeficiency virus

<400> SEQUENCE: 144

Asn Leu Thr Asn Asn Ala Lys Ile
1               5

<210> SEQ ID NO 145
<211> LENGTH: 13
<212> TYPE: PRT
<213> ORGANISM: human immunodeficiency virus

<400> SEQUENCE: 145

Gln Pro His Ser Gly Gly Asp Leu Glu Val Val Thr His
1               5                   10

<210> SEQ ID NO 146
<211> LENGTH: 12
<212> TYPE: PRT
<213> ORGANISM: human immunodeficiency virus

<400> SEQUENCE: 146

Gly Gly Lys Asp Asn Asn Met Thr Glu Ile Phe Arg
1               5                   10

<210> SEQ ID NO 147
<211> LENGTH: 8
<212> TYPE: PRT
<213> ORGANISM: human immunodeficiency virus

<400> SEQUENCE: 147

Asn Leu Thr Asn Asn Ile Lys Thr
1               5

<210> SEQ ID NO 148
<211> LENGTH: 13
<212> TYPE: PRT
<213> ORGANISM: human immunodeficiency virus

<400> SEQUENCE: 148

Glu Pro Ser Ser Gly Gly Asp Leu Glu Val Thr Thr His
1               5                   10

<210> SEQ ID NO 149
<211> LENGTH: 11
<212> TYPE: PRT
<213> ORGANISM: human immunodeficiency virus

<400> SEQUENCE: 149

Gly Gly Glu Asn Ser Thr Glu Gly Val Phe Arg
1               5                   10

<210> SEQ ID NO 150
<211> LENGTH: 13
<212> TYPE: PRT
<213> ORGANISM: human immunodeficiency virus

<400> SEQUENCE: 150

Glu Ser His Ser Gly Gly Asp Leu Glu Ile Thr Thr His
1               5                   10

<210> SEQ ID NO 151
<211> LENGTH: 11
<212> TYPE: PRT
<213> ORGANISM: human immunodeficiency virus

<400> SEQUENCE: 151

Gly Gly Pro Asn Ser Thr Asn Glu Thr Phe Arg
1               5                   10

<210> SEQ ID NO 152
<211> LENGTH: 14
<212> TYPE: PRT
<213> ORGANISM: human immunodeficiency virus

<400> SEQUENCE: 152

Lys Pro Ala Val Val Gly Gly Asp Leu Glu Ile Thr Thr His
1               5                   10

<210> SEQ ID NO 153
<211> LENGTH: 12
<212> TYPE: PRT
<213> ORGANISM: human immunodeficiency virus

<400> SEQUENCE: 153

Gly Gly Asn Asn Thr Asn Gly Thr Glu Thr Phe Arg
1               5                   10

<210> SEQ ID NO 154
<211> LENGTH: 13
<212> TYPE: PRT
<213> ORGANISM: human immunodeficiency virus

<400> SEQUENCE: 154

Ala Pro Ser Ser Gly Gly Asp Leu Glu Ile Thr Thr His

```
<210> SEQ ID NO 155
<211> LENGTH: 12
<212> TYPE: PRT
<213> ORGANISM: human immunodeficiency virus

<400> SEQUENCE: 155

Gly Gly Lys Glu Lys Asn Asp Thr Glu Thr Phe Arg
1               5                   10

<210> SEQ ID NO 156
<211> LENGTH: 8
<212> TYPE: PRT
<213> ORGANISM: human immunodeficiency virus

<400> SEQUENCE: 156

Asn Val Thr Asn Asn Ala Lys Thr
1               5

<210> SEQ ID NO 157
<211> LENGTH: 13
<212> TYPE: PRT
<213> ORGANISM: human immunodeficiency virus

<400> SEQUENCE: 157

Ser Pro Ser Ser Gly Gly Asp Pro Glu Ile Thr Thr His
1               5                   10

<210> SEQ ID NO 158
<211> LENGTH: 12
<212> TYPE: PRT
<213> ORGANISM: human immunodeficiency virus

<400> SEQUENCE: 158

Gly Gly Leu Asn Thr Ser Asn Asn Glu Thr Phe Arg
1               5                   10

<210> SEQ ID NO 159
<211> LENGTH: 8
<212> TYPE: PRT
<213> ORGANISM: human immunodeficiency virus

<400> SEQUENCE: 159

Asn Leu Thr Asn Asn Ala Lys Val
1               5

<210> SEQ ID NO 160
<211> LENGTH: 13
<212> TYPE: PRT
<213> ORGANISM: human immunodeficiency virus

<400> SEQUENCE: 160

Asn Ser Pro Ala Gly Gly Asp Leu Glu Ile Thr Thr His
1               5                   10

<210> SEQ ID NO 161
<211> LENGTH: 14
<212> TYPE: PRT
<213> ORGANISM: human immunodeficiency virus

<400> SEQUENCE: 161

Gly Val Asn Asp Thr His Asp Lys Glu Asn Glu Thr Phe Arg
1               5                   10
```

<210> SEQ ID NO 162
<211> LENGTH: 13
<212> TYPE: PRT
<213> ORGANISM: human immunodeficiency virus

<400> SEQUENCE: 162

Asn Ala Ser Ser Gly Gly Asp Pro Glu Ile Thr Thr His
1               5                   10

<210> SEQ ID NO 163
<211> LENGTH: 14
<212> TYPE: PRT
<213> ORGANISM: human immunodeficiency virus

<400> SEQUENCE: 163

Gly Gly Gly Ala Asp Asn Asn Arg Gln Asn Glu Thr Phe Arg
1               5                   10

<210> SEQ ID NO 164
<211> LENGTH: 8
<212> TYPE: PRT
<213> ORGANISM: human immunodeficiency virus

<400> SEQUENCE: 164

Asn Ile Ser Asn Asn Val Lys Thr
1               5

<210> SEQ ID NO 165
<211> LENGTH: 13
<212> TYPE: PRT
<213> ORGANISM: human immunodeficiency virus

<400> SEQUENCE: 165

Ala Pro Pro Val Gly Gly Asp Leu Glu Ile Thr Thr His
1               5                   10

<210> SEQ ID NO 166
<211> LENGTH: 15
<212> TYPE: PRT
<213> ORGANISM: human immunodeficiency virus

<400> SEQUENCE: 166

Gly Gly Glu Asn Lys Thr Glu Asn Asn Asp Thr Glu Ile Phe Arg
1               5                   10                  15

<210> SEQ ID NO 167
<211> LENGTH: 8
<212> TYPE: PRT
<213> ORGANISM: human immunodeficiency virus

<400> SEQUENCE: 167

Asn Ile Ser Ala Asn Ala Lys Thr
1               5

<210> SEQ ID NO 168
<211> LENGTH: 13
<212> TYPE: PRT
<213> ORGANISM: human immunodeficiency virus

<400> SEQUENCE: 168

Thr Lys Pro Ser Gly Gly Asp Leu Glu Ile Thr Thr His
1               5                   10

<210> SEQ ID NO 169

```
<211> LENGTH: 12
<212> TYPE: PRT
<213> ORGANISM: human immunodeficiency virus

<400> SEQUENCE: 169

Gly Glu Gly Asp Glu Lys Ala Asn Glu Thr Phe Arg
1               5                   10

<210> SEQ ID NO 170
<211> LENGTH: 8
<212> TYPE: PRT
<213> ORGANISM: human immunodeficiency virus

<400> SEQUENCE: 170

Asn Phe Thr Gln Asn Ala Glu Thr
1               5

<210> SEQ ID NO 171
<211> LENGTH: 14
<212> TYPE: PRT
<213> ORGANISM: human immunodeficiency virus

<400> SEQUENCE: 171

Asn Pro Pro Ile Arg Gly Gly Asp Pro Glu Ile Val Met His
1               5                   10

<210> SEQ ID NO 172
<211> LENGTH: 13
<212> TYPE: PRT
<213> ORGANISM: human immunodeficiency virus

<400> SEQUENCE: 172

Gly Gly Lys Asn Gly Thr Glu Gly Thr Glu Ile Phe Arg
1               5                   10

<210> SEQ ID NO 173
<211> LENGTH: 8
<212> TYPE: PRT
<213> ORGANISM: human immunodeficiency virus

<400> SEQUENCE: 173

Asn Leu Thr Glu Asn Thr Lys Thr
1               5

<210> SEQ ID NO 174
<211> LENGTH: 13
<212> TYPE: PRT
<213> ORGANISM: human immunodeficiency virus

<400> SEQUENCE: 174

Lys Pro His Ala Gly Asp Ile Glu Ile Thr Met His
1               5                   10

<210> SEQ ID NO 175
<211> LENGTH: 13
<212> TYPE: PRT
<213> ORGANISM: human immunodeficiency virus

<400> SEQUENCE: 175

Gly Gly Phe Asn Thr Thr Asn Asn Thr Glu Thr Phe Arg
1               5                   10

<210> SEQ ID NO 176
<211> LENGTH: 8
<212> TYPE: PRT
```

```
<213> ORGANISM: human immunodeficiency virus

<400> SEQUENCE: 176

Asp Leu Asn Asn Thr Gly Asn Thr
1               5

<210> SEQ ID NO 177
<211> LENGTH: 13
<212> TYPE: PRT
<213> ORGANISM: human immunodeficiency virus

<400> SEQUENCE: 177

Ser Pro His Pro Gly Gly Asp Leu Glu Val Thr Met His
1               5                   10

<210> SEQ ID NO 178
<211> LENGTH: 14
<212> TYPE: PRT
<213> ORGANISM: human immunodeficiency virus

<400> SEQUENCE: 178

Gly Asp Lys Thr Ser Asn Asp Pro Asp Thr Asp Val Phe Arg
1               5                   10

<210> SEQ ID NO 179
<211> LENGTH: 8
<212> TYPE: PRT
<213> ORGANISM: human immunodeficiency virus

<400> SEQUENCE: 179

Asn Phe Ser Arg Asn Thr Lys Asn
1               5

<210> SEQ ID NO 180
<211> LENGTH: 13
<212> TYPE: PRT
<213> ORGANISM: human immunodeficiency virus

<400> SEQUENCE: 180

Gln Pro His Ser Gly Gly Asp Pro Glu Val Val Arg His
1               5                   10

<210> SEQ ID NO 181
<211> LENGTH: 15
<212> TYPE: PRT
<213> ORGANISM: human immunodeficiency virus

<400> SEQUENCE: 181

Gly Gly Asn Asn Pro Glu Gly Lys Asn Asn Thr Glu Ile Phe Arg
1               5                   10                  15

<210> SEQ ID NO 182
<211> LENGTH: 8
<212> TYPE: PRT
<213> ORGANISM: human immunodeficiency virus

<400> SEQUENCE: 182

Asn Phe Ser Arg Asp Thr Lys Asn
1               5

<210> SEQ ID NO 183
<211> LENGTH: 12
<212> TYPE: PRT
<213> ORGANISM: human immunodeficiency virus
```

```
<400> SEQUENCE: 183

Gly Gly Asn Lys Asn Thr Thr Lys Glu Ile Phe Arg
1               5                   10

<210> SEQ ID NO 184
<211> LENGTH: 8
<212> TYPE: PRT
<213> ORGANISM: human immunodeficiency virus

<400> SEQUENCE: 184

Asn Phe Ser Asp Asn Asn Lys Asn
1               5

<210> SEQ ID NO 185
<211> LENGTH: 13
<212> TYPE: PRT
<213> ORGANISM: human immunodeficiency virus

<400> SEQUENCE: 185

Asp Ala His Ser Gly Gly Asp Pro Glu Val Val Met His
1               5                   10

<210> SEQ ID NO 186
<211> LENGTH: 15
<212> TYPE: PRT
<213> ORGANISM: human immunodeficiency virus

<400> SEQUENCE: 186

Gly Gly Asn Asn Ile Gly Gly Glu Asn Asn Thr Glu Ile Phe Arg
1               5                   10                  15

<210> SEQ ID NO 187
<211> LENGTH: 8
<212> TYPE: PRT
<213> ORGANISM: human immunodeficiency virus

<400> SEQUENCE: 187

Asn Ile Ser Asp Asn Ala Lys Thr
1               5

<210> SEQ ID NO 188
<211> LENGTH: 12
<212> TYPE: PRT
<213> ORGANISM: human immunodeficiency virus

<400> SEQUENCE: 188

Gly Gly Lys Asn Glu Ser Glu Ile Glu Thr Phe Arg
1               5                   10

<210> SEQ ID NO 189
<211> LENGTH: 8
<212> TYPE: PRT
<213> ORGANISM: human immunodeficiency virus

<400> SEQUENCE: 189

Asn Leu Thr Asp Asn Ala Lys Thr
1               5

<210> SEQ ID NO 190
<211> LENGTH: 8
<212> TYPE: PRT
<213> ORGANISM: human immunodeficiency virus

<400> SEQUENCE: 190
```

Asn Leu Thr Asp Asn Thr Lys Thr
1               5

<210> SEQ ID NO 191
<211> LENGTH: 8
<212> TYPE: PRT
<213> ORGANISM: human immunodeficiency virus

<400> SEQUENCE: 191

Asn Leu Thr Glu Asn Lys Lys Thr
1               5

<210> SEQ ID NO 192
<211> LENGTH: 13
<212> TYPE: PRT
<213> ORGANISM: human immunodeficiency virus

<400> SEQUENCE: 192

Lys Gln Ser Ser Gly Gly Asp Ile Glu Ile Thr Met His
1               5                   10

<210> SEQ ID NO 193
<211> LENGTH: 8
<212> TYPE: PRT
<213> ORGANISM: human immunodeficiency virus

<400> SEQUENCE: 193

Asn Phe Thr Asp Asn Ala Glu Thr
1               5

<210> SEQ ID NO 194
<211> LENGTH: 8
<212> TYPE: PRT
<213> ORGANISM: human immunodeficiency virus

<400> SEQUENCE: 194

Asn Phe Thr Gln Asn Ala Lys Thr
1               5

<210> SEQ ID NO 195
<211> LENGTH: 13
<212> TYPE: PRT
<213> ORGANISM: human immunodeficiency virus

<400> SEQUENCE: 195

Lys Gln Ser Ser Gly Gly Asp Pro Glu Ile Val Met His
1               5                   10

<210> SEQ ID NO 196
<211> LENGTH: 8
<212> TYPE: PRT
<213> ORGANISM: human immunodeficiency virus

<400> SEQUENCE: 196

Asn Phe Ser Asp Asn Ala Lys Thr
1               5

<210> SEQ ID NO 197
<211> LENGTH: 8
<212> TYPE: PRT
<213> ORGANISM: human immunodeficiency virus

<400> SEQUENCE: 197

Asn Phe Ser Asp Asn Thr Lys Asn
1               5

```
<210> SEQ ID NO 198
<211> LENGTH: 8
<212> TYPE: PRT
<213> ORGANISM: human immunodeficiency virus

<400> SEQUENCE: 198

Asn Phe Ser Arg Asn Ala Lys Asn
1               5

<210> SEQ ID NO 199
<211> LENGTH: 8
<212> TYPE: PRT
<213> ORGANISM: human immunodeficiency virus

<400> SEQUENCE: 199

Asn Phe Ser Arg Asn Thr Lys Thr
1               5
```